(12) United States Patent
Hachtel et al.

(10) Patent No.: US 8,501,981 B2
(45) Date of Patent: *Aug. 6, 2013

(54) CXCR2 INHIBITORS

(75) Inventors: Stephanie Hachtel, Frankfurt am Main (DE); Juergen Dedio, Frankfurt am Main (DE); Elisabeth DeFossa, Frankfurt am Main (DE); Sven Grueneberg, Frankfurt am Main (DE); Holger Heitsch, Frankfurt am Main (DE); William Bock, Oro Valley, AZ (US); Charlie Chen, Tucson, AZ (US); Raymond Kosley, Bridgewater, NJ (US); Chung-Yi Kung, Tucson, AZ (US); Marcel Patek, Tucson, AZ (US); Rosy Sher, Bridgewater, NJ (US); Stephen Shimshock, Hillsborough, NJ (US); Aleksandra Weichsel, Tucson, AZ (US)

(73) Assignee: SANOFI, Paris (FR)

( * ) Notice: Subject to any disclaimer, the term of this patent is extended or adjusted under 35 U.S.C. 154(b) by 728 days.

This patent is subject to a terminal disclaimer.

(21) Appl. No.: 12/337,040

(22) Filed: Dec. 17, 2008

(65) Prior Publication Data

US 2009/0227625 A1 Sep. 10, 2009

Related U.S. Application Data

(63) Continuation of application No. PCT/EP2007/005576, filed on Jun. 25, 2007.

(30) Foreign Application Priority Data

Jun. 28, 2006 (EP) .................................. 06013323

(51) Int. Cl.
| | | |
|---|---|---|
| *C07C 229/00* | (2006.01) | |
| *C07C 69/76* | (2006.01) | |
| *C07C 61/00* | (2006.01) | |
| *A01N 37/12* | (2006.01) | |

(52) U.S. Cl.
USPC .............. 560/19; 560/100; 562/433; 562/511

(58) Field of Classification Search
None
See application file for complete search history.

(56) References Cited

U.S. PATENT DOCUMENTS

| | | | |
|---|---|---|---|
| 4,962,224 A | 10/1990 | Wrobel et al. | |
| 4,994,477 A | 2/1991 | Kempf et al. | |
| 7,919,628 B2 * | 4/2011 | Hachtel et al. ................ | 548/179 |
| 2002/0123522 A1 | 9/2002 | Fritz et al. | |
| 2004/0204417 A1 | 10/2004 | Perez et al. | |
| 2005/0059705 A1 | 3/2005 | Mjalli et al. | |
| 2008/0090854 A1 * | 4/2008 | Hachtel et al. ................ | 514/274 |

FOREIGN PATENT DOCUMENTS

| | | |
|---|---|---|
| EP | 1676834 | 7/2006 |
| FR | 2825706 | 12/2002 |
| WO | WO 9907351 | 2/1999 |
| WO | WO01/58852 | 8/2001 |
| WO | WO 0158852 | 8/2001 |
| WO | WO2004/108681 | 12/2004 |
| WO | WO 2004108681 | 12/2004 |
| WO | WO2005/023818 | 3/2005 |
| WO | WO 2005023818 | 3/2005 |
| WO | WO2005/033102 | 4/2005 |
| WO | WO 2005033102 | 4/2005 |
| WO | WO 2005070906 | 4/2005 |
| WO | WO2005/051940 | 6/2005 |
| WO | WO 2005051940 | 6/2005 |
| WO | WO2005/070906 | 8/2005 |
| WO | WO2006/040646 | 4/2006 |
| WO | WO 2006040646 | 4/2006 |
| WO | WO2006/052722 | 5/2006 |
| WO | WO 2006052722 | 5/2006 |
| WO | WO 2006/099610 | 9/2006 |
| WO | WO2006/099610 | 9/2006 |

OTHER PUBLICATIONS

Database CAPLUS Chemical Abstracts Service, Columbus, Ohio, US; Database Accession No. 1972:47393, Abstract of Van Den Eynde et al.: DE 2108189, Sep. 9, 1971.*
Database CAPLUS Chemical Abstracts Service, Columbus, Ohio, US; Database Accession No. 2006:649653, Abstract of WO 2006069656, Published Jul. 6, 2006.*
Kubinyi (3D QSAR in Drug Design: Ligand-Protein Interactions and Molecular Similarity, vol. 2-3, Springer, 1998, 800 pages).
Boschelli et al., Inhibition of E-Selectin-, ICAM-I-, and VCAM-1-Mediated Cell Adhesion by Benzo(b)thiophene-, Benzofuran-. Indole. and Naphthalene-2-carboxamides: Identification of PD 144795 as a Antiinflammatory Agent, J. Med. Chem., 1995, pp. 4597-4614, vol. 38.

(Continued)

*Primary Examiner* — Karl J Puttlitz
(74) *Attorney, Agent, or Firm* — Scully, Scott, Murphy & Presser, P.C.

(57) ABSTRACT

The invention relates to compounds of the formula I

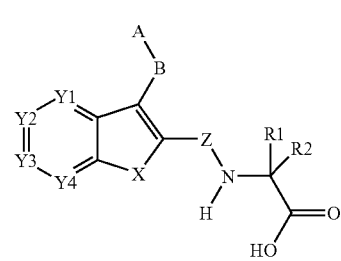

in which R1, R2, X, A, B, Z and Y1 to Y4 have the meanings indicated in the claims, and/or a pharmaceutically acceptable salt and/or a prodrug thereof. Because of their properties as inhibitors of chemokine receptors, especially as CXCR2 inhibitors, the compounds of the formula I and the pharmaceutically acceptable salts and prodrugs thereof are suitable for the prevention and treatment of chemokine mediated diseases.

34 Claims, No Drawings

OTHER PUBLICATIONS

CAPLUS Abstract of: Jodlbauer et al. (J. Chromatography, A (2002), 945(1-2), 45-63).
International Search Report dated Mar. 29, 2006 issued in PCT/EP2005/013624.
International Search Report dated Sep. 14, 2007 issued in PCT/EP2007/005574.
International Search Report dated Sep. 3, 2007 issued in PCT/EP2007/005575.
International Search Report dated Oct. 2, 2007 issued in PCT/EP2007/005576.
International Search Report dated Sep. 3, 2007 issued in PCT/EP2007/005577.
U.S. Office Action dated Nov. 18, 2011 received in related U.S. Appl. No. 13/079,522.
Wermuth, The Practice of Medicinal Chemistry, 2d ed., 768 pages, Chapters 9-10 provided.
U.S. Office Action dated Jan. 12, 2012 received in related U.S. Appl. No. 12/337,040.
U.S. Office Action dated Sep. 26, 2011 received in related U.S. Appl. No. 12/337,040.
U.S. Final Office Action dated Feb. 29, 2012 received in related U.S. Appl. No. 12/337,107.
Huff J.R., "HIV Protease: A Novel Chemotherapeutic Target for AIDS", *Journal of Medicinal Chemistry*, 34(8):2305-2314 (Aug. 1991).
The Merck Manual of Diagnosis and Therapy (16$^{th}$ Ed., pp. 52-55) (1999).
Johnson J. et al., "Relationships Between Drug Activity in NCI Preclinical In Vitro and In Vivo Models and Early Clinical Trials", *British Journal of Cancer*, 84(10):1424-1431 (2001).
Lala P.K. et al., "Role of Nitric Oxide in Tumor Progression: Lessons from Experimental Tumors", *Cancer and Metastasis Reviews*, 17:91-106 (1998).
Sausville E.A. et al., "Contributions of Human Tumor Xenografts to Anticancer Drug Development", *Cancer Research* 66(7):3351-3354 (Apr. 1, 2006).
Golub T.R. et al., "Molecular Classification of Cancer: Class Discovery and Class Prediction by Gene Expression Monitoring", *Science*, 286:531-537 (1999).
U.S. Office Action dated Jul. 12, 2011 received in related U.S. Appl. No. 12/337,107.
U.S. Final Office Action dated Feb. 8, 2012 received in related U.S. Appl. No. 12/337,970.
U.S. Office Action dated Sep. 15, 2011 received in related U.S. Appl. No. 12/337,970.
U.S. Final Office Action dated Mar. 22, 2012 received in related U.S. Appl. No. 12/337,980.
U.S. Office Action dated Nov. 2, 2011 received in related U.S. Appl. No. 12/337,980.

* cited by examiner

CXCR2 INHIBITORS

Chemokines are a family of low molecular weight proteins (8-13 kDa) that are classified into four distinct groups depending on the positioning of the cysteine motif at the amino terminus. The family members comprise CXC, CC, XC, and CX3C chemokines of which CXC and CC are the largest and most characterized. The CXC chemokines include interleukin-8 (IL-8), neutrophil-activating protein-2 (NAP-2), growth-related oncogenes GRO-α, GRO-β, GRO-γ, epithelial cell-derived neutrophil activating factor-78 (ENA-78), granulocyte chemoattractant protein-2 (GCP-2), γ-interferon-inducible protein-10 (γIP-10), interferon-inducible T cell α-chemoattractant (I-TAC), monokine induced by γ-interferon (Mig) and platelet factor-4 (PF-4). CC chemokines include RANTES (regulated on activation normal T cell expressed and secreted), macrophage inflammatory proteins MIP-1α, MIP-1β, monocyte chemoattractant proteins MCP-1, MCP-2, MCP-3 and eotaxin. The XC family comprises two members, lymphotactin-α and lymphotactin-β, and the CX3C family consists only of a single chemokine named fractalkine (Murphy et al., Pharmacol. Rev. 52: 145-176, 2000).

Chemokines mediate their biological effects by binding to cell surface molecules, which belong to the superfamily of seven-transmembrane spanning receptors that signal through coupling to heterotrimeric G proteins. Although most chemokine receptors recognize more than one chemokine, they are almost always restricted to a single subclass. Chemokine receptor binding initiates a cascade of intracellular events of which the first step is the binding of the receptor by its high-affinity ligand. This induces a conformational change leading to a dissociation of the receptor-associated heterotrimeric G proteins into α and βγ subunits. These G protein subunits are able to activate various effector proteins, including phospholipases leading to generation of inositol trisphosphate, an increase in cytosolic calcium, and activation of protein kinases. This cascade of intracellular events mediates a wide range of functions in different leukocytes such as chemotaxis, degranulation, oxidative burst, phagocytosis, and lipid mediator synthesis.

Interleukin-8 (IL-8) is a key mediator of immunological reactions in inflammatory disorders such as atherosclerosis, ischemia/reperfusion injury, rheumatoid arthritis, chronic obstructive pulmonary disease, respiratory distress syndrome, asthma, cystic fibrosis, and psoriasis (Bizarri et al., Curr. Med. Chem. 2: 67-79, 2003). IL-8 is the most characterized member of the CXC subfamily of chemokines. Leukocyte responses to IL-8 are mediated via specific cell surface receptors, CXCR1 and CXCR2. Whereas CXCR1 is selectively activated by IL-8, CXCR2 responds to several additional chemokines including growth-related oncogenes GRO-α, GRO-β, GRO-γ, neutrophil-activating protein-2 (NAP-2), epithelial cell-derived neutrophil activating factor-78 (ENA-78), and granulocyte chemoattractant protein-2 (GCP-2). The common denominator shared by all chemokines that activate CXCR2 is a Glu-Leu-Arg (ELR) sequence in the amino terminus, which appears to serve as a recognition sequence for receptor binding and activation (Herbert et al., J. Biol. Chem. 266: 18989-18994, 1991).

Early investigations concentrated on the effect of IL-8 on neutrophils, which respond to IL-8 with calcium mobilization, actin polymerization, enzyme release, chemotaxis, and the respiratory burst. Despite similar affinities for IL-8 and similar receptor numbers of CXCR1 and CXCR2 on neutrophils, both receptors are functionally different. Responses such as calcium mobilization and the release of granule enzymes are mediated through both receptors, whereas the respiratory burst and the activation of phospholipase D depend exclusively on stimulation of CXCR1 (Jones et al., Proc. Natl. Acad. Sci. USA 93: 6682-6686, 1996). Due to their prominent role in neutrophil recruitment, CXCR1 and CXCR2 are thought to be important in several acute neutrophil-mediated diseases such as acute respiratory distress syndrome and ischemia/reperfusion injuries, as well as in chronic diseases such as asthma, psoriasis, dermatitis, and arthritis.

It has been shown that CXCR2 is also expressed by monocytes. Despite IL-8's inactivity in monocyte chemotaxis assay, this factor induces calcium flux and respiratory burst in monocytes and enhances adhesion of monocytes in static assays. Similarly, GRO-α enhances adhesion of monocytes to stimulated endothelial cells.

Moreover, IL-8 is able to induce firm arrest of monocytes on endothelial cells under conditions of physiological flow (Gerszten et al., Nature 398: 718-723, 1999). Since CXCR2 is strongly expressed on monocytes and macrophages in atherosclerotic lesions where it is suggested to play a key role in chemoattraction, retension, expansion, and activation of monocytes and macrophages, this strongly suggests that CXCR2 and one or more of its ligands (IL-8, GRO-α) play a pathophysiological role in atherosclerosis (Huo et al., J. Clin. Invest. 108: 1307-1314, 2001).

Apart from neutrophils and monocytes, numerous cell types have been shown to express IL-8 receptors. These cell types include neurons, various cancer cells, keratinocytes, and endothelial cells. Several lines of evidence indicate that IL-8 plays a direct role in angiogenesis via stimulation of CXCR2 expressed on endothelial cells. IL-8 has been shown to bind specifically to endothelial cells and induce chemotaxis. IL-8 is able to induce neovascularization in the absence of inflammatory responses (Koche et al., Science 258: 1798-1801, 1992). Moreover, there is accumulating evidence that IL-8 could play a key role in melanoma progression and metastasis as patients with melanoma metastases have elevated serum levels of IL-8. IL-8 is supposed to act as an autocrine growth and metastatic factor for melanoma cells (Schadendorf et al., J. Immunol: 151-157, 1993).

Due to the wide range of actions of IL-8, such as attraction and activation of neutrophils and monocytes/macrophages as well as promotion of endothelial cell proliferation and cancer cell growth, the inhibition of chemokine receptors CXCR1 and CXCR2 is expected to be beneficial in the prevention and treatment of numerous diseases. Besides acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78 or GCP-2) mediated diseases include adult respiratory distress syndrome, inflammatory bowel disease, ulcerative colitis, Crohn's disease, atopic dermatitis, cystic fibrosis, psoriasis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer.

U.S. Pat. No. 4,962,224 (American Home) relates to 2-0xy-N-naphthaloyl-methylglycines useful in the treatment of diabetis melitus. FR 2 825 706 (Piere Fabre) describes inole-1-aryl-2-carbonyl-alanine derivatives. US 2005/059705 (Mjalli et al.) discloses substituted isoquinoline-2-carbonyl-alanine derivatives with multiple substitutions on the hetero ring useful as antithrombotic agents. EP 1 676 834 (Sanofi-Aventis) relates to fused bicyclic aromaticv carboxamide derivatives useful as CXCR2 inhibitors having a shorter linker B. WO 2004/108681 (Fibrogen Inc) describes 2-carbonyl-alanine-isoquinoline derivatives effective in the prevention of tissue damage caused by ischemia. WO 2005/023818 (Axima) discloses heterobicyclic compounds with the carboxamide moiety connected on the position 1 instead of the position 2 of the heteroring. WO 01/58852 (Dompe Spa.) relates to N-(2-aryl-propionyl)-amides useful in the inhibition of the chemotaxis of neutrophils induced by IL-8.

The invention provides novel compounds represented by the formula I and pharmaceutically acceptable salts, solvates, isomers or prodrugs thereof, which are inhibitors of chemokine receptors, in particular of CXC-chemokine receptors, more particular of CXCR2, and therefore useful for the prevention and treatment of chemokine mediated diseases.

The present invention relates to a compound of formula I

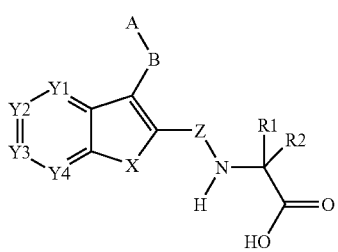

wherein
X is —CR3=CR4-, —CR5=N—, —N=CR6-, —NR7- or —S—;
R3, R4, R5 and R6
  are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR27R28, C(O)R29, C(O)NR30R31, $S(O)_oR32$, $S(O)_p$NR33R34, aryl, heteroaryl, arylalkyl with alkyl having 1, 2, 3 or 4 carbon atoms or heteroarylalkyl with alkyl having 1, 2, 3 or 4 carbon atoms;
  R27 is hydrogen or alkyl having 1, 2, 3 or 4 carbon atoms;
  R28 is hydrogen, alkyl having 1, 2, 3 or 4 carbon atoms, aryl, C(O)H, C(O)alkyl with alkyl having 1, 2, 3 or 4 carbon atoms or C(O)aryl;
  R29 is hydrogen, OH, alkyl with 1, 2, 3 or 4 carbon atoms, alkoxy with 1, 2, 3 or 4 carbon atoms or aryl;
  R30, R31, R33 and R34
    are, independently of one another, hydrogen, alkyl having 1, 2, 3 or 4 carbon atoms or aryl;
  R32 is OH, alkyl having 1, 2, 3 or 4 carbon atoms, alkoxy with 1, 2, 3 or 4 carbon atoms or aryl;
  o and p
    are, independently of one another, 1 or 2;
  R7 is hydrogen, alkyl having 1, 2, 3 or 4 carbon atoms or C(O)R35;
  R35 is hydrogen, alkyl with 1, 2, 3 or 4 carbon atoms or aryl;
Y1, Y2, Y3 and Y4
  are, independently of one another, —CR8- or nitrogen, with the proviso that at least two of Y1, Y2, Y3 and Y4 are defined as —CR8-;
  R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR36R37, C(O)R38, C(O)NR39R40, $S(O)_qR41$, $S(O)_r$NR42R43, aryl, heteroaryl, arylalkyl with alkyl having 1, 2, 3 or 4 carbon atoms or heteroarylalkyl with alkyl having 1, 2, 3 or 4 carbon atoms;
  R36 is hydrogen or alkyl having 1, 2, 3 or 4 carbon atoms;
  R37 is hydrogen, alkyl having 1, 2, 3 or 4 carbon atoms, aryl, C(O)H, C(O)alkyl with alkyl having 1, 2, 3 or 4 carbon atoms or C(O)aryl;
  R38 is hydrogen, OH, alkyl with 1, 2, 3 or 4 carbon atoms, alkoxy with 1, 2, 3 or 4 carbon atoms or aryl;
  R39, R40, R42 and R43
    are, independently of one another, hydrogen, alkyl having 1, 2, 3 or 4 carbon atoms or aryl;
  R41 is OH, alkyl having 1, 2, 3 or 4 carbon atoms, alkoxy with 1, 2, 3 or 4 carbon atoms or aryl;
  q and r
    are, independently of one another, 1 or 2;
Z is —C(O)—, —S(O)— or —S(O)$_2$—;
A is cycloalkyl having 3, 4, 5, 6, 7 or 8 carbon atoms, heterocyclyl having 5, 6, 7 or 8 atoms, phenyl or heteroaryl having 5 or 6 atoms;
  in which the said cycloalkyl, heterocyclyl, phenyl or heteroaryl can be condensed to a cycloalkyl radical having 3, 4, 5, 6, 7 or 8 atoms, a heterocyclyl radical having 5, 6, 7 or 8 atoms, a phenyl radical or a heteroaryl radical having 5 or 6 atoms,
  and in which said cycloalkyl, heterocyclyl, phenyl or heteroaryl and the optionally condensed cycloalkyl radical, heterocyclyl radical, phenyl radical or heteroaryl radical are unsubstituted or substituted by 1, 2, 3, 4 or 5 radicals selected from the group consisting of F, Cl, Br, I, OH, CN, NO$_2$, SF$_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms or —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

B is a linear linker consisting of 3, 4 or 5 carbon atoms, in which 1 or 2 carbon atoms can be replaced by a member of a heteroatom containing group consisting of O, NR19 or S(O)$_y$, and which linker may contain 0, 1 or 2 double or triple bonds between carbon atoms within the linker, with the provisos, that 2 of said heteroatom containing groups are separated by at least 2 carbon atoms, that heteroatom containing groups are not adjacent to a double or triple bond within the linker or to a non-aromatic double bond, which might be part of A, that double or triple bonds are not cumulated, and that, if A is connected to the linker via a nitrogen atom being part of A, the atom of the linker which is connected to A is a carbon atom;

and in which linker saturated carbon atoms, which are not adjacent to heteroatom containing groups, which are not adjacent to double or triple bonds within the linker or which are not adjacent to a heteroatom, which might be part of A, can, independently of one another, be substituted by hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms; cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

and in which linker saturated carbon atoms, which are adjacent to heteroatom containing groups, which are adjacent to double or triple bonds in the linker, or which are adjacent to a heteroatom, which might be part of A, or carbon atoms being part of a double bond, can, independently of one another, be substituted by hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is hydrogen, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

R44, R45 and R46
are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms;

y is 0, 1 or 2;

R1 is alkyl having 1, 2, 3, 4, 5 or 6 carbon atoms;
which can be unsubstituted or substituted by 1, 2, 3, 4 or 5 radicals selected from the group consisting of F, Cl, Br, I, —O$_m$—(CH$_2$)$_n$—R26;
m is 0 or 1;
n is 0, 1, 2 or 3;
R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from F, Cl, Br or I;

R2 is alkyl having 1, 2, 3, 4, 5 or 6 carbon atoms, phenyl, heteroaryl having 5 or 6 atoms, cycloalkyl having 3, 4, 5, 6, 7 or 8 carbon atoms or heterocyclyl having 3, 4, 5, 6, 7 or 8 atoms;
wherein alkyl is unsubstituted or substituted by 1, 2, 3, 4 or 5 radicals selected from the group consisting of F, Cl, Br, I, —O$_m$—(CH$_2$)$_n$—R26;
m is 0 or 1;
n is 0, 1, 2 or 3;
R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from F, Cl, Br or I;
and wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2, 3, 4 or 5 radicals selected from the group consisting of F, Cl, Br, I, OH, CN, NO$_2$, SCF$_3$, SF$_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

or

R1 and R2 form, together with the carbon atom to which they are attached, a 3-, 4-, 5- or 6-membered carbon ring, wherein one carbon atom, which is not adjacent to the carbon atom, to which R1 and R2 are attached, can be replaced by —O—, —NR57- or —S(O)$_w$—, and in which the formed ring can be saturated or partially unsaturated, and in which the formed ring can optionally be condensed to phenyl, heteroaryl having 5 or 6 atoms, cycloalkyl having 3, 4, 5, 6, 7 or 8 carbon atoms or heterocyclyl having 3, 4, 5, 6, 7 or 8 atoms;

wherein the formed ring and the optionally condensed phenyl, heteroaryl, cycloalkyl or heterocyclyl radical can be unsubstituted or substituted by 1, 2, 3, 4 or 5 radicals selected from the group consisting of F, Cl, Br, I, CN, NO$_2$, SCF$_3$, SF$_5$ or alkyl having 1, 2, 3 or 4 carbon atoms;

R57 is hydrogen, alkyl having 1, 2, 3 or 4 carbon atoms or C(O)R58;

R58 is hydrogen, alkyl with 1, 2, 3 or 4 carbon atoms or phenyl;

w is 0, 1 or 2;

and/or a pharmaceutically acceptable salt and/or a prodrug thereof.

In one embodiment X in compounds of formula I is described by —CR3=CR4-, —CR5=N—, —N=CR6-, —NR7- or —S—, wherein R3, R4, R5 and R6, are independently of one another, hydrogen, F, Cl, Br, I, alkyl having 1, 2, 3 or 4 carbon atoms or alkoxy having 1, 2, 3 or 4 carbon atoms, and R7 is hydrogen or alkyl having 1, 2, 3 or 4 carbon atoms, preferably hydrogen;

preference is given to compounds, in which X is described by —CR3=CR4-, —CR5=N—, —N=CR6-, —NH— or —S—, wherein R3, R4, R5 and R6 are, independently of one another, hydrogen, F, Cl, Br, I or alkyl having 1, 2, 3 or 4 carbon atoms, preferably R3, R4, R5 and R6 are, independently of one another, hydrogen, F, Cl or Br;

particular preference is given to compounds, in which X is described as —CR3=CH—, —CH=N—, —N=CH, NH or —S—, wherein R3 is defined as hydrogen, F, Cl or Br;

more particular preference is given to compounds, in which X is described as —CR3=CH— or —S—, wherein R3 is defined as hydrogen, F, Cl or Br.

In another embodiment X in compounds of formula I is —CR3=CR4- or —S—; wherein R3 and R4 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN or NO$_2$;

preference is given to compounds, in which R3 and R4 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

particular preference is given to compounds, wherein R3 and R4 are, independently of one another, hydrogen, F, Cl, Br, I or alkyl having 1, 2, 3 or 4 carbon atoms;

more particular preference is given to compounds, wherein R3 and R4 are, independently of one another, hydrogen, F, Cl or Br.

Linker X is attached with its left hand side to the carbon atom in the six-membered ring and with its right hand side to the other carbon atom.

In a further embodiment Y1, Y2, Y3 and Y4 in compounds of formula I are, independently of one another, described by —CR8- or nitrogen, with the proviso that at least two of Y1, Y2, Y3 and Y4 are defined as —CR8-, wherein R8 is hydrogen, F, Cl, Br, I or alkyl having 1, 2, 3 or 4 carbon atoms; preferably at least three of Y1, Y2, Y3 and Y4 are defined as —CR8, wherein R8 is hydrogen, F, Cl, Br, I or alkyl having 1, 2, 3 or 4 carbon atoms, preferably hydrogen or Cl, for example hydrogen; for example Y1, Y2 and Y3 are CH and Y4 is N or Y1, Y2, Y3 and Y4 are CR8, wherein R8 is hydrogen, F or Cl, in particular hydrogen.

In another embodiment Y1, Y2, Y3 and Y4 in compounds of formula I are, independently of one another, —CR8-, wherein R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN or NO$_2$;

preference is given to compounds, wherein R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

particular preference is given to compounds, wherein R8 is hydrogen, F, Cl, Br, I or alkyl having 1, 2, 3 or 4 carbon atoms;

more particular preference is given to compounds, wherein R8 is, independently of one another, hydrogen, F or Cl, in particular hydrogen.

In a further embodiment X in compounds of formula I is described by —CR3=CR4-, —CR5=N—, —N=CR6-, —NR7- or —S—, wherein R3, R4, R5 and R6, are independently of one another, F, Cl, Br, I, alkyl having 1, 2, 3 or 4 carbon atoms or alkoxy having 1, 2, 3 or 4 carbon atoms, and R7 is hydrogen or alkyl having 1, 2, 3 or 4 carbon atoms, preferably hydrogen;
and
Y1, Y2, Y3 and Y4 in compounds of formula I are, independently of one another, described by —CR8- or nitrogen, with the proviso that at least two of Y1, Y2, Y3 and Y4 are defined as —CR8-, wherein R8 is hydrogen, F, Cl, Br, I or alkyl having 1, 2, 3 or 4 carbon atoms.

In a preferred embodiment X in compounds of formula I is described by —CR3=CR4-, —CR5=N—, —N=CR6-, —NH— or —S—, wherein R3, R4, R5 and R6 are, independently of one another, hydrogen, F, Cl, Br, I or alkyl having 1, 2, 3 or 4 carbon atoms, preferably R3, R4, R5 and R6 are, independently of one another, hydrogen, F, Cl or Br; more preferably X is described as —CR3=CH—, —CH=N—, —N=CH, NH or —S—, wherein R3 is defined as hydrogen, F, Cl or Br; more preferably X is described as —CR3=CH— or —S—, wherein R3 is defined as hydrogen, F, Cl or Br;
and
Y1, Y2, Y3 and Y4 in compounds of formula I are, independently of one another, described by —CR8- or nitrogen, with the proviso that at least three of Y1, Y2, Y3 and Y4 are defined as —CR8-, wherein R8 is hydrogen, F, Cl, Br, I or alkyl having 1, 2, 3 or 4 carbon atoms, preferably hydrogen or Cl, for example hydrogen; for example Y1, Y2 and Y3 are CH and Y4 is N or Y1, Y2, Y3 and Y4 are CR8, wherein R8 is hydrogen, F or Cl, in particular hydrogen.

In another embodiment X in compounds of formula I is —CR3=CR4- or —S—; wherein R3 and R4 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN or NO$_2$;
and
Y1, Y2, Y3 and Y4 in compounds of formula I are, independently of one another, —CR8-, wherein R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN or NO$_2$;

In a preferred embodiment X in compounds of formula I is —CR3=CR4- or —S—, in which R3 and R4 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms; preferably R3 and R4 are, independently of one another, hydrogen, F, Cl, Br, I or alkyl having 1, 2, 3 or 4 carbon atoms; more preferably, R3 and R4 are, independently of one another, hydrogen, F, Cl or Br;
and
Y1, Y2, Y3 and Y4 in compounds of formula I are, independently of one another, —CR8-, wherein R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms; preferably R8 is hydrogen, F, Cl, Br, I or alkyl having 1, 2, 3 or 4 carbon atoms; more preferably, R8 Is is hydrogen, F or, Cl, most preferably hydrogen.

In a further embodiment of compounds of formula I Z is —S(O)$_2$— or —C(O)—.

In a preferred embodiment Z is —C(O)—. In the embodiment, where Z is —C(O)—, the compound of formula I has the formula I-I.

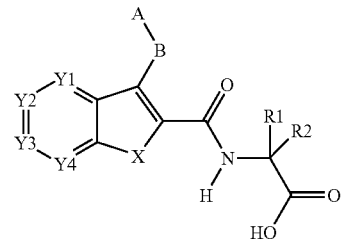

I-I

In a further embodiment of the compounds of formula I A is cycloalkyl having 3, 4, 5, 6, 7 or 8 carbon atoms, heterocyclyl having 5, 6, 7 or 8 atoms, phenyl or heteroaryl having 5 or 6 atoms;
  in which the said phenyl can be condensed to a cycloalkyl radical having 3, 4, 5, 6, 7 or 8 atoms, a heterocyclyl radical having 5, 6, 7 or 8 atoms, a phenyl radical or a heteroaryl radical having 5 or 6 atoms; preferably, the said phenyl is not condensed or condensed to form a naphthyl or an indanyl, more preferably, the said phenyl is not condensed;
  and in which said cycloalkyl, heterocyclyl, phenyl or heteroaryl and the optionally condensed cycloalkyl radical, heterocyclyl radical, phenyl radical or heteroaryl radical are unsubstituted or substituted by 1, 2, 3, 4 or 5 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

In a preferred embodiment A is cycloalkyl having 3, 4, 5, 6, 7 or 8 carbon atoms, heterocyclyl having 5, 6, 7 or 8 atoms, phenyl or heteroaryl having 5 or 6 atoms;

in which the said phenyl can be condensed to form a naphthyl or an indanyl, more preferably, the said phenyl is not condensed;

in which said cycloalkyl, heterocyclyl, phenyl, heteroaryl or the optionally formed naphthyl or indanyl are unsubstituted or substituted by 1, 2, 3, 4 or 5 radicals selected from the group consisting of F, Cl, Br, I, OH, CN, $NO_2$, $SF_5$, $SCF_3$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms.

In a more preferred embodiment,

A is cyclohexyl, piperidyl, phenyl, naphthyl, indanyl, thienyl, pyridinyl or imidazolyl;

in which the phenyl radical is unsubstituted or substituted by 1, 2 or 3 radicals selected from the group consisting of F, Cl, Br, methoxy, alkyl having 1, 2 or 3 carbon atoms in which 1, 2, 3, 4, 5, 6 or 7 hydrogen atoms may be substituted by fluorine atoms;

in which pyridinyl is unsubstituted or substituted by Cl.

In a most preferred embodiment

A is cyclohexyl, phenyl, naphthyl, indanyl or thienyl;

in which the phenyl radical is unsubstituted or substituted by 1, 2 or 3 radicals selected from the group consisting of F, Cl, Br, methoxy, methyl, ethyl, propyl, iso-propyl or trifluoromethyl.

In some of the embodiments of A there is the possibility that A is cycloalkyl having 3, 4, 5, 6, 7 or 8 carbon atoms, heterocyclyl having 5, 6, 7 or 8 atoms, phenyl or heteroaryl having 5 or 6 atoms in which the said cycloalkyl, heterocyclyl, phenyl or heteroaryl can be condensed to a cycloalkyl radical having 3, 4, 5, 6, 7 or 8 atoms, a heterocyclyl radical having 5, 6, 7 or 8 atoms, a phenyl radical or a heteroaryl radical having 5 or 6 atoms. Representative examples for condensed radicals resulting from the mentioned combinations are given in the list below. In case where two different radicals are condensed the examples apply to both situations, where either the one or the other ring in the condensed radical is attached to B. For example, if cycloalkyl is attached to B and is condensed with a heterocyclyl, the same examples also apply to the situation where heterocyclyl is attached to B and is condensed with a cycloalkyl;

Cycloalkyl-cycloalkyl:
Octahydro-pentalene, bicyclo[4.1.0]heptane, octahydro-indene, decahydro-naphthalene, decahydro-azulene Cycloalkyl-heterocyclyl:
Hexahydro-cyclopenta[b]furane, 7-oxa-bicyclo[4.1.0]heptane, octahydro-cyclopenta[1,4]oxazine, octahydro-benzo[1,4]dioxine, octahydro-cyclohepta[b]thiophene;

Cycloalkyl-phenyl:
Bicyclo[4.2.0]octa-1,3,5-triene, indane, 1,2,3,4-tetrahydro-naphthalene, 6,7,8,9-tetrahydro-5H-benzocycloheptene, 5,6,7,8,9,10-hexahydro-benzocyclooctene;

Cycloalkyl-heteroaryl:
6,7-Dihydro-5H-[1]pyrindine, 5,6,7,8-tetrahydro-isoquinoline, 6,7,8,9-tetrahydro-5H-cyclohepta[b]pyridine, 4,5,6,7-tetrahydro-benzooxazole, 4,5,6,7-tetrahydro-benzo[b]thiophene;

Heterocyclyl-heterocyclyl:
Hexahydro-pyrrolizine, 3,7-dioxa-bicyclo[4.1.0]heptane, octahydro-pyrano[3,2-b]pyridine, hexahydro-furo[3,2-b]pyrane, hexahydro-1,4-dioxa-6-thia-naphthalene;

Heterocyclyl-phenyl:
2,3-Dihydro-benzofuran, benzo[1,3]dioxole, 1,2,3,4-tetrahydro-isoquinoline, 2,3,4,5-tetrahydro-1H-benzo[b]azepine, 2,3-dihydro-benzo[d]isoxazole;

Heterocyclyl-heteroaryl:
5,6,7,8-Tetrahydro-4H-thieno[3,2-c]azepine, 5,8-dihydro-6H-pyrano[3,4-b]pyridine, 5,6-dihydro-[1,4]dioxino[2,3-d]thiazole, 6,7-dihydro-5H-pyrrolo[1,2-c]imidazole;

Phenyl-Phenyl:
Naphthyl;

Phenyl-heteroaryl:
Benzofuran, isoquinoline, benzo[d]isoxazole, 1H-benzotriazole, benzothiazole;

Heteroaryl-heteroaryl:
Thiazolo[4,5-c]pyridine, thieno[2,3-d]isoxazole, [1,6]naphthyridine, imidazo[1,2-a]pyridine, furo[2,3-b]pyridine.

Preferred examples of condensed radicals are naphtyl or indanyl. All these examples may be substituted as mentioned above.

The terms cycloalkyl, heterocyclyl, phenyl or heteroaryl are used here interchangeable for being either directly attached as a substituent or being the condensed radical.

In a further embodiment of the compounds of formula I B is

—C(R11R12)-C(R13R14)-O—, —C(R11R12)-C(R15R16)-C(R15R16)-, —C(R13R14)-C≡C—, —C(R13R14)-C(R17)=C(R18)-, —C(R11R12)-C(R13R14)-NR19-, —C(R11R12)-C(R13R14)-S(O)$_y$—, —O—C(R13R14)-C(R15R16), —C≡C—C(R13R14)-, —C(R17)=C(R18)-C(R13R14)-, —C(R13R14)-O—C(R13R14)-, —C(R11R12)-C(R15R16)-C(R13R14)-O—, —C(R11R12)-C(R15R16)-C(R13R14)-NR19-, —C(R11R12)-C(R15R16)-C(R15R16)-C(R15R16)-, —O—C(R13R14)-C(R13R14)-O—, —O—C(R13R14)-C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R13R14)-O—C(R13R14)-C(R15R16)-, —C(R11R12)-C(R13R14)-O—C(R13R14)-,

—C(R11R12)-C(R15R16)-C(R13R14)-S(O)$_y$—,
—O—C(R13R14)-C(R13R14)-S(O)$_y$—, —O—C(R13R14)-C(R17)=C(R18)-, —C≡C—C(R13R14)-C(R15R16)-, —C(R17)=C(R18)-C(R13R14)-C(R15R16)-, —C(R13R14)-C≡C—C(R13R14)-,
—C(R13R14)-C(R17)=C(R18)-C(R13R14)-,
—C(R11R12)-C(R15R16)-C(R15R16)-C(R15R16)-C(R15R16)-, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C—, —C(R13R14)-O—C(R13R14)-C(R13R14)-O—, —C(R13R14)-O—C(R13R14)-C(R15R16)-C(R15R16)-, —C(R11R12)-C(R15R16)-C(R13R14)-C(R17)=C(R18)-, —C(R13R14)-C(R17)=C(R18)-C(R13R14)-O—, —C(R13R14)-C≡C—C(R13R14)-O—, —C(R17)=C(R18)-C(R13R14)-C(R13R14)-O—, —C≡C—C(R13R14)-C(R13R14)-O—, —C(R11R12)-C(R15R16)-C(R13R14)-O—C(R13R14)-, —C(R11R12)-C(R13R14)-O—C(R13R14)-C(R15R16)-, —O—C(R13R14)-C(R15R16)-C(R15R16)-C(R15R16)- or —O—C(R13R14)-C(R13R14)-O—C(R13R14)-;
with the proviso that, if A is connected to the linker B via a nitrogen atom being part of A, the atom of the linker which is connected to A is a carbon atom;

R11 and R12
are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;
with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14, R17 and R18
are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16
are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19
is hydrogen, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

R44, R45 and R46
are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms;

y is 0, 1 or 2.

In a preferred embodiment of a compound of formula I B is —C(R11R12)-C(R13R14)-O—, —C(R11R12)-C(R15R16)-C(R13R14)-O—, —C(R11R12)-C(R15R16)-C(R13R14)-NR19-, —C(R11R12)-C(R15R16)-C(R15R16)-C(R15R16)-, —O—C(R13R14)-C(R13R14)-O—, —O—C(R13R14)-C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R11R12)-C(R15R16)-C(R15R16)-C(R15R16)-C(R15R16)-, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C— or —C(R13R14)-O—C(R13R14)-C(R13R14)-O—,
with the proviso that, if A is connected to the linker via a nitrogen atom being part of A, the atom of the linker which is connected to A is a carbon atom;

R11 and R12
are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14, R17 and R18 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16 are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is H or alkyl having 1, 2, 3, 4, 5 or 6 carbon atoms.

In a more preferred embodiment of a compound of formula I

B is —C(R11R12)-C(R13R14)-O—, —C(R11R12)-C(R15R16)-C(R13R14)-O—, —O—C(R13R14)-C(R13R14)-O—, —C(R17)=C(R18)-C(R13R14)-O—, —C≡C—C(R13R14)-O—, —C(R11R12)-C(R13R14)-C≡C—, —O—C(R13R14)-C≡C—, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C— or —C(R13R14)-O—C(R13R14)-C(R13R14)-O—, with the proviso that, if A is connected to the linker via a nitrogen atom being part of A, the atom of the linker which is connected to A is a carbon atom;

R1 and R12 are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14, R17 and R18 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16 are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

Within the embodiments of B those are preferred, wherein R11-R18 are, independently of each other, hydrogen, F or alkyl having 1, 2, 3, 4 carbon atoms, preferably alkyl being methyl, more preferably R11-R18 are hydrogen or methyl, preferably hydrogen.

Also, within the embodiments of B those are preferred, wherein R19 is hydrogen or methyl, preferably hydrogen.

Also, within the embodiments of B those are preferred, wherein y is 0.

In a more preferred embodiment of B, R11-R19 are, independently of each other, hydrogen or methyl, preferably hydrogen.

Linker B is attached with its left hand side to the residue A and with its right hand side to the ring system.

In a further embodiment of compounds of formula I
R1 is alkyl having 1, 2, 3, 4, 5 or 6 carbon atoms;
  which can be unsubstituted or substituted by 1, 2, 3, 4 or 5 radicals selected from the group consisting of F, Cl, Br, I, $-O_m-(CH_2)_n-R26$;
    m is 0 or 1;
    n is 0, 1, 2 or 3;
    R26 is hydrogen or phenyl, heteroaryl having 5 or 6 atoms, cycloalkyl having 3, 4, 5 or 6 carbon atoms or heterocyclyl having 3, 4 5, 6, 7 or 8 atoms;
and
R2 is alkyl having 1, 2, 3, 4, 5 or 6 carbon atoms or phenyl;
  wherein alkyl is unsubstituted or substituted by 1, 2, 3, 4 or 5 radicals selected from the group consisting of F, Cl, Br, I, $-O_m-(CH_2)_n-R26$;
    m is 0 or 1;
    n is 0, 1, 2 or 3;
    R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from F, Cl, Br or I;
  and wherein phenyl is unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms,
or
R1 and R2
  form, together with the carbon atom to which they are attached, a 3-, 4,5- or 6-membered saturated or partly saturated carbon ring, which can be condensed to phenyl;
    wherein the formed ring and the optionally condensed phenyl can be unsubstituted or substituted by 1, 2, 3, 4 or 5 radicals selected from the group consisting of F, Cl, Br, I, CN, $NO_2$, $SCF_3$, $SF_5$ or alkyl having 1, 2, 3 or 4 carbon atoms;
    preferably, the formed ring is not condensed to phenyl;
or
R1 and R2
  form, together with the carbon atom to which they are attached, a 4-, 5- or 6-membered saturated or partly saturated carbon ring, wherein one carbon atom, which is not adjacent to the carbon atom, to which R1 and R2 are attached, is replaced by —O—, —NR57- or $-S(O)_w-$, and in which the formed ring can optionally be condensed to phenyl,
    wherein the formed ring and the optionally condensed phenyl can be unsubstituted or substituted by 1, 2, 3, 4 or 5 radicals selected from the group consisting of F, Cl, Br, I, CN, $NO_2$, $SCF_3$, $SF_5$ or alkyl having 1, 2, 3 or 4 carbon atoms;
      R57 is hydrogen, alkyl having 1, 2, 3 or 4 carbon atoms or C(O)R58;
        R58 is hydrogen, alkyl with 1, 2, 3 or 4 carbon atoms or phenyl;
      preferably, R57 is hydrogen or alkyl having 1, 2, 3 or 4 carbon atoms;
    w is 0, 1 or 2;
    preferably, w is 0, and preferably, the formed ring is not condensed to phenyl.

In a preferred embodiment of compounds of formula I
R1 is alkyl having 1, 2, 3, 4, 5 or 6 carbon atoms;
and
R2 is alkyl having 1, 2, 3, 4, 5 or 6 carbon atoms or phenyl;
  wherein alkyl is unsubstituted or substituted by 1, 2, 3, 4 or 5 radicals selected from the group consisting of F, Cl, Br, I, $-O_m-(CH_2)_n-R26$;
    m is 0 or 1;
    n is 0, 1, 2 or 3;
    R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from F, Cl, Br or I;
    preferably, R26 is hydrogen or phenyl;
or
R1 and R2
  form, together with the carbon atom to which they are attached, a 3-, 4, 5- or 6-membered saturated or partly saturated carbon ring, which can be condensed to phenyl; preferably, the formed ring is not condensed to phenyl;
or
R1 and R2
  form, together with the carbon atom to which they are attached, a 4-, 5- or 6-membered saturated or partly saturated carbon ring, wherein one carbon atom, which is not adjacent to the carbon atom, to which R1 and R2 are attached, is replaced by —O—, —NH— or —S—.

In a more preferred embodiment
R1 is alkyl having 1, 2, 3 or 4 carbon atoms;
and
R2 is alkyl having 1, 2, 3 or 4 carbon atoms, phenyl or benzyl;
or
R1 and R2
  form, together with the carbon atom to which they are attached, a cyclopropane, cyclobutane, cyclopentane, cyclohexane, cyclopentene ring or indene;
  preferably R1 and R2 form a cyclopropane, cyclobutane, cyclopentane, cyclohexane or cyclopent-3-ene ring;
or
R1 and R2
  form, together with the carbon atom to which they are attached, a tetrahydro-thiophene, a tetrahydro-thiopyrane or a tetrahydro-furane ring; preferably, a tetrahydro-thiophene or a tetrahydro-thiopyrane ring, more preferably a 3-tetrahydro-thiophene or a 4-tetrahydro-thiopyrane ring.

In a most preferred embodiment
R1 is methyl or ethyl;
and
R2 is methyl or ethyl; preferably methyl;
or
R1 and R2
  form, together with the carbon atom to which they are attached, a cyclobutane or cyclopentane ring.

In given embodiments of the present invention one or more or all of the groups contained in the compounds of formula I can independently of each other have any of the given, preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention.

Preference is given to compounds of formula I in which
X is —CR3=CR4-, —CR5=N—, —N=CR6-, —NR7- or —S—, wherein
  R3, R4, R5 and R6,
    are independently of one another, hydrogen, F, Cl, Br, I, alkyl having 1, 2, 3 or 4 carbon atoms or alkoxy having 1, 2, 3 or 4 carbon atoms, and
  R7 is hydrogen or alkyl having 1, 2, 3 or 4 carbon atoms;
Y1, Y2, Y3 and Y4
  are, independently of one another, —CR8- or nitrogen, with the proviso that at least two of Y1, Y2, Y3 and Y4 are defined as —CR8-, wherein
    R8 is hydrogen, F, Cl, Br, I or alkyl having 1, 2, 3 or 4 carbon atoms;
Z is —S(O)$_2$— or —C(O)—;
A is cycloalkyl having 3, 4, 5, 6, 7 or 8 carbon atoms, heterocyclyl having 5, 6, 7 or 8 atoms, phenyl or heteroaryl having 5 or 6 atoms;
  in which the said phenyl can be condensed to a cycloalkyl radical having 3, 4, 5, 6, 7 or 8 atoms, a heterocyclyl radical having 5, 6, 7 or 8 atoms, a phenyl radical or a heteroaryl radical having 5 or 6 atoms,
    and in which said cycloalkyl, heterocyclyl, phenyl or heteroaryl and the optionally condensed cycloalkyl radical, heterocyclyl radical, phenyl radical or heteroaryl radical are unsubstituted or substituted by 1, 2, 3, 4 or 5 radicals selected from the group consisting of F, Cl, Br, I, OH, CN, NO$_2$, SF$_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
B is —C(R11R12)-C(R13R14)-O—, —C(R11R12)-C(R15R16)-C(R15R16)-, —C(R13R14)-C≡C—, —C(R13R14)-C(R17)=C(R18)-, —C(R11R12)-C(R13R14)-NR19-, —C(R11R12)-C(R13R14)-S(O)$_y$—, —O—C(R13R14)-C(R15R16), —C≡C—C(R13R14)-, —C(R17)=C(R18)-C(R13R14)-, —C(R13R14)-O—C(R13R14)-, —C(R11R12)-C(R15R16)-C(R13R14)-O—, —C(R11R12)-C(R15R16)-C(R13R14)-NR19-, —C(R11R12)-C(R15R16)-C(R15R16)-, —O—C(R13R14)-C(R13R14)-O—, —O—C(R13R14)-C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R13R14)-O—C(R13R14)-C(R15R16)-, —C(R11R12)-C(R13R14)-O—C(R13R14)-, —C(R11R12)-C(R15R16)-C(R13R14)-S(O)$_y$—, —O—C(R13R14)-C(R13R14)-S(O)$_y$—, —O—C(R13R14)-C(R17)=C(R18)-, —C≡C—C(R13R14)-C(R15R16)-, —C(R17)=C(R18)-C(R13R14)-C(R15R16)-, —C(R13R14)-C≡C—C(R13R14)-, —C(R13R14)-C(R17)=C(R18)-C(R13R14)-, —C(R11R12)-C(R15R16)-C(R15R16)-C(R15R16)-, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-O—, —C(R13R14)-C≡C—, —C(R13R14)-O—C(R13R14)-C(R13R14)-O—, —C(R13R14)-O—C(R13R14)-C(R15R16)-, —C(R11R12)-C(R15R16)-C(R13R14)-C(R17)=C(R 8)-, —C(R13R14)-C(R17)=C(R18)-C(R13R14)-O—, —C(R13R14)-C≡C—C(R13R14)-O—, —C(R17)=C(R18)-C(R13R14)-C(R13R14)-O—, —C≡C—C(R13R14)-C(R13R14)-O—, —C(R11R12)-C(R15R16)-C(R13R14)-O—C(R13R14)-, —C(R11R12)-C(R13R14)-O—C(R13R14)-C(R15R16)-, —O—C(R13R14)-C(R15R16)-C(R15R16)- or —O—C(R13R14)-C(R13R14)-O—C(R13R14)-,
with the proviso that, if A is connected to the linker B via a nitrogen atom being part of A, the atom of the linker which is connected to A is a carbon atom,
R11 and R12
  are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;
  with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14, R17 and R18
are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16
are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is hydrogen, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

R44, R45 and R46
are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms;

y is 0, 1 or 2;

R1 is alkyl having 1, 2, 3, 4, 5 or 6 carbon atoms; and

R2 is alkyl having 1, 2, 3, 4, 5 or 6 carbon atoms or phenyl; wherein alkyl is unsubstituted or substituted by 1, 2, 3, 4 or 5 radicals selected from the group consisting of F, Cl, Br, I, —O$_m$—(CH$_2$)$_n$—R26;

m is 0 or 1;

n is 0, 1, 2 or 3;

R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from F, Cl, Br or I;

or

R1 and R2
form, together with the carbon atom to which they are attached, a 3-, 4-, 5- or 6-membered saturated or partly saturated carbon ring, which can be condensed to phenyl;

or

R1 and R2
form, together with the carbon atom to which they are attached, a 4-, 5- or 6-membered saturated or partly saturated carbon ring, wherein one carbon atom, which is not adjacent to the carbon atom to which R1 and R2 are attached, is replaced by —O—, —NH— or —S—;

and/or a pharmaceutically acceptable salt and/or prodrug thereof.

Also, preference is given to compounds of formula I, in which

X is —CR3=CR4- or —S—; wherein

R3 and R4
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN or NO$_2$;

Y1, Y2, Y3 and Y4
are, independently of one another, —CR8-, wherein

R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN or NO$_2$;

Z is —S(O)₂— or —C(O)—.

A is cycloalkyl having 3, 4, 5, 6, 7 or 8 carbon atoms, heterocyclyl having 5, 6, 7 or 8 atoms, phenyl or heteroaryl having 5 or 6 atoms;
in which the said phenyl can be condensed to a cycloalkyl radical having 3, 4, 5, 6, 7 or 8 carbon atoms, a heterocyclyl radical having 5, 6, 7 or 8 atoms, a phenyl radical or a heteroaryl radical having 5 or 6 atoms,
and in which said cycloalkyl, heterocyclyl, phenyl or heteroaryl and the optionally condensed cycloalkyl radical, heterocyclyl radical, phenyl radical or heteroaryl radical are unsubstituted or substituted by 1, 2, 3, 4 or 5 radicals selected from the group consisting of F, Cl, Br, I, OH, CN, NO₂, SF₅, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

B is —C(R11R12)-C(R13R14)-O—, —C(R11R12)-C(R15R16)-C(R15R16)-, —C(R13R14)-C≡C—, —C(R13R14)-C(R17)=C(R18)-, —C(R11R12)-C(R13R14)-NR19-, —C(R11R12)-C(R13R14)-S(O)$_y$—, —O—C(R13R14)-C(R15R16), —C≡C—C(R13R14)-, —C(R17)=C(R18)-C(R13R14)-, —C(R13R14)-O—C(R13R14)-, —C(R11R12)-C(R15R16)-C(R13R14)-O—, —C(R11R12)-C(R15R16)-C(R13R14)-NR19-, —C(R11R12)-C(R15R16)-C(R15R16)-, —O—C(R13R14)-C(R13R14)-O—, —O—C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R13R14)-O—C(R13R14)-C(R15R16)-, —C(R11R12)-C(R13R14)-O—C(R13R14)-, —C(R11R12)-C(R15R16)-C(R13R14)-S(O)$_y$—, —O—C(R13R14)-C(R13R14)-S(O)$_y$—, —O—C(R13R14)-C(R17)=C(R18)-, —C≡C—C(R13R14)-C(R15R16)-, —C(R17)=C(R18)-C(R13R14)-C(R15R16)-, —C(R13R14)-C≡C—C(R13R14)-, —C(R13R14)-C(R17)=C(R18)-C(R13R14)-, —C(R11R12)-C(R15R16)-C(R15R16)-C(R15R16)-, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-O—, —C(R13R14)-C≡C—, —C(R13R14)-O—C(R13R14)-C(R13R14)-O—, —C(R13R14)-O—C(R13R14)-C(R15R16)-C(R15R16)-, —C(R11R12)-C(R15R16)-C(R13R14)-C(R17)=C(R18)-, —C(R13R14)-C(R17)=C(R18)-C(R13R14)-C(R17)=C(R18)-C(R13R14)-O—, —C(R13R14)-C≡C—C(R13R14)-O—, —C≡C—C(R13R14)-C(R13R14)-O—, —C(R11R12)-C(R15R16)-C(R13R14)-O—C(R13R14)-, —C(R11R12)-C(R13R14)-O—C(R13R14)-, —O—C(R13R14)-C(R15R16)-C(R15R16)-C(R15R16)- or —O—C(R13R14)-C(R13R14)-O—C(R13R14)-, with the proviso that, if A is connected to the linker B via a nitrogen atom being part of A, the atom of the linker which is connected to A is a carbon atom, R11 and R12
are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14, R17 and R18
are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16
are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is hydrogen, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

R44, R45 and R46 are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms;

y is 0, 1 or 2;

R1 is alkyl having 1, 2, 3, 4, 5 or 6 carbon atoms;
and
R2 is alkyl having 1, 2, 3, 4, 5 or 6 carbon atoms or phenyl;
wherein alkyl is unsubstituted or substituted by 1, 2, 3, 4 or 5 radicals selected from the group consisting of F, Cl, Br, I, —O$_m$—(CH$_2$)$_n$—R26;

m is 0 or 1;

n is 0, 1, 2 or 3;

R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from F, Cl, Br or I;

or
R1 and R2
form, together with the carbon atom to which they are attached, a 3-, 4-, 5- or 6-membered saturated or partly saturated carbon ring, which can be condensed to phenyl;
or
R1 and R2
form, together with the carbon atom to which they are attached, a 4-, 5- or 6-membered saturated or partly saturated carbon ring, wherein one carbon atom, which is not adjacent to the carbon atom to which R1 and R2 are attached, is replaced by —O—, —NH— or —S—;
and/or a pharmaceutically acceptable salt and/or prodrug thereof.

Particular preference is given to compounds of formula I, in which

X is —CR3=CR4-, —CR5=N—, —N=CR6-, —NH— or —S—, wherein
R3, R4, R5 and R6,
are independently of one another, hydrogen, F, Cl or Br;
Y1, Y2, Y3 and Y4
are, independently of one another, —CR8- or nitrogen, with the proviso that at least three of Y1, Y2, Y3 and Y4 are defined as —CR8-, wherein R8 is hydrogen, F or Cl;
Z is —C(O)—;

A is cycloalkyl having 3, 4, 5, 6, 7 or 8 carbon atoms, heterocyclyl having 5, 6, 7 or 8 atoms, phenyl or heteroaryl having 5 or 6 atoms;
in which the said phenyl can be condensed to form a naphthyl or an indanyl;
in which said cycloalkyl, heterocyclyl, phenyl, heteroaryl or the optionally formed naphthyl or indanyl are unsubstituted or substituted by 1, 2, 3, 4 or 5 radicals selected from the group consisting of F, Cl, Br, I, OH, CN, NO$_2$, SF$_5$, SCF$_3$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

B is —C(R11R12)-C(R13R14)-O—, —C(R11R12)-C(R15R16)-C(R13R14)-O—, —C(R11R12)-C(R15R16)-C(R13R14)-NR19-, —C(R11R12)-C(R15R16)-C(R15R16)-C(R15R16)-, —O—C(R13R14)-C(R13R14)-O—, —O—C(R13R14)-C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R11R12)-C(R15R16)-C(R15R16)-C(R15R16)-, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C— or —C(R13R14)-O—C(R13R14)-C(R13R14)-O—, with the proviso that, if A is connected to the linker via a nitrogen atom being part of A, the atom of the linker which is connected to A is a carbon atom;

R11-R18 are, independently of one another, hydrogen, F or alkyl having 1, 2, 3, 4 carbon atoms R19 is H or alkyl having 1, 2, 3, 4, 5 or 6 carbon atoms;

R1 is alkyl having 1, 2, 3 or 4 carbon atoms;
and
R2 is alkyl having 1, 2, 3 or 4 carbon atoms, phenyl or benzyl;
or
R1 and R2
form, together with the carbon atom to which they are attached, a cyclopropane, cyclobutane, cyclopentane, cyclohexane, cyclopentene ring or indene;
or
R1 and R2
form, together with the carbon atom to which they are attached, a tetrahydro-thiophene, a tetrahydro-thiopyrane or a tetrahydro-furane ring; preferably a tetrahydro-thiophene or a tetrahydro-thiopyrane ring.
and/or a pharmaceutically acceptable salt and/or prodrug thereof.

Also particular preference is given to compounds of formula I, in which

X is —CR3=CR4- or —S—; in which
R3 and R4
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

Y1, Y2, Y3 and Y4
  are, independently of one another, —CR8-, wherein
    R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
Z is —C(O)—;
A is cycloalkyl having 3, 4, 5, 6, 7 or 8 carbon atoms, heterocyclyl having 5, 6, 7 or 8 atoms, phenyl or heteroaryl having 5 or 6 atoms;
  in which the said phenyl can be condensed to form a naphthyl or an indanyl;
  in which said cycloalkyl, heterocyclyl, phenyl, heteroaryl or the optionally formed naphthyl or indanyl are unsubstituted or substituted by 1, 2, 3, 4 or 5 radicals selected from the group consisting of F, Cl, Br, I, OH, CN, $NO_2$, $SF_5$, $SCF_3$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
B is —C(R11R12)-C(R13R14)-O—, —C(R11R12)-C(R15R16)-C(R13R14)-O—, —C(R11R12)-C(R15R16)-C(R13R14)-NR19-, —C(R11R12)-C(R15R16)-C(R15R16)-C(R15R16)-, —O—C(R13R14)-C(R13R14)-O—, —O—C(R13R14)-C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R11R12)-C(R15R16)-C(R15R16)-C(R15R16)-C(R15R16)-, —C(R11R12)-C(R15R16)-C(R13R14)-O—, —O—C(R13R14)-C(R15R16)-C(R13R14)-O—, —C(R11R12)-C(R15R16)-C(R13R14)-C≡C— or —C(R13R14)-O—C(R13R14)-C(R13R14)-O—,
  with the proviso that, if A is connected to the linker via a nitrogen atom being part of A, the atom of the linker which is connected to A is a carbon atom;
    R11-R18 are, independently of one another, hydrogen, F or alkyl having 1, 2, 3, 4 carbon atoms
    R19 is H or alkyl having 1, 2, 3, 4, 5 or 6 carbon atoms;
R1 is alkyl having 1, 2, 3 or 4 carbon atoms;
and
R2 is alkyl having 1, 2, 3 or 4 carbon atoms, phenyl or benzyl;
or
R1 and R2
  form, together with the carbon atom to which they are attached, a cyclopropane, cyclobutane, cyclopentane, cyclohexane, cyclopentene ring or indene;
or
R1 and R2
  form, together with the carbon atom to which they are attached, a tetrahydro-thiophene, a tetrahydro-thiopyrane or a tetrahydro-furane ring; preferably a tetrahydro-thiophene or a tetrahydro-thiopyrane ring.
and/or a pharmaceutically acceptable salt and/or prodrug thereof.

Special preference is given to compounds of formula I, in which
X is —CR3=CR4- or —S—; in which
  R3 and R4
    are, independently of one another, hydrogen, F, Cl or Br;
Y1, Y2, Y3 and Y4
  are, independently of one another, —CR8-, wherein R8 is hydrogen, F or Cl;
Z is —C(O)—;
A is cyclohexyl, phenyl, naphthyl, indanyl or thienyl;
  in which the phenyl radical is unsubstituted or substituted by 1, 2 or 3 radicals selected from the group consisting of F, Cl, Br, methoxy, methyl, ethyl, propyl, iso-propyl or trifluoromethyl;
B is —C(R11R12)-C(R13R14)-O—, —C(R11R12)-C(R15R16)-C(R13R14)-O—, —O—C(R13R14)-C(R13R14)-O—, —C(R17)=C(R18)-C(R13R14)-O—, —C≡C—C(R13R14)-O—, —C(R11R12)-C(R13R14)-C≡C—, —O—C(R13R14)-C≡C—, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C— or —C(R13R14)-O—C(R13R14)-C(R13R14)-O—,
  R11-R18 are, independently of each other, hydrogen or methyl.
R1 is methyl or ethyl;
and
R2 is methyl or ethyl;
or
R1 and R2
  form, together with the carbon atom to which they are attached, a cyclobutane or cyclopentane ring;
and/or a pharmaceutically acceptable salt and/or prodrug thereof.

A particular compound of the formula I of the present invention is selected from the group consisting of:
2-{[1-(2-Phenoxy-ethoxy)-naphthalene-2-carbonyl]-amino}-2-propyl-pentanoic acid,
2-Ethyl-2-({1-[2-(4-fluoro-phenyl)-ethoxy]-naphthalene-2-carbonyl}-amino)-hexanoic acid,
2-Ethyl-2-[(1-phenethyloxy-naphthalene-2-carbonyl)-amino]-hexanoic acid,
1-{[1-(3-Cyclohexyl-propoxy)-naphthalene-2-carbonyl]-amino}-cyclobutanecarboxylic acid,
2-Methyl-2-({1-[2-(naphthalen-2-yloxy)-ethoxy]-naphthalene-2-carbonyl}-amino)-propionic acid,
2-({1-[2-(2,3-Dichloro-phenoxy)-ethoxy]-naphthalene-2-carbonyl}-amino)-2-methyl-propionic acid,
2-({1-[2-(2-Chloro-4-fluoro-phenoxy)-ethoxy]-naphthalene-2-carbonyl}-amino)-2-methyl-propionic acid,
2-Methyl-2-{[1-((E)-3-phenyl-allyloxy)-naphthalene-2-carbonyl]-amino}-propionic acid,
2-Methyl-2-{[1-(3-phenoxy-propyl)-naphthalene-2-carbonyl]-amino}-propionic acid,
2-({1-[2-(4-Methoxy-phenoxy)-ethoxy]-naphthalene-2-carbonyl}-amino)-2-methyl-propionic acid,
2-Methyl-2-({1-[2-(4-trifluoromethyl-phenoxy)-ethoxy]-naphthalene-2-carbonyl}-amino)-propionic acid
2-Methyl-2-{[1-(2-phenoxy-ethylamino)-naphthalene-2-carbonyl]-amino}-propionic acid,
2-Methyl-2-[1-(2-phenoxy-ethoxy)-naphthalene-2-sulfonylamino]-propionic acid,
2-{[1-(3-Cyclohexyl-propoxy)-naphthalene-2-carbonyl]-amino}-2-methyl-propionic acid,
2-Methyl-2-{[1-(3-pyridin-2-yl-propoxy)-naphthalene-2-carbonyl]-amino}-propionic acid, 1-{[1-(1-Methyl-3-phenyl-propoxy)-naphthalene-2-carbonyl]-amino}-cyclohexanecarboxylic acid,
3-({1-[2-(4-Fluoro-phenoxy)-ethoxy]-naphthalene-2-carbonyl}-amino)-tetrahydro-thiophene-3-carboxylic acid,
4-({1-[2-(4-Fluoro-phenoxy)-ethoxy]-naphthalene-2-carbonyl}-amino)-tetrahydro-thiopyran-4-carboxylic acid,
2-({1-[2-(4-Fluoro-phenoxy)-ethoxy]-naphthalene-2-carbonyl}-amino)-2-phenyl-butyric acid,
1-{[1-(2-Phenoxy-ethoxy)-naphthalene-2-carbonyl]-amino}-cyclopent-3-enecarboxylic acid,
2,4-Dimethyl-2-{[1-(2-phenoxy-ethoxy)-naphthalene-2-carbonyl]-amino}-pentanoic acid,
2-{[4-Fluoro-1-(2-phenoxy-ethoxy)-naphthalene-2-carbonyl]-amino}-2-methyl-butyric acid,
1-{[1-(2-Phenoxy-ethoxy)-naphthalene-2-carbonyl]-amino}-indan-1-carboxylic acid,
1-{[1-(2-Cyclohexyl-ethoxy)-4-fluoro-naphthalene-2-carbonyl]-amino}-cyclopentanecarboxylic acid,
1-({4-Fluoro-1-[2-(4-fluoro-phenoxy)-ethoxy]-naphthalene-2-carbonyl}-amino)-cyclopentanecarboxylic acid,
1-{[4-Fluoro-1-(3-phenoxy-propoxy)-naphthalene-2-carbonyl]-amino}-cyclopentanecarboxylic acid,
1-{[4-Fluoro-1-(2-phenoxy-ethoxy)-naphthalene-2-carbonyl]-amino}-cyclopentanecarboxylic acid,
1-[(4-Fluoro-1-phenethyloxy-naphthalene-2-carbonyl)-amino]-cyclopentanecarboxylic acid,
1-{[4-Fluoro-1-(3-phenyl-propoxy)-naphthalene-2-carbonyl]-amino}-cyclopentanecarboxylic acid,
2-({1-[2-(4-Fluoro-phenoxy)-ethoxy]-naphthalene-2-carbonyl}-amino)-2-methyl-3-phenyl-propionic acid,
2-{[1-(2-Cyclohexyl-ethoxy)-naphthalene-2-carbonyl]-amino}-2-ethyl-hexanoic acid,
2-{[1-(3-Cyclohexyl-propoxy)-naphthalene-2-carbonyl]-amino}-2-ethyl-hexanoic acid,
2-Ethyl-2-{[1-(3-phenyl-propoxy)-naphthalene-2-carbonyl]-amino}-hexanoic acid,
2-({1-[2-(4-Chloro-phenoxy)-ethoxy]-naphthalene-2-carbonyl}-amino)-2-ethyl-hexanoic acid,
2-Ethyl-2-{[1-(2-phenoxy-ethoxy)-naphthalene-2-carbonyl]-amino}-hexanoic acid,
2-Ethyl-2-({1-[2-(4-fluoro-phenoxy)-ethoxy]-naphthalene-2-carbonyl}-amino)-hexanoic acid,
1-({4-Chloro-1-[2-(4-fluoro-phenyl)-ethoxy]-naphthalene-2-carbonyl}-amino)-cyclobutanecarboxylic acid,
1-{[4-Chloro-1-(2-cyclohexyl-ethoxy)-naphthalene-2-carbonyl]-amino}-cyclobutanecarboxylic acid,
1-[(4-Chloro-1-phenethyloxy-naphthalene-2-carbonyl)-amino]-cyclobutanecarboxylic acid,
1-{[4-Chloro-1-(3-phenyl-propoxy)-naphthalene-2-carbonyl]-amino}-cyclobutanecarboxylic acid,
1-{[4-Chloro-1-(2-phenoxy-ethoxy)-naphthalene-2-carbonyl]-amino}-cyclobutanecarboxylic acid,
1-({4-Chloro-1-[2-(4-fluoro-phenoxy)-ethoxy]-naphthalene-2-carbonyl}-amino)-cyclobutanecarboxylic acid,
1-({1-[2-(4-Fluoro-phenyl)-ethoxy]-naphthalene-2-carbonyl}-amino)-cyclobutanecarboxylic acid,
1-{[1-(2-Cyclohexyl-ethoxy)-naphthalene-2-carbonyl]-amino}-cyclobutanecarboxylic acid,
1-({1-[2-(4-Chloro-phenyl)-ethoxy]-naphthalene-2-carbonyl}-amino)-cyclobutanecarboxylic acid,
1-[(1-Phenethyloxy-naphthalene-2-carbonyl)-amino]-cyclobutanecarboxylic acid,
1-{[1-(3-Phenyl-propoxy)-naphthalene-2-carbonyl]-amino}-cyclobutanecarboxylic acid,
1-({1-[2-(4-Chloro-phenoxy)-ethoxy]-naphthalene-2-carbonyl}-amino)-cyclobutanecarboxylic acid,
1-{[1-(2-Phenoxy-ethoxy)-naphthalene-2-carbonyl]-amino}-cyclobutanecarboxylic acid,
1-({1-[2-(4-Fluoro-phenoxy)-ethoxy]-naphthalene-2-carbonyl}-amino)-cyclobutanecarboxylic acid,
2-{[4-Fluoro-1-(2-thiophen-2-yl-ethoxy)-naphthalene-2-carbonyl]-amino}-2-methyl-propionic acid,
2-{[4-Fluoro-1-(1-methyl-3-phenyl-propoxy)-naphthalene-2-carbonyl]-amino}-2-methyl-propionic acid,
2-({4-Fluoro-1-[2-(4-fluoro-phenoxy)-ethoxy]-naphthalene-2-carbonyl}-amino)-2-methyl-propionic acid,
2-{[4-Fluoro-1-(3-phenoxy-propoxy)-naphthalene-2-carbonyl]-amino}-2-methyl-butyric acid,
2-({4-Fluoro-1-[2-(4-fluoro-phenyl)-ethoxy]-naphthalene-2-carbonyl}-amino)-2-methyl-propionic acid,
2-{[4-Fluoro-1-(3-phenyl-propoxy)-naphthalene-2-carbonyl]-amino}-2-methyl-propionic acid,
2-{[4-Fluoro-1-(3-phenoxy-propoxy)-naphthalene-2-carbonyl]-amino}-2-methyl-propionic acid,
2-[(4-Fluoro-1-phenethyloxy-naphthalene-2-carbonyl)-amino]-2-methyl-propionic acid,
2-{[4-Fluoro-1-(2-phenoxy-ethoxy)-naphthalene-2-carbonyl]-amino}-2-methyl-propionic acid,
2-{[1-(2-Cyclohexyl-ethoxy)-naphthalene-2-carbonyl]-amino}-2-methyl-propionic acid,
2-({1-[3-(4-Chloro-phenyl)-propoxy]-naphthalene-2-carbonyl}-amino)-2-methyl-propionic acid,
1-{[1-((R)-1-Methyl-3-phenyl-propoxy)-naphthalene-2-carbonyl]-amino}-cyclopentanecarboxylic acid,
1-{[1-((S)-1-Methyl-3-phenyl-propoxy)-naphthalene-2-carbonyl]-amino}-cyclopentanecarboxylic acid,
(R)-2-Methyl-2-{[1-(2-phenoxy-ethoxy)-naphthalene-2-carbonyl]-amino}-butyric acid,
(S)-2-Methyl-2-{[1-(2-phenoxy-ethoxy)-naphthalene-2-carbonyl]-amino}-butyric acid,
2-({1-[2-(5-Chloro-pyridin-3-yloxy)-ethoxy]-naphthalene-2-carbonyl}-amino)-2-methyl-propionic acid,
2-({4-Chloro-1-[2-(4-fluoro-phenoxy)-ethoxy]-naphthalene-2-carbonyl}-amino)-2-methyl-butyric acid,
2-({4-Chloro-1-[2-(4-fluoro-phenoxy)-ethoxy]-naphthalene-2-carbonyl}-amino)-2-methyl-propionic acid,
2-({1-[2-(3-Chloro-4-fluoro-phenoxy)-ethoxy]-naphthalene-2-carbonyl}-amino)-2-methyl-propionic acid,
2-{[4-Bromo-1-(2-phenoxy-ethoxy)-naphthalene-2-carbonyl]-amino}-2-methyl-propionic acid,
2-({1-[2-(4-Fluoro-3-trifluoromethyl-phenoxy)-ethoxy]-naphthalene-2-carbonyl}-amino)-2-methyl-propionic acid,
2-({1-[2-(4-Bromo-phenoxy)-ethoxy]-naphthalene-2-carbonyl}-amino)-2-methyl-propionic acid,
2-({1-[2-(4-Fluoro-phenoxy)-ethoxy]-naphthalene-2-carbonyl}-amino)-2-methyl-butyric acid,
2-({4-Bromo-1-[2-(4-fluoro-phenoxy)-ethoxy]-naphthalene-2-carbonyl}-amino)-2-methyl-propionic acid,
2-Methyl-2-{[1-((S)-1-methyl-2-phenoxy-ethoxy)-naphthalene-2-carbonyl]-amino}-propionic acid,
2-Methyl-2-{[1-((R)-1-methyl-2-phenoxy-ethoxy)-naphthalene-2-carbonyl]-amino}-propionic acid,
2-({1-[2-(2-Isopropyl-phenoxy)-ethoxy]-naphthalene-2-carbonyl}-amino)-2-methyl-propionic acid,
2-Methyl-2-{[1-(2-m-tolyloxy-ethoxy)-naphthalene-2-carbonyl]-amino}-propionic acid,
2-({1-[2-(3-Methoxy-phenoxy)-ethoxy]-naphthalene-2-carbonyl}-amino)-2-methyl-propionic acid,
2-({1-[2-(3,5-Dichloro-phenoxy)-ethoxy]-naphthalene-2-carbonyl}-amino)-2-methyl-propionic acid,
2-({1-[2-(2,6-Dichloro-phenoxy)-ethoxy]-naphthalene-2-carbonyl}-amino)-2-methyl-propionic acid, 2-({1-[2-(3-Chloro-5-fluoro-phenoxy)-ethoxy]-naphthalene-2-carbonyl}-amino)-2-methyl-propionic acid,
2-({1-[2-(3,4-Dichloro-phenoxy)-ethoxy]-naphthalene-2-carbonyl}-amino)-2-methyl-propionic acid,
2-({1-[2-(Indan-5-yloxy)-ethoxy]-naphthalene-2-carbonyl}-amino)-2-methyl-propionic acid,
2-({1-[2-(2,4-Dimethyl-phenoxy)-ethoxy]-naphthalene-2-carbonyl}-amino)-2-methyl-propionic acid,
2-({1-[2-(2,3-Dimethyl-phenoxy)-ethoxy]-naphthalene-2-carbonyl}-amino)-2-methyl-propionic acid,
2-({1-[2-(3-Isopropyl-phenoxy)-ethoxy]-naphthalene-2-carbonyl}-amino)-2-methyl-propionic acid,
2-({1-[2-(2-Chloro-phenoxy)-ethoxy]-naphthalene-2-carbonyl}-amino)-2-methyl-propionic acid,
2-({1-[2-(3-Chloro-phenoxy)-ethoxy]-naphthalene-2-carbonyl}-amino)-2-methyl-propionic acid,
2-({1-[2-(2-Chloro-4-fluoro-phenoxy)-ethoxy]-naphthalene-2-carbonyl}-amino)-2-methyl-propionic acid,
2-({1-[2-(3,4-Difluoro-phenoxy)-ethoxy]-naphthalene-2-carbonyl}-amino)-2-methyl-propionic acid,
2-({1-[2-(3-Fluoro-phenoxy)-ethoxy]-naphthalene-2-carbonyl}-amino)-2-methyl-propionic acid,
2-({1-[2-(2-Methoxy-phenoxy)-ethoxy]-naphthalene-2-carbonyl}-amino)-2-methyl-propionic acid,
2-Methyl-2-{[1-(3-phenyl-prop-2-ynyloxy)-naphthalene-2-carbonyl]-amino}-propionic acid,
2-({1-[3-(4-Chloro-phenyl)-prop-2-ynyloxy]-naphthalene-2-carbonyl}-amino)-2-methyl-propionic acid,
2,3-Dimethyl-2-{[1-(2-phenoxy-ethoxy)-naphthalene-2-carbonyl]-amino}-butyric acid,
1-{[1-(1-Methyl-3-phenyl-propoxy)-naphthalene-2-carbonyl]-amino}-cyclopentanecarboxylic acid,
1-({1-[2-(4-Fluoro-phenoxy)-ethoxy]-naphthalene-2-carbonyl}-amino)-cyclopentanecarboxylic acid,
2,3-Dimethyl-2-{[1-(1-methyl-3-phenyl-propoxy)-naphthalene-2-carbonyl]-amino}-butyric acid,
2-({1-[2-(4-Chloro-phenoxy)-ethoxy]-naphthalene-2-carbonyl}-amino)-2,3-dimethyl-butyric acid,
2-({1-[2-(4-Fluoro-phenoxy)-ethoxy]-naphthalene-2-carbonyl}-amino)-2,3-dimethyl-butyric acid,
2-Methyl-2-{[1-(1-methyl-2-phenoxy-ethoxy)-naphthalene-2-carbonyl]-amino}-propionic acid,
2-Methyl-2-{[1-(5-phenyl-pentyl)-naphthalene-2-carbonyl]-amino}-propionic acid,
2-Methyl-2-{[1-(5-phenyl-pent-1-ynyl)-naphthalene-2-carbonyl]-amino}-propionic acid,
2-Methyl-2-{[1-(3-phenyl-butoxy)-naphthalene-2-carbonyl]-amino}-propionic acid,
2-({1-[2-(4-Chloro-phenoxy)-ethoxy]-naphthalene-2-carbonyl}-amino)-2-methyl-butyric acid,
2-({1-[2-(4-Chloro-phenoxy)-ethoxy]-naphthalene-2-carbonyl}-amino)-2-methyl-propionic acid,
2-({1-[2-(2,4-Dichloro-phenyl)-ethoxy]-naphthalene-2-carbonyl}-amino)-2-methyl-propionic acid,
2-Methyl-2-{[1-(3-phenoxy-prop-1-ynyl)-naphthalene-2-carbonyl]-amino}-propionic acid,
2-({1-[2-(4-Chloro-phenyl)-ethoxy]-naphthalene-2-carbonyl}-amino)-2-methyl-propionic acid,
2-Methyl-2-{[1-(2-p-tolyl-ethoxy)-naphthalene-2-carbonyl]-amino}-propionic acid,
2-{[1-(2-Benzyloxy-ethoxy)-naphthalene-2-carbonyl]-amino}-2-methyl-propionic acid,
2-Methyl-2-{[1-(2-phenoxy-ethoxy)-naphthalene-2-carbonyl]-amino}-butyric acid,
2-{[6-Chloro-3-(2-phenoxy-ethoxy)-benzo[b]thiophene-2-carbonyl]-amino}-2-methyl-butyric acid,
2-{[6-Chloro-3-(2-phenoxy-ethoxy)-benzo[b]thiophene-2-carbonyl]-amino}-2-methyl-propionic acid,
2-({1-[2-(3,5-Difluoro-phenoxy)-ethoxy]-naphthalene-2-carbonyl}-amino)-2-methyl-propionic acid,
2-Methyl-2-{[1-((E)-4-phenyl-but-1-enyl)-naphthalene-2-carbonyl]-amino}-propionic acid,
2-Methyl-2-{[1-(4-phenyl-butyl)-naphthalene-2-carbonyl]-amino}-propionic acid,
2-({1-[2-(4-Fluoro-phenoxy)-ethoxy]-naphthalene-2-carbonyl}-amino)-2-methyl-propionic acid,
2-Methyl-2-{[1-(1-methyl-3-phenyl-propoxy)-naphthalene-2-carbonyl]-amino}-butyric acid,
2-Methyl-2-{[1-(4-phenyl-but-1-ynyl)-naphthalene-2-carbonyl]-amino}-propionic acid,
2-Methyl-2-{[3-(2-phenoxy-ethoxy)-benzo[b]thiophene-2-carbonyl]-amino}-butyric acid,
2-Methyl-2-{[3-(2-phenoxy-ethoxy)-benzo[b]thiophene-2-carbonyl]-amino}-propionic acid,
2-[(4-Bromo-1-phenethyloxy-naphthalene-2-carbonyl)-amino]-2-methyl-propionic acid,
2-{[4-Bromo-1-(1-methyl-3-phenyl-propoxy)-naphthalene-2-carbonyl]-amino}-2-methyl-propionic acid,
2-Methyl-2-({1-[2-(3-trifluoromethyl-phenyl)-ethoxy]-naphthalene-2-carbonyl}-amino)-propionic acid,
2-({1-[2-(4-Fluoro-phenyl)-ethoxy]-naphthalene-2-carbonyl}-amino)-2-methyl-propionic acid,
2-({1-[2-(3-Bromo-phenyl)-ethoxy]-naphthalene-2-carbonyl}-amino)-2-methyl-propionic acid,
2-Methyl-2-{[1-(2-phenoxy-ethoxy)-naphthalene-2-carbonyl]-amino}-propionic acid,
2-Methyl-2-{[1-((S)-1-methyl-3-phenyl-propoxy)-naphthalene-2-carbonyl]-amino}-propionic acid,
2-Methyl-2-{[1-(3-phenyl-propoxy)-naphthalene-2-carbonyl]-amino}-propionic acid,
2-Methyl-2-{[1-((R)-1-methyl-3-phenyl-propoxy)-naphthalene-2-carbonyl]-amino}-propionic acid,
2-Methyl-2-[(1-phenethyloxy-naphthalene-2-carbonyl)-amino]-propionic acid, or
2-Methyl-2-{[1-(1-methyl-3-phenyl-propoxy)-naphthalene-2-carbonyl]-amino}-propionic acid,
2-({4-Fluoro-1-[2-(3-fluoro-phenyl)-ethoxy]-naphthalene-2-carbonyl}-amino)-2-methyl-propionic acid,
2-{[4-Fluoro-1-(4-phenyl-butoxy)-naphthalene-2-carbonyl]-amino}-2-methyl-propionic acid,
2-({4-Fluoro-1-[2-(2-fluoro-phenoxy)-ethoxy]-naphthalene-2-carbonyl}-amino)-2-methyl-propionic acid,
2-({1-[2-(4-Chloro-phenyl)-ethoxy]-4-fluoro-naphthalene-2-carbonyl}-amino)-2-methyl-propionic acid,
2-({4-Fluoro-1-[3-(2-fluoro-phenoxy)-propoxy]-naphthalene-2-carbonyl}-amino)-2-methyl-propionic acid,
2-({4-Fluoro-1-[3-(4-fluoro-phenoxy)-propoxy]-naphthalene-2-carbonyl}-amino)-2-methyl-propionic acid,
2-({4-Fluoro-1-[2-(naphthalen-2-yloxy)-ethoxy]-naphthalene-2-carbonyl}-amino)-2-methyl-propionic acid,
2-({1-[2,2-Difluoro-2-(4-fluoro-phenoxy)-ethoxy]-naphthalene-2-carbonyl}-amino)-2-methyl-propionic acid,
3-({1-[2-(4-Fluoro-phenoxy)-ethoxy]-naphthalene-2-carbonyl}-amino)-tetrahydro-furan-3-carboxylic acid
and/or a pharmaceutically acceptable salt and/or a prodrug thereof.

Particular preference is given to the following compounds of the formula I, selected from the group consisting of:
2-({1-[2-(4-Fluoro-phenoxy)-ethoxy]-naphthalene-2-carbonyl}-amino)-2-phenyl-butyric acid,
1-{[1-(2-Phenoxy-ethoxy)-naphthalene-2-carbonyl]-amino}-cyclopent-3-enecarboxylic acid, 2,4-Dimethyl-2-{[1-(2-phenoxy-ethoxy)-naphthalene-2-carbonyl]-amino}-pentanoic acid,
2-{[4-Fluoro-1-(2-phenoxy-ethoxy)-naphthalene-2-carbonyl]-amino}-2-methyl-butyric acid,
1-{[1-(2-Phenoxy-ethoxy)-naphthalene-2-carbonyl]-amino}-indan-1-carboxylic acid,
1-{[1-(2-Cyclohexyl-ethoxy)-4-fluoro-naphthalene-2-carbonyl]-amino}-cyclopentanecarboxylic acid,
1-({4-Fluoro-1-[2-(4-fluoro-phenoxy)-ethoxy]-naphthalene-2-carbonyl}-amino)-cyclopentanecarboxylic acid,
1-{[4-Fluoro-1-(3-phenoxy-propoxy)-naphthalene-2-carbonyl]-amino}-cyclopentanecarboxylic acid,
1-{[4-Fluoro-1-(2-phenoxy-ethoxy)-naphthalene-2-carbonyl]-amino}-cyclopentanecarboxylic acid,
1-[(4-Fluoro-1-phenethyloxy-naphthalene-2-carbonyl)-amino]-cyclopentanecarboxylic acid,
1-{[4-Fluoro-1-(3-phenyl-propoxy)-naphthalene-2-carbonyl]-amino}-cyclopentanecarboxylic acid,
2-({1-[2-(4-Fluoro-phenoxy)-ethoxy]-naphthalene-2-carbonyl}-amino)-2-methyl-3-phenyl-propionic acid,
2-{[1-(2-Cyclohexyl-ethoxy)-naphthalene-2-carbonyl]-amino}-2-ethyl-hexanoic acid,
2-{[1-(3-Cyclohexyl-propoxy)-naphthalene-2-carbonyl]-amino}-2-ethyl-hexanoic acid,
2-Ethyl-2-{[1-(3-phenyl-propoxy)-naphthalene-2-carbonyl]-amino}-hexanoic acid,
2-({1-[2-(4-Chloro-phenoxy)-ethoxy]-naphthalene-2-carbonyl}-amino)-2-ethyl-hexanoic acid,
2-Ethyl-2-{[1-(2-phenoxy-ethoxy)-naphthalene-2-carbonyl]-amino}-hexanoic acid,
2-Ethyl-2-({1-[2-(4-fluoro-phenoxy)-ethoxy]-naphthalene-2-carbonyl}-amino)-hexanoic acid,
1-({4-Chloro-1-[2-(4-fluoro-phenyl)-ethoxy]-naphthalene-2-carbonyl}-amino)-cyclobutanecarboxylic acid,
1-{[4-Chloro-1-(2-cyclohexyl-ethoxy)-naphthalene-2-carbonyl]-amino}-cyclobutanecarboxylic acid,
1-[(4-Chloro-1-phenethyloxy-naphthalene-2-carbonyl)-amino]-cyclobutanecarboxylic acid,
1-{[4-Chloro-1-(3-phenyl-propoxy)-naphthalene-2-carbonyl]-amino}-cyclobutanecarboxylic acid,
1-{[4-Chloro-1-(2-phenoxy-ethoxy)-naphthalene-2-carbonyl]-amino}-cyclobutanecarboxylic acid,
1-({4-Chloro-1-[2-(4-fluoro-phenoxy)-ethoxy]-naphthalene-2-carbonyl}-amino)-cyclobutanecarboxylic acid,
1-({1-[2-(4-Fluoro-phenyl)-ethoxy]-naphthalene-2-carbonyl}-amino)-cyclobutanecarboxylic acid,
1-{[1-(2-Cyclohexyl-ethoxy)-naphthalene-2-carbonyl]-amino}-cyclobutanecarboxylic acid,
1-({1-[2-(4-Chloro-phenyl)-ethoxy]-naphthalene-2-carbonyl}-amino)-cyclobutanecarboxylic acid,
1-[(1-Phenethyloxy-naphthalene-2-carbonyl)-amino]-cyclobutanecarboxylic acid,
1-{[1-(3-Phenyl-propoxy)-naphthalene-2-carbonyl]-amino}-cyclobutanecarboxylic acid,
1-({1-[2-(4-Chloro-phenoxy)-ethoxy]-naphthalene-2-carbonyl}-amino)-cyclobutanecarboxylic acid,
1-{[1-(2-Phenoxy-ethoxy)-naphthalene-2-carbonyl]-amino}-cyclobutanecarboxylic acid,
1-({1-[2-(4-Fluoro-phenoxy)-ethoxy]-naphthalene-2-carbonyl}-amino)-cyclobutanecarboxylic acid,
2-{[4-Fluoro-1-(2-thiophen-2-yl-ethoxy)-naphthalene-2-carbonyl]-amino}-2-methyl-propionic acid,
2-{[4-Fluoro-1-(1-methyl-3-phenyl-propoxy)-naphthalene-2-carbonyl]-amino}-2-methyl-propionic acid,
2-({4-Fluoro-1-[2-(4-fluoro-phenoxy)-ethoxy]-naphthalene-2-carbonyl}-amino)-2-methyl-propionic acid,
2-{[4-Fluoro-1-(3-phenoxy-propoxy)-naphthalene-2-carbonyl]-amino}-2-methyl-butyric acid,
2-({4-Fluoro-1-[2-(4-fluoro-phenyl)-ethoxy]-naphthalene-2-carbonyl}-amino)-2-methyl-propionic acid,
2-{[4-Fluoro-1-(3-phenyl-propoxy)-naphthalene-2-carbonyl]-amino}-2-methyl-propionic acid,
2-{[4-Fluoro-1-(3-phenoxy-propoxy)-naphthalene-2-carbonyl]-amino}-2-methyl-propionic acid,
2-[(4-Fluoro-1-phenethyloxy-naphthalene-2-carbonyl)-amino]-2-methyl-propionic acid,
2-{[4-Fluoro-1-(2-phenoxy-ethoxy)-naphthalene-2-carbonyl]-amino}-2-methyl-propionic acid,
2-{[1-(2-Cyclohexyl-ethoxy)-naphthalene-2-carbonyl]-amino}-2-methyl-propionic acid,
2-({1-[3-(4-Chloro-phenyl)-propoxy]-naphthalene-2-carbonyl}-amino)-2-methyl-propionic acid,
1-{[1-((R)-1-Methyl-3-phenyl-propoxy)-naphthalene-2-carbonyl]-amino}-cyclopentanecarboxylic acid,
1-{[1-((S)-1-Methyl-3-phenyl-propoxy)-naphthalene-2-carbonyl]-amino}-cyclopentanecarboxylic acid,
(R)-2-Methyl-2-{[1-(2-phenoxy-ethoxy)-naphthalene-2-carbonyl]-amino}-butyric acid,
(S)-2-Methyl-2-{[1-(2-phenoxy-ethoxy)-naphthalene-2-carbonyl]-amino}-butyric acid,
2-({1-[2-(5-Chloro-pyridin-3-yloxy)-ethoxy]-naphthalene-2-carbonyl}-amino)-2-methyl-propionic acid,
2-({4-Chloro-1-[2-(4-fluoro-phenoxy)-ethoxy]-naphthalene-2-carbonyl}-amino)-2-methyl-butyric acid,
2-({4-Chloro-1-[2-(4-fluoro-phenoxy)-ethoxy]-naphthalene-2-carbonyl}-amino)-2-methyl-propionic acid,
2-({1-[2-(3-Chloro-4-fluoro-phenoxy)-ethoxy]-naphthalene-2-carbonyl}-amino)-2-methyl-propionic acid,
2-{[4-Bromo-1-(2-phenoxy-ethoxy)-naphthalene-2-carbonyl]-amino}-2-methyl-propionic acid,
2-({1-[2-(4-Fluoro-3-trifluoromethyl-phenoxy)-ethoxy]-naphthalene-2-carbonyl}-amino)-2-methyl-propionic acid,
2-({1-[2-(4-Bromo-phenoxy)-ethoxy]-naphthalene-2-carbonyl}-amino)-2-methyl-propionic acid,
2-({1-[2-(4-Fluoro-phenoxy)-ethoxy]-naphthalene-2-carbonyl}-amino)-2-methyl-butyric acid,
2-({4-Bromo-1-[2-(4-fluoro-phenoxy)-ethoxy]-naphthalene-2-carbonyl}-amino)-2-methyl-propionic acid,
2-Methyl-2-{[1-((S)-1-methyl-2-phenoxy-ethoxy)-naphthalene-2-carbonyl]-amino}-propionic acid,
2-Methyl-2-{[1-((R)-1-methyl-2-phenoxy-ethoxy)-naphthalene-2-carbonyl]-amino}-propionic acid,
2-({1-[2-(2-Isopropyl-phenoxy)-ethoxy]-naphthalene-2-carbonyl}-amino)-2-methyl-propionic acid,
2-Methyl-2-{[1-(2-m-tolyloxy-ethoxy)-naphthalene-2-carbonyl]-amino}-propionic acid,
2-({1-[2-(3-Methoxy-phenoxy)-ethoxy]-naphthalene-2-carbonyl}-amino)-2-methyl-propionic acid,
2-({1-[2-(3,5-Dichloro-phenoxy)-ethoxy]-naphthalene-2-carbonyl}-amino)-2-methyl-propionic acid,
2-({1-[2-(2,6-Dichloro-phenoxy)-ethoxy]-naphthalene-2-carbonyl}-amino)-2-methyl-propionic acid,
2-({1-[2-(3-Chloro-5-fluoro-phenoxy)-ethoxy]-naphthalene-2-carbonyl}-amino)-2-methyl-propionic acid,
2-({1-[2-(3,4-Dichloro-phenoxy)-ethoxy]-naphthalene-2-carbonyl}-amino)-2-methyl-propionic acid,
2-({1-[2-(Indan-5-yloxy)-ethoxy]-naphthalene-2-carbonyl}-amino)-2-methyl-propionic acid,
2-({1-[2-(2,4-Dimethyl-phenoxy)-ethoxy]-naphthalene-2-carbonyl}-amino)-2-methyl-propionic acid,
2-({1-[2-(2,3-Dimethyl-phenoxy)-ethoxy]-naphthalene-2-carbonyl}-amino)-2-methyl-propionic acid, 2-({1-[2-(3-Isopropyl-phenoxy)-ethoxy]-naphthalene-2-carbonyl}-amino)-2-methyl-propionic acid,
2-({1-[2-(2-Chloro-phenoxy)-ethoxy]-naphthalene-2-carbonyl}-amino)-2-methyl-propionic acid,
2-({1-[2-(3-Chloro-phenoxy)-ethoxy]-naphthalene-2-carbonyl}-amino)-2-methyl-propionic acid,
2-({1-[2-(2-Chloro-4-fluoro-phenoxy)-ethoxy]-naphthalene-2-carbonyl}-amino)-2-methyl-propionic acid,
2-({1-[2-(3,4-Difluoro-phenoxy)-ethoxy]-naphthalene-2-carbonyl}-amino)-2-methyl-propionic acid,
2-({1-[2-(3-Fluoro-phenoxy)-ethoxy]-naphthalene-2-carbonyl}-amino)-2-methyl-propionic acid,
2-({1-[2-(2-Methoxy-phenoxy)-ethoxy]-naphthalene-2-carbonyl}-amino)-2-methyl-propionic acid,
2-Methyl-2-{[1-(3-phenyl-prop-2-ynyloxy)-naphthalene-2-carbonyl]-amino}-propionic acid,
2-({1-[3-(4-Chloro-phenyl)-prop-2-ynyloxy]-naphthalene-2-carbonyl}-amino)-2-methyl-propionic acid,
2,3-Dimethyl-2-{[1-(2-phenoxy-ethoxy)-naphthalene-2-carbonyl]-amino}-butyric acid,
1-{[1-(1-Methyl-3-phenyl-propoxy)-naphthalene-2-carbonyl]-amino}-cyclopentanecarboxylic acid,
1-({1-[2-(4-Fluoro-phenoxy)-ethoxy]-naphthalene-2-carbonyl}-amino)-cyclopentanecarboxylic acid,
2,3-Dimethyl-2-{[1-(1-methyl-3-phenyl-propoxy)-naphthalene-2-carbonyl]-amino}-butyric acid,
2-({1-[2-(4-Chloro-phenoxy)-ethoxy]-naphthalene-2-carbonyl}-amino)-2,3-dimethyl-butyric acid,
2-({1-[2-(4-Fluoro-phenoxy)-ethoxy]-naphthalene-2-carbonyl}-amino)-2,3-dimethyl-butyric acid,
2-Methyl-2-{[1-(1-methyl-2-phenoxy-ethoxy)-naphthalene-2-carbonyl]-amino}-propionic acid,
2-Methyl-2-{[1-(5-phenyl-pentyl)-naphthalene-2-carbonyl]-amino}-propionic acid,
2-Methyl-2-{[1-(5-phenyl-pent-1-ynyl)-naphthalene-2-carbonyl]-amino}-propionic acid,
2-Methyl-2-{[1-(3-phenyl-butoxy)-naphthalene-2-carbonyl]-amino}-propionic acid,
2-({1-[2-(4-Chloro-phenoxy)-ethoxy]-naphthalene-2-carbonyl}-amino)-2-methyl-butyric acid,
2-({1-[2-(4-Chloro-phenoxy)-ethoxy]-naphthalene-2-carbonyl}-amino)-2-methyl-propionic acid,
2-({1-[2-(2,4-Dichloro-phenyl)-ethoxy]-naphthalene-2-carbonyl}-amino)-2-methyl-propionic acid,
2-Methyl-2-{[1-(3-phenoxy-prop-1-ynyl)-naphthalene-2-carbonyl]-amino}-propionic acid,
2-({1-[2-(4-Chloro-phenyl)-ethoxy]-naphthalene-2-carbonyl}-amino)-2-methyl-propionic acid,
2-Methyl-2-{[1-(2-p-tolyl-ethoxy)-naphthalene-2-carbonyl]-amino}-propionic acid,
2-{[1-(2-Benzyloxy-ethoxy)-naphthalene-2-carbonyl]-amino}-2-methyl-propionic acid,
2-Methyl-2-{[1-(2-phenoxy-ethoxy)-naphthalene-2-carbonyl]-amino}-butyric acid,
2-{[6-Chloro-3-(2-phenoxy-ethoxy)-benzo[b]thiophene-2-carbonyl]-amino}-2-methyl-butyric acid,
2-{[6-Chloro-3-(2-phenoxy-ethoxy)-benzo[b]thiophene-2-carbonyl]-amino}-2-methyl-propionic acid,
2-({1-[2-(3,5-Difluoro-phenoxy)-ethoxy]-naphthalene-2-carbonyl}-amino)-2-methyl-propionic acid,
2-Methyl-2-{[1-((E)-4-phenyl-but-1-enyl)-naphthalene-2-carbonyl]-amino}-propionic acid,
2-Methyl-2-{[1-(4-phenyl-butyl)-naphthalene-2-carbonyl]-amino}-propionic acid,
2-({1-[2-(4-Fluoro-phenoxy)-ethoxy]-naphthalene-2-carbonyl}-amino)-2-methyl-propionic acid,
2-Methyl-2-{[1-(1-methyl-3-phenyl-propoxy)-naphthalene-2-carbonyl]-amino}-butyric acid,
2-Methyl-2-{[1-(4-phenyl-but-1-ynyl)-naphthalene-2-carbonyl]-amino}-propionic acid,
2-Methyl-2-{[3-(2-phenoxy-ethoxy)-benzo[b]thiophene-2-carbonyl]-amino}-butyric acid,
2-Methyl-2-{[3-(2-phenoxy-ethoxy)-benzo[b]thiophene-2-carbonyl]-amino}-propionic acid,
2-[(4-Bromo-1-phenethyloxy-naphthalene-2-carbonyl)-amino]-2-methyl-propionic acid,
2-{[4-Bromo-1-(1-methyl-3-phenyl-propoxy)-naphthalene-2-carbonyl]-amino}-2-methyl-propionic acid,
2-Methyl-2-({1-[2-(3-trifluoromethyl-phenyl)-ethoxy]-naphthalene-2-carbonyl}-amino)-propionic acid,
2-({1-[2-(4-Fluoro-phenyl)-ethoxy]-naphthalene-2-carbonyl}-amino)-2-methyl-propionic acid,
2-({1-[2-(3-Bromo-phenyl)-ethoxy]-naphthalene-2-carbonyl}-amino)-2-methyl-propionic acid,
2-Methyl-2-{[1-(2-phenoxy-ethoxy)-naphthalene-2-carbonyl]-amino}-propionic acid,
2-Methyl-2-{[1-((S)-1-methyl-3-phenyl-propoxy)-naphthalene-2-carbonyl]-amino}-propionic acid,
2-Methyl-2-{[1-(3-phenyl-propoxy)-naphthalene-2-carbonyl]-amino}-propionic acid,
2-Methyl-2-{[1-((R)-1-methyl-3-phenyl-propoxy)-naphthalene-2-carbonyl]-amino}-propionic acid,
2-Methyl-2-[(1-phenethyloxy-naphthalene-2-carbonyl)-amino]-propionic acid, or
2-Methyl-2-{[1-(1-methyl-3-phenyl-propoxy)-naphthalene-2-carbonyl]-amino}-propionic acid,
2-({4-Fluoro-1-[2-(3-fluoro-phenyl)-ethoxy]-naphthalene-2-carbonyl}-amino)-2-methyl-propionic acid,
2-{[4-Fluoro-1-(4-phenyl-butoxy)-naphthalene-2-carbonyl]-amino}-2-methyl-propionic acid,
2-({4-Fluoro-1-[2-(2-fluoro-phenoxy)-ethoxy]-naphthalene-2-carbonyl}-amino)-2-methyl-propionic acid,
2-({1-[2-(4-Chloro-phenyl)-ethoxy]-4-fluoro-naphthalene-2-carbonyl}-amino)-2-methyl-propionic acid,
2-({4-Fluoro-1-[3-(2-fluoro-phenoxy)-propoxy]-naphthalene-2-carbonyl}-amino)-2-methyl-propionic acid,
2-({4-Fluoro-1-[3-(4-fluoro-phenoxy)-propoxy]-naphthalene-2-carbonyl}-amino)-2-methyl-propionic acid,
2-({4-Fluoro-1-[2-(naphthalen-2-yloxy)-ethoxy]-naphthalene-2-carbonyl}-amino)-2-methyl-propionic acid,
2-({1-[2,2-Difluoro-2-(4-fluoro-phenoxy)-ethoxy]-naphthalene-2-carbonyl}-amino)-2-methyl-propionic acid,
3-({1-[2-(4-Fluoro-phenoxy)-ethoxy]-naphthalene-2-carbonyl}-amino)-tetrahydro-furan-3-carboxylic acid
and/or a pharmaceutically acceptable salt and/or a prodrug thereof.

The compounds of the formula I can be present in the form of their salts. An overview of pharmaceutically employed salts can be found in the "Handbook of Pharmaceutical Salts", edited by P. Heinrich Stahl, Camille G. Wermuth, Verlag Helvetica Chimica Acta, Switzerland, 2002. Suitable base addition salts are salts of all pharmacologically acceptable bases, for example alkali metal, earth alkali metal or metal salts, preferably sodium, potassium, magnesium, calcium or zinc salts, or as ammonium salts, for example as salts with ammonia or organic amines or amino acids, preferably as salts formed with ammonia, arginine, benethamine, benzathine, choline, deanol, diethanolamine, diethylamine, 2-(diethylamino)-ethanol, ethanolamine, ethylendiamine, N-methyl-glucamine, hydrabamine, 1H-imidazole, lysine, 4-(2-hydroxyethyl)-morpholine, piperazine, 1-(2-hydroxyethyl)-pyrrolidine, triethanolamine or tromethamine; If the compounds contain a basic group, they are capable of forming salts with acid, for example halides, in particular hydrochlorides, hydrobromides, lactates, sulfates, citrates, tartrates, acetates, phosphates, methylsulfonates, benzenesulfonates, p-toluenesulfonates, adipinates, fumarates, gluconates, glutamates, glycerol phosphates, maleates, benzoates, oxalates and pamoates. This group also corresponds to the physiologically acceptable anions; but also trifluoroacetates. They can also be present as zwitterions.

If the compounds of the present invention contain one or more centers of asymmetry, these may independently of one another have the S and the R configuration. Thus, the compounds may be in the form of optical isomers, of diastereomers, of racemates or of mixtures thereof in any ratio.

The compounds of the formula I according to the invention can contain mobile hydrogen atoms, that is be present in various tautomeric forms. The present invention relates to all the tautomers of the compounds of the formula I.

The present invention furthermore encompasses derivatives of compounds of the formula I, for example solvates, such as hydrates and adducts with alcohols, esters, prodrugs and other physiologically tolerated derivatives of compounds of the formula I, and also active metabolites of compounds of the formula I. Further the compounds of formula I of the present invention may also exist in various polymorphous forms, for example as amorphous and crystalline polymorphous forms. All polymorphous forms belong to and are another aspect of the invention.

The invention relates, in particular, to prodrugs of the compounds of the formula I which are not necessarily pharmacologically active in vitro but which are converted in vivo, under physiological conditions, into active compounds of the formula I, for example by hydrolysis in blood. The skilled person is familiar with suitable prodrugs for the compounds of the formula I, that is chemically modified derivatives of the compounds of the formula I possessing properties which have been improved in a desired manner. Further details with regard to prodrugs can be found, for example, in Fleisher et al., Advanced Drug Delivery Reviews 19 (1996) 115-130; Design of Prodrugs, H. Bundgaard, Ed., Elsevier, 1985; or H. Bundgaard, Drugs of the Future 16 (1991) 443. Prodrugs which are especially suitable for the compounds of the formula I are ester prodrugs of carboxylic acid groups, amide prodrugs of carboxylic acid groups and alcohol prodrugs of carboxylic acid groups as well as acyl prodrugs and carbamate prodrugs of acylatable nitrogen-containing groups such as amino groups, amidino groups and guanidino groups. In the acyl prodrugs or carbamate prodrugs, a hydrogen atom which is located on a nitrogen atom is replaced with an acyl group or carbamate group. Examples of ester prodrugs and amide prodrugs which may be prepared from the carboxylic acid group in a compound of formula I and which may be mentioned are $(C_1-C_4)$-alkyl esters such as methyl esters, ethyl esters, n-propyl esters, isopropyl esters, n-butyl esters and isobutyl esters, substituted alkyl esters such as hydroxyalkyl esters, acyloxyalkyl esters, aminoalkyl esters, acylaminoalkyl esters and dialkylaminoalkyl esters, unsubstituted amides and N—$(C_1$-$C_4)$-alkylamides, such as methylamides or ethylamides. For example the methyl and ethyl esters of the compounds listed above are included.

Alkyl radicals are linear, ie. a straight-chain, or branched hydrocarbons, which, where indicated, contain a specified number of carbon atoms, e.g. 1, 2, 3 or 4 atoms, 1, 2, 3, 4, 5 or 6 atoms or 1, 2, 3, 4, 5, 6, 7 or 8 atoms. This also applies if they carry substituents or occur as substituents of other radicals, for example in alkoxy, arylalkyl, heteroarylalkyl, fluoroalkyl or —S-alkyl radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), pentyl or hexyl. Preferred alkyl radicals are methyl, ethyl, n-propyl, isopropyl, tert-butyl and isobutyl. Where indicated one or more, for example 1, 2, 3, 4, 5, 6, 7, 8, 9, 10, 11, 12 or 13, hydrogen atoms in alkyl radicals may be replaced by fluorine atoms to form fluoroalkyl radicals. Examples of such radicals are difluoromethyl, trifluoromethyl, pentafluoroethyl, 2,2,2-trifluoroethyl; 3,3,3-trifluoropropyl; 3,3,3-trifluorobutyl or 4,4,4-trifluorobutyl.

Cycloalkyl radicals are hydrocarbon rings, which, where indicated, contain a specified number of carbon atoms, for example 3, 4, 5 or 6 carbon atoms or 3, 4, 5, 6, 7 or 8 carbon atoms. Examples of cycloalkyl groups are cyclopropyl, cyclobutyl, cyclopentyl, cyclohexyl, cycloheptyl or cyclooctyl. Cycloalkyl radicals may be unsubstituted or be substituted one or more times, for example once, twice or three times, by identical or different specified radicals in identical or different positions. Cycloalkyl radicals can be saturated or partly unsaturated (contain double bonds). For example a cycloalkyl radical may contain zero, one or two double bonds. This also applies if they carry substituents or occur as substituents of other radicals, for example in the radical cycloalkylalkyl. Where indicated, a cycloalkyl radical may be condensed to a cycloalkyl, aryl, heterocyclyl or heteroaryl radical. Where for a cycloalkylalkyl or cycloalkylalkoxy radical the number of carbon atoms has been given, this is the sum of the number of the carbon atoms in the cycloalkyl and in the alkyl or alkoxy radical, respectively.

Heterocyclyl radicals or heterocycle radicals are hydrocarbon ring compounds, which where indicated, contain a specified number of carbon atoms, for example 3, 4, 5, 6, 7 or 8 atoms or 5, 6, 7 or 8 atoms, respectively, in which one or more ring atoms are replaced by oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. Heterocyclyl radicals can be saturated or partly unsaturated (contain double bonds). For example a heterocyclyl radical may contain zero, one or two double bonds.

The heterocyclyl radicals may be attached at all positions, for example at the 1 position, 2 position, 3 position, 4 position, 5 position, 6 position, 7 position or 8 position. Heterocycle radicals may be unsubstituted or be substituted one or more times, for example once, twice or three times, by identical or different specified radicals in identical or different positions. Substitutions can occur on free carbon atoms or on nitrogen atoms. Examples of heterocycles are oxirane, aziridine, tetrahydrofurane, tetrahydropyrane, dioxolane, for example 1,3-dioxolane, dioxane, for example 1,4-dioxan, piperidine, pyrrolidin, imidazolidine, triazolidine, hexahydropyrimidine, piperazine, tetrahydropyridazine, triazinane, for example, 1,3,5-triazinane, 1,2,3-triazinane or 1,2,4-triazinane, tetrahydrothiophene, tetrahydrothiopyrane, dithiolane, for example 1,3-dithiolane, dithiane, thiazolidine, oxazolidine, oxathiolane, for example 1,3-oxathiolane, morpholine or thiomorpholine. Where indicated, the heterocyclyl radical may be condensed to a cycloalkyl, heterocyclyl or heteroaryl.

The term "aryl" means phenyl, 1-naphthyl, 2-naphthyl and indenyl. The aryl radical may be unsubstituted or be substituted one or more times, for example once, twice, three or four times, by identical or different specified radicals. If an aryl radical is substituted, it preferably has one, two or three identical or different substituents. This likewise applies to substituted aryl radicals in groups such as arylalky. Where indicated, aryl radicals may be condensed to e.g. a cycloalkyl or heterocyclyl radical.

"Heteroaryl" radicals are aromatic 5 or 6-membered carbon ring compounds, in which one or more ring atoms are replaced by oxygen atoms, sulfur atoms or nitrogen atoms, e.g. 1, 2, 3 or 4 nitrogen atoms, 1 oxygen atom, 1 sulfur atom or a combination of various heteroatoms. The heteroaryl radicals may be attached by all positions, for example at the 1 position, 2 position, 3 position, 4 position, 5 position or 6 position. Heteroaryls may be unsubstituted or substituted one or more times, for example once, twice, three or four times, by identical or different specified radicals. This applies likewise to heteroaryl radicals such as, for example, in the radical heteroarylalkyl. Examples of heteroaryls are furyl, thienyl, pyrrolyl, imidazolyl, pyrazolyl, oxazolyl, isoxazolyl, thiazolyl, isothiazolyl, pyridyl, triazolyl, oxadiazolyl, thiadiazolyl, pyrazinyl, pyrimidinyl, pyridazinyl or tetrazolyl, in particular pyridyl, thienyl or imidazolyl. Pyridyl stands both for 2-, 3- and 4-pyridyl, Thienyl stands both for 2- and 3-thienyl. Where indicated, a heteroaryl radical may be condensed to e.g. a cycloalkyl or heterocyclyl radical.

When any variable (e.g. aryl, R1) occurs more than one time in any constituent, its definition on each occurrence is independent of its definition at every other occurrence. Also, combinations of substituents and/or variables are permissible only if such combinations result in stable compounds.

In the definition of R1 and R2 there is the possibility that R1 and R2
form, together with the carbon atom to which they are attached, a 3,4-, 5- or 6-membered carbon ring, wherein one carbon atom, which is not adjacent to the carbon atom, to which R1 and R2 are attached, can be replaced by —O—, —NR57- or —S(O)$_w$—, and in which the formed ring can be saturated or partially unsaturated, and in which the formed ring can optionally be condensed to phenyl, heteroaryl having 5 or 6 atoms, cycloalkyl having 3, 4, 5, 6, 7 or 8 carbon atoms or heterocyclyl having 3, 4, 5, 6, 7 or 8 atoms,
wherein the formed ring and the condensed phenyl, heteroaryl, cycloalkyl or heterocyclyl radical can be unsubstituted or substituted by 1, 2, 3, 4 or 5 radicals selected from the group consisting of F, Cl, Br, I, CN, NO$_2$,
SCF$_3$, SF$_5$ or alkyl having 1, 2, 3 or 4 carbon atoms;
R57 is hydrogen, alkyl having 1, 2, 3 or 4 carbon atoms or C(O)R58;
R58 is hydrogen, alkyl with 1, 2, 3 or 4 carbon atoms or phenyl,
w is 0, 1 or 2.

Examples of said rings formed by R1 and R1 and the carbon atom, to which they are attached, are described in the following text and structures. The carbon atom, to which R1 and R2 are attached, is indicated by an asterix (*) in the structures.

Examples of saturated carbon rings are cyclopropane, cyclobutane cyclopentane or cyclohexane:

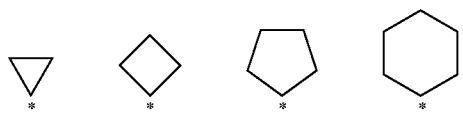

Examples of carbons rings formed by R1 and R2 and the carbon atom, to which they are attached, which are partially unsaturated, are cyclopentene, cyclohexene or cyclohexadiene:

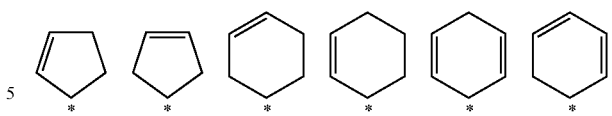

Examples of saturated rings formed by R1 and R2 and the carbon atom, to which they are attached, wherein a carbon atom, which is not adjacent to the carbon atom to which R1 and R2 are attached, is replaced by —O— are oxetane, tetrahydrofurane, tetrahydropyrane:

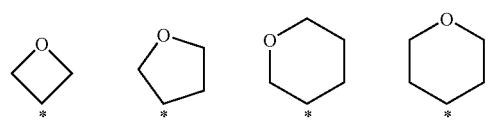

Examples of saturated rings formed by R1 and R2 and the carbon atom, to which they are attached, wherein a carbon atom, which is not adjacent to the carbon atom to which R1 and R2 are attached, is replaced by —S(O)$_w$—, are, for the case, that w is 0, thietane, tetrahydro-thiophene or tetrahydro-thiopyrane:

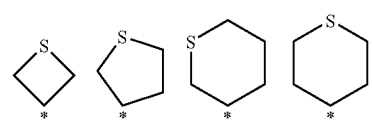

The corresponding mono- or dioxides thereof are also examples of saturated rings formed by R1 and R2 and the carbon atom, to which they are attached, wherein a carbon atom, which is not adjacent to the carbon atom to which R1 and R2 are attached, is replaced by —S(O)$_w$— (in cases where w is 1 or 2).

Examples of saturated rings formed by R1 and R2 and the carbon atom, to which they are attached, wherein a carbon atom, which is not adjacent to the carbon atom to which R1 and R2 are attached, is replaced by —NR57- are, for the case, that R57 is hydrogen, azetidine, pyrrolidine or piperidine:

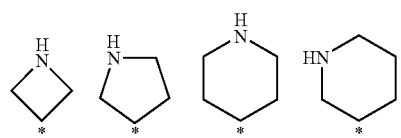

5- or 6-membered carbon rings, which are formed by R1 and R2 and the carbon atom, to which they are attached, and wherein one carbon atom, which is not adjacent to the carbon atom to which R1 and R2 are attached, is replaced by —O—, —NR57- or —S(O)$_w$— may be partially unsaturated and can contain for example one double bond in five membered rings or one or two double bonds in six membered rings as exemplified in the following structures for the cases, where for rings containing —S(O)$_w$— w is 0 and for rings containing NR57 and R57 is hydrogen:

The rings formed by R1 and R2 and the carbon atom, to which they are attached, can be optionally condensed to phenyl, heteroaryl having 5 or 6 atoms, cycloalkyl having 3, 4, 5, 6, 7 or 8 carbon atoms or heterocyclyl having 3, 4, 5, 6, 7 or 8 atoms.

The rings formed by R1 and R2 and the carbon atom, to which they are attached, and the optionally condensed phenyl, heteroaryl, cycloalkyl or heterocyclyl may be further substituted as described.

The heteroatoms may be at different positions in the ring as shown for example in some of the structures above. There is no double bond in the ring formed by R1 and R2 at the carbon atom to which R1 and R2 are attached in a compound of formula I.

The invention further relates to the following processes for preparing the compounds of the formula I.

Compounds of formula I wherein Z is —C(O)— and the atom in B linked to the ring system is oxygen can be prepared as described in Scheme 1

Scheme 1 which comprises
a) coupling of an acid of formula III with an amino compound of formula IV to an amide of formula V,
b) reacting a compound of formula V with a reagent R—U to an compound of formula VI,
c) converting an ester of formula VI to an acid of formula Ia
wherein in the compounds of the formulae Ia, III, IV, V and VI
X, Y1 to Y4, R1 and R2 are defined as in formula I,
R' is alkyl having 1, 2, 3, 4, 5 or 6 carbon atoms,
R—U is A-B1-L or A-B1-OH and R— is A-B1-,
   wherein A is defined as in formula I and —B1- is defined in a manner so that —B1-O— is contained in the definition of B as given in formula I;
   U is OH or L, wherein L is a leaving group, which can undergo nucleophilic substitution with an amine.

The procedure for preparing the compounds of the formula I is initially a coupling of an amino compound of formula IV with an acid of formula III for preparing the compound of formula V generally in the presence of an coupling agent, for example EDC, DIC or HATU and optionally an additional base, for example triethylamine or Hünig's base, in an appropriate solvent, in particular in an aprotic polar solvent such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range.

Subsequently, the transformation of the compound of formula V to the compound of formula VI can be achieved by adding the reagent R-L (U=L) in the presence of a suitable base, for example potassium or cesium carbonate. L is a leaving group which can undergo nucleophilic substitution, for example Cl, Br, I or OTos. The reaction temperature in this case is generally from −30° C. to 200° C., preferably from 20° C. to 150°. The reaction time is generally from 2 min to 6 days, preferably from 15 min to 16 h, depending on the composition of the mixture and the chosen temperature range. Alternatively the reaction of the compound of formula V with R—OH(U=OH) can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 80°, more preferably from 0° C. to 25° C. The reaction time is generally from 15 min to 6 days, preferably from 15 min to 16 h, depending on the composition of the mixture and the chosen temperature range.

The cleavage of the ester of formula VI to the acid of formula Ia in can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range.

Optionally, compounds VI or Ia in Scheme 1, which contain within R triple bonds or non-aromatic double bonds, can be (partially) reduced, so that triple bonds are converted to double bonds, or so that triple bonds are converted to single bonds, or so that non-aromatic double bonds are converted to single bonds, or so that triple bonds and non-aromatic double bonds are converted to single bonds. These transformations can be carried out in analogy to the processes which are described in the literature and are known to those skilled in the art, for example by (partial) hydrogenation of said compounds in the presence of homogenous or heterogenous catalysts.

Alternatively compounds of formula I wherein U is —C(O)— and the atom in B linked to the ring system is oxygen can be prepared as described in Scheme 2

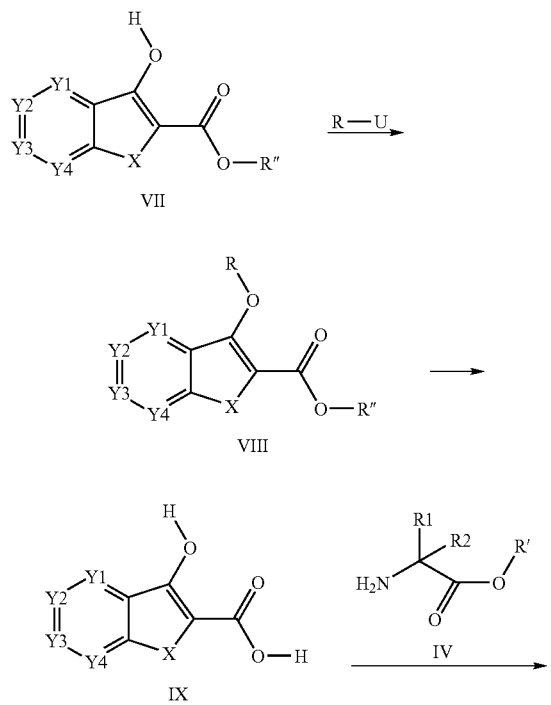

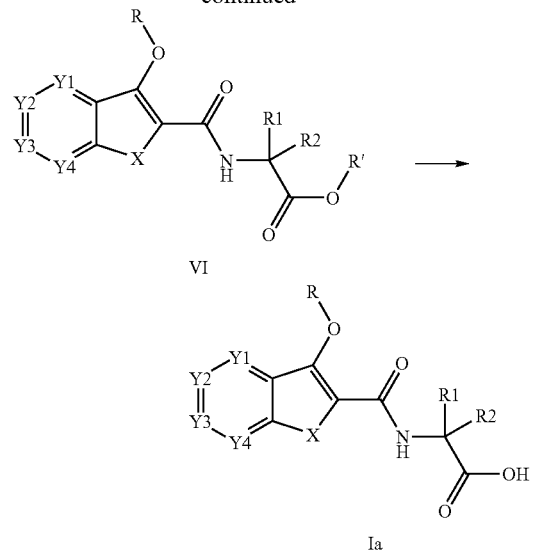

which comprises
a) reacting a compound of formula VII with an reagent R—U to a compound of formula VIII
b) converting an ester of formula VIII to an acid of formula IX
c) coupling of an acid of formula IX with an amino compound of formula IV to an amide of formula VI
d) converting an ester of formula VI to an acid of formula Ia
wherein in the compounds of the formulae Ia, IV, VI, VII, VIII and IX
X, Y1 to Y4, R1 and R2 are defined as in formula I,
R' is alkyl having 1, 2, 3, 4, 5 or 6 carbon atoms,
R" is alkyl having 1, 2, 3, 4, 5 or 6 carbon atoms or aryl,
R—Z is A-B1-L or A-B1-OH and R— is A-B1-,
wherein A is defined as in formula I and —B1- is defined in a manner so that —B1-O— is contained in the definition of B as given in formula I;
U is OH or L, wherein L is a leaving group, which can undergo nucleophilic substitution with an amine.

The procedure for preparing the compounds of the formula I is initially a transformation of the compound of formula VII to the compound of formula VIII which can be achieved by adding the reagent R-L (U=L) in the presence of a suitable base, for example potassium or cesium carbonate. L is a leaving group which can undergo nucleophilic substitution, for example Cl, Br, I or OTos. The reaction temperature in this case is generally from −30° C. to 200° C., preferably from 20° C. to 1500. The reaction time is generally from 2 min to 6 days, preferably from 15 min to 16 h depending on the composition of the mixture and the chosen temperature range Alternatively, the reaction of the compound of formula VII with R—OH(U=OH) can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 80°, more preferably from 0° C. to 25° C. The reaction time is generally from 15 min to 6 days, preferably from 15 min to 16 h, depending on the composition of the mixture and the chosen temperature range.

The subsequent cleavage of the ester of formula VIII to the acid of formula IX can be achieved in a manner known by the person skilled in the art, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160° C. The reaction time is generally from 2 min to 6 days, preferably from 2 min to 16 h.

The resulting compound of formula IX can be coupled with the amino compound of formula IV to form the compound of formula VI generally in the presence of an coupling agent, for example EDC, DIC or HATU and optionally an additional base, for example triethylamine or Hünig's base, in an appropriate solvent, in particular in an aprotic polar solvents such as, for example, DMF. The reaction temperature in this case is or non-aromatic double bonds, can be (partially) reduced, so that triple bonds are converted to double bonds, or so that triple bonds are converted to single bonds, or so that non-aromatic double bonds are converted to single bonds, or so that triple bonds and non-aromatic double bonds are converted to single bonds. These transformations can be carried out in analogy to the processes which are described in the literature and are known to those skilled in the art, for example by (partial) hydrogenation of said compounds in the presence of homogenous or heterogenous catalysts.

Alternatively, compounds of formula I wherein Z is —C(O)— and the atom in B linked to the ring system is —N(R19)- or a carbon atom can be prepared as described in Scheme 3

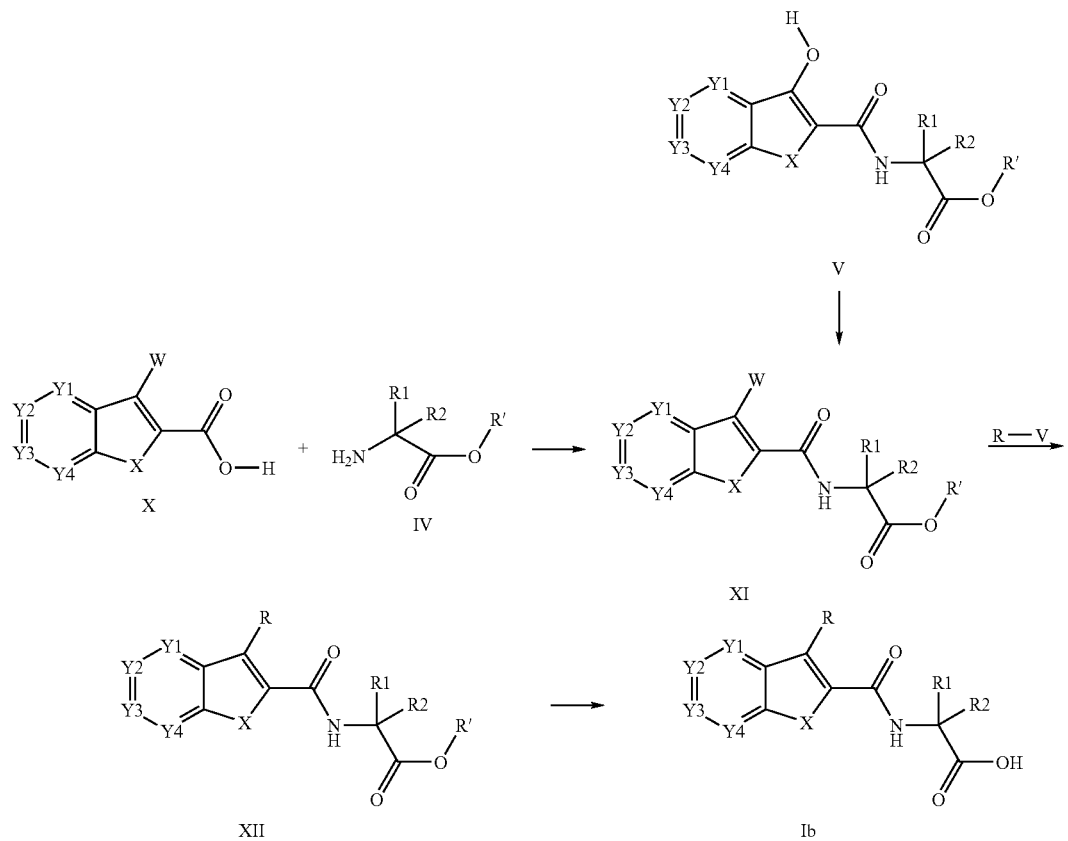

generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The cleavage of the ester of formula VI to the acid of formula Ia in can be achieved as mentioned above, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160. The reaction time is generally from 2 min to 6 days, preferably from 2 min to 16 h, depending on the composition of the mixture and the chosen temperature range. Optionally, compounds Ia, VI, VIII or IX in Scheme 2, which contain within R triple bonds which comprises
a) coupling of an acid of formula X with an amino compound of formula IV to an amide of formula XI,
or, alternatively, the conversion of a compound of formula V to a compound of formula XI (if W is triflate, mesylate or tosylate),
b) reacting a compound of formula XI with an reagent R—V to an compound of formula XII,
c) converting an ester of formula XII to an acid of formula Ib
wherein in the compounds of the formulae Ib, IV, V, X, XI and XII
X, Y1 to Y4, R1 and R2 are defined as in formula I,
W is halogen, for example 1, Br or Cl, or triflate, mesylate or tosylate,
R' is alkyl having 1, 2, 3, 4, 5 or 6 carbon atoms,
R—V is A-B2-NR19-H and R— is A-B2-NR19- or R—V is A-B3-CR17=CR18-H and R— is A-B3-CR17=CR18-
or R—V is A-B3-CR17=CR18-B(OR''')$_2$ and R— is A-B3-CR17=CR18-
or R—V is A-B3-CR17=CR18-Sn(R'''')$_3$ and R is A-B3-CR17=CR18- or
or R—V is A-B3-CR17=CR18-ZnHal and R— is A-B3-CR17=CR18-
or R—V is A-B4-C≡C—H and R— is A-B4-C≡C—,
wherein
A is defined as in formula I,
—B2- is defined in a manner so that —B2-NR19- is contained in the definition of B as given in formula I,
—B3- is defined in a manner, so that —B3-CR17=CR18- is contained in the definition of B as given in formula I,
—B4- is defined in a manner, so that —B4-C≡C— is contained in the definition of B as given in formula I,
R17 and R18 are substituents at a carbon atom being part of a double bond as defined for B in formula I and R19 is defined as in formula I,
R''' is H or alkyl having 1, 2, 3, 4, 5 or 6 carbon atoms, or alternatively both R''' form, together with the oxygen atoms they are attached to and with the boron atom the oxygen atoms are attached to, a five, six or seven membered ring, which can be unsubstituted or substituted by 1, 2, 3, 4, 5, 6, 7 or 8 alkyl groups,
R'''' is alkyl having 1, 2, 3, 4, 5 or 6 carbon atoms,
Hal is halogen, for example 1, Br or Cl.

The procedure for preparing the compounds of the formula I is initially a coupling of an amino compound of formula IV with an acid of formula X for preparing the compound of formula XI generally in the presence of a coupling agent, for example EDC, DIC or HATU and optionally an additional base, for example triethylamine or Hünig's base, in an appropriate solvent, in particular in an aprotic polar solvent such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range.

Alternatively, a compound of formula V can be converted into a compound of formula XI, in which W is defined as triflate, tosylate or mesylate, by reacting it with an anhydride or chloride of trifluoromethane sulfonic acid, para-toluene sulfonic acid or methyl sulfonic acid in the presence of a suitable base, for example triethylamine in an appropriate solvent, for example dichloromethane. The reaction temperature in this case is generally from −80° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range.

Subsequently, the transformation of the compound of formula XI to the compound of formula XII can be achieved by reacting with a reagent R—V, often under inert conditions and in an appropriate solvent, in the presence of a suitable catalytic system, which can contain a palladium and/or copper complex and/or salt, for example Pd$_2$ dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAc, K$_3$PO$_4$, LiHMDS, NaHMDS or KHMDS. The reaction temperature in this case is generally from −30° C. to 250° C., preferably from 0° C. to 2500, more preferably from 20° C. to 200° C. The reaction time is generally from 15 min to 6 days, preferably from 15 min to 16 h, depending on the composition of the mixture and the chosen temperature range.

The cleavage of the ester of formula XII to the acid of formula Ib can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range.

Optionally, compounds Ib or XII in Scheme 3, which contain within R triple bonds or non-aromatic double bonds, can be (partially) reduced, so that triple bonds are converted to double bonds, or so that triple bonds are converted to single bonds, or so that non-aromatic double bonds are converted to single bonds, or so that triple bonds and non-aromatic double bonds are converted to single bonds. These transformations can be carried out in analogy to the processes which are described in the literature and are known to those skilled in the art, for example by (partial) hydrogenation of said compounds in the presence of homogenous or heterogenous catalysts.

Alternatively compounds of formula I wherein Z is —C(O)— and the atom in B linked to the ring system is —N(R19)- or a carbon atom can be prepared as described in Scheme 4

Scheme 4

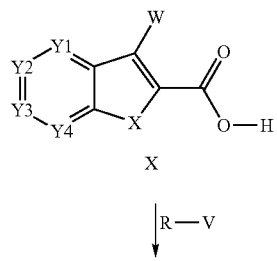

X

R—V

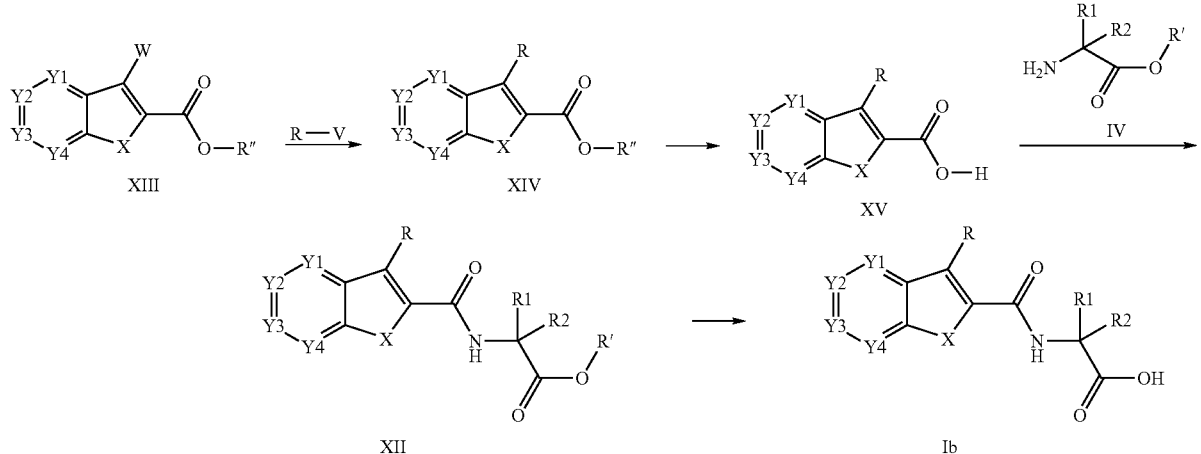

-continued which comprises
a) reacting a compound of formula XIII with a reagent R—V to a compound of formula
b) converting an ester of formula XIV to an acid of formula XV
or, alternatively, reacting a compound of formula X with a reagent R—V to a compound of formula XV
c) coupling of an acid of formula XV with an amino compound of formula IV to an amide of formula XII
d) converting an ester of formula XII to an acid of formula Ib
wherein in the compounds of the formulae Ib, IV, X, XII, XIII, XIV and XV
X, Y1 to Y4, R1 and R2 are defined as in formula I,
W is halogen, for example 1, Br or Cl, or triflate, mesylate or tosylate,
R' is alkyl having 1, 2, 3, 4, 5 or 6 carbon atoms,
R" is alkyl having 1, 2, 3, 4, 5 or 6 carbon atoms or aryl,
R—V is A-B2-NR19-H and R— is A-B2-NR19-
or R—V is A-B3-CR17=CR18-H and R— is A-B3-CR17=CR18-
or R—V is A-B3-CR17=CR18-B(OR''')$_2$ and R— is A-B3-CR17=CR18-
or R—V is A-B3-CR17=CR18-Sn(R'''')$_3$ and R is A-B3-CR17=CR18-
or R—V is A-B3-CR17=CR18-ZnHal and R— is A-B3-CR17=CR18-
or R—V is A-B4-C≡C—H and R— is A-B4-C≡C—,
  wherein
  A is defined as in formula I,
  —B2- is defined in a manner so that —B2-NR19- is contained in the definition of B as given in formula I,
  —B3- is defined in a manner, so that —B3-CR17=CR18- is contained in the definition of B as given in formula I,
  —B4 is defined in a manner, so that —B4-C≡C— is contained in the definition of B as given in formula I,
  R17, R18 are substituents at a carbon atom being part of a double bond as defined for B in formula I and R19 is defined as in formula I,
  R''' is H or alkyl having 1, 2, 3, 4, 5 or 6 carbon atoms, or alternatively both R''' form, together with the oxygen atoms they are attached to and with the boron atom the oxygen atoms are attached to, a five, six or seven membered ring, which can be unsubstituted or substituted by 1, 2, 3, 4, 5, 6, 7 or 8 alkyl groups,
  R'''' is alkyl having 1, 2, 3, 4, 5 or 6 carbon atoms,
  Hal is halogen, for example 1, Br or Cl.

The procedure for preparing the compounds of the formula I is initially a transformation of the compound of formula XIII to the compound of formula XIV which can be achieved by reacting with a reagent R—V, often under inert conditions and in an appropriate solvent, in the presence of a suitable catalytic system, which can contain a palladium and/or copper complex and/or salt, for example Pd$_2$ dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAc, K$_3$PO$_4$, LiHMDS, NaHMDS or KHMDS. The reaction temperature in this case is generally from −30° C. to 250° C., preferably from 0° C. to 2500, more preferably from 20° C. to 200° C. The reaction time is generally from 15 min to 6 days, preferably from 15 min to 16 h, depending on the composition of the mixture and the chosen temperature range.

The subsequent cleavage of the ester of formula XIV to the acid of formula XV can be achieved in a manner known by the person skilled in the art, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160° C. The reaction time is generally from 2 min to 6 days, preferably from 2 min to 16 h.

Alternatively, a transformation of a compound of formula X to the compound of formula XV can be achieved by reacting with a reagent R—V, often under inert conditions and in an appropriate solvent, in the presence of a suitable catalytic system, which can contain a palladium and/or copper complex and/or salt, for example Pd$_2$ dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAc, K$_3$PO$_4$, LiHMDS, NaHMDS or KHMDS. The reaction temperature in this case is generally from −30° C. to 250° C., preferably from 0° C. to 2500, more preferably from 20° C. to 200° C. The reaction time is generally from 15 min to 6 days, preferably from 15 min to 16 h, depending on the composition of the mixture and the chosen temperature range.

The resulting compound of formula XV can be coupled with the amino compound of formula IV to form the compound of formula XII generally in the presence of a coupling agent, for example EDC, DIC or HATU and optionally an additional base, for example triethylamine or Hünig's base, in an appropriate solvent, in particular in aprotic polar solvents such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The cleavage of the ester of formula XII to the acid of formula Ib in can be achieved as mentioned above, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160. The reaction time is generally from 2 min to 6 days, preferably from 2 min to 16 h, depending on the composition of the mixture and the chosen temperature range.

Optionally, compounds Ib, XII, XIV or XV in Scheme 4, which contain within R triple bonds or non-aromatic double bonds, can be (partially) reduced, so that triple bonds are converted to double bonds, or so that triple bonds are converted to single bonds, or so that non-aromatic double bonds are converted to single bonds, or so that triple bonds and non-aromatic double bonds are converted to single bonds. These transformations can be carried out in analogy to the processes which are described in the literature and are known to those skilled in the art, for example by (partial) hydrogenation of said compounds in the presence of homogenous or heterogenous catalysts.

Alternatively, compounds of formula I wherein Z is —S(O)2- and the atom in B linked to the ring system is oxygen can be prepared as described in Scheme 5

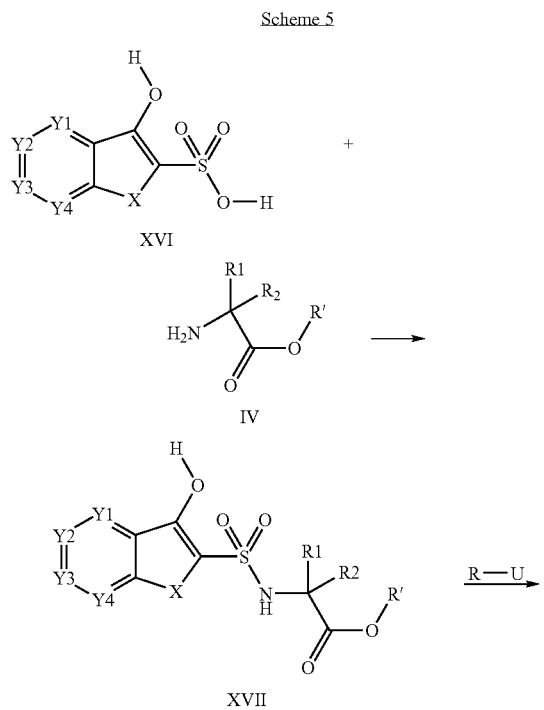

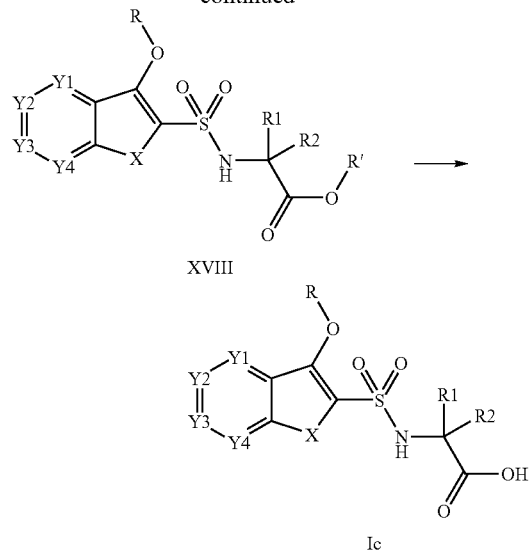

which comprises
a) coupling of a sulfonic acid of formula XVI with an amino compound of formula IV to a sulfonamide of formula XVII,
b) reacting a compound of formula XVII with a reagent R—U to an compound of formula XVIII,
c) converting an ester of formula XVIII to an acid of formula Ic,
wherein in the compounds of the formulae Ic, IV, XVI, XVII and XVIII
X, Y1 to Y4, R1 and R2 are defined as in formula I,
R' is alkyl having 1, 2, 3, 4, 5 or 6 carbon atoms,
R—U is A-B1-L and R— is A-B1-,
wherein A is defined as in formula I and —B1- is defined in a manner so that —B1-O— is contained in the definition of B as given for formula I;
U is L, wherein L is a leaving group, which can undergo nucleophilic substitution with an amine.

The procedure for preparing the compounds of the formula Ic is initially a coupling of an amino compound of formula IV with a sulfonic acid of formula XVI for preparing the compound of formula XVII generally by transforming the sulfonic acid XVI or an alkali salt of the sulfonic acid XVI into a sulfonic acid chloride, for example ba action of phsosphorous pentachloride, optionally in a suitable solvent such as, for example, chloroform, and optionally in the presence of a base, and by then reacting the sulfonyl chloride with an amino acid of formula IV in a suitable solvent, for example dioxane or THF, and optionally in the presence of a suitable base, for example N,N-diisopropyl-ethyl amine or N,N-diisopropylamine. The reaction temperature in this case in the first step is generally from 0° C. to 200° C., preferably from 0° C. to 1000, more preferably from 20° C. to 80° C., and the reaction time is generally from 15 min to 16 h, preferably from 15 min to 6 h depending on the composition of the mixture and the chosen temperature range; the reaction temperature in the second step is generally from −30° C. to 200° C., preferably from −20° C. to 80°, more preferably from 0° C. to 20° C., and the reaction time is generally from 15 min to 6 days, preferably from 15 min to 16 h, depending on the composition of the mixture and the chosen temperature range.

Subsequently, the transformation of the compound of formula XVII to the compound of formula XVIII can be achieved by adding the reagent R-L (U=L) in the presence of a suitable base, for example potassium or cesium carbonate in a suitable solvent, such as, for example, THF or DMF. L is a leaving group which can undergo nucleophilic substitution, for example Cl, Br, I or OTos. The reaction temperature in this case is generally from −30° C. to 200° C., preferably from 20° C. to 1500. The reaction time is generally from 2 min to 6 days, preferably from 15 min to 16 h, depending on the composition of the mixture and the chosen temperature range.

The cleavage of the ester of formula XVIII to the acid of formula Ic can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range.

Optionally, compounds Ic or XVIII in Scheme 5, which contain within R triple bonds or non-aromatic double bonds, can be (partially) reduced, so that triple bonds are converted to double bonds, or so that triple bonds are converted to single bonds, or so that non-aromatic double bonds are converted to single bonds, or so that triple bonds and non-aromatic double bonds are converted to single bonds. These transformations can be carried out in analogy to the processes which are described in the literature and are known to those skilled in the art, for example by (partial) hydrogenation of said compounds in the presence of homogenous or heterogenous catalysts.

Alternatively compounds of formula I, wherein Z is —C(O)— and A-B— can be described as RO(CH$_2$)$_{2-3}$O—, where R is A, wherein A is phenyl or heteroaryl, can be prepared as described in Scheme 6

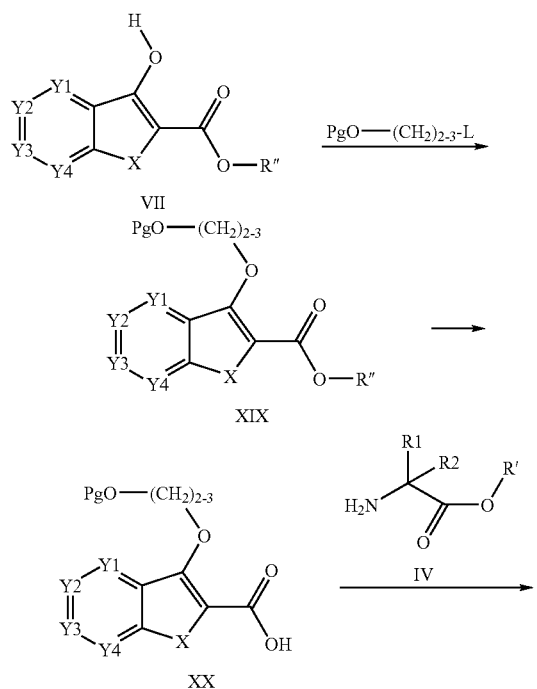

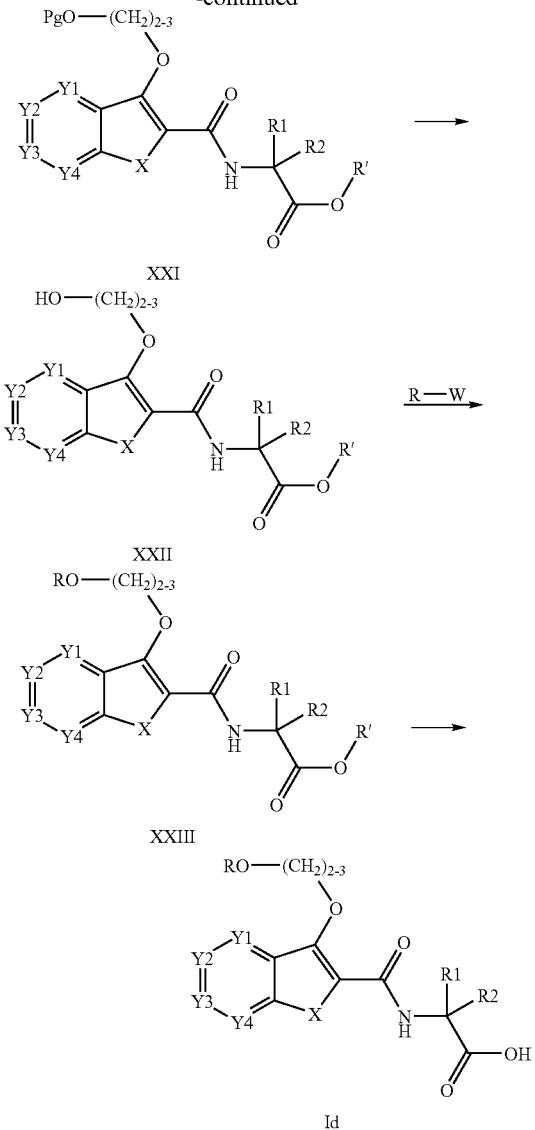

which comprises
a) reacting a compound of formula VII with an reagent PgO—(CH$_2$)$_{2-3}$-L a to compound of formula XIX
b) converting an ester of formula XIX to an acid of formula XX
c) coupling of an acid of formula XX with an amino compound of formula IV to an amide of formula XXI
d) cleaving of the hydroxyl-protecting group of a compound of formula XXI to an alcohol of formula XXII
e) reacting an alcohol of formula XXII with a reagent R—W to a compound of formula XXIII
f) converting an ester of formula XXIII to an acid of formula Id;
wherein in the compounds of the formulae Id, IV, VII, XIX, XX, XXI, XXII and XXIII
X, Y1 to Y4, R1 and R2 are defined as in formula I,
R' is alkyl having 1, 2, 3, 4, 5 or 6 carbon atoms,
R" is alkyl having 1, 2, 3, 4, 5 or 6 carbon atoms or aryl,
R—W is R—OH and R is A, for cases, where A is phenyl or heteroaryl, which both can be condensed or substituted as described in formula I;
L is a leaving group, which can undergo nucleophilic substitution with an amine.

Pg is a hydroxyl-protecting group, which can be cleaved in the presence of esters and amides, and in whose presence an ester can be cleaved, for example a silyl protecting group, as tert-butyl-dimethylsilyl or triisopropylsilyl.

The procedure for preparing the compounds of the formula I is initially the reaction of a compound of formula VII with a reagent RO(CH$_2$)$_{2-3}$L, wherein Pg is a hydroxyl-protecting group, which can be cleaved in the presence of esters and amides, and in whose presence an ester can be cleaved, for example a silyl protecting group, as tert-butyl-dimethylsilyl or triisopropylsilyl, and L is a leaving group, which can undergo nucleophilic substitution with an amine, for example L can be Cl, Br, I or OTos. The reaction can be carried out in the presence of a suitable base, for example potassium or cesium carbonate in a suitable solvent, such as, for example, THF or DMF. The reaction temperature in this case is generally from 0° C. to 250° C., preferably from 20° C. to 150°. The reaction time is generally from 2 min to 6 days, preferably from 15 min to 16 h, depending on the composition of the mixture and the chosen temperature range. The subsequent cleavage of the ester of formula XIX to the acid of formula XX can be achieved in a manner known by the person skilled in the art, for example by the use of a base, like potassium trimethylsilanoate, for example in case of primary or secondary alkyl esters, in a suitable solvent, for example DMF. The reaction temperature in this case is generally from −30° C. to 150° C., preferably from 0° C. to 100° C. The reaction time is generally from 2 min to 6 days, preferably from 2 min to 16 h. The resulting compound of formula XX can be coupled with the amino compound of formula IV to form the compound of formula XXI generally in the presence of a coupling agent, for example EDC, DIC or HATU and optionally an additional base, for example triethylamine or Hünig's base, in an appropriate solvent, in particular in an aprotic polar solvent such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The subsequent cleavage of the hydroxyl-protecting group of a compound of formula XXI to an alcohol of formula XXII can be achieved in a manner known by the person skilled in the art, for example in case of silyl protecting groups as tert-butyldimethylsilyl or triisopropylsilyl by the use of a fluoride source, for example by treatment with tetrabutylammonium fluoride, in a suitable solvent, for example THF. The reaction temperature in this case is generally from −80° C. to 150° C., preferably from −10° C. to 50° C. The reaction time is generally from 2 min to 6 days, preferably from 2 min to 16 h, depending on the composition of the mixture and the chosen temperature range. The reaction of the compound of formula XXIII with R—OH(W═OH) to a compound of formula XXIII can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 80°, more preferably from 0° C. to 25° C. The reaction time is generally from 15 min to 6 days, preferably from 15 min to 16 h, depending on the composition of the mixture and the chosen temperature range. The cleavage of the ester of formula XXIII to the acid of formula Id can be achieved as mentioned above, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range.

The compounds of formulae Ia, Ib, Ic and Id are contained in the compound of formula I.

The starting compounds of the formulae III, IV, V, VII, X, XIII and XVI are commercially available or can be prepared by a skilled artisan according to procedures described in the literature.

The workup and optionally the purification of the products and/or intermediates are effected by customary methods such as extraction, chromatography or crystallization and customary dryings.

Alternative processes for preparing the compounds are described in the examples and are also part of the invention.

Functional groups in the starting compounds may be present in protected form or in the form of precursors, and then be converted into the desired groups in the compounds of the formula I prepared by the process described above. Corresponding protective group techniques are known to the skilled artisan.

It is likewise possible for appropriate functional groups to be derivatized by methods known to the skilled artisan.

| List of abbreviations: | |
| --- | --- |
| O-(7-Azabenzotriazol-1-yl)-N,N,N',N'-tetramethyl-uronium Hexafluorophosphate | HATU |
| [2-(1H)-benzotriazol-1yl]-1,1,3,3-tetramethyluronium tetra-fluoroborate | TBTU |
| (dibenzyliden)acetone | dba |
| 4-Dimethylaminopyridine | DMAP |
| Diethylazodicarboxylate | DEAD |
| Diisoppropylazodicarboxylate | DIAD |
| N,N'-Diisopropylcarbodiimid | DIC |
| 1-(3-Dimethylaminopropyl)-3-ethylcarbodiimide-Hydrochloride | EDC |
| N,N-Dimethylformamide | DMF |
| Electron spray ionisation Positive mode | ESI+ or ESI |
| Electron spray ionisation Negative mode | ESI− |
| enantiomeric excess in percent | % ee |
| Hexamethyldisilazide | HMDS |
| high pressure/performance liquid chromatography | HPLC |
| liquid chromatography - mass spectroscopy | LCMS |
| nuclear magnetic resonance | NMR |
| meta-chloro perbenzoic acid | MCPBA |
| Tetrahydrofuran | THF |
| N,N,N',N'-Tetramethylethylendiamine | TMEDA |
| Retention time | Rt |
| reversed phase | RP |

Another aspect of the invention is the use of a compound of the formula I and/or a pharmaceutically acceptable salt and/or a prodrug thereof alone or in combination with other medicaments or active ingredients as for producing a medicament for the treatment or prophylaxis of chemokine mediated diseases.

The invention further relates to the use of a compound of the formula I and/or a pharmaceutically acceptable salt and/or a prodrug thereof alone or in combination with other medicaments or active ingredients for producing a medicament for the treatment or prophylaxis of a chemokine mediated disease, wherein the chemokine binds to a CXC receptor.

Another aspect of the invention is the use of a compound of the formula I and/or the pharmaceutically acceptable salt and/or a prodrug thereof alone or in combination with other medicaments or active ingredients for producing a medicament for the treatment or prophylaxis of a chemokine mediated disease, wherein the chemokine binds to a CXCR2 and/or CXCR1 receptor, in particular to a CXCR2 receptor.

The invention further relates to the use of a compound of the formula I and/or a pharmaceutically acceptable salt and/or a prodrug thereof alone or in combination with other medicaments or active ingredients for producing a medicament for the treatment or prophylaxis of rheumatoid arthritis, chronic obstructive pulmonary disease, adult or acute respiratory distress syndrome, asthma, atherosclerosis, myocardial and renal ischemia/reperfusion injury, peripheral limb ischemia/reperfusion injury, inflammatory bowel disease, ulcerative colitis, Crohn's disease, meconium apriration syndrome, atopic dermatitis, cystic fibrosis, psoriasis, psoriatic arthritis, multiple sclerosis, angiogenesis, restenosis, osteoarthritis, osteoporosis, septic shock, endotoxic shock, gram negative sepsis, toxic shock syndrome, stroke, glomerulonephritis, thrombosis, graft vs. host reaction, allograft rejections, transplant reperfusion injury, early transplantation rejection, acute inflammation, alzheimers disease, malaria, respiratory viruses, herpes viruses, hepatitis viruses, HIV, Kaposi's sarcoma-associated viruses, meningitis, gingivitis, herpes encephalitis, CNS vasculitis, traumatic brain injury, brain ischemia/reperfusion injury, migraine, CNS tumors, subarachnoid hemorrhage, post surgical trauma, interstitial pneumonitis, hypersensitivity, crystal induced arthritis, acute and chronic pancreatitis, hepatic ischemia/reperfusion injury, acute alcoholic hepatitis, necrotizing enterocolitis, chronic sinusitis, uveitis, polymyositis, vasculitis, acne, gastric and duodenal ulcers, intestinal ischemia/reperfusion injury, celiac disease, esophagitis, glossitis, rhinitis, airflow obstruction, airway hyperresponsiveness, bronchiolitis, bronchiolitis obliterans, bronchiolitis obliterans organizing pneumonia, bronchiectasis, chronic bronchitis, cor pulmonae, dyspnea, emphysema, hypercapnea, hyperinflation, hyperoxia-induced inflammations, hypoxemia, hypoxia, lung ischemia/reperfusion injury, surgerical lung volume reduction, pulmonary fibrosis, pulmonary hypertension, right ventricular hypertrophy, peritonitis associated with continuous ambulatory peritoneal dialysis, granulocytic ehrlichiosis, sarcoidosis, small airway disease, ventilation-perfusion mismatching, wheeze, colds, gout, alcoholic liver disease, lupus, burn therapy, periodontitis, pre-term labor, cough, pruritis, multi-organ dysfunction, trauma, sprains, contusions, undesired hematopoietic stem cell release, angiogenic ocular disease, ocular inflammation, retinopathy or prematurity, diabetic retinopathy, macular degeneration with the wet type preferred and corneal neovasularization, tumor angiogenesis, cancer and metastasis.

In particular, the invention further relates to the use of a compound of the formula I and/or a pharmaceutically acceptable salt and/or a prodrug thereof alone or in combination with other medicaments or active ingredients for producing a medicament for the treatment or prophylaxis of acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78 or GCP-2) mediated diseases which include adult respiratory distress syndrome, inflammatory bowel disease, ulcerative colitis, Crohn's disease, atopic dermatitis, cystic fibrosis, psoriasis, dermatitis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer.

A further aspect of the present invention is the use of a compound of the formula II

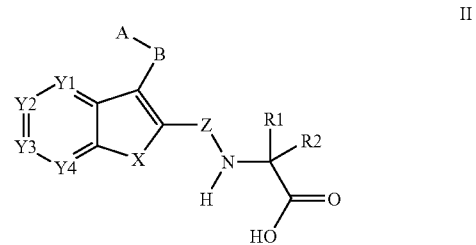

wherein
X is —CR3=CR4-, —CR5=N—, —N=CR6-, —NR7- or —S—;
R3, R4, R5 and R6
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, NO$_2$, NR27R28, C(O)R29, C(O)NR30R31, S(O)OR32, S(O)$_p$NR33R34, aryl, heteroaryl, arylalkyl with alkyl having 1, 2, 3 or 4 carbon atoms or heteroarylalkyl with alkyl having 1, 2, 3 or 4 carbon atoms;
R27 is hydrogen or alkyl having 1, 2, 3 or 4 carbon atoms;
R28 is hydrogen, alkyl having 1, 2, 3 or 4 carbon atoms, aryl, C(O)H, C(O)alkyl with alkyl having 1, 2, 3 or 4 carbon atoms or C(O)aryl;
R29 is hydrogen, OH, alkyl with 1, 2, 3 or 4 carbon atoms, alkoxy with 1, 2, 3 or 4 carbon atoms or aryl;
R30, R31, R33 and R34
are, independently of one another, hydrogen, alkyl having 1, 2, 3 or 4 carbon atoms or aryl;
R32 is OH, alkyl having 1, 2, 3 or 4 carbon atoms, alkoxy with 1, 2, 3 or 4 carbon atoms or aryl;
o and p
are, independently of one another, 1 or 2;
R7 is hydrogen, alkyl having 1, 2, 3 or 4 carbon atoms or C(O)R35;
R35 is hydrogen, alkyl with 1, 2, 3 or 4 carbon atoms or aryl;
Y1, Y2, Y3 and Y4
are, independently of one another, —CR8- or nitrogen, with the proviso that at least two of Y1, Y2, Y3 and Y4 are defined as —CR8-;

R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, $NR36R37$, $C(O)R38$, $C(O)NR39R40$, $S(O)_qR41$, $S(O)_rNR42R43$, aryl, heteroaryl, arylalkyl with alkyl having 1, 2, 3 or 4 carbon atoms or heteroarylalkyl with alkyl having 1, 2, 3 or 4 carbon atoms;

R36 is hydrogen or alkyl having 1, 2, 3 or 4 carbon atoms;

R37 is hydrogen, alkyl having 1, 2, 3 or 4 carbon atoms, aryl, C(O)H, C(O)alkyl with alkyl having 1, 2, 3 or 4 carbon atoms or C(O)aryl;

R38 is hydrogen, OH, alkyl with 1, 2, 3 or 4 carbon atoms, alkoxy with 1, 2, 3 or 4 carbon atoms or aryl;

R39, R40, R42 and R43
are, independently of one another, hydrogen, alkyl having 1, 2, 3 or 4 carbon atoms or aryl;

R41 is OH, alkyl having 1, 2, 3 or 4 carbon atoms, alkoxy with 1, 2, 3 or 4 carbon atoms or aryl;

q and r
are, independently of one another, 1 or 2;

Z is —C(O)—, S(O)— or —$S(O)_2$—;

A is cycloalkyl having 3, 4, 5, 6, 7 or 8 carbon atoms, heterocyclyl having 5, 6, 7 or 8 atoms, phenyl or heteroaryl having 5 or 6 atoms;

in which the said cycloalkyl, heterocyclyl, phenyl or heteroaryl can be condensed to a cycloalkyl radical having 3, 4, 5, 6, 7 or 8 atoms, a heterocyclyl radical having 5, 6, 7 or 8 atoms, a phenyl radical or a heteroaryl radical having 5 or 6 atoms, and in which said cycloalkyl, heterocyclyl, phenyl or heteroaryl and the optionally condensed cycloalkyl radical, heterocyclyl radical, phenyl radical or heteroaryl radical are unsubstituted or substituted by 1, 2, 3, 4 or 5 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms or —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

B is a linear linker consisting of 3, 4 or 5 carbon atoms, in which 1 or 2 carbon atoms can be replaced by a member of a heteroatom containing group consisting of O, NR19 or $S(O)_y$, and which linker may contain 0, 1 or 2 double or triple bonds between carbon atoms within the linker, with the provisos, that 2 of said heteroatom containing groups are separated by at least 2 carbon atoms, that heteroatom containing groups are not adjacent to a double or triple bond within the linker or to a non-aromatic double bond, which might be part of A, that double or triple bonds are not cumulated, and that, if A is connected to the linker via a nitrogen atom being part of A, the atom of the linker which is connected to A is a carbon atom;

and in which linker saturated carbon atoms, which are not adjacent to heteroatom containing groups, which are not adjacent to double or triple bonds within the linker or which are not adjacent to a heteroatom, which might be part of A, can, independently of one another, be substituted by hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms; cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

and in which linker saturated carbon atoms, which are adjacent to heteroatom containing groups, which are adjacent to double or triple bonds in the linker, or which are adjacent to a heteroatom, which might be part of A, or carbon atoms being part of a double bond, can, independently of one another, be substituted by hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is hydrogen, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

R44, R45 and R46 are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms;

y is 0, 1 or 2;

R1 is hydrogen;

and

R2 is alkyl having 1, 2, 3, 4, 5 or 6 carbon atoms, phenyl, heteroaryl having 5 or 6 atoms, cycloalkyl having 3, 4, 5, 6, 7 or 8 carbon atoms or heterocyclyl having 3, 4, 5, 6, 7 or 8 atoms;
  wherein alkyl is unsubstituted or substituted by 1, 2, 3, 4 or 5 radicals selected from the group consisting of F, Cl, Br, I, —$O_m$—$(CH_2)_n$—R26;
  m is 0 or 1;
  n is 0, 1, 2 or 3;
  R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from F, Cl, Br or I;
  and wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

and/or a pharmaceutically acceptable salt and/or a prodrug thereof alone or in combination with other medicaments or active ingredients for producing a medicament for the treatment or prophylaxis of chemokine mediated diseases.

Further embodiments of X, Y1, Y2, Y3, Y4, A, B, Z and R2 in a compound of formula II are those as defined in the various embodiments for X, Y1, Y2, Y3, Y4, A, B, Z and R2 of a compound of formula I, wherein R1 and R2 do not form a ring in formula I.

The invention further relates to the use of a compound of the formula II and/or a pharmaceutically acceptable salt and/or a prodrug thereof alone or in combination with other medicaments or active ingredients for producing a medicament for the treatment or prophylaxis of a chemokine mediated disease, wherein the chemokine binds to a CXC receptor, for example wherein the chemokine binds to a CXCR2 and/or CXCR1 receptor, in particular to a CXCR2 receptor.

Another aspect of the invention is the use of a compound of the formula II and/or a pharmaceutically acceptable salt and/ or a prodrug thereof alone or in combination with other medicaments or active ingredients for producing a medicament for the treatment or prophylaxis of arthritis, chronic obstructive pulmonary disease, adult or acute respiratory distress syndrome, asthma, atherosclerosis, myocardial and renal ischemia/reperfusion injury, peripheral limb ischemia/reperfusion injury, inflammatory bowel disease, ulcerative colitis, Crohn's disease, meconium apriration syndrome, atopic dermatitis, cystic fibrosis, psoriasis, psoriatic arthritis, multiple sclerosis, angiogenesis, restenosis, osteoarthritis, osteoporosis, septic shock, endotoxic shock, gram negative sepsis, toxic shock syndrome, stroke, glomerulonephritis, thrombosis, graft vs. host reaction, allograft rejections, transplant reperfusion injury, early transplantation rejection, acute inflammation, alzheimers disease, malaria, respiratory viruses, herpes viruses, hepatitis viruses, HIV, Kaposi's sarcoma-associated viruses, meningitis, gingivitis, herpes encephalitis, CNS vasculitis, traumatic brain injury, brain ischemia/reperfusion injury, migraine, CNS tumors, subarachnoid hemorrhage, post surgical trauma, interstitial pneumonitis, hypersensitivity, crystal induced arthritis, acute and chronic pancreatitis, hepatic ischemia/reperfusion injury, acute alcoholic hepatitis, necrotizing enterocolitis, chronic sinusitis, uveitis, polymyositis, vasculitis, acne, gastric and duodenal ulcers, intestinal ischemia/reperfusion injury, celiac disease, esophagitis, glossitis, rhinitis, airflow obstruction, airway hyperresponsiveness, bronchiolitis, bronchiolitis obliterans, bronchiolitis obliterans organizing pneumonia, bronchiectasis, chronic bronchitis, cor pulmonae, dyspnea, emphysema, hypercapnea, hyperinflation, hyperoxia-induced inflammations, hypoxemia, hypoxia, lung ischemia/reperfusion injury, surgerical lung volume reduction, pulmonary fibrosis, pulmonary hypertension, right ventricular hypertrophy, peritonitis associated with continuous ambulatory peritoneal dialysis, granulocytic ehrlichiosis, sarcoidosis, small airway disease, ventilation-perfusion mismatching, wheeze, colds, gout, alcoholic liver disease, lupus, burn therapy, periodontitis, pre-term labor, cough, pruritis, multi-organ dysfunction, trauma, sprains, contusions, undesired hematopoietic stem cell release, angiogenic ocular disease, ocular inflammation, retinopathy or prematurity, diabetic retinopathy, macular degeneration with the wet type preferred and corneal neovasularization, tumor angiogenesis, cancer and metastasis.

In particular, the invention further relates to the use of a compound of the formula II and/or a pharmaceutically acceptable salt and/or a prodrug thereof alone or in combination with other medicaments or active ingredients for producing a medicament for the treatment or prophylaxis of acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78 or GCP-2) mediated diseases which include adult respiratory distress syndrome, inflammatory bowel disease, ulcerative colitis, Crohn's disease, atopic dermatitis, cystic fibrosis, psoriasis, dermatitis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer. In particular, a compound of formula I is used alone.

Examples Nos. 21, 32, 41, 42, 125, 127, 130, 132, 133, 139, 142, 143, 144, 145, 147, 149, 150, 151, 152, 154, 155, 156, 160 and 164 vide infra represent compounds of the formula II in the context of the above described uses. All other example compounds exemplify compounds of the formula I.

As a further aspect of the present invention, certain compounds of formula I or formula II may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma).

Also claimed is a medicine or pharmaceutical composition for human or veterinary use, comprising an effective amount of a compound of the formula I and/or a pharmaceutically acceptable salt and/or a prodrug thereof, together with pharmaceutically acceptable carriers and additives, alone or in combination with other active pharmaceutical ingredients or medicaments.

Medicaments which comprise a compound of the formula I and/or a pharmaceutically acceptable salt and/or a prodrug thereof can in this connection be administered, for example, orally, parenterally, intravenously, rectally, transdermally or by inhalation, the preferred administration being dependent on the particular characteristics of the disorder. The compounds of the formula I may moreover be used alone or together with pharmaceutical excipients, both in veterinary medicine and in human medicine. The medicaments generally comprise active ingredients of the formula I and/or a pharmaceutically acceptable salt and/or a prodrug thereof in an amount of from 0.01 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I and/or a pharmaceutically acceptable salt and/or a prodrug thereof in a pharmaceutically acceptable solvent such as, in particular, ethanol or water, or a mixture of such solvents. The formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3% by weight.

The dosage of the active ingredient of the formula I to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of the formula I and/or a pharmaceutically acceptable salt and/or a prodrug thereof for a patient weighing about 75 kg is at least 0.001 mg/kg, preferably 0.01 mg/kg, to a maximum of 50 mg/kg, preferably 1 mg/kg, of body weight. For acute episodes of the disorder, for example immediately after suffering a myocardial infarction, higher and, in particular, more frequent dosages may also be necessary, e.g. up to 4 single doses a day. Up to 700 mg a day may be necessary, in particular on i.v. administration, for example for a patient with infarction in the intensive care unit, and the compounds of the invention can be administered by infusion.

DESCRIPTION OF THE EXPERIMENTS AND EXAMPLES

Example 1

2-({4-Bromo-1-[2-(4-fluoro-phenoxy)-ethoxy]-naphthalene-2-carbonyl}-amino)-2-methyl-propionic acid

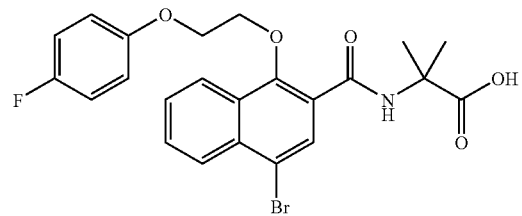 [SMILES: CC(C)(NC(=O)c1cc(Br)c2ccccc2c1OCCOc1ccc(F)cc1)C(=O)O]

a) 2-[(4-Bromo-1-hydroxy-naphthalene-2-carbonyl)-amino]-2-methyl-propionic acid methyl ester To a solution of 1.5 g 4-bromo-1-hydroxy-2-naphthoic acid in 20 ml abs. DMF under inert atmosphere 0.84 g 1-hydroxybenzotriazole, 1.18 g 1-ethyl-3-(3-dimethylaminopropyl)carbodiimide hydrochloride and 1.1 ml of N,N-diisopropylethylamine were added. After 15 minutes 0.86 g of 2-amino-2-methyl-propionic acid methyl ester hydrochloride, followed by 1.1 ml of N,N-diisopropylethylamine were added. After 24 h at room temperature and 2 h at 50° C. the reaction mixture was concentrated, the residue was taken up in ethyl acetate and washed with 2 M HCl, aqueous sodium carbonate solution (10%) and brine. The organic layer was dried over magnesium sulphate, and concentrated to yield 1.44 g of 2-[(4-bromo-1-hydroxy-naphthalene-2-carbonyl)-amino]-2-methyl-propionic acid methyl ester.

$C_{16}H_{16}BrNO_4$ (366.21), LCMS (ESI): 366.00, 368.00 (MH$^+$, Br-pattern).

b) 2-({4-Bromo-1-[2-(4-fluoro-phenoxy)-ethoxy]-naphthalene-2-carbonyl}-amino)-2-methyl-propionic acid methyl ester To 90 mg cesium carbonate and 92 mg 2-[(4-bromo-1-hydroxy-naphthalene-2-carbonyl)-amino]-2-methyl-propionic acid methyl ester in 1 ml abs. DMF 60 mg 4-fluorophenoxyethylbromide was added. After 16 h at room temperature the reaction was poured unto ice-water and extracted with ethyl acetate twice. The combined organic layers were washed with brine, dried over magnesium sulphate and concentrated in vacuo. After purification by RP-HPLC 61 mg of 2-({4-Bromo-1-[2-(4-fluoro-phenoxy)-ethoxy]-naphthalene-2-carbonyl}-amino)-2-methyl-propionic acid methyl ester were obtained.

$C_{24}H_{23}BrFNO_5$ (504.36), LCMS (ESI): 504.05, 506.05 (MH$^+$, bromo-pattern).

c) 2-({4-Bromo-1-[2-(4-fluoro-phenoxy)-ethoxy]-naphthalene-2-carbonyl}-amino)-2-methyl-propionic acid 61 mg 2-({4-bromo-1-[2-(4-fluoro-phenoxy)-ethoxy]-naphthalene-2-carbonyl}-amino)-2-methyl-propionic acid methyl ester in 0.5 ml THF, 0.36 ml of 2 M sodium hydroxide and 1.7 ml methanol were reacted in a microwave at 120° C. for 6 min. The reaction was then acidified with 2 M hydrochloric acid and extracted with ethyl acetate twice. The combined organic layers were dried over magnesium sulphate, and concentrated. After purification of the residue by RP-HPLC 27 mg of 2-({4-bromo-1-[2-(4-fluoro-phenoxy)-ethoxy]-naphthalene-2-carbonyl}-amino)-2-methyl-propionic acid were obtained.

$C_{23}H_{21}BrFNO_5$ (490.33), LCMS (ESI): 490.05, 492.05 (MH$^+$, bromo-pattern).

Example 2

2-Methyl-2-{[1-(3-phenyl-butoxy)-naphthalene-2-carbonyl]-amino}-propionic acid

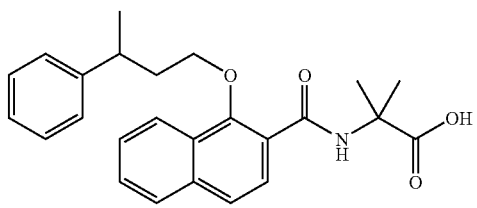 [SMILES: CC(CCOc1c(C(=O)NC(C)(C)C(=O)O)ccc2ccccc12)c1ccccc1]

a) 2-[(1-Hydroxy-naphthalene-2-carbonyl)-amino]-2-methyl-propionic acid methyl ester To a solution of 4.70 g 1-hydroxy-2-naphthalene carboxylic acid in 40 ml abs. DMF under inert atmosphere 3.72 g 1-hydroxybenzotriazole, 8.89 g N,N'-diisopropyl carbodiimide and 7 ml of N,N-diisopropylethylamine were added at 0° C. After 30 minutes at 0° C. 4.22 g of methyl 2-aminoisobutyrate hydrochloride, followed by 5 ml of N,N-diisopropylethylamine were added. After 16 h at room temperature the reaction mixture was concentrated, the residue was taken up in ethyl acetate and washed with 2 M HCl and brine. The organic layer was dried over magnesium sulphate, concentrated and the resulting residue was crystallized from toluene to yield 4.18 g of 2-[(1-hydroxy-naphthalene-2-carbonyl)-amino]-2-methyl-propionic acid methyl ester.

$C_{16}H_{17}NO_4$ (287.12), LCMS (ESI): 287.97 (MH$^+$).

b) 2-Methyl-2-{[1-(3-phenyl-butoxy)-naphthalene-2-carbonyl]-amino}-propionic acid methyl ester At 0° C. to a solution of 80 mg of 2-[(1-hydroxy-naphthalene-2-carbonyl)-amino]-2-methyl-propionic acid methyl ester, 42 mg 3-phenyl-1-butanol and 73 mg triphenyl phosphine in 3 ml of dry THF 56 mg of diisopropylazodicarboxylate were added. After 2 h and again after 4 h at room temperature 36 mg of triphenylphosphine and 25 mg of diisopropylazodicarboxylate were added. After additional 12 h the reaction was concentrated in vacuo and after chromatography on silica (ethyl acetate/heptane) 110 mg of 2-methyl-2-{[1-(3-phenyl-butoxy)-naphthalene-2-carbonyl]-amino}-propionic acid methyl ester were obtained.

$C_{26}H_{29}NO_4$ (419.53), LCMS (ESI): 420.25 (MH$^+$).

c) 2-Methyl-2-{[1-(3-phenyl-butoxy)-naphthalene-2-carbonyl]-amino}-propionic acid A solution of 105 mg 2-methyl-2-{[1-(3-phenyl-butoxy)-naphthalene-2-carbonyl]-amino}-propionic acid methyl ester in 2.5 ml THF was treated with 0.2 ml of 2 M aqueous sodium hydroxide. After 3 h at 60° C. another 0.1 ml of 2 M NaOH was added, and after 6 h at 65° C. the reaction was concentrated, the residue was taken up in 3 ml of water, treated with 2 M hydrochloric acid and extracted with ethyl acetate twice. The combined organic layers were dried over magnesium sulphate and evaporated. After purification by RP-HPLC 15 mg 2-methyl-2-{[1-(3-phenyl-butoxy)-naphthalene-2-carbonyl]-amino}-propionic acid were obtained.

$C_{25}H_{27}NO_4$ (405.50), LCMS (ESI-): 406.19 (M-H$^+$).

Example 3

2-Methyl-2-{[1-(2-phenoxy-ethoxy)-naphthalene-2-carbonyl]-amino}-butyric acid

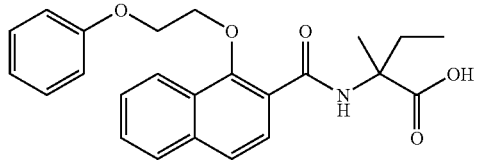 [SMILES: CCC(C)(NC(=O)c1ccc2ccccc2c1OCCOc1ccccc1)C(=O)O]

a) 1-(2-Phenoxy-ethoxy)-naphthalene-2-carboxylic acid methyl ester

To 22.81 g cesium carbonate and 7.08 g methyl 1-hydroxy-2-naphthoate in 70 ml abs. DMF was added 7.39 g (2-bromo-ethoxy)-benzene and the mixture was reacted for 16 h at 80° C. The reaction was poured unto ice, neutralized with 2 M hydrochloric acid, and extracted with ethyl acetate twice. The combined organic phases were washed with brine, dried over magnesium sulphate and concentrated in vacuo. The resulting residue was purified by crystallization from pentane to yield 9.60 g of 1-(2-phenoxy-ethoxy)-naphthalene-2-carboxylic acid methyl ester.

$C_{20}H_{18}O_4$ (322.36), LCMS (ESI): 323.10 (MH$^+$).

b) 1-(2-Phenoxy-ethoxy)-naphthalene-2-carboxylic acid

To 9.60 g of 1-(2-phenoxy-ethoxy)-naphthalene-2-carboxylic acid methyl ester in 105 ml of THF were added 30 ml of 2 M aqueous sodium hydroxide and 40 ml of methanol. After 3 h at reflux the organic solvents were removed in vacuo. The residue was treated with 2 M hydrochloric acid, and three times extracted with ethyl acetate. The combined organic layers were dried over magnesium sulphate, and concentrated and dried in vacuo to yield 7.62 g of 1-(2-phenoxy-ethoxy)-naphthalene-2-carboxylic acid.

$C_{19}H_{16}O_4$ (308.34), LCMS (ESI): 309.10 (MH$^+$—H$_2$O).

c) 2-Methyl-2-{[1-(2-phenoxy-ethoxy)-naphthalene-2-carbonyl]-amino}-butyric acid methyl ester To a solution of 487 mg 1-(2-phenoxy-ethoxy)-naphthalene-2-carboxylic acid in 6 ml abs. DMF under inert atmosphere 216 mg 1-hydroxybenzotriazole, 306 mg 1-ethyl-3-(3-dimethylaminopropyl)carbodiimide hydrochloride and 293 μl of N,N-diisopropylethylamine were added at 0° C. After 30 minutes at 0° C. 252 mg of 2-amino-2-methyl-butyric acid methyl ester hydrochloride, followed by 293 μl of N,N-diisopropylethylamine were added. After 16 h at room temperature the reaction mixture was concentrated, the residue was taken up in ethyl acetate and washed with 2 M HCl, aqueous sodium carbonate solution (10%) and brine. The organic layer was dried over magnesium sulphate and concentrated. The resulting residue was purified by chromatography on silica (ethyl acetate/heptane) to yield 419 mg of 2-methyl-2-{[1-(2-phenoxy-ethoxy)-naphthalene-2-carbonyl]-amino}-butyric acid methyl ester.

$C_{25}H_{27}NO_5$ (421.50), LCMS (ESI): 422.10 (MH$^+$).

d) 2-Methyl-2-{[1-(2-phenoxy-ethoxy)-naphthalene-2-carbonyl]-amino}-butyric acid 419 mg 2-methyl-2-{[1-(2-phenoxy-ethoxy)-naphthalene-2-carbonyl]-amino}-butyric acid methyl ester in 25 ml THF, 1.5 ml of 2 M sodium hydroxide and 8 ml methanol were heated under reflux for 3 h. The organic solvents were then removed in vacuo, and the residue was acidified with 2 M hydrochloric acid and extracted with ethyl acetate twice. The combined organic layers were dried over magnesium sulphate, and concentrated. After recrystallization from toluene 240 mg of 2-methyl-2-{[1-(2-phenoxy-ethoxy)-naphthalene-2-carbonyl]-amino}-butyric acid were obtained.

$C_{24}H_{25}NO_5$ (407.47), LCMS (ESI): 408.10 (MH$^+$).

Example 4

2-Methyl-2-{[1-(1-methyl-2-phenoxy-ethoxy)-naphthalene-2-carbonyl]-amino}-propionic acid

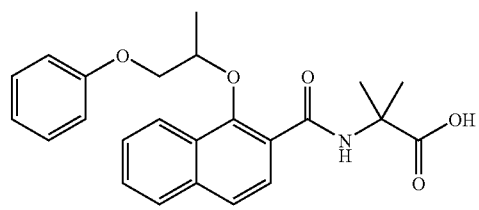 [SMILES: CC(COc1ccccc1)Oc1c(C(=O)NC(C)(C)C(=O)O)ccc2ccccc12]

a) 1-(1-Methyl-2-phenoxy-ethoxy)-naphthalene-2-carboxylic acid methyl ester

To a solution of 1.00 g 1-hydroxy-naphthalene-2-carboxylic acid methyl ester, 0.75 g 1-phenoxy-propan-2-ol and 3.89 g triphenyl phosphine in 60 ml dry THF at 0° C. 3.00 g diisopropylazodicarboxylate were added. After 48 h at room temperature the reaction was concentrated in vacuo, the residue was taken up in ethyl acetate, washed with sat. sodium hydrogen carbonate solution and dryed over magnesium sulphate. The solvent was removed in vacuo and after chromatography on silica (ethyl acetate/heptane) 0.47 g 1-(1-methyl-2-phenoxy-ethoxy)-naphthalene-2-carboxylic acid methyl ester were obtained.

$C_{21}H_{20}O_4$ (336.39), LCMS (ESI): 337.10 (MH$^+$).

b) 1-(1-Methyl-2-phenoxy-ethoxy)-naphthalene-2-carboxylic acid

To 0.47 g of 1-(1-methyl-2-phenoxy-ethoxy)-naphthalene-2-carboxylic acid methyl ester in 5 ml of THF and 2 ml methanol were added 10 ml of 2 M aqueous sodium hydroxide. After 16 h at room temperature and 2 h at reflux the organic solvents were removed in vacuo. The residue was treated with 2 M hydrochloric acid, and three times extracted with ethyl acetate. The combined organic layers were washed with brine, dried over magnesium sulphate, concentrated and dried in vacuo to yield 0.36 g of 1-(1-methyl-2-phenoxy-ethoxy)-naphthalene-2-carboxylic acid.

$C_{20}H_{18}O_4$ (322.36), LCMS (ESI$^-$): 321.10 (M-H$^+$).

c) 2-Methyl-2-{[1-(1-methyl-2-phenoxy-ethoxy)-naphthalene-2-carbonyl]-amino}-propionic acid methyl ester To a solution of 100 mg—(1-methyl-2-phenoxy-ethoxy)-naphthalene-2-carboxylic acid in 1.5 ml abs. DMF under inert atmosphere 45 mg 1-hydroxybenzotriazole, 83 mg 1-ethyl-3-(3-dimethylaminopropyl)carbodiimide hydrochloride and 70 μl of N,N-diisopropylethylamine were added at 0° C. After 30 minutes at 0° C. 36 mg of 2-aminoisobutyric acid methyl ester hydrochloride, followed by 70 μl of N,N-diisopropylethylamine were added. After 16 h at room temperature the reaction mixture was concentrated, the residue was taken up in ethyl acetate and washed with 2 M HCl, aqueous sodium carbonate solution (10%) and brine. The organic layer was dried over magnesium sulphate, and concentrated to yield 114 mg of 2-methyl-2-{[1-(1-methyl-2-phenoxy-ethoxy)-naphthalene-2-carbonyl]-amino}-propionic acid methyl ester.

$C_{25}H_{27}NO_5$ (421.50), LCMS (ESI): 422.05 (MH$^+$).

d) 2-Methyl-2-{[1-(1-methyl-2-phenoxy-ethoxy)-naphthalene-2-carbonyl]-amino}-propionic acid 110 mg 2-methyl-2-{[1-(1-methyl-2-phenoxy-ethoxy)-naphthalene-2-carbonyl]-amino}-propionic acid methyl ester in 1 ml THF, 0.3 ml of 2 M sodium hydroxide and 0.3 ml methanol were heated under reflux for 2 h. The organic solvents were then removed in vacuo, and the residue was acidified with 2 M hydrochloric acid and extracted with ethyl acetate twice. The combined organic layers were dried over magnesium sulphate and concentrated. After purification by RP-HPLC 10 mg of 2-methyl-2-{[1-(1-methyl-2-phenoxy-ethoxy)-naphthalene-2-carbonyl]-amino}-propionic acid were obtained.

$C_{24}H_{25}NO_5$ (407.47), LCMS (ESI): 408.15 (MH$^+$).

Example 5

2-({1-[2-(3,5-Difluoro-phenoxy)-ethoxy]-naphthalene-2-carbonyl}-amino)-2-methyl-propionic acid

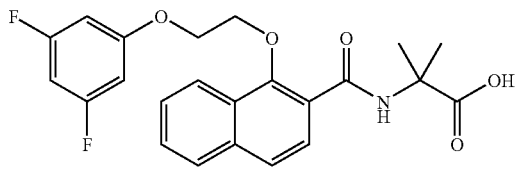 [SMILES: CC(C)(NC(=O)c1ccc2ccccc2c1OCCOc1cc(F)cc(F)c1)C(=O)O]

a) 1-[2-(tert-Butyl-dimethyl-silanyloxy)-ethoxy]-naphthalene-2-carboxylic acid methyl ester To 5.2 g cesium carbonate and 1.6 g methyl 1-hydroxy-2-naphthoate in 10 ml abs. DMF was added 1.9 g (2-bromethoxy)-tert.butyldimethylsilane and the mixture was reacted for 4 h at 60-80° C. The reaction was poured unto ice and extracted with ethyl acetate twice. The combined organic layers were washed with aqueous sat. sodium hydrogen carbonate solution and brine, dried over magnesium sulphate and concentrated in vacuo to yield 2.7 g of 1-[2-(tert-butyl-dimethyl-silanyloxy)-ethoxy]-naphthalene-2-carboxylic acid methyl ester.

$C_{20}H_{28}O_4Si$ (360.53), NMR (400 MHz, CDCl$_3$): δ [ppm]= 8.4 (d, 1H), 7.7 (m, 2H), 7.5-7.3 (m, 3H), 4.1 (m, 2H), 3.9 (m, 2H), 3.8 (s, 3H), 0.8 (s, 9H), 0.0 (s, 6H).

b) 1-[2-(tert-Butyl-dimethyl-silanyloxy)-ethoxy]-naphthalene-2-carboxylic acid 2.53 g 1-[2-(tert-butyl-dimethyl-silanyloxy)-ethoxy]-naphthalene-2-carboxylic acid methyl ester were dissolved in 25 ml abs. DMF and after addition of 1.35 g of potassium trimethylsilanoate the reaction was stirred for 16 h at room temperature. The precipitated potassium salt of the product was isolated by filtration, washed with diethyl ether, dissolved in water, acidified with 2 M hydrochloric acid, extracted with ethyl acetate, dried over sodium sulphate and concentrated in vacuo to yield 2.00 g of 1-[2-(tert-butyl-dimethyl-silanyloxy)-ethoxy]-naphthalene-2-carboxylic acid.

$C_{19}H_{26}O_4Si$ (346.50), NMR (400 MHz, CDCl$_3$): δ [ppm]= 13.0 (s, 1H), 8.4 (d, 1H), 7.9 (d, 1H), 7.65 (m, 2H), 7.55 (t, 1H), 7.45 (t, 1H), 4.1 (m, 2H), 3.9 (m, 2H), 0.8 (s, 9H), 0.0 (s, 6H).

c) 2-({1-[2-(tert-Butyl-dimethyl-silanyloxy)-ethoxy]-naphthalene-2-carbonyl}-amino)-2-methyl-propionic acid methyl ester To a solution of 1.49 g 1-[2-(tert-butyl-dimethyl-silanyloxy)-ethoxy]-naphthalene-2-carboxylic acid in 15 ml abs. DMF under inert atmosphere 0.64 g 1-hydroxybenzo-triazole and 0.91 g 1-ethyl-3-(3-dimethylaminopropyl)carbodiimide hydrochloride were added. After addition of 0.73 g aminoiosbutyric acid methyl ester hydrochloride and 1.9 ml of N,N-diisopropylethylamine the reaction was stirred for 16 h at room temperature. Then, the reaction mixture was concentrated, the residue was taken up in ethyl acetate and washed with 2 M HCl and aqueous sat. sodium hydrogen carbonate solution. The organic layer was dried over sodium sulphate, concentrated and recrystallized from n-heptane to yield 0.90 g of 2-({1-[2-(tert-butyl-dimethyl-silanyloxy)-ethoxy]-naphthalene-2-carbonyl}-amino)-2-methyl-propionic acid methyl ester.

$C_{24}H_{35}NO_5Si$ (445.64), NMR (400 MHz, CDCl$_3$): δ [ppm]=8.3 (m, 2H), 7.85 (d, 1H), 7.65 (m, 1H), 7.5 (d, 1H), 7.35 (m, 2H), 4.05 (m, 2H), 3.95 (m, 2H), 3.6 (s, 3H), 1.6 (s, 6H), 0.85 (s, 9H), 0.0 (s, 6H).

d) 2-{[1-(2-Hydroxy-ethoxy)-naphthalene-2-carbonyl]-amino}-2-methyl-propionic acid methyl ester To 112 mg 2-({1-[2-(tert-butyl-dimethyl-silanyloxy)-ethoxy]-naphthalene-2-carbonyl}-amino)-2-methyl-propionic acid methyl ester in 1 ml abs. THF at −10° C. 0.25 ml tetra-butylammonium fluoride (1 M in THF) was added, and the reaction was stirred at 0° C. for 3 h. It was then poured onto ice-water and extracted with ethyl acetate three times. The combined organic layers were then washed with water, dried over sodium sulphate, concentrated in vacuo and crystallized from n-pentane to yield 67 mg 2-{[1-(2-hydroxy-ethoxy)-naphthalene-2-carbonyl]-amino}-2-methyl-propionic acid methyl ester.

$C_{18}H_{21}NO_5$ (331.37), LCMS (ESI): 332.13 (MH$^+$).

e) 2-({1-[2-(3,5-Difluoro-phenoxy)-ethoxy]-naphthalene-2-carbonyl}-amino)-2-methyl-propionic acid methyl ester To a solution of 67 mg 2-{[1-(2-hydroxy-ethoxy)-naphthalene-2-carbonyl]-amino}-2-methyl-propionic acid methyl ester and 29 mg 3,5-difluorophenol in 1 ml THF at 0° C. 58 mg triphenyl phosphine and 46 µl diisopropylazodicarboxylate were added. After 16 h at room temperature the reaction was concentrated in vacuo and after chromatography on silica (ethyl acetate/heptane) 80 mg 2-({1-[2-(3,5-difluoro-phenoxy)-ethoxy]-naphthalene-2-carbonyl}-amino)-2-methyl-propionic acid methyl ester were obtained.

$C_{24}H_{23}F_2NO_5$ (443.45), LCMS (ESI): 444.16 (MH$^+$).

f) 2-({1-[2-(3,5-Difluoro-phenoxy)-ethoxy]-naphthalene-2-carbonyl}-amino)-2-methyl-propionic acid 22 mg 2-({1-[2-(3,5-difluoro-phenoxy)-ethoxy]-naphthalene-2-carbonyl}-amino)-2-methyl-propionic acid methyl ester were reacted with 0.2 ml of 2 M sodium hydroxide in 1 ml methanol at 65° C. for 1 h. The organic solvents were then removed in vacuo, and the residue was acidified with 2 M hydrochloric acid and extracted with ethyl acetate twice. The combined organic layers were dried over sodium sulphate, and concentrated. After recrystallization from n-heptane 3 mg of 2-({1-[2-(3,5-difluoro-phenoxy)-ethoxy]-naphthalene-2-carbonyl}-amino)-2-methyl-propionic acid were obtained.

$C_{23}H_{21}F_2NO_5$ (429.42), LCMS (ESI): 430.11 (MH$^+$).

Example 6

2-({1-[2-(Indan-5-yloxy)-ethoxy]-naphthalene-2-carbonyl}-amino)-2-methyl-propionic acid

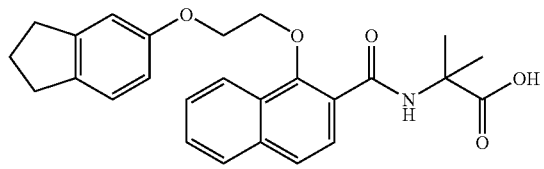 [SMILES: CC(C)(NC(=O)c1ccc2ccccc2c1OCCOc1ccc2c(c1)CCC2)C(=O)O]

Under inert atmosphere to 166 mg 2-{[1-(2-hydroxy-ethoxy)-naphthalene-2-carbonyl]-amino}-2-methyl-propionic acid methyl ester, 74 mg indan-5-ol and 208 mg polystyrene-bound triphenyl phosphine (3 mmol/g) in 5 ml THF at 0° C. 98 µl diethylazodicarboxylate were added. After 16 h at room temperature the reaction was filtered, the filtrate concentrated in vacuo and after RP-HPLC the obtained 2-({1-[2-(Indan-5-yloxy)-ethoxy]-naphthalene-2-carbonyl}-amino)-2-methyl-propionic acid methyl ester was dissolved in 3 ml of dioxane and reacted with 3 ml 1N NaOH for 5 h at 50° C. The reaction was then diluted with ethyl acetate and treated with citric acid (5%). The organic layer was separated, dried and concentrated in vacuo. After purification by RP-HPLC 22 mg 2-{[1-(2-hydroxy-ethoxy)-naphthalene-2-carbonyl]-amino}-2-methyl-propionic acid were obtained.

$C_{26}H_{27}NO_5$ (433.51), LCMS (ESI): 434.09 (MH$^+$).

Example 7

1-({1-[2-(4-Chloro-phenoxy)-ethoxy]-naphthalene-2-carbonyl}-amino)-cyclobutanecarboxylic acid

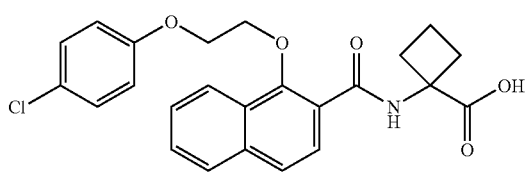 [SMILES: O=C(NC1(C(=O)O)CCC1)c1ccc2ccccc2c1OCCOc1ccc(Cl)cc1]

To 94 mg 1-[(1-hydroxy-naphthalene-2-carbonyl)-amino]-cyclobutanecarboxylic acid ethyl ester, 195 mg cesium carbonate and 5 mg sodium iodide in 3 ml of abs. DMF 78 mg of 4-Chlorphenyl 2-bromoethyl ether were added. The reaction mixture was stirred for 2 h at room temperature, then for 5 h at 80° C. The cooled reaction mixture was filtrated, and the filtrate was diluted with 20 ml ethyl acetate and washed twice with brine. The organic phase was concentrated in vacuo, and the resulting residue was dissolved in 2 ml methanol and 1 ml THF. After addition of 0.75 ml 2M NaOH (aq) the mixture was stirred for 1 h at 45° C. and then overnight at room temperature. The solution was neutralized with 0.75 ml 2 M hydrochloride acid, evaporated, and the resulting residue was purified by RP-HPLC to yield 42 mg 1-({1-[2-(4-chloro-phenoxy)-ethoxy]-naphthalene-2-carbonyl}-amino)-cyclobutanecarboxylic acid.

$C_{24}H_{22}ClNO_5$ (439.90), LCMS (ESI): 440.14 (MH$^+$).

Example 8

2-Methyl-2-{[1-(3-phenyl-propoxy)-naphthalene-2-carbonyl]-amino}-propionic acid

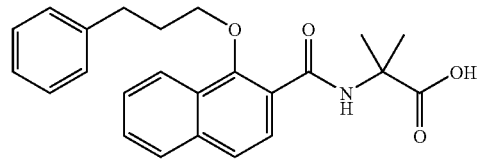 [SMILES: CC(C)(NC(=O)c1ccc2ccccc2c1OCCCc1ccccc1)C(=O)O]

To 1 g Wang polystyrene resin (1.7 mmol/g) swelled in dichloromethane a solution of 1.38 g 2-(9H-fluoren-9-yl-methoxycarbonylamino)-2-methyl-propionic acid, 0.65 g 1-hydroxybenzotriazole hydrate and 0.54 g N,N'-diisopropylcarbodiimide in 6 ml of DMF were added. After addition of 20 mg of 4-dimethylaminopyridine the reaction mixture was shaken for 4 h at room temperature. Then the resin was washed with dichloromethane five times. To cap unreacted hydroxyl groups on the Wang resin a solution of 350 mg of acetic anhydride and 270 mg of pyridine in 6 ml DMF was added and the reaction mixture was stirred for 30 min at room temperature before the resin was washed with DMF six times. The resin was then suspended in 5 ml DMF and 5 ml piperidine and reacted for 30 min at room temperature to remove the 9-fluorenylmethoxycarbonyl protecting group. Then a solution of 0.96 g of 1-hydroxy-naphthalene-2-carboxylic acid, 0.78 g of 1-hydroxybenzotriazole hydrate, 0.64 g of N,N'-diisopropylcarbodiimide in 6 ml DMF and 3 ml dichloromethane was added to the resin, and the reaction was shaken for 5 h at room temperature. Then the resin was washed five times each with DMF, dichloromethane and THF. A solution of 2.31 g 3-phenyl-propan-1-ol and 4.46 g of triphenyl phosphine in 34 ml of dry THF was added to the resin. The suspension was cooled to 4° C. A solution of 2.15 g of diisopropylazodicarboxylate in 2 ml of dry THF was then added and the reaction mixture cooled to −20° C. for 15 min. After shaking the mixture 5 h at room temperature, the resin was washed five time each with THF and dichloromethane. The resin suspended in dichloromethane was then sonicated, washed three times each with DMF and dichloromethane and dried. It was then suspended in 3 ml of trifluoroacetic acid and 3 ml dichlormethane and shaken for 2 h at room temperature. The resin was then filtered off, the filtrate was concentrated in vacuo and purified by RP-HPLC to obtain 30 mg of 2-methyl-2-{[1-(3-phenyl-propoxy)-naphthalene-2-carbonyl]-amino}-propionic acid.

$C_{24}H_{25}NO_4$ (391.47), LCMS (ESI): 392.14 (MH$^+$).

Example 9

2-Methyl-2-[1-(2-phenoxy-ethoxy)-naphthalene-2-sulfonylamino]-propionic acid

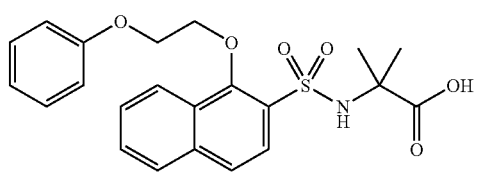 [SMILES: CC(C)(NS(=O)(=O)c1ccc2ccccc2c1OCCOc1ccccc1)C(=O)O]

a) 2-(1-Hydroxy-naphthalene-2-sulfonylamino)-2-methyl-propionic acid methyl ester To a suspension of 2.62 g potassium 1-naphthol-2-sulfonate in 10 ml of dry chloroform was added 2.60 g of phosphorous pentachloride in several portions. With exclusion of moisture the reaction was refluxed for 1.5 h. Then the mixture was filtrated, the filtrate was concentrated and the residue crystallized from benzene to obtain 0.48 g of 1-Hydroxy-naphthalene-2-sulfonyl chloride, which was used without further purification. A suspension of 77 mg 2-Amino-2-methyl-propionic acid methyl ester hydrochloride in 3 ml of dry THF was treated with 90 µl of N,N-diisopropylamine. After 5 min a solution of 120 mg of 1-Hydroxy-naphthalene-2-sulfonyl chloride in 0.5 ml benzene and 0.5 ml dry THF was added and the reaction was stirred under inert atmosphere overnight.

Then the solvents were removed in vacuo and the residue was treated with water and ethyl acetate. The organic phase was dried over magnesium sulphate and concentrated. After chromatography on silica (dichloromethane/methanol) 44 mg of 2-(1-hydroxy-naphthalene-2-sulfonylamino)-2-methyl-propionic acid methyl ester were obtained.

$C_{15}H_{17}NO_5S$ (323.37), LCMS (ESI): 324.25 (MH$^+$).

b) 2-Methyl-2-[1-(2-phenoxy-ethoxy)-naphthalene-2-sulfonylamino]-propionic acid To a suspension of 44 mg of 2-(1-hydroxy-naphthalene-2-sulfonylamino)-2-methyl-propionic acid methyl ester and 40 mg cesium carbonate in 1 ml DMF 25 mg (2-bromo-ethoxy)-benzene were added. After 3 h at 80° C. the solvent was removed, and the residue was taken up in ethyl acetate and water and the pH of the aqueous phase was adjusted to 7. The organic phase was separated and concentrated to yield 25 mg of a mixture of a mono- and dialkylated product. This was dissolved in 1 ml methanol, and 0.2 ml of 2 M NaOH and 0.2 ml of THF were added. After 16 h at room temperature the organic solvents were removed in vacuo, the residue was acidified with 2 M HCl and extracted with ethyl acetate twice. The combined organic layers were concentrated, and the crude product was purified by RP-HPLC to yield 11 mg of 2-methyl-2-[1-(2-phenoxy-ethoxy)-naphthalene-2-sulfonylamino]-propionic acid.

$C_{22}H_{23}NO_6S$ (429.50), LCMS (ESI): 430.08 (MH$^+$).

Example 10

2-Methyl-2-{[1-(3-phenyl-propylamino)-naphthalene-2-carbonyl]-amino}-propionic acid

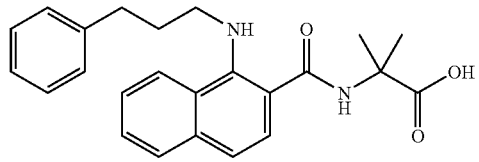 [SMILES: CC(C)(NC(=O)c1ccc2ccccc2c1NCCCc1ccccc1)C(=O)O]

a) 1-Bromo-naphthalene-2-carboxylic acid methyl ester

To 2.00 g 1-bromo-naphthalene-2-carboxylic acid in 20 ml of dry methanol 5 ml of sulfuric acid were added. After 5 h at reflux, the reaction was poured onto ice-water, and the precipitated product was collected by filtration and washed until neutral. After recrystallization from heptane 1.90 g 1-bromo-naphthalene-2-carboxylic acid methyl ester were obtained.

$C_{12}H_9BrO_2$ (265.11), NMR (400 MHz, CDCl$_3$): δ [ppm]= 8.45 (d, 1H), 7.85 (m, 2H), 7.7-7.55 (m, 3H), 4.0 (s, 3H).

b) 1-(3-Phenyl-propylamino)-naphthalene-2-carboxylic acid methyl ester 3 mg copper(I)iodide, 127 mg potassium phosphate and 80 mg 1-bromo-naphthalene-2-carboxylic acid methyl ester were placed in a reaction vial, which was evaporated and backfilled with argon three times. A solution of 61 mg 3-phenylpropylamine and 12 mg N,N-diethylsalicylaminde in 0.5 ml of dry DMF was then added via septum. Under inert conditions the reaction mixture was heated to 10° C. for 20 h. It was then diluted with ethyl acetate and water, the pH was adjusted to neutral, the layers were separated and the aqueous layer was extracted with ethyl acetate twice. The combined organic layers were dried over magnesium sulphate and evaporated. After purification by chromatography on silica (ethyl acetate/heptane) 48 mg 1-(3-phenyl-propylamino)-naphthalene-2-carboxylic acid methyl ester were obtained.

$C_{21}H_{21}NO_2$ (319.41), LCMS (ESI): 320.23 (MH$^+$).

c) 1-(3-Phenyl-propylamino)-naphthalene-2-carboxylic acid 48 mg 1-(3-phenyl-propylamino)-naphthalene-2-carboxylic acid methyl ester were reacted with 0.14 ml of 2 M sodium hydroxide in 1 ml methanol and 1 ml of THF at 65° C. for 2 h. The organic solvents were then removed in vacuo, and the residue was taken up in water and ethyl acetate. The pH was brought to 3-4 with 2 M hydrochloric acid. The layers were separated and the aqueous layer was extracted with ethyl acetate twice. The combined organic layers were dried over sodium sulphate, and concentrated. After purification by chromatography on silica (ethyl acetate/heptane) 18 mg of 1-(3-phenyl-propylamino)-naphthalene-2-carboxylic acid were obtained.

$C_{20}H_{19}NO_2$ (305.38), LCMS (ESI): 306.25 (MH$^+$).

d) 2-Methyl-2-{[1-(3-phenyl-propylamino)-naphthalene-2-carbonyl]-amino}-propionic acid methyl ester Under argon atmosphere 16 mg 1-(3-phenyl-propylamino)-naphthalene-2-carboxylic acid, 10 mg 1-hydroxybenzotriazole, 12 mg 1-ethyl-3-(3-dimethylaminopropyl) carbodiimide hydrochloride and 18 μl of N,N-diisopropylethylamine in 1 ml of dry DMF were stirred at 0° C. After 30 minutes at 0° C. 8 mg of 2-aminoisobutyric acid methyl ester hydrochloride, followed by 18 μl of N,N-diisopropylethylamine were added. After 16 h at room temperature the reaction mixture was concentrated, and the residue was purified by RP-HPLC to yield 7 mg of 2-methyl-2-{[1-(3-phenyl-propylamino)-naphthalene-2-carbonyl]-amino}-propionic acid methyl ester.
$C_{25}H_{28}N_2O_3$ (404.51), LCMS (ESI): 405.20 (MH$^+$).

e) 2-Methyl-2-{[1-(3-phenyl-propylamino)-naphthalene-2-carbonyl]-amino}-propionic acid 6 mg 2-methyl-2-{[1-(3-phenyl-propylamino)-naphthalene-2-carbonyl]-amino}-propionic acid methyl ester in 0.2 ml THF, 40 μl of 2 M sodium hydroxide and 0.2 ml methanol were reacted at room temperature for 3 h. To the mixture 0.5 ml of water were added and the pH was adjusted to 3-4 with 2 M hydrochloride acid. The volatiles were then removed by freeze drying, the resultic residue was suspended in methanol and filtrated. Concentration of the filtrate yielded 3 mg of 2-methyl-2-{[1-(3-phenyl-propylamino)-naphthalene-2-carbonyl]-amino}-propionic acid.
$C_{24}H_{26}N_2O_3$ (390.49), LCMS (ESI): 391.20 (MH$^+$).

Example 11

2-Methyl-2-{[1-(2-phenoxy-ethylamino)-naphthalene-2-carbonyl]-amino}-propionic acid

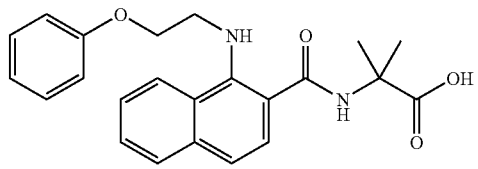 [SMILES: CC(C)(NC(=O)c1ccc2ccccc2c1NCCOc1ccccc1)C(=O)O]

a) 2-[(1-Bromo-naphthalene-2-carbonyl)-amino]-2-methyl-propionic acid methyl ester 1.0 g 1-bromo-naphthalene-2-carboxylic acid and 0.61 g 2,2-dimethylglycine methyl ester hydrochloride were suspended in 30 ml of dichloromethane and 10 ml of DMF. 1.31 ml N-methylmorpholine, 0.70 g 1-hydroxybenzotriazole and, finally, 0.99 g 1-(3-dimethylaminopropyl)-3-ethylcarbodiimide hydrochloride were added and the reaction stirred at room temperature for 14 h. The reaction mixture was chromatographed on silica (ethyl acetate/heptane) without aqueous work-up to give 1.3 g 2-[(1-bromo-naphthalene-2-carbonyl)-amino]-2-methyl-propionic acid methyl ester.
$C_{16}H_{16}BrNO_3$ (350.21), LCMS (ESI): 350.07, 352.07 (MH$^+$, bromo-pattern).

b) 2-Methyl-2-{[1-(2-phenoxy-ethylamino)-naphthalene-2-carbonyl]-amino}-propionic acid 3 mg copper(I)iodide, 127 mg potassium phosphate and 105 mg 2-[(1-bromo-naphthalene-2-carbonyl)-amino]-2-methyl-propionic acid methyl ester were placed in a reaction vial, which was evaporated and backfilled with argon three times. A solution of 62 mg 2-phenoxyethylamine and 12 mg N,N-diethylsalicylaminde in 0.5 ml of dry DMF was then added via septum. Under inert conditions the reaction mixture was heated to 100° C. for 20 h. It was then diluted with ethyl acetate and water, the pH was adjusted to neutral, the layers were separated and the aqueous layer was extracted with ethyl acetate twice. The combined organic layers were dried over magnesium sulphate and evaporated. After purification by RP-HPLC 12 mg 2-methyl-2-{[1-(2-phenoxy-ethylamino)-naphthalene-2-carbonyl]-amino}-propionic acid were obtained.
$C_{23}H_{24}N_2O_4$ (392.46), LCMS (ESI): 393.16 (MH$^+$).

Example 12

2-Methyl-2-{[1-(4-phenyl-but-1-ynyl)-naphthalene-2-carbonyl]-amino}-propionic acid

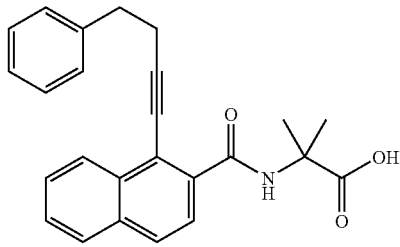 [SMILES: CC(C)(NC(=O)c1ccc2ccccc2c1C#CCCc1ccccc1)C(=O)O]

a) 2-Methyl-2-{[1-(4-phenyl-but-1-ynyl)-naphthalene-2-carbonyl]-amino}-propionic acid methyl ester 40 mg 2-[(1-bromo-naphthalene-2-carbonyl)-amino]-2-methyl-propionic acid methyl ester and 0.8 mg bis(triphenylphosphine)palladium(II)chloride were placed in a reaction vial, which was evaporated and backfilled with argon three times. Via septum 18 mg of 4-phenyl-1-butyne, 180 μl diethylamine and 0.2 ml abs. DMF were added. In a microwave reactor the reaction was heated to 130° C. for 5 min. Then, water and ethyl acetate were added, the layers were separated, and the aqueous phase was extracted with ethyl acetate twice. The combined organic layers were dried over magnesium sulphate and concentrated. The resulting residue was purified by chromatography on silica (ethyl acetate/heptane) to yield 25 mg of 2-methyl-2-{[1-(4-phenyl-but-1-ynyl)-naphthalene-2-carbonyl]-amino}-propionic acid methyl ester.
$C_{26}H_{25}NO_3$ (399.49), LCMS (ESI): 400.19 (MH$^+$).

b) 2-Methyl-2-{[1-(4-phenyl-but-1-ynyl)-naphthalene-2-carbonyl]-amino}-propionic acid 20 mg 2-methyl-2-{[1-(4-phenyl-but-1-ynyl)-naphthalene-2-carbonyl]-amino}-propionic acid methyl ester were reacted with 60 μl of 2 M sodium hydroxide in 0.5 ml methanol and 0.5 ml THF for 48 h room temperature and for 4 h at 60° C. The organic solvents were then removed in vacuo, and the residue was treated with water, acidified with 2 M hydrochloric acid and extracted with ethyl acetate twice. The combined organic layers were dried over sodium sulphate, and concentrated. After chromatography on silica (ethyl acetate/ heptane) 11 mg of 2-methyl-2-{[1-(4-phenyl-but-1-ynyl)-naphthalene-2-carbonyl]-amino}-propionic acid were obtained.

$C_{25}H_{23}NO_3$ (385.47), LCMS (ESI): 386.16 (MH$^+$).

Example 13

2-Methyl-2-{[1-(4-phenyl-butyl)-naphthalene-2-carbonyl]-amino}-propionic acid

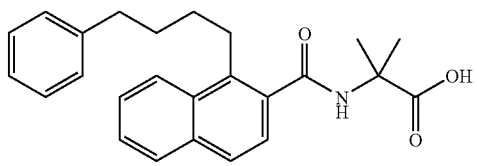

a) 2-Methyl-2-{[1-(4-phenyl-butyl)-naphthalene-2-carbonyl]-amino}-propionic acid methyl ester 50 mg of 2-methyl-2-{[1-(4-phenyl-but-1-ynyl)-naphthalene-2-carbonyl]-amino}-propionic acid methyl ester were dissolved in 5 ml methanol, and after addition of 10 mg of Pd/C (10%) hydrogenated for 6 h. The reaction was then filtrated and the filtrate was concentrated to yield 48 mg of 2-methyl-2-{[1-(4-phenyl-butyl)-naphthalene-2-carbonyl]-amino}-propionic acid methyl ester.

$C_{26}H_{29}NO_3$ (403.53), LCMS (ESI): 404.18 (MH$^+$).

b) 2-Methyl-2-{[1-(4-phenyl-butyl)-naphthalene-2-carbonyl]-amino}-propionic acid 40 mg 2-methyl-2-{[1-(4-phenyl-butyl)-naphthalene-2-carbonyl]-amino}-propionic acid methyl ester were reacted with 150 µl of 2 M sodium hydroxide in 1 ml methanol and 1 ml THF for 1 h at 60° C. The reaction mixture was then acidified with 2 M hydrochloric acid and the precipitated product was collected by filtration and dried in vacuo to yield 26 mg of 2-methyl-2-{[1-(4-phenyl-butyl)-naphthalene-2-carbonyl]-amino}-propionic acid.

$C_{25}H_{27}NO_3$ (389.50), LCMS (ESI): 390.18 (MH$^+$).

Example 14

2-Methyl-2-{[1-(4-phenyl-but-1-enyl)-naphthalene-2-carbonyl]-amino}-propionic acid

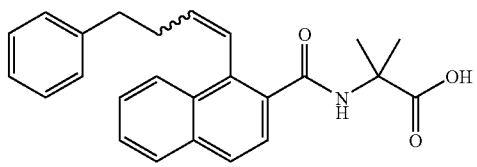 [SMILES: CC(C)(NC(=O)c1ccc2ccccc2c1C=CCCc1ccccc1)C(=O)O]

a) 1-(4-Phenyl-but-1-enyl)-naphthalene-2-carboxylic acid methyl ester 530 mg g 1-bromo-naphthalene-2-carboxylic acid methyl ester and 9 mg tris(dibenzylideneacetone)dipalladium(0) were placed in a reaction vial, which was evacuated and backfilled with argon three times. Via septum 125 µl tri-tert.butylphosphine (10% in hexane), 291 mg 4-phenyl-1-butene, 470 µl N,N-dicyclohexylmethylamine and 1.8 ml dioxane were added. After 2 h at 80° C., the reaction mixture was cooled and filtrated over silica with diethyl ether. After concentration of the organic phase the resulting residue was purified by chromatography on silica (ethyl acetate/heptane) to yield 175 mg of a mixture of the (E)- and (Z)-isomers of 1-(4-phenyl-but-1-enyl)-naphthalene-2-carboxylic acid methyl ester.

$C_{22}H_{20}O_2$ (316.40), LCMS (ESI): 317.23 (MH$^+$).

b) 1-(4-Phenyl-but-1-enyl)-naphthalene-2-carboxylic acid 175 mg 1-(4-phenyl-but-1-enyl)-naphthalene-2-carboxylic acid methyl ester were reacted with 1 ml of 2 M aqueous sodium hydroxide in 1.5 ml methanol and 4 ml THF for 1 h at 60° C. The organic solvents were removed in vacuo, the mixture was acidified with 2 M hydrochloric acid and extracted with ethyl acetate twice. The combined organic layers were washed with brine, dried over magnesium sulphate and concentrated to yield 165 mg of a mixture of the (E)- and (Z)-isomers of 1-(4-phenyl-but-1-enyl)-naphthalene-2-carboxylic acid.

$C_{21}H_{18}O_2$ (302.38), LCMS (ESI): 303.15 (MH$^+$).

c) 2-Methyl-2-{[1-(4-phenyl-but-1-enyl)-naphthalene-2-carbonyl]-amino}-propionic acid methyl ester At 0° C. to a solution of 165 mg of a mixture of the (E)- and (Z)-isomers of 1-(4-phenyl-but-1-enyl)-naphthalene-2-carboxylic acid in 2 ml abs. DMF under inert atmosphere 95 mg 1-hydroxybenzotriazole, 110 µl N,N'-diisopropylcarbodiimide and 98 µl N,N-diisopropylethylamine were added. After 15 min at 0° C. 86 mg amino-isobutyric acid methyl ester hydrochloride and 98 µl N,N-diisopropylethylamine were added and the reaction was stirred for 0.5 h at 0° C. and for 4 h at room temperature. Then, the reaction mixture was concentrated, the residue was taken up in ethyl acetate and washed with 2 M HCl, aqueous sat. sodium hydrogen carbonate solution and brine. The organic layer was dried over sodium sulphate, concentrated and purified by chromatography on silica (ethyl acetate/heptane) to yield 85 mg of a mixture of the (E)- and (Z)-isomers of 2-methyl-2-{[1-(4-phenyl-but-1-enyl)-naphthalene-2-carbonyl]-amino}-propionic acid methyl ester.

$C_{26}H_{27}NO_3$ (401.51), LCMS (ESI): 402.23 (MH$^+$).

d) 2-Methyl-2-{[1-(4-phenyl-but-1-enyl)-naphthalene-2-carbonyl]-amino}-propionic acid 80 mg of a mixture of the (E)- and (Z)-isomers of 2-methyl-2-{[1-(4-phenyl-but-1-enyl)-naphthalene-2-carbonyl]-amino}-propionic acid methyl ester were reacted with 0.5 ml of 2 M sodium hydroxide in 1 ml methanol and 2 ml THF for 15 min at 60° C. The organic solvents were removed in vacuo, the mixture was acidified with 2 M hydrochloric acid and extracted with ethyl acetate twice. The combined organic layers were washed with brine, dried over magnesium sulphate and concentrated to yield 75 mg of a mixture of the (E)- and (Z)-isomers of 2-methyl-2-{[1-(4-phenyl-but-1-enyl)-naphthalene-2-carbonyl]-amino}-propionic acid.

$C_{25}H_{25}NO_3$ (387.48), LCMS (ESI): 388.19 (MH$^+$).

The following examples were prepared in analogy to example 1 via a sequence of a coupling of a suitable (ortho-)hydroxy-arene-carboxylic acid with a corresponding amino acid ester using coupling reagents as for example EDC/HOBT, DIC/HOBT, HATU, TBTU/DMAP, followed by an alkylation reaction to attach a suitably substituted alkylating agent to the aromatic hydroxy group and finally a basic hydrolysis of the amino acid ester to the free amino acid:

| No. | Structure | Name | ESI+ or ESI− |
|---|---|---|---|
| 15 | 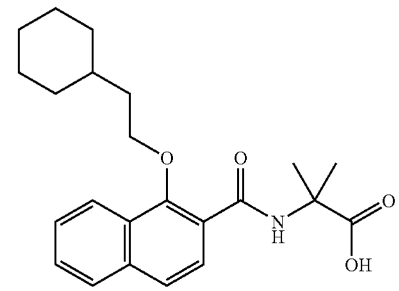 [SMILES: CC(C)(NC(=O)c1ccc2ccccc2c1OCCC1CCCCC1)C(=O)O] | 2-{[1-(2-Cyclohexyl-ethoxy)-naphthalene-2-carbonyl]-amino}-2-methyl-propionic acid | 384.25 |
| 16 | 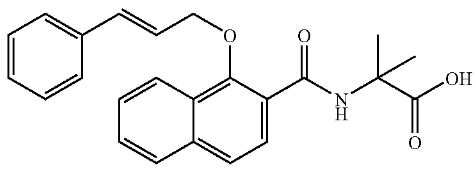 [SMILES: CC(C)(NC(=O)c1ccc2ccccc2c1OC/C=C/c1ccccc1)C(=O)O] | 2-Methyl-2-{[1-((E)-3-phenyl-allyloxy)-naphthalene-2-carbonyl]-amino}propionic acid | 390.16 |
| 17 | 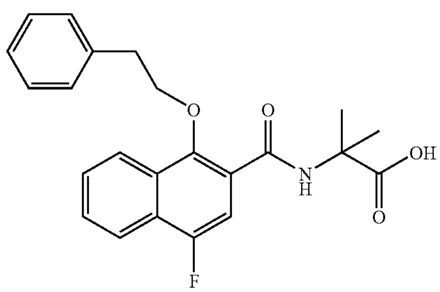 [SMILES: CC(C)(NC(=O)c1cc(F)c2ccccc2c1OCCc1ccccc1)C(=O)O] | 2-[(4-Fluoro-1-phenethyloxy-naphthalene-2-carbonyl)-amino]-2-methyl-propionic acid | 396.16 |
| 18 | 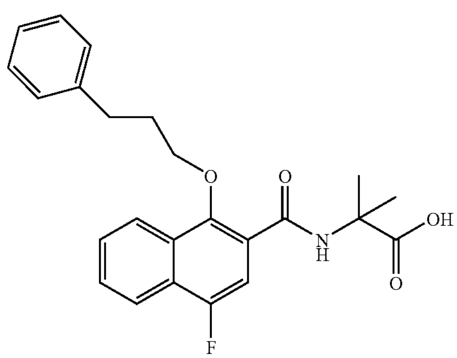 [SMILES: CC(C)(NC(=O)c1cc(F)c2ccccc2c1OCCCc1ccccc1)C(=O)O] | 2-{[4-Fluoro-1-(3-phenyl-propoxy)-naphthalene-2-carbonyl]-amino}-2-methyl-propionic acid | 410.13 |
| 19 | 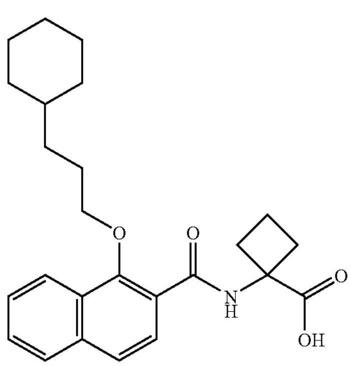 [SMILES: O=C(NC1(C(=O)O)CCC1)c1ccc2ccccc2c1OCCCC1CCCCC1] | 1-{[1-(3-Cyclohexyl-propoxy)-naphthalene-2-carbonyl]-amino}-cyclobutanecarboxylic acid | 410.32 |

| No. | Structure | Name | ESI+ or ESI− |
|---|---|---|---|
| 20 | 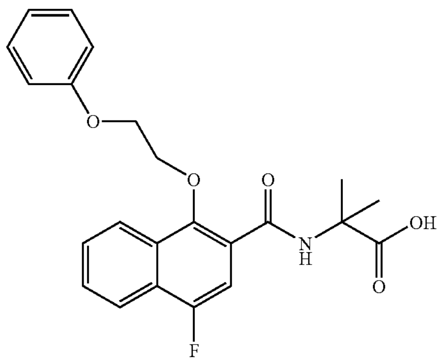 [SMILES: CC(C)(NC(=O)c1cc(F)c2ccccc2c1OCCOc1ccccc1)C(=O)O] | 2-{[4-Fluoro-1-(2-phenoxy-ethoxy)-naphthalene-2-carbonyl]-amino}-2-methyl-propionic acid | 412.12 |
| 21 | 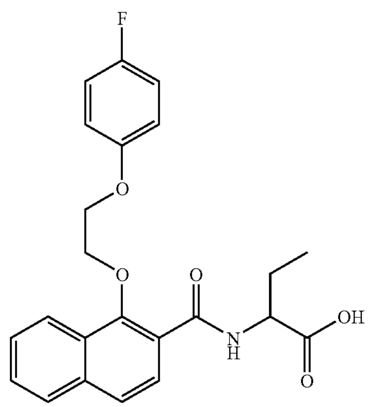 [SMILES: CCC(NC(=O)c1ccc2ccccc2c1OCCOc1ccc(F)cc1)C(=O)O] | 2-({1-[2-(4-Fluoro-phenoxy)-ethoxy]-naphthalene-2-carbonyl}-amino)-butyric acid | 412.16 |
| 22 | 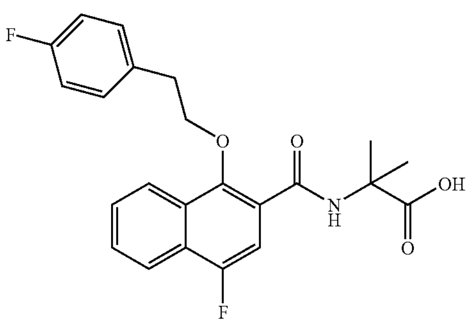 [SMILES: CC(C)(NC(=O)c1cc(F)c2ccccc2c1OCCc1ccc(F)cc1)C(=O)O] | 2({4-Fluoro-1-[2-(4-fluoro-phenyl)-ethoxy]-naphthalene-2-carbonyl}-amino)-2-methyl-propionic acid | 414.1 |
| 23 | 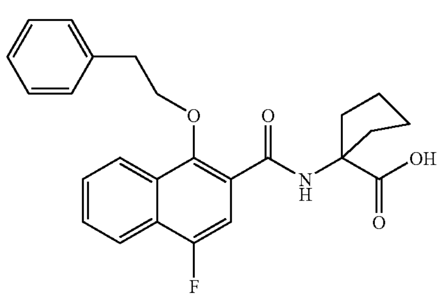 [SMILES: O=C(NC1(C(=O)O)CCCC1)c1cc(F)c2ccccc2c1OCCc1ccccc1] | 1-[(4-Fluoro-1-phenethyloxy-naphthalene-2-carbonyl)-amino]-cyclopentanecarboxylic acid | 422.18 |

-continued

| No. | Structure | Name | ESI+ or ESI− |
|---|---|---|---|
| 24 | 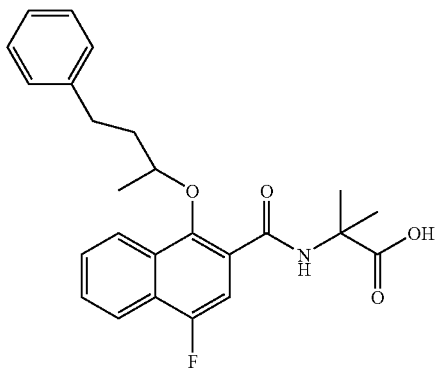 [SMILES: CC(CCc1ccccc1)Oc1c(C(=O)NC(C)(C)C(=O)O)cc(F)c2ccccc12] | 2-{[4-Fluoro-1-(1-methyl-3-phenyl-propoxy)-naphthalene-2-carbonyl]-amino}-2-methyl-propionic acid | 424.2 |
| 25 | 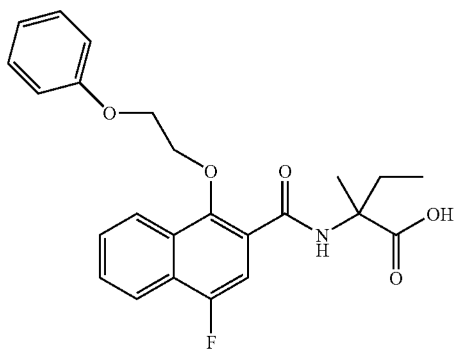 [SMILES: CCC(C)(NC(=O)c1cc(F)c2ccccc2c1OCCOc1ccccc1)C(=O)O] | 2-{[4-Fluoro-1-(2-phenoxy-ethoxy)-naphthalene-2-carbonyl]-amino}-2-methyl-butyric acid | 426.18 |
| 26 | 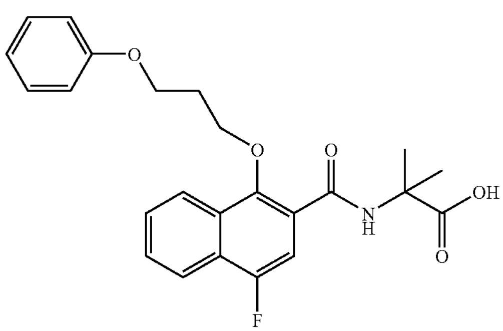 [SMILES: CC(C)(NC(=O)c1cc(F)c2ccccc2c1OCCCOc1ccccc1)C(=O)O] | 2-{[4-Fluoro-1-(3-phenoxy-propoxy)-naphthalene-2-carbonyl]-amino}-2-methyl-propionic acid | 426.18 |
| 27 | 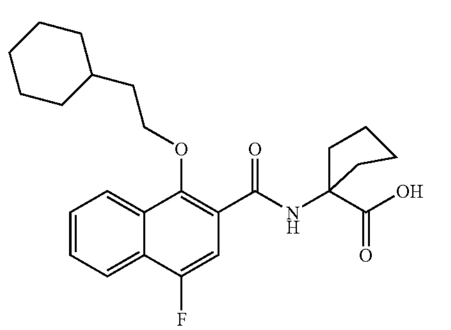 [SMILES: O=C(NC1(C(=O)O)CCCC1)c1cc(F)c2ccccc2c1OCCC1CCCCC1] | 1-{[1-(2-Cyclohexyl-ethoxy)-4-fluoro-naphthalene-2-carbonyl]-amino}-cyclopentanecarboxylic acid | 428.25 |

| No. | Structure | Name | ESI+ or ESI− |
|---|---|---|---|
| 28 | 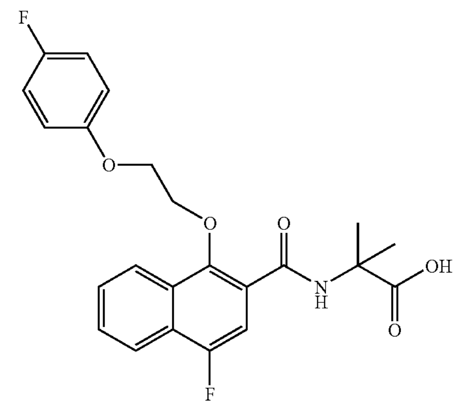 [SMILES: CC(C)(NC(=O)c1cc(F)c2ccccc2c1OCCOc1ccc(F)cc1)C(=O)O] | 2-({4-Fluoro-1-[2-(4-fluoro-phenoxy)-ethoxy]-naphthalene-2-carbonyl}-amino)-2-methyl-propionic acid | 430.1 |
| 29 | 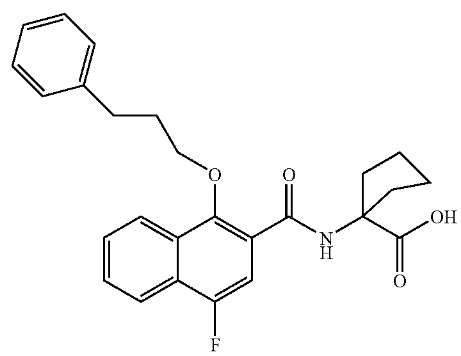 [SMILES: O=C(NC1(C(=O)O)CCCC1)c1cc(F)c2ccccc2c1OCCCc1ccccc1] | 1-{[4-Fluoro-1-(3-phenyl-propoxy)-naphthalene-2-carbonyl]-amino}-cyclopentanecarboxylic acid | 436.14 |
| 30 | 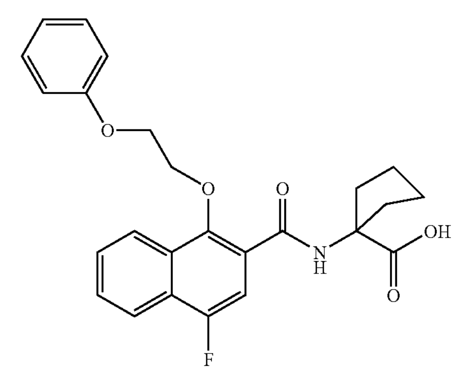 [SMILES: O=C(NC1(C(=O)O)CCCC1)c1cc(F)c2ccccc2c1OCCOc1ccccc1] | 1-{[4-Fluoro-1-(2-phenoxy-ethoxy)-naphthalene-2-carbonyl]-amino}-cyclopentanecarboxylic acid | 438.2 |
| 31 | 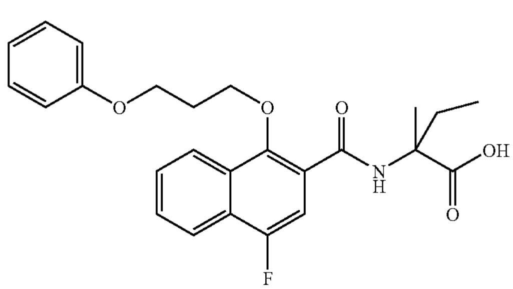 [SMILES: CCC(C)(NC(=O)c1cc(F)c2ccccc2c1OCCCOc1ccccc1)C(=O)O] | 2-{[4-Fluoro-1-(3-phenoxy-propoxy)-naphthalene-2-carbonyl]-amino}-2-methyl-butyric acid | 440.1 |

-continued

| No. | Structure | Name | ESI+ or ESI− |
|---|---|---|---|
| 32 | 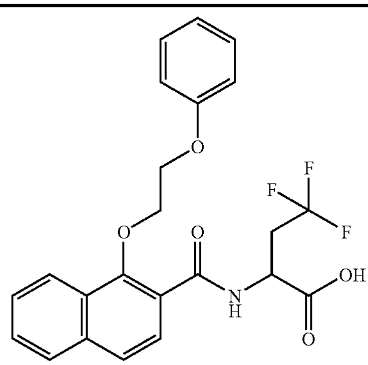 | 4,4,4-Trifluoro-2-{[1-(2-phenoxy-ethoxy)-naphthalene-2-carbonyl]-amino}-butyric acid | 448.13 |
| 33 | 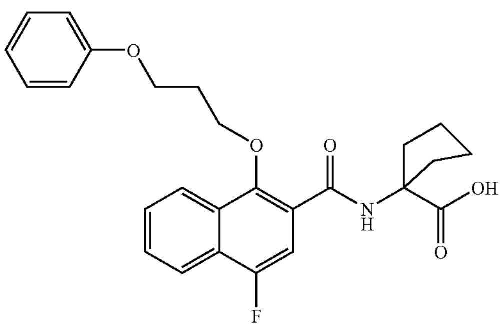 [SMILES: O=C(NC1(C(=O)O)CCCC1)c1cc(F)c2ccccc2c1OCCCOc1ccccc1] | 1-{[4-Fluoro-1-(3-phenoxy-propoxy)-naphthalene-2-carbonyl]-amino}-cyclopentanecarboxylic acid | 450.19 |
| 34 | 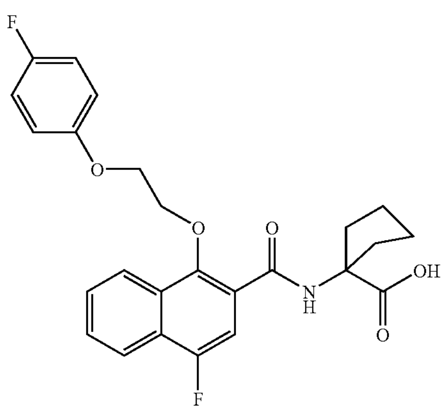 [SMILES: O=C(NC1(C(=O)O)CCCC1)c1cc(F)c2ccccc2c1OCCOc1ccc(F)cc1] | 1-({4-Fluoro-1-[2-(4-fluoro-phenoxy)-ethoxy]-naphthalene-2-carbonyl}-amino)-cyclopentanecarboxylic acid | 454.19 |
| 35 | 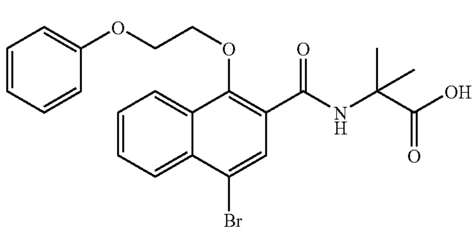 [SMILES: CC(C)(NC(=O)c1cc(Br)c2ccccc2c1OCCOc1ccccc1)C(=O)O] | 2-{[4-Bromo-1-(2-phenoxy-ethoxy)-naphthalene-2-carbonyl]-amino}-2-methyl-propionic acid | 472.10 474.05 (br-pattern) |

The following examples were prepared in analogy to example 2 via a sequence of a coupling of a suitable (ortho-) hydroxy-arene-carboxylic acid with a corresponding amino acid ester using coupling reagents as for example EDC/HOBT, DIC/HOBT, HATU, TBTU/DMAP, followed by a Mitsunobu reaction of a suitably substituted alcohol with the aromatic hydroxy group and finally a basic hydrolysis of the amino acid ester to the free amino acid:

| No. | Structure | Name | ESI+ or ESI− |
|---|---|---|---|
| 36 | 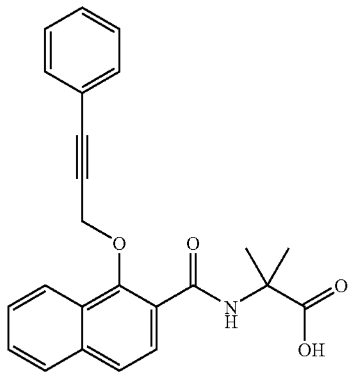 [SMILES: CC(C)(NC(=O)c1ccc2ccccc2c1OCC#Cc1ccccc1)C(=O)O] | 2-Methyl-2-{[1-(3-phenyl-prop-2-ynyloxy)-naphthalene-2-carbonyl]-amino}-propionic acid | 388.05 |
| 37 | 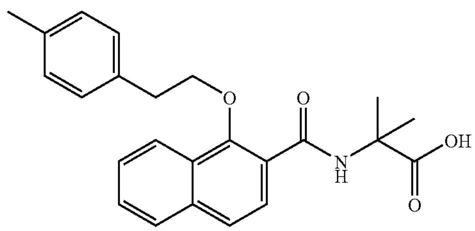 [SMILES: Cc1ccc(CCOc2c(C(=O)NC(C)(C)C(=O)O)ccc3ccccc23)cc1] | 2-Methyl-2-{[1-(2-p-tolyl-ethoxy)-naphthalene-2-carbonyl]-amino}-propionic acid | 392.13 |
| 38 | 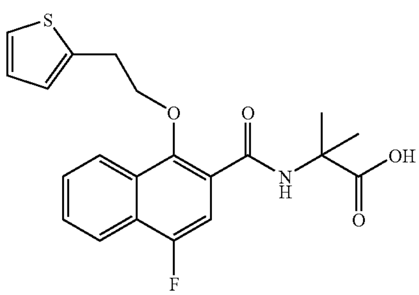 [SMILES: CC(C)(NC(=O)c1cc(F)c2ccccc2c1OCCc1cccs1)C(=O)O] | 2-{[4-Fluoro-1-(2-thiophen-2-yl-ethoxy)-naphthalene-2-carbonyl]-amino}-2-methyl-propionic acid | 402.23 |
| 39 | 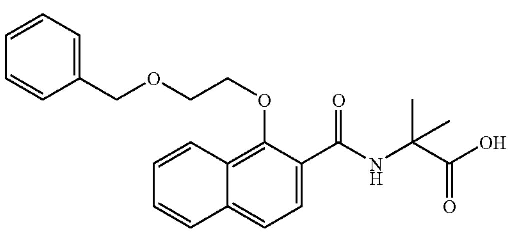 [SMILES: CC(C)(NC(=O)c1ccc2ccccc2c1OCCOCc1ccccc1)C(=O)O] | 2-{[1-(2-Benzyloxy-ethoxy)-naphthalene-2-carbonyl]-amino}-2-methyl-propionic acid | 408.12 |
| 40 | 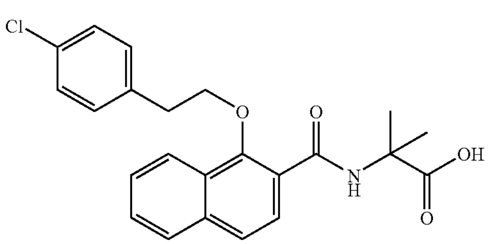 [SMILES: CC(C)(NC(=O)c1ccc2ccccc2c1OCCc1ccc(Cl)cc1)C(=O)O] | 2-({1-[2-(4-Chloro-phenyl)-ethoxy]-naphthalene-2-carbonyl}-amino)-2-methyl-propionic acid | 412.07 |
| 41 | CHIRAL | (S)-3-Methyl-2-{[1-(1-methyl-3-phenyl-propoxy)-naphthalene-2-carbonyl]-amino}-butyric acid | 420.29 |

| No. | Structure | Name | ESI+ or ESI– |
|---|---|---|---|
| 42 | CHIRAL | (R)-3-Methyl-2-{[1-(1-methyl-3-phenyl-propoxy)-naphthalene-2-carbonyl]-amino}-butyric acid | 420.30 |
| 43 | 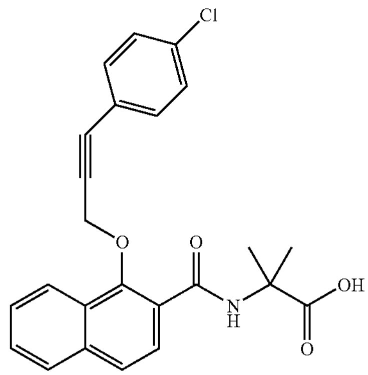 [SMILES: CC(C)(NC(=O)c1ccc2ccccc2c1OCC#Cc1ccc(Cl)cc1)C(=O)O] | 2-({1-[3-(4-Chloro-phenyl)-prop-2-ynyloxy]-naphthalene-2-carbonyl}-amino)-2-methyl-propionic acid | 422.02 |
| 44 | 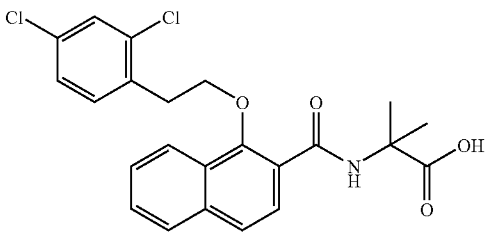 [SMILES: CC(C)(NC(=O)c1ccc2ccccc2c1OCCc1ccc(Cl)cc1Cl)C(=O)O] | 2-({1-[2-(2,4-Dichloro-phenyl)-ethoxy]-naphthalene-2-carbonyl}-amino)-2-methyl-propionic acid | 445.98 447.99 (di-Cl-pattern) |

The following examples were prepared in analogy to example 3 via a sequence of an alkylation of a suitable (ortho-)hydroxy-arene-carboxylic ester with a corresponding alkylating agent, followed by a basic hydrolysis of this ester, and a coupling of the resulting acid with a corresponding amino acid ester using coupling reagents as for example EDC/HOBT, DIC/HOBT, HATU, TBTU/DMAP, and finally a basic hydrolysis of the amino acid ester to the free amino acid:

| No. | Structure | Name | ESI+ or ESI– |
|---|---|---|---|
| 45 | 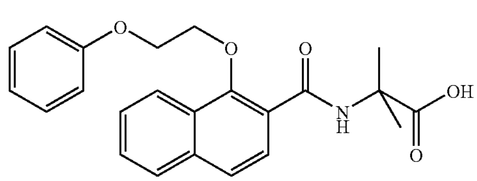 [SMILES: CC(C)(NC(=O)c1ccc2ccccc2c1OCCOc1ccccc1)C(=O)O] | 2-Methyl-2-{[1-(2-phenoxy-ethoxy)-naphthalene-2-carbonyl]-amino}-propionic acid | 394.21 |
| 46 | 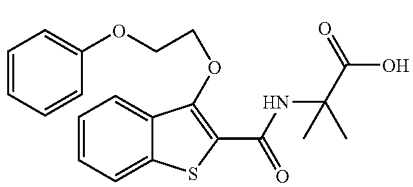 [SMILES: CC(C)(NC(=O)c1sc2ccccc2c1OCCOc1ccccc1)C(=O)O] | 2-Methyl-2-{[3-(2-phenoxy-ethoxy)-benzo[b]thiophene-2-carbonyl]-amino}-propionic acid | 400.26 |

-continued

| No. | Structure | Name | ESI+ or ESI− |
|---|---|---|---|
| 47 | 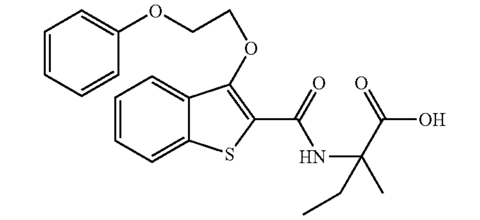 [SMILES: CCC(C)(NC(=O)c1sc2ccccc2c1OCCOc1ccccc1)C(=O)O] | 2-Methyl-2-{[3-(2-phenoxy-ethoxy)-benzo[b]thiophene-2-carbonyl]-amino}-butyric acid | 414.2 |
| 48 | 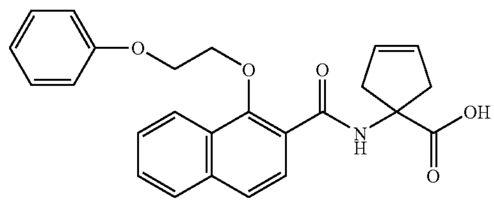 [SMILES: O=C(NC1(C(=O)O)CC=CC1)c1ccc2ccccc2c1OCCOc1ccccc1] | 1-{[1-(2-Phenoxy-ethoxy)-naphthalene-2-carbonyl]-amino}-cyclopent-3-enecarboxylic acid | 418.15 |
| 49 | 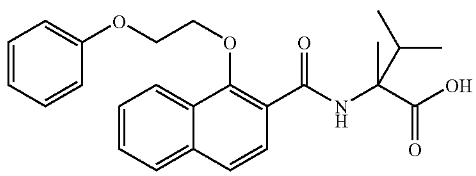 [SMILES: CC(C)C(C)(NC(=O)c1ccc2ccccc2c1OCCOc1ccccc1)C(=O)O] | 2,3-Dimethyl-2-{[1-(2-phenoxy-ethoxy)-naphthalene-2-carbonyl]-amino}-butyric acid | 422.1 |
| 50 | 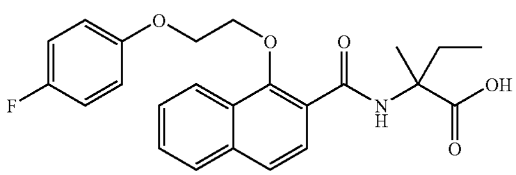 [SMILES: CCC(C)(NC(=O)c1ccc2ccccc2c1OCCOc1ccc(F)cc1)C(=O)O] | 2-({1-[2-(4-Fluoro-phenoxy)-ethoxy]-naphthalene-2-carbonyl}-amino)-2-methyl-butyric acid | 426.45 |
| 51 | 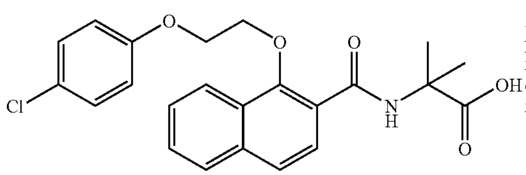 [SMILES: CC(C)(NC(=O)c1ccc2ccccc2c1OCCOc1ccc(Cl)cc1)C(=O)O] | 2-({1-[2-(4-Chloro-phenoxy)-ethoxy]-naphthalene-2-carbonyl}-amino)-2-methyl-propionic acid | 428.09 |
| 52 | 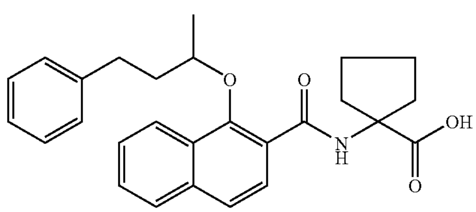 [SMILES: CC(CCc1ccccc1)Oc1c(C(=O)NC2(C(=O)O)CCCC2)ccc2ccccc12] | 1-{[1-(1-Methyl-3-phenyl-propoxy)-naphthalene-2-carbonyl]-amino}-cyclopentanecarboxylic acid | 432.2 |
| 53 | 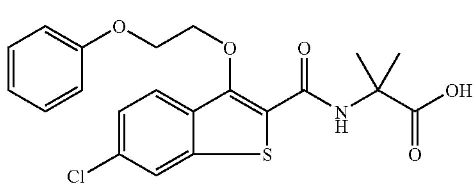 [SMILES: CC(C)(NC(=O)c1sc2cc(Cl)ccc2c1OCCOc1ccccc1)C(=O)O] | 2-{[6-Chloro-3-(2-phenoxy-ethoxy)-benzo[b]thiophene-2-carbonyl]-amino}-2-methyl-propionic acid | 434.03 |
| 54 | 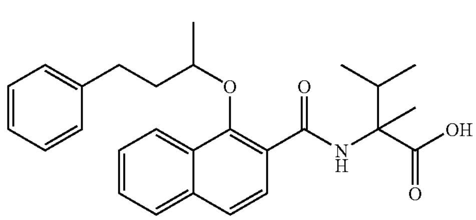 [SMILES: CC(CCc1ccccc1)Oc1c(C(=O)NC(C)(C(=O)O)C(C)C)ccc2ccccc12] | 2,3-Dimethyl-2-{[1-(1-methyl-3-phenyl-propoxy)-naphthalene-2-carbonyl]-amino}-butyric acid | 434.21 |

| No. | Structure | Name | ESI+ or ESI− |
|---|---|---|---|
| 55 | 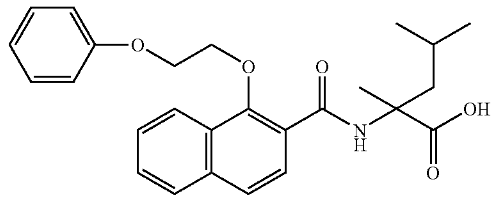 [SMILES: CC(C)CC(C)(NC(=O)c1ccc2ccccc2c1OCCOc1ccccc1)C(=O)O] | 2,4-Dimethyl-2-{1-(2-phenoxy-ethoxy)-naphthalene-2-carbonyl]-amino}-pentanoic acid | 436.5 |
| 56 | 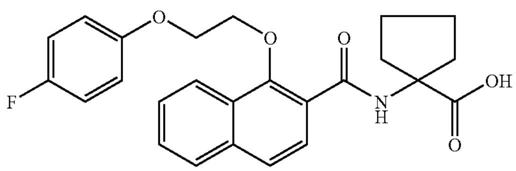 [SMILES: O=C(NC1(C(=O)O)CCCC1)c1ccc2ccccc2c1OCCOc1ccc(F)cc1] | 1-{[2-(4-Fluoro-naphthalene-2-carbonyl}-amino)-cyclopentanecarboxylic acid | 438.11 |
| 57 | 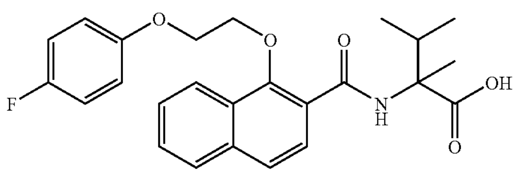 [SMILES: CC(C)C(C)(NC(=O)c1ccc2ccccc2c1OCCOc1ccc(F)cc1)C(=O)O] | 2-({1-[2-(4-Fluoro-phenoxy)-ethoxy]-naphthalene-2-carbonyl}-amino)-2,3-dimethyl-butyric acid | 440.17 |
| 58 | 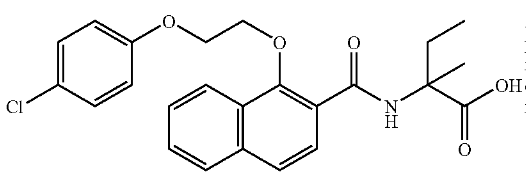 | 2-({1-[2-(4-Chloro-phenoxy)-ethoxy]-naphthalene-2-carbonyl}-amino)-2-methyl-butyric acid | 442.14 |
| 59 | 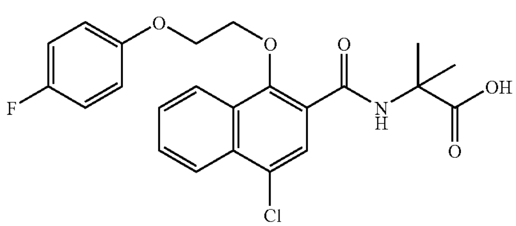 [SMILES: CC(C)(NC(=O)c1cc(Cl)c2ccccc2c1OCCOc1ccc(F)cc1)C(=O)O] | 2-({4-Chloro-1-[2-(4-fluoro-phenoxy)-ethoxy]-naphthalene-2-carbonyl}-amino)-2-methyl-propionic acid | 446.18 |
| 60 | 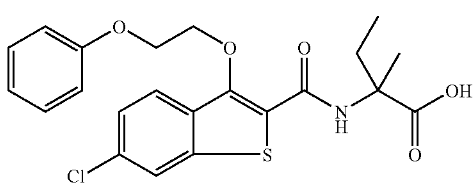 [SMILES: CCC(C)(NC(=O)c1sc2cc(Cl)ccc2c1OCCOc1ccccc1)C(=O)O] | 2-{[6-Chloro-3-(2-phenoxy-ethoxy)-benzo[b]thiophene-2-carbonyl]-amino}-2-methyl-butyric acid | 448.03 |
| 61 | 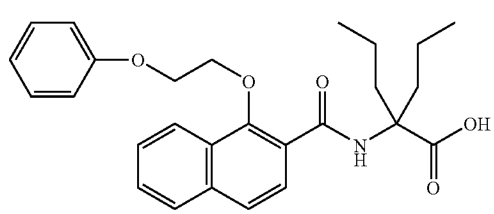 [SMILES: CCCC(CCC)(NC(=O)c1ccc2ccccc2c1OCCOc1ccccc1)C(=O)O] | 2-{[1-(2-Phenoxy-ethoxy)-naphthalene-2-carbonyl]-amino}-2-propyl-pentanoic acid | 450.24 |

-continued

| No. | Structure | Name | ESI+ or ESI− |
|---|---|---|---|
| 62 | 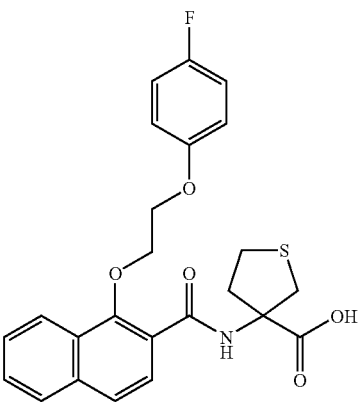 [SMILES: O=C(NC1(C(=O)O)CCSC1)c1ccc2ccccc2c1OCCOc1ccc(F)cc1] | 3-({1-[2-(4-Fluoro-phenoxy)-ethoxy]-naphthalene-2-carbonyl}-amino)-tetrahydro-thiophene-3-carboxylic acid | 456.08 |
| 63 | 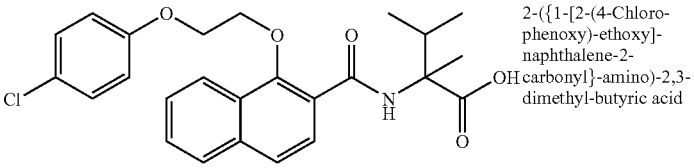 | 2-({1-[2-(4-Chloro-phenoxy)-ethoxy]-naphthalene-2-carbonyl}-amino)-2,3-dimethyl-butyric acid | 456.13 |
| 64 | 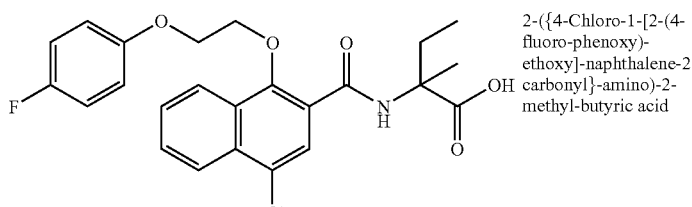 | 2-({4-Chloro-1-[2-(4-fluoro-phenoxy)-ethoxy]-naphthalene-2-carbonyl}-amino)-2-methyl-butyric acid | 460.26 |
| 65 | 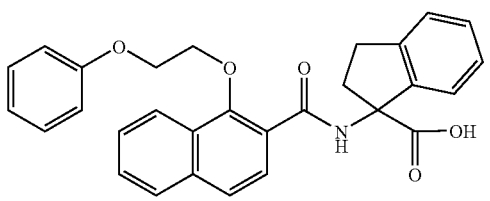 [SMILES: O=C(NC1(C(=O)O)CCc2ccccc21)c1ccc2ccccc2c1OCCOc1ccccc1] | 1-{[1-(2-Phenoxy-ethoxy)-naphthalene-2-carbonyl]-amino}-indan-1-carboxylic acid | 468.18 |
| 66 | 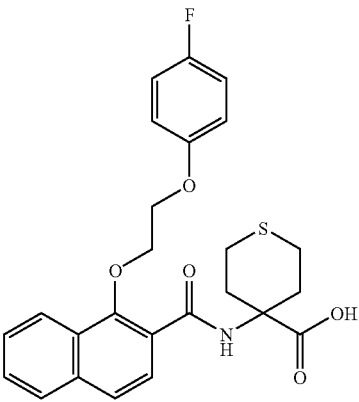 [SMILES: O=C(NC1(C(=O)O)CCSCC1)c1ccc2ccccc2c1OCCOc1ccc(F)cc1] | 4-({1-[2-(4-Fluoro-phenoxy)-ethoxy]-naphthalene-2-carbonyl}-amino)-tetrahydro-thiopyran-4-carboxylic acid | 470.14 |

| No. | Structure | Name | ESI+ or ESI− |
|---|---|---|---|
| 67 | 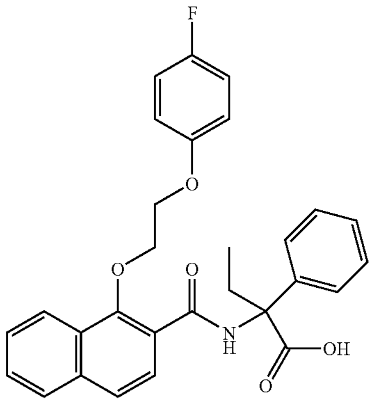 [SMILES: CCC(NC(=O)c1ccc2ccccc2c1OCCOc1ccc(F)cc1)(C(=O)O)c1ccccc1] | 2-({1-[2-(4-Fluoro-phenoxy)-ethoxy]-naphthalene-2-carbonyl}-amino)-2-phenyl-butyric acid | 488.24 |
| 68 | 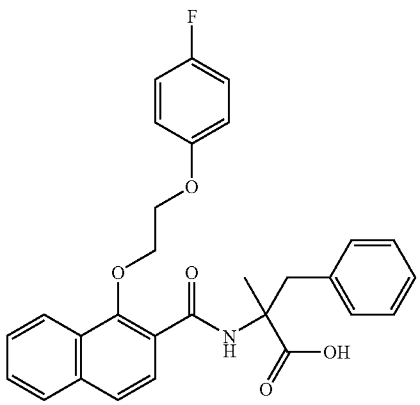 [SMILES: CC(Cc1ccccc1)(NC(=O)c1ccc2ccccc2c1OCCOc1ccc(F)cc1)C(=O)O] | 2-({1-[2-(4-Fluoro-phenoxy)-ethoxy]-naphthalene-2-carbonyl}-amino)-2-methyl-3-phenyl-propionic acid | 488.44 |

The following example was prepared in analogy to example 4 via a sequence of a Mitsunobu of a suitable (ortho-)hydroxy-arene-carboxylic ester with a corresponding alcohol, followed by a basic hydrolysis of this ester, and a coupling of the resulting acid with a corresponding amino acid ester using coupling reagents as for example EDC/HOBT, DIC/HOBT, HATU, TBTU/DMAP, and finally a basic hydrolysis of the amino acid ester to the free amino acid:

hoxy)-tert.butyldimethylsilane, followed by a basic hydrolysis of this ester, preferably with potassium trimethylsilanoate, a coupling of the resulting acid with a corresponding amino acid ester using coupling reagents as for example EDC/HOBT, DIC/HOBT, HATU, TBTU/DMAP, a removal of the tert.butyldimethylsilyl protecting group by treatment with fluoride, e.g. with tetrabutylammoniumfluoride solution in THF, a Mitsunobu reaction of the deprotected hydroxy group

| No. | Structure | Name | ESI+ or ESI− |
|---|---|---|---|
| 69 | 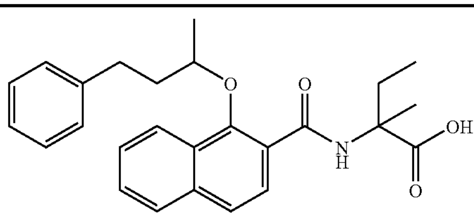 | 2-Methyl-2-{[1-(1-methyl-3-phenyl-propoxy)-naphthalene-2-carbonyl]-amino}-butyric acid | 420.22 |

The following example was prepared in analogy to example 5 via a sequence of an alkylation of a suitable (ortho-)hydroxy-arene-carboxylic ester with a (2-bromoet- and a suitably substituted (hetero)aromatic hydroxy group, and finally a basic hydrolysis of the amino acid ester to the free amino acid:

| No. | Structure | Name | ESI+ or ESI– |
|---|---|---|---|
| 70 | 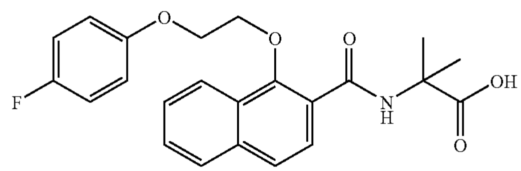 [SMILES: CC(C)(NC(=O)c1ccc2ccccc2c1OCCOc1ccc(F)cc1)C(=O)O] | 2-({1-[2-(4-Fluoro-phenoxy)-ethoxy]-naphthalene-2-carbonyl}-amino)-2-methyl-propionic acid | 412.14 |
| 71 | 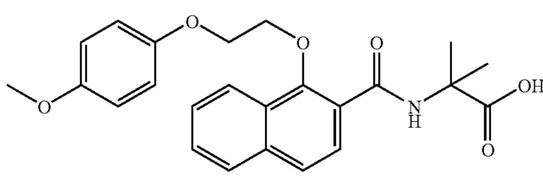 [SMILES: COc1ccc(OCCOc2c(C(=O)NC(C)(C)C(=O)O)ccc3ccccc23)cc1] | 2-({1-[2-(4-Methoxy-phenoxy)-ethoxy]-naphthalene-2-carbonyl}-amino)-2-methyl-propionic acid | 424.14 |
| 72 | 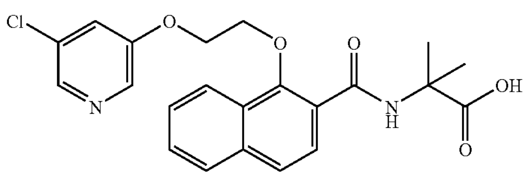 [SMILES: CC(C)(NC(=O)c1ccc2ccccc2c1OCCOc1cncc(Cl)c1)C(=O)O] | 2-({1-[2-(5-Chloro-pyridin-3-yloxy)-ethoxy]-naphthalene-2-carbonyl}-amino)-2-methyl-propionic acid | 429.16 |
| 73 | 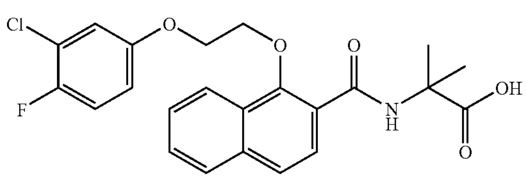 [SMILES: CC(C)(NC(=O)c1ccc2ccccc2c1OCCOc1ccc(F)c(Cl)c1)C(=O)O] | 2-({1-[2-(3-Chloro-4-fluoro-phenoxy)-ethoxy]-naphthalene-2-carbonyl}-amino)-2-methyl-propionic acid | 446.21 |
| 74 | 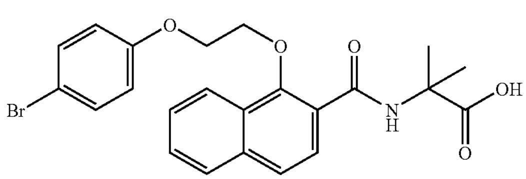 [SMILES: CC(C)(NC(=O)c1ccc2ccccc2c1OCCOc1ccc(Br)cc1)C(=O)O] | 2-({1-[2-(4-Bromo-phenoxy)-ethoxy]-naphthalene-2-carbonyl}-amino)-2-methyl-propionic acid | 472.31 |
| 75 | 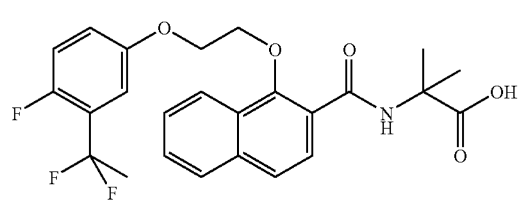 [SMILES: CC(C)(NC(=O)c1ccc2ccccc2c1OCCOc1ccc(F)c(C(C)(F)F)c1)C(=O)O] | 2-({1-[2-(4-Fluoro-3-trifluoromethyl-phenoxy)-ethoxy]-naphthalene-2-carbonyl}-amino)-2-methyl-propionic acid | 480.17 |
| 76 | 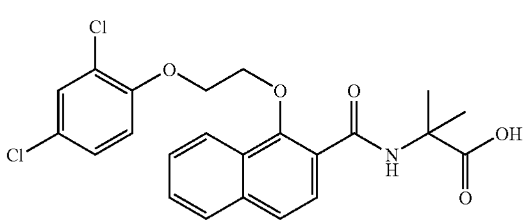 [SMILES: CC(C)(NC(=O)c1ccc2ccccc2c1OCCOc1ccc(Cl)cc1Cl)C(=O)O] | 2-({1-[2-(2,4-Dichloro-phenoxy)-ethoxy]-naphthalene-2-carbonyl}-amino)-2-methyl-propionic acid | 359.02 361.03 (di-Cl— pattern) |

The following examples were prepared in analogy to example 6:

| No. | Structure | Name | ESI+ or ESI− |
|---|---|---|---|
| 77 | 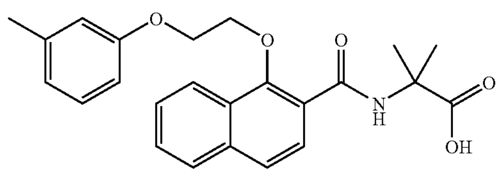 [SMILES: Cc1cccc(OCCOc2c(C(=O)NC(C)(C)C(=O)O)ccc3ccccc23)c1] | 2-Methyl-2-{1-(2-m-tolyloxy-ethoxy)-naphthalene-2-carbonyl]-amino}-propionic acid | 408.07 |
| 78 | 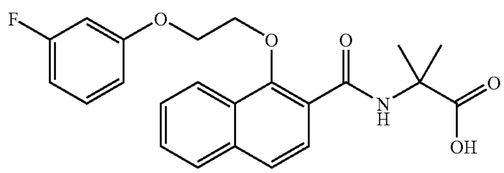 [SMILES: CC(C)(NC(=O)c1ccc2ccccc2c1OCCOc1cccc(F)c1)C(=O)O] | 2-({1-[2-(3-Fluoro-phenoxy)-ethoxy]-naphthalene-2-carbonyl}-amino)-2-methyl-propionic acid | 412.04 |
| 79 | 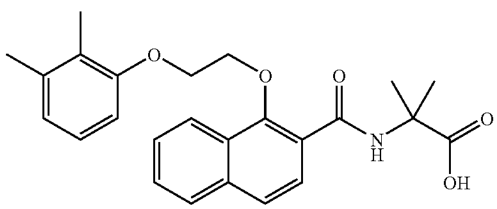 [SMILES: Cc1cccc(OCCOc2c(C(=O)NC(C)(C)C(=O)O)ccc3ccccc23)c1C] | 2-({1-[2-(2,3-Dimethyl-phenoxy)-ethoxy]-naphthalene-2-carbonyl}-amino)-2-methyl-propionic acid | 422.05 |
| 80 | 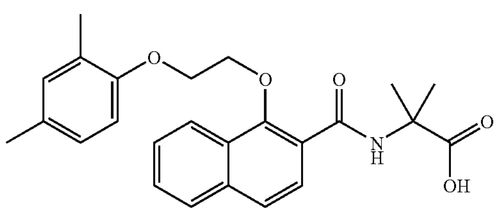 [SMILES: Cc1ccc(OCCOc2c(C(=O)NC(C)(C)C(=O)O)ccc3ccccc23)c(C)c1] | 2-({1-[2-(2,4-Dimethyl-phenoxy)-ethoxy]-naphthalene-2-carbonyl}-amino)-2-methyl-propionic acid | 422.07 |
| 81 | 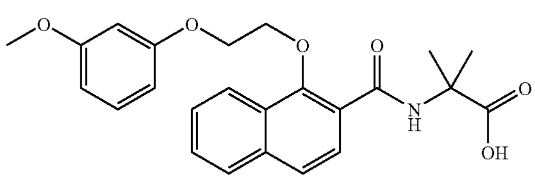 [SMILES: COc1cccc(OCCOc2c(C(=O)NC(C)(C)C(=O)O)ccc3ccccc23)c1] | 2-({1-[2-(3-Methoxy-phenoxy)-ethoxy]-naphthalene-2-carbonyl}-amino)-2-methyl-propionic acid | 424.06 |
| 82 | 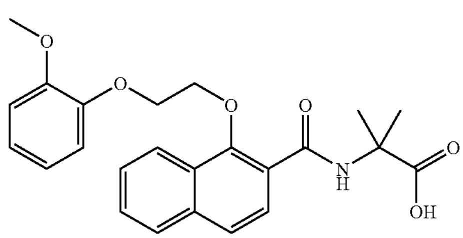 [SMILES: COc1ccccc1OCCOc1c(C(=O)NC(C)(C)C(=O)O)ccc2ccccc12] | 2-({1-[2-(2-Methoxy-phenoxy)-ethoxy]-naphthalene-2-carbonyl}-amino)-2-methyl-propionic acid | 424.06 |
| 83 | 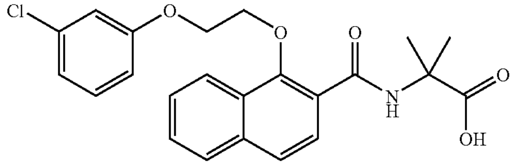 [SMILES: CC(C)(NC(=O)c1ccc2ccccc2c1OCCOc1cccc(Cl)c1)C(=O)O] | 2-({1-[2-(3-Chloro-phenoxy)-ethoxy]-naphthalene-2-carbonyl}-amino)-2-methyl-propionic acid | 428.01 |

-continued

| No. | Structure | Name | ESI+ or ESI− |
|---|---|---|---|
| 84 | 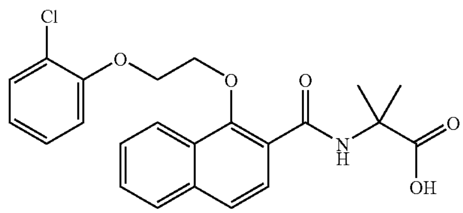 [SMILES: CC(C)(NC(=O)c1ccc2ccccc2c1OCCOc1ccccc1Cl)C(=O)O] | 2-({1-[2-(2-Chloro-phenoxy)-ethoxy]-naphthalene-2-carbonyl}-amino)-2-methyl-propionic acid | 428.02 |
| 85 | 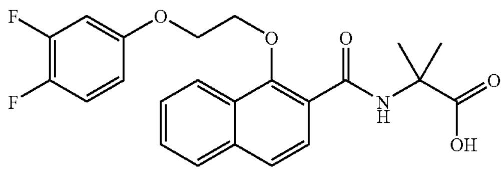 [SMILES: CC(C)(NC(=O)c1ccc2ccccc2c1OCCOc1ccc(F)c(F)c1)C(=O)O] | 2-({1-[2-(3,4-Difluoro-phenoxy)-ethoxy]-naphthalene-2-carbonyl}-amino)-2-methyl-propionic acid | 430.03 |
| 86 | 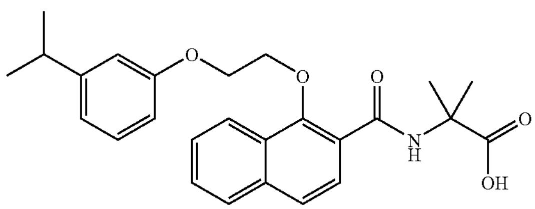 [SMILES: CC(C)c1cccc(OCCOc2c(C(=O)NC(C)(C)C(=O)O)ccc3ccccc23)c1] | 2-({1-[2-(3-Isopropyl-phenoxy)-ethoxy]-naphthalene-2-carbonyl}-amino)-2-methyl-propionic acid | 436.07 |
| 87 | 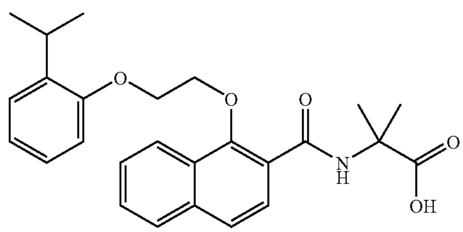 [SMILES: CC(C)c1ccccc1OCCOc1c(C(=O)NC(C)(C)C(=O)O)ccc2ccccc12] | 2-({1-[2-(2-Isopropyl-phenoxy)-ethoxy]-naphthalene-2-carbonyl}-amino)-2-methyl-propionic acid | 436.09 |
| 88 | 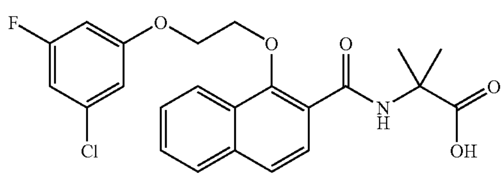 [SMILES: CC(C)(NC(=O)c1ccc2ccccc2c1OCCOc1cc(F)cc(Cl)c1)C(=O)O] | 2-({1-[2-(3-Chloro-5-fluoro-phenoxy)-ethoxy]-naphthalene-2-carbonyl}-amino)-2-methyl-propionic acid | 445.97 |
| 89 | 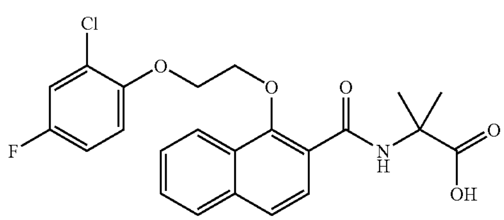 [SMILES: CC(C)(NC(=O)c1ccc2ccccc2c1OCCOc1ccc(F)cc1Cl)C(=O)O] | 2-({1-[2-(2-Chloro-4-fluoro-phenoxy)-ethoxy]-naphthalene-2-carbonyl}-amino)-2-methyl-propionic acid | 446 |
| 90 | 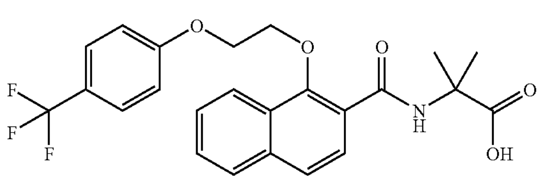 [SMILES: CC(C)(NC(=O)c1ccc2ccccc2c1OCCOc1ccc(C(F)(F)F)cc1)C(=O)O] | 2-Methyl-2-({1-[2-(4-trifluoromethyl-phenoxy)-ethoxy]-naphthalene-2-carbonyl}-amino)-propionic acid | 462.01 |

| No. | Structure | Name | ESI+ or ESI− |
|---|---|---|---|
| 91 | 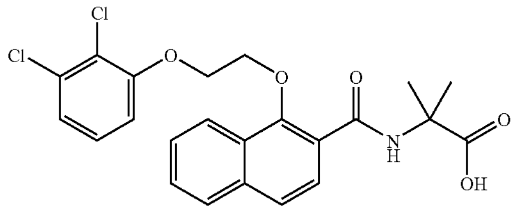 [SMILES: CC(C)(NC(=O)c1ccc2ccccc2c1OCCOc1cccc(Cl)c1Cl)C(=O)O] | 2-({1-[2-(2,3-Dichloro-phenoxy)-ethoxy]-naphthalene-2-carbonyl}-amino)-2-methyl-propionic acid | 461.95 463.96 (di-Cl— pattern) |
| 92 | 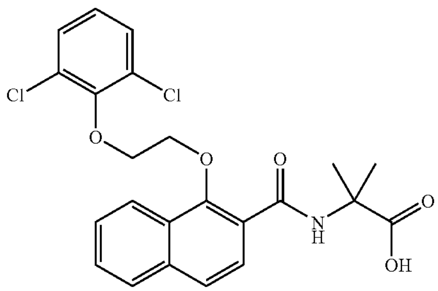 [SMILES: CC(C)(NC(=O)c1ccc2ccccc2c1OCCOc1c(Cl)cccc1Cl)C(=O)O] | 2-({1-[2-(2,6-Dichloro-phenoxy)-ethoxy]-naphthalene-2-carbonyl}-amino)-2-methyl-propionic acid | 461.96 463.95 (di-Cl— pattern) |
| 93 | 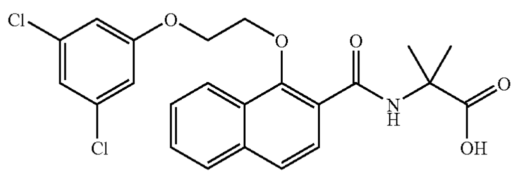 [SMILES: CC(C)(NC(=O)c1ccc2ccccc2c1OCCOc1cc(Cl)cc(Cl)c1)C(=O)O] | 2-({1-[2-(3,5-Dichloro-phenoxy)-ethoxy]-naphthalene-2-carbonyl}-amino)-2-methyl-propionic acid | 461.97 463.96 (di-Cl— pattern) |
| 94 | 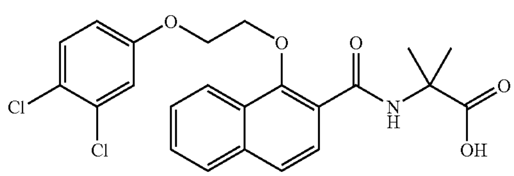 [SMILES: CC(C)(NC(=O)c1ccc2ccccc2c1OCCOc1ccc(Cl)c(Cl)c1)C(=O)O] | 2-({1-[2-(3,4-Dichloro-phenoxy)-ethoxy]-naphthalene-2-carbonyl}-amino)-2-methyl-propionic acid | 461.97 463.97 (di-Cl— pattern) |

The following examples were prepared in analogy to example 7:

| No. | Structure | Name | ESI+ or ESI− |
|---|---|---|---|
| 95 | 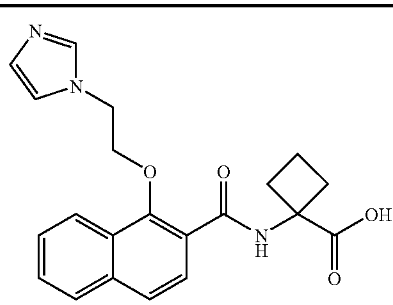 | 1-{1[1-(2-Imidazol-1-yl-ethoxy)-naphthalene-2-carbonyl]-amino}-cyclobutanecarboxylic acid | 380.16 |

-continued

| No. | Structure | Name | ESI+ or ESI− |
|---|---|---|---|
| 96 | 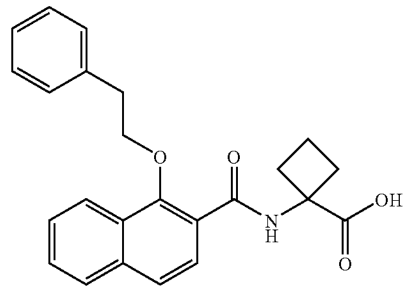 [SMILES: O=C(NC1(C(=O)O)CCC1)c1ccc2ccccc2c1OCCc1ccccc1] | 1-[(1-Phenethyloxy-naphthalene-2-carbonyl)-amino]-cyclobutanecarboxylic acid | 390.2 |
| 97 | 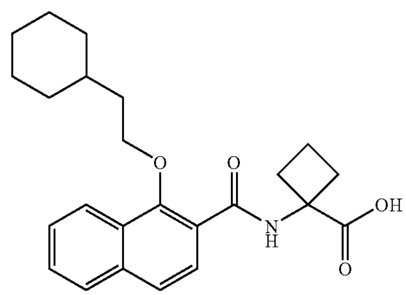 [SMILES: O=C(NC1(C(=O)O)CCC1)c1ccc2ccccc2c1OCCC1CCCCC1] | 1-{[1-(2-Cyclohexyl-ethoxy)-naphthalene-2-carbonyl]-amino}-cyclobutanecarboxylic acid | 396.22 |
| 98 | 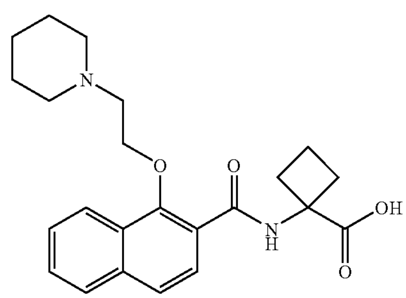 [SMILES: O=C(NC1(C(=O)O)CCC1)c1ccc2ccccc2c1OCCN1CCCCC1] | 1-{[1-(2-Piperidin-1-yl-ethoxy)-naphthalene-2-carbonyl]-amino}-cyclobutanecarboxylic acid | 397.2 |
| 99 | 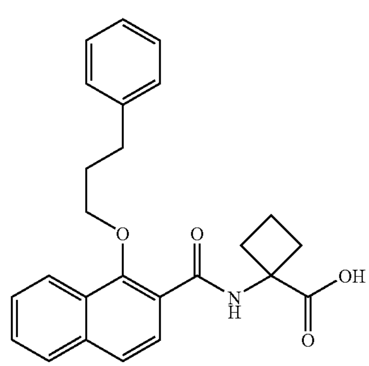 [SMILES: O=C(NC1(C(=O)O)CCC1)c1ccc2ccccc2c1OCCOc1ccccc1] | 1-{[1-(3-Phenyl-propoxy)-naphthalene-2-carbonyl]-amino}-cyclobutanecarboxylic acid | 404.21 |

| No. | Structure | Name | ESI+ or ESI– |
|---|---|---|---|
| 100 | 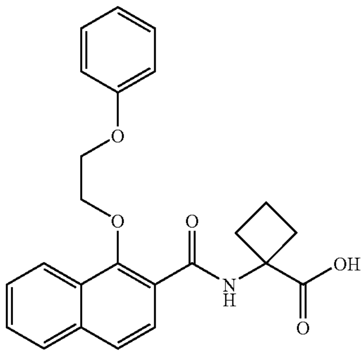 | 1-{1-(2-Phenoxy-ethoxy)-naphthalene-2-carbonyl]-amino}-cyclobutanecarboxylic acid | 406.18 |
| 101 | 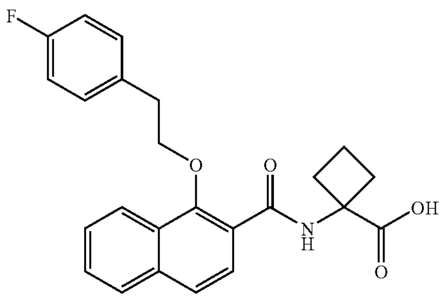 [SMILES: O=C(NC1(C(=O)O)CCC1)c1ccc2ccccc2c1OCCc1ccc(F)cc1] | 1-({1-[2-(4-Fluoro-pheny)-ethoxy]-naphthalene-2-carbonyl}-amino)-cyclobutanecarboxylic acid | 408.18 |
| 102 | 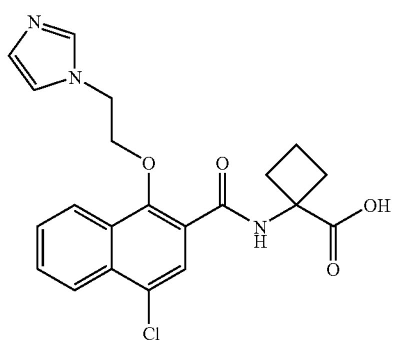 [SMILES: O=C(NC1(C(=O)O)CCC1)c1cc(Cl)c2ccccc2c1OCCn1ccnc1] | 1-{[4-Chloro-1-(2-imidazol-1-yl-ethoxy)-naphthalene-2-carbonyl]-amino}-cyclobutanecarboxylic acid | 414.1 |
| 103 | 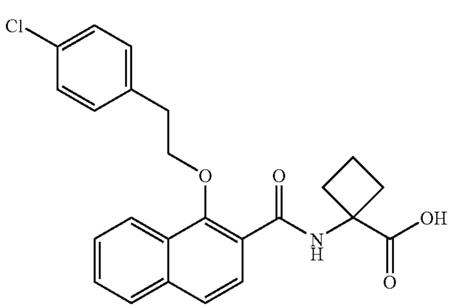 [SMILES: O=C(NC1(C(=O)O)CCC1)c1ccc2ccccc2c1OCCc1ccc(Cl)cc1] | 1-({1-[2-(4-Chloro-phenyl)-ethoxy]-naphthalene-2-carbonyl}-amino)-cyclobutanecarboxylic acid | 424.15 |

-continued

| No. | Structure | Name | ESI+ or ESI− |
|---|---|---|---|
| 104 | 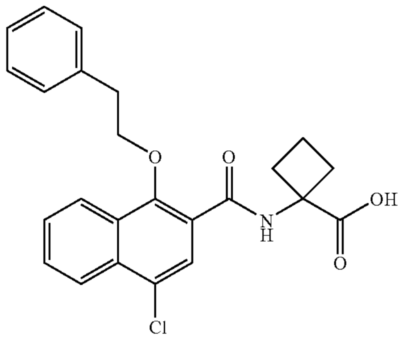 [SMILES: O=C(NC1(C(=O)O)CCC1)c1cc(Cl)c2ccccc2c1OCCc1ccccc1] | 1-[(4-Chloro-1-phenethyloxy-naphthalene-2-carbonyl)-amino]-cyclobutanecarboxylic acid | 424.16 |
| 105 | 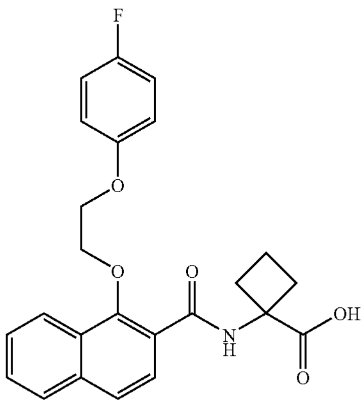 [SMILES: O=C(NC1(C(=O)O)CCC1)c1ccc2ccccc2c1OCCOc1ccc(F)cc1] | 1-({1-[2-(4-Fluoro-phenoxy)-ethoxy]-naphthalene-2-carbonyl}-amino)-cyclobutanecarboxylic acid | 424.17 |
| 106 | 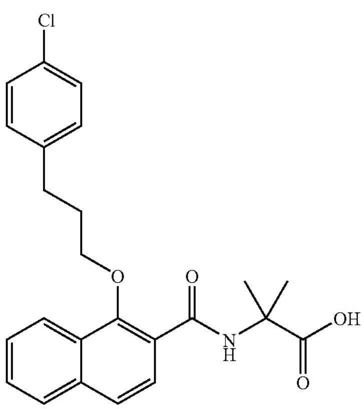 [SMILES: CC(C)(NC(=O)c1ccc2ccccc2c1OCCCc1ccc(Cl)cc1)C(=O)O] | 2-({1-[3-(4-Chloro-phenyl)-propoxy]-naphthalene-2-carbonyl}-amino)-2-methyl-propionic acid | 426.21 |
| 107 | 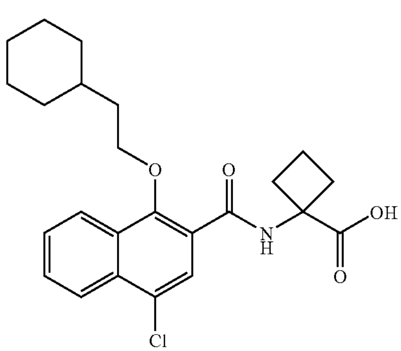 | 1-{1[4-Chloro-1-(2-cyclohexyl-ethoxy)-naphthalene-2-carbonyl]-amino}-cyclobutanecarboxylic acid | 430.22 |

-continued
| No. | Structure | Name | ESI+ or ESI− |
|---|---|---|---|
| 108 | 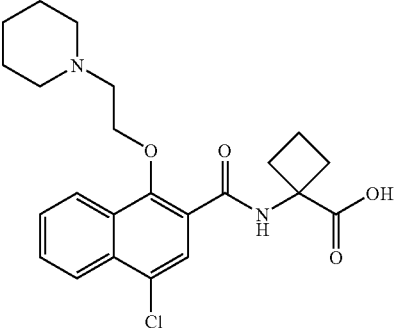 [SMILES: O=C(NC1(C(=O)O)CCC1)c1cc(Cl)c2ccccc2c1OCCN1CCCCC1] | 1-{[4-Chloro-1-(2-piperidin-1-yl-ethoxy)-naphthalene-2-carbonyl]-amino}-cyclobutanecarboxylic acid | 431.15 |
| 109 | 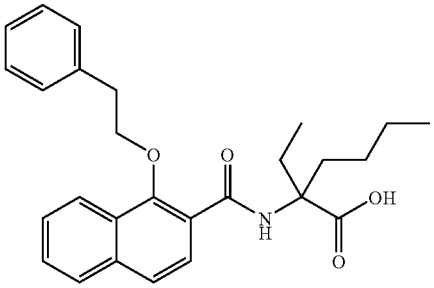 [SMILES: CCCCC(CC)(NC(=O)c1ccc2ccccc2c1OCCc1ccccc1)C(=O)O] | 2-Ethyl-2-[(1-phenethyloxy-naphthalene-2-carbonyl)-amino]-hexanoic acid | 434.27 |
| 110 | 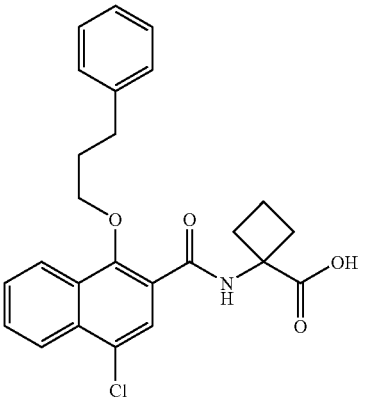 [SMILES: O=C(NC1(C(=O)O)CCC1)c1cc(Cl)c2ccccc2c1OCCOc1ccccc1] | 1-{[4-Chloro-1-(3-phenyl-propoxy)-naphthalene-2-carbonyl]-amino}-cyclobutanecarboxylic acid | 438.17 |
| 111 | 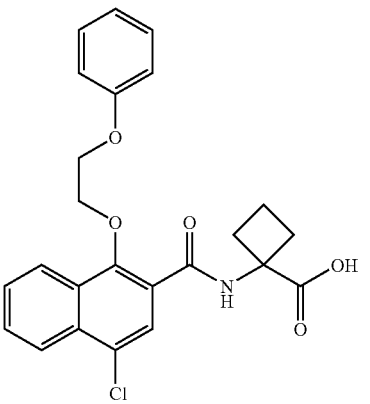 | 1-{[4-Chloro-1-(2-phenoxy-ethoxy)-naphthalene-2-carbonyl]-amino}-cyclobutanecarboxylic acid | 440.16 |

-continued

| No. | Structure | Name | ESI+ or ESI− |
|---|---|---|---|
| 112 | 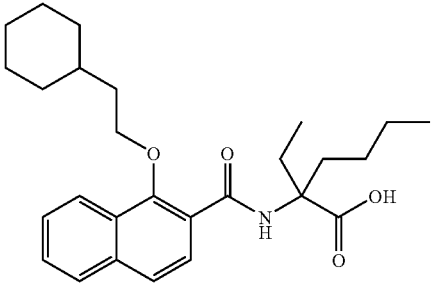 [SMILES: CCCCC(CC)(NC(=O)c1ccc2ccccc2c1OCCC1CCCCC1)C(=O)O] | 2-{[1-(2-Cyclohexyl-ethoxy)-naphthalene-2-carbonyl]-amino}-2-ethyl-hexanoic acid | 440.25 |
| 113 | 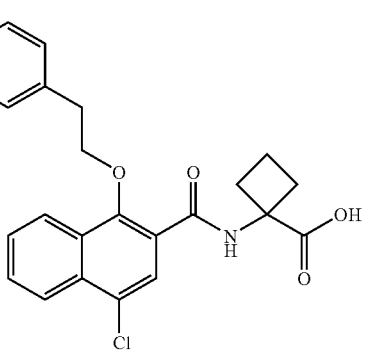 | 1-({4-Chloro-1-[2-(4-fluoro-phenyl)-ethoxy]-naphthalene-2-carbonyl}-amino)-cyclobutanecarboxylic acid | 442.15 |
| 114 | 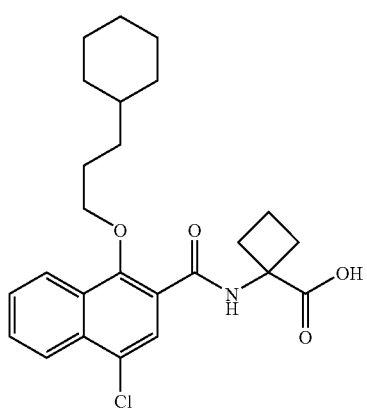 [SMILES: O=C(NC1(C(=O)O)CCC1)c1cc(Cl)c2ccccc2c1OCCCC1CCCCC1] | 1-{[4-Chloro-1-(3-cyclohexyl-propoxy)-naphthalene-2-carbonyl]-amino}-cyclobutanecarboxylic acid | 444.24 |
| 115 | 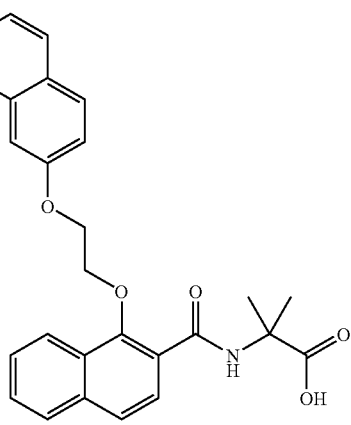 | 2-Methyl-2-({1-[2-(naphthalen-2-yloxy)-ethoxy]-naphthalene-2-carbonyl}-amino)-propionic acid | 444.29 |

-continued

| No. | Structure | Name | ESI+ or ESI− |
|---|---|---|---|
| 116 | 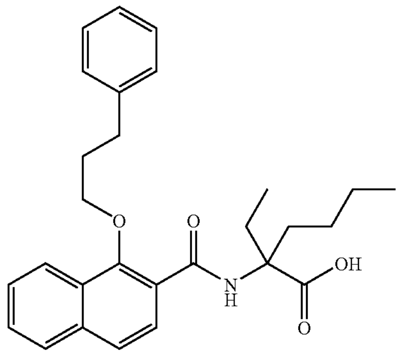 [SMILES: CCCCC(CC)(NC(=O)c1ccc2ccccc2c1OCCCc1ccccc1)C(=O)O] | 2-Ethyl-2-{[1-(3-phenyl-propoxy)-naphthalene-2-carbonyl]-amino}-hexanoic acid | 448.23 |
| 117 | 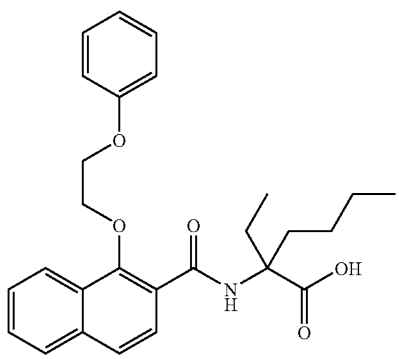 [SMILES: CCCCC(CC)(NC(=O)c1ccc2ccccc2c1OCCOc1ccccc1)C(=O)O] | 2-Ethyl-2-{[1-(2-phenoxy-ethoxy)-naphthalene-2-carbonyl]-amino}-hexanoic acid | 450.26 |
| 118 | 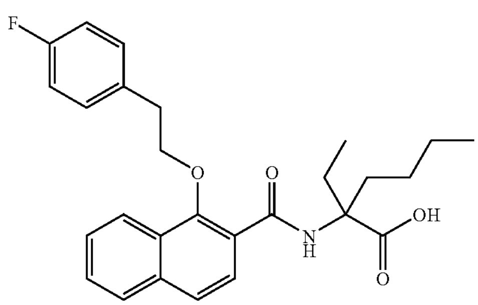 [SMILES: CCCCC(CC)(NC(=O)c1ccc2ccccc2c1OCCc1ccc(F)cc1)C(=O)O] | 2-Ethyl-2-({1-[2-(4-fluoro-phenyl)-ethoxy]-naphthalene-2-carbonyl}-amino)-hexanoic acid | 452.27 |
| 119 | 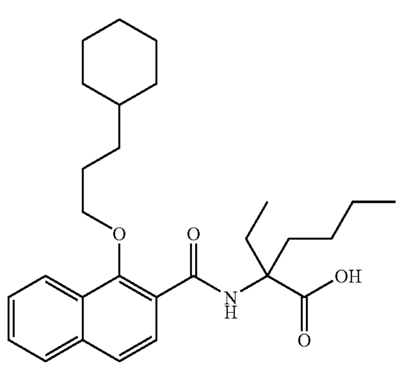 [SMILES: CCCCC(CC)(NC(=O)c1ccc2ccccc2c1OCCCC1CCCCC1)C(=O)O] | 2-{[1-(3-Cyclohexyl-propoxy)-naphthalene-2-carbonyl]-amino}-2-ethyl-hexanoic acid | 454.31 |

-continued

| No. | Structure | Name | ESI+ or ESI− |
|---|---|---|---|
| 120 | 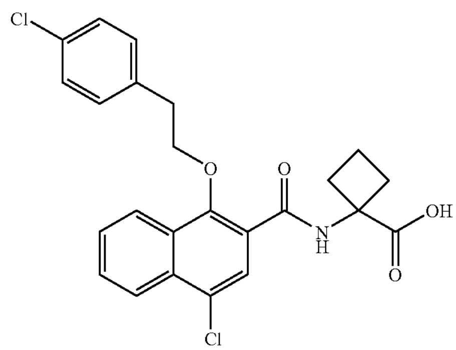 [SMILES: O=C(NC1(C(=O)O)CCC1)c1cc(Cl)c2ccccc2c1OCCc1ccc(Cl)cc1] | 1-({4-Chloro-1-[2-(4-chloro-phenyl)-ethoxy]-naphthalene-2-carbonyl}-amino)-cyclobutanecarboxylic acid | 458.15 |
| 121 | 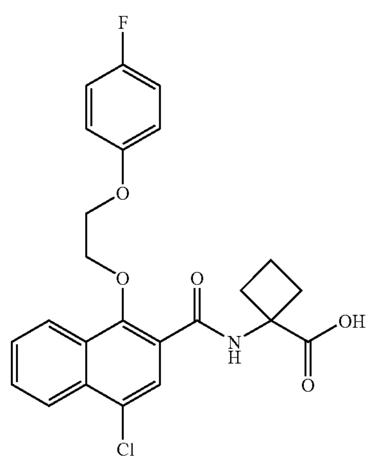 [SMILES: O=C(NC1(C(=O)O)CCC1)c1cc(Cl)c2ccccc2c1OCCOc1ccc(F)cc1] | 1-({4-Chloro-1-[2-(4-fluoro-phenoxy)-ethoxy]-naphthalene-2-carbonyl}-amino)-cyclobutanecarboxylic acid | 458.15 |
| 122 | 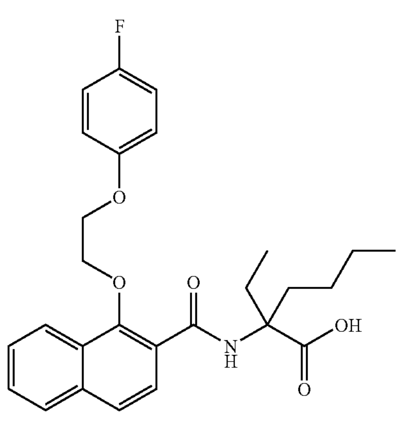 [SMILES: CCCCC(CC)(NC(=O)c1ccc2ccccc2c1OCCOc1ccc(F)cc1)C(=O)O] | 2-Ethyl-2-({1-[2-(4-fluoro-phenoxy)-ethoxy]-naphthalene-2-carbonyl}-amino)-hexanoic acid | 468.2 |

| No. | Structure | Name | ESI+ or ESI− |
|---|---|---|---|
| 123 | 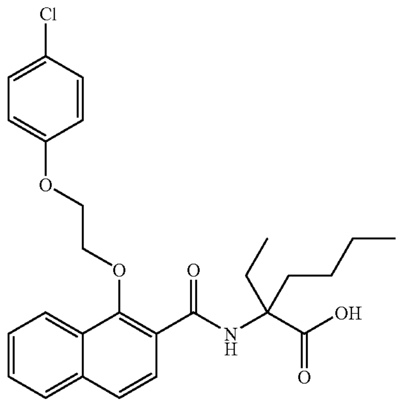 [SMILES: CCCCC(CC)(NC(=O)c1ccc2ccccc2c1OCCOc1ccc(Cl)cc1)C(=O)O] | 2-({1-[2-(4-Chloro-phenoxy)-ethoxy]-naphthalene-2-carbonyl}-amino)-2-ethyl-hexanoic acid | 484.18 |
| 124 | 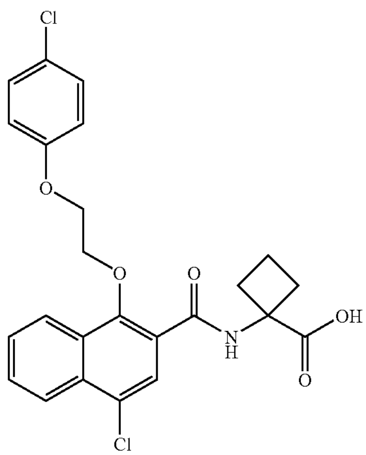 [SMILES: O=C(NC1(C(=O)O)CCC1)c1cc(Cl)c2ccccc2c1OCCOc1ccc(Cl)cc1] | 1-({4-Chloro-1-[2-(4-chloro-phenoxy)-ethoxy]-naphthalene-2-carbonyl}-amino)-cyclobutanecarboxylic acid | 474.12 476.13 (diCl— pattern) |

The following examples were prepared in analogy to example 8:

| No. | Structure | Autonom-Name | ESI+ or ESI− |
|---|---|---|---|
| 125 | CHIRAL | (S)-1-{[1-(3-Phenyl-propoxy)-naphthalene-2-carbonyl]-amino}-propionic acid | 378.2 |
| 126 | 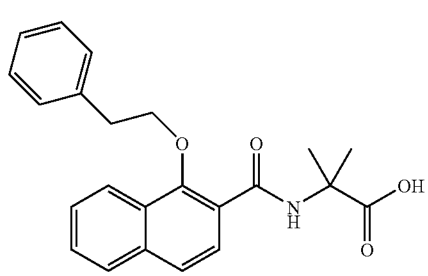 [SMILES: CC(C)(NC(=O)c1ccc2ccccc2c1OCCc1ccccc1)C(=O)O] | 2-Methyl-2-[(1-phenethyloxy-naphthalene-2-carbonyl)-amino]-propionic acid | 378.2 |

-continued

| No. | Structure | Autonom-Name | ESI+ or ESI− |
|---|---|---|---|
| 127 | CHIRAL | (S)-2-{[1-(3-Pyridin-2-yl-propoxy)-naphthalene-2-carbonyl]-amino}-propionic acid | 379.2 |
| 128 | 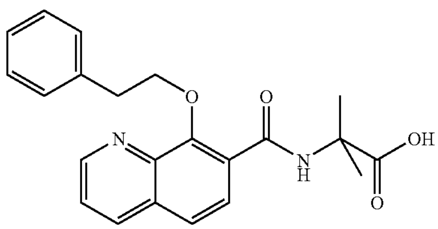 [SMILES: CC(C)(NC(=O)c1ccc2cccnc2c1OCCc1ccccc1)C(=O)O] | 2-Methyl-2-[(8-phenethyloxy-quinoline-7-carbonyl)-amino]-propionic acid | 379.2 |
| 129 | 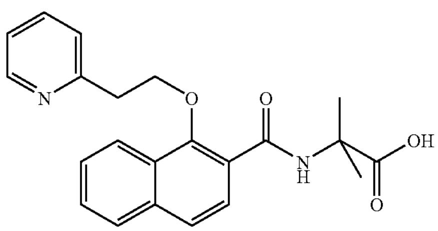 [SMILES: CC(C)(NC(=O)c1ccc2ccccc2c1OCCc1ccccn1)C(=O)O] | 2-Methyl-2-{[1-(2-pyridin-2-yl-ethoxy)-naphthalene-2-carbonyl]-amino}-propionic acid | 379.2 |
| 130 | CHIRAL | (R)-2-({1-[2-(4-Fluoro-phenyl)-ethoxy]-naphthalene-2-carbonyl}-amino)-propionic acid | 382.16 |
| 131 | 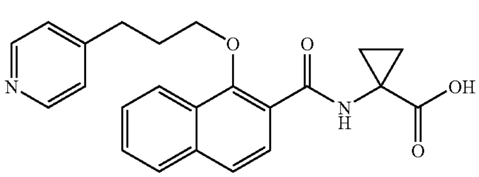 [SMILES: O=C(NC1(C(=O)O)CC1)c1ccc2ccccc2c1OCCCc1ccncc1] | 1-{[1-(3-Pyridin-4-yl-propoxy)-naphthalene-2-carbonyl]-amino}-cyclopropanecarboxylic acid | 391.2 |
| 132 | CHIRAL | (S)-2-{[1[1-(1-Methyl-3-phenyl-propoxy)-naphthalene-2-carbonyl]-amino}-propionic acid | 392.19 |

-continued

| No. | Structure | Autonom-Name | ESI+ or ESI– |
|---|---|---|---|
| 133 | CHIRAL | (S)-3-Methyl-2-[(1-phenethyloxy-naphthalene-2-carbonyl)-amino]-butyric acid | 392.2 |
| 134 | 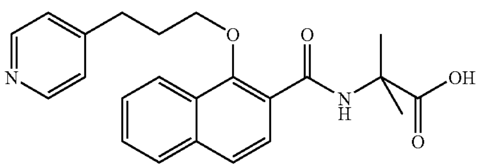 [SMILES: CC(C)(NC(=O)c1ccc2ccccc2c1OCCCc1ccncc1)C(=O)O] | 2-Methyl-2-{[1-(3-pyridin-4-yl-propoxy)-naphthalene-2-carbonyl]-amino}-propionic acid | 393.2 |
| 135 | 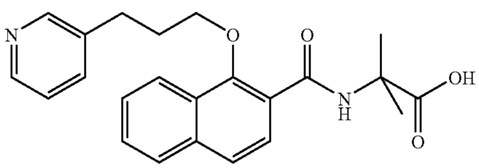 [SMILES: CC(C)(NC(=O)c1ccc2ccccc2c1OCCCc1cccnc1)C(=O)O] | 2-Methyl-2-{[1-(3-pyridin-3-yl-propoxy)-naphthalene-2-carbonyl]-amino}-propionic acid | 393.2 |
| 136 | 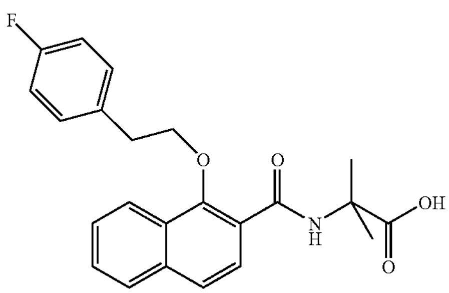 [SMILES: CC(C)(NC(=O)c1ccc2ccccc2c1OCCc1ccc(F)cc1)C(=O)O] | 2-({1-[2-(4-Fluoro-phenyl)-ethoxy]-naphthalene-2-carbonyl}-amino)-2-methyl-propionic acid | 396.17 |
| 137 | 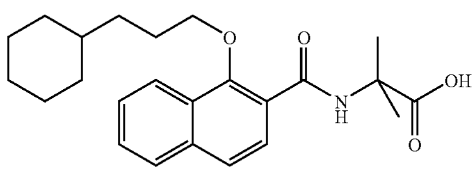 [SMILES: CC(C)(NC(=O)c1ccc2ccccc2c1OCCCC1CCCCC1)C(=O)O] | 2-{[1-(3-Cyclohexyl-propoxy)-naphthalene-2-carbonyl]-amino}-2-methyl-propionic acid | 398.2 |
| 138 | 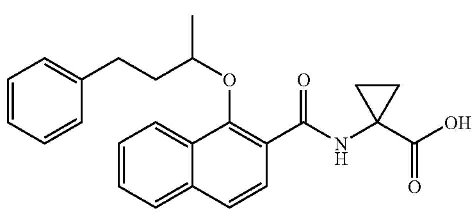 [SMILES: CC(CCc1ccccc1)Oc1c(C(=O)NC2(C(=O)O)CC2)ccc2ccccc12] | 1-{[1-(1-Methyl-3-phenyl-propoxy)-naphthalene-2-carbonyl]-amino}-cyclopropanecarboxylic acid | 404.2 |
| 139 | CHIRAL | (2S,3S)-3-Methyl-2-[(1-phenethyloxy-naphthalene-2-carbonyl)-amino]-pentanoic acid | 406.2 |

| No. | Structure | Autonom-Name | ESI+ or ESI− |
|---|---|---|---|
| 140 | 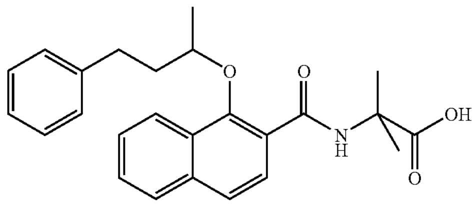 | 2-Methyl-2-{[1-(1-methyl-3-phenyl-propoxy)-naphthalene-2-carbonyl]-amino}-propionic acid | 406.26 |
| 141 | 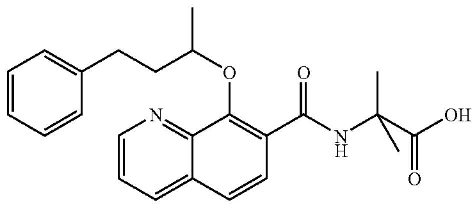 [SMILES: CC(CCc1ccccc1)Oc1c(C(=O)NC(C)(C)C(=O)O)ccc2cccnc12] | 2-Methyl-2-{[8-(1-methyl-3-phenyl-propoxy)-quinoline-7-carbonyl]-amino}-propionic acid | 407.2 |
| 142 | CHIRAL | (S)-3-Methyl-2-{[1-(2-phenoxy-ethoxy)-naphthalene-2-carbonyl]-amino}-butyric acid | 408.2 |
| 143 | CHIRAL | (2S,3S)-3-Methyl-2-{[1-(2-phenoxy-ethoxy)-naphthalene-2-carbonyl]-amino}-pentanoic acid | 422.2 |
| 144 | CHIRAL | (2S,3S)-3-Methyl-2-{[1-(1-methyl-3-phenyl-propoxy-naphthalene-2-carbonyl]-amino}-prantanoic acid | 434.32 |
| 145 | CHIRAL | (S)-2-[(1-Phenethyloxy-naphthalene-2-carbonyl)-amino]-3-phenyl-propionic acid | 440.2 |
| 146 | 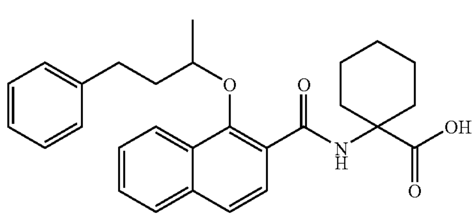 [SMILES: CC(CCc1ccccc1)Oc1c(C(=O)NC2(C(=O)O)CCCCC2)ccc2ccccc12] | 1-{[1-(1-Methyl-3-pheyl-propoxy)-naphthalene-2-carbonyl]-amino}-cyclohexanecarboxylic acid | 446.3 |

| No. | Structure | Autonom-Name | ESI+ or ESI− |
|---|---|---|---|
| 147 | CHIRAL | (S)-2-{[1-(2-Phenoxy-ethoxy)-naphthalene-2-carbonyl]-amino}-3-phenyl-propionic acid | 456.3 |
| 148 | 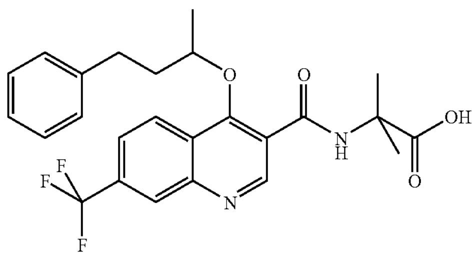 [SMILES: CC(CCc1ccccc1)Oc1c(C(=O)NC(C)(C)C(=O)O)cnc2cc(C(F)(F)F)ccc12] | 2-Methyl-2-{[4-(1-methyl-3-phenyl-propoxy)-7-trifluoromethyl-quinoline-3-carbonyl]-amino}-propionic acid | 475.3 |
| 149 | CHIRAL | (S)-3-(4-Fluoro-phenyl)-2-{[1-(1-methyl-3-phenyl-propoxy)-naphthalene-2-carbonyl]-amino}-propionic acid | 486.3 |
| 150 | CHIRAL | (S)-2-[(1-Phenethyloxy-naphthalene-2-carbonyl)-amino]-propionic acid | 386.2 (M + H + 22) |
| 151 | CHIRAL | (R)-2-[(1-Phenethyloxy-naphthalene-2-carbonyl)-amino]-propionic acid | 386.2 (M + H + 22) |
| 152 | CHIRAL | (R)-2-{[1-(3-Phenyl-propoxy)-naphthalene-2-carbonyl]-amino}-propionic acid | 400.2 (M + H + 22) |

-continued

| No. | Structure | Autonom-Name | ESI+ or ESI− |
|---|---|---|---|
| 153 | 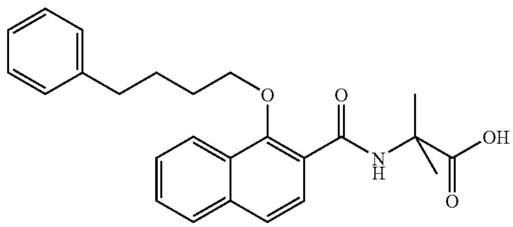 [SMILES: CC(C)(NC(=O)c1ccc2ccccc2c1OCCCCc1ccccc1)C(=O)O] | 2-Methyl-2-{[1-(4-phenyl-butoxy)-naphthalene-2-carbonyl]-amino}-propionic acid | 406.2 |
| 154 | CHIRAL | (S)-2-{[1-(4-Phenyl-butoxy)-naphthalene-2-carbonyl]-amino}-propionic acid | 414.2 (M + H + 22) |
| 155 | CHIRAL | (R)-2-{[1-(4-Phenyl-butoxy)-naphthalene-2-carbonyl]-amino}-propionic acid | 414.2 (M + H + 22) |
| 156 | CHIRAL | (R)-2-{[1-(1-Methyl-3-phenyl-propoxy)-naphthalene-2-carbonyl]-amino}-propionic acid | 414.2 (M + H + 22) |
| 157 | 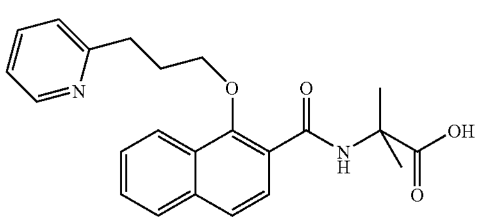 [SMILES: CC(C)(NC(=O)c1ccc2ccccc2c1OCCCc1ccccn1)C(=O)O] | 2-Methyl-2-{[1-(3-pyridin-2-yl-propoxy)-naphthalene-2-carbonyl]-amino}-propionic acid | 415.2 (M + H + 22) |
| 158 | 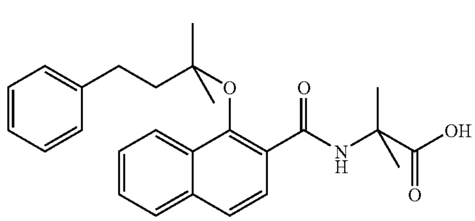 [SMILES: CC(C)(CCc1ccccc1)Oc1c(C(=O)NC(C)(C)C(=O)O)ccc2ccccc12] | 2-{[1-(1,1-Dimethyl-3-phenyl-propoxy)-naphthalene-2-carobnyl]-amino}-2-methyl-propionic acid | 442.2 (M + H + 22) |

-continued

| No. | Structure | Autonom-Name | ESI+ or ESI− |
|---|---|---|---|
| 159 | 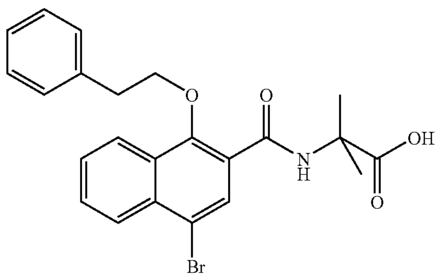 [SMILES: CC(C)(NC(=O)c1cc(Br)c2ccccc2c1OCCc1ccccc1)C(=O)O] | 2-[(4-Bromo-1-phenethyloxy-naphthalene-2-carbonyl)-amino]-2-methyl-propionic acid | 456.3 458.3 (Br— pattern) |
| 160 | CHIRAL | (S)-3-(4-Fluoro-phenyl)-2-[(1-phenethyloxy-naphthalene-2-carbonyl)-amino]-propionic acid | 458.3 |
| 161 | 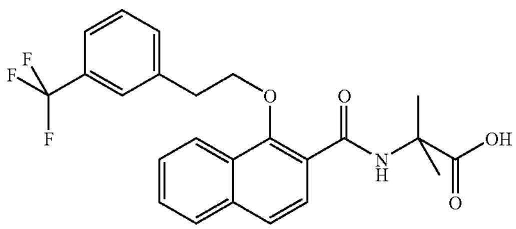 [SMILES: CC(C)(NC(=O)c1ccc2ccccc2c1OCCc1cccc(C(F)(F)F)c1)C(=O)O] | 2-Methyl-2-({1-[2-(3-trifluoromethyl-phenyl)-ethoxy]-naphthalene-2-carbonyl}-amino)-propionic acid | 468.3 (M + H + 22) |
| 162 | 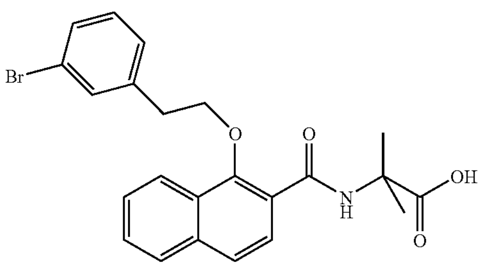 [SMILES: CC(C)(NC(=O)c1ccc2ccccc2c1OCCc1cccc(Br)c1)C(=O)O] | 2-({1-[2-(3-Bromo-phenyl)-ethoxy]-naphthalene-2-carbonyl}-amino)-2-methyl-propionic acid | 478.3 480.3 (M + H + 22, Br— pattern) |
| 163 | 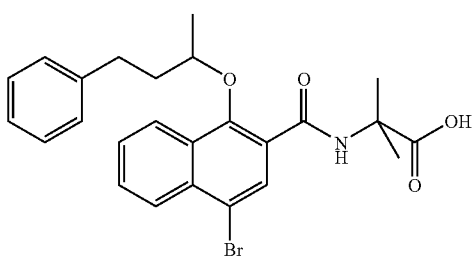 [SMILES: CC(CCc1ccccc1)Oc1c(C(=O)NC(C)(C)C(=O)O)cc(Br)c2ccccc12] | 2-{[4-Bromo-1-(1-methyl-3-phenyl-propoxy)-naphthalene-2-carbonyl]-amino}-2-methyl-propionic acid | 484.3 484.3 (Br— pattern) |
| 164 | CHIRAL | (S)-3-(4-Fluoro-phenyl)-2-{[1-(2-phenoxy-ethoxy)-naphthalene-2-carbonyl]-amino}-propionic acid | 496.3 |

The following examples were prepared in analogy to example 12 via a sequence of a Sonogashira coupling of a suitable alkyne with 2-[(1-bromo-naphthalene-2-carbonyl)-amino]-2-methyl-propionic acid methyl ester and a subsequent ester hydrolysis:

| No. | Structure | Name | ESI+ or ESI− |
|---|---|---|---|
| 165 | 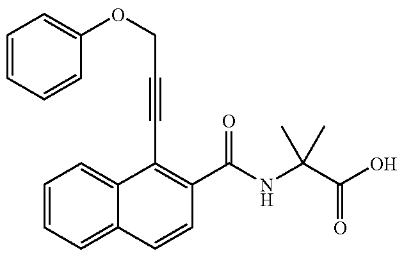 [SMILES: CC(C)(NC(=O)c1ccc2ccccc2c1C#CCOc1ccccc1)C(=O)O] | 2-Methyl-2-{[1-(3-phenoxy-prop-1-ynyl)-naphthalene-2-carbonyl]-amino}-propionic acid | 388.13 |
| 166 | 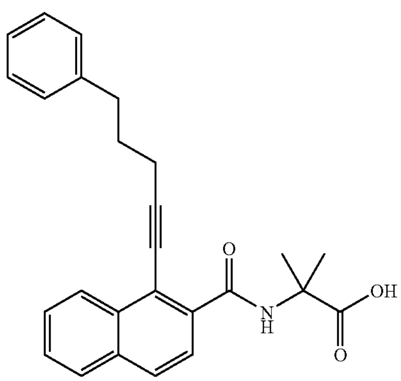 [SMILES: CC(C)(NC(=O)c1ccc2ccccc2c1C#CCCCc1ccccc1)C(=O)O] | 2-Methyl-2-{[1-(5-phenyl-pent-1-ynyl)-naphthalene-2-carbonyl]-amino}-propionic acid | 400.18 |

The following examples were prepared in analogy to example 13 via a sequence of a hydrogenation of a suitable alkyne and a subsequent ester hydrolysis:

| No. | Structure | Name | ESI+ or ESI− |
|---|---|---|---|
| 167 | 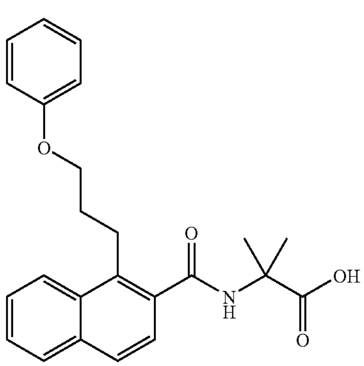 [SMILES: CC(C)(NC(=O)c1ccc2ccccc2c1CCCOc1ccccc1)C(=O)O] | 2-Methyl-2-{[1-(3-phenoxy-propyl)-naphthalene-2-carbonyl]-amino}-propionic acid | 392.16 |

-continued

| No. | Structure | Name | ESI+ or ESI– |
|---|---|---|---|
| 168 | 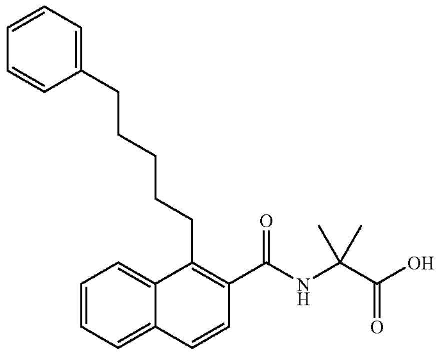 [SMILES: CC(C)(NC(=O)c1ccc2ccccc2c1CCCCCc1ccccc1)C(=O)O] | 2-Methyl-2-{[1-(5-phenyl-pentyl)-naphthalene-2-carbonyl]-amino}-propionic acid | 404.15 |

The following enantiomers were obtained after separation of the racemates by preparative HPLC using a Waters Alliance 2695 system with chiral columns and solvent mixtures at a flow rate of 1 ml/min as given in the following table.

| Exp. No. | Structure of racemate | Conditions of separation | No. of enantiomer | Rt [min] | % ee |
|---|---|---|---|---|---|
| 169 | | Chiralcel OJ 250 × 4.6 mm; heptane/EtOH/ MeOH 15/1/1 + 0.1% TFA | 1 | 7.6 | >98 |
| 217 | | | 2 | 10.9 | >98 |
| 171 | | Chiralpak AD-H 250 × 4.6 mm, heptane/EtOH/ MeOH 15/1/1 + 0.1% TFA | 1 | 9.8 | >98 |
| 172 | | | 2 | 12.0 | 87 |
| 173 | | Chiralcel OD-H 250 × 4.6 mm; heptane/EtOH/ MeOH 25/1/1 + 0.1% TFA | 1 | 8.1 | >98 |
| 174 | | | 2 | 9.4 | 94 |
| 175 | | Chiracel OJ 250 × 4.6 mm, heptane/EtOH/ MeOH 15/1/1 + 0.1% TFA | 1 | 10.1 | >98 |
| 176 | | | 2 | 13.1 | 93 |

The following examples were prepared in analogy to example 1 via a sequence of a coupling of a suitable (ortho-)hydroxy-arene-carboxylic acid with a corresponding amino acid ester using coupling reagents as for example EDC/HOBT, DIC/HOBT, HATU, TBTU/DMAP, followed by an alkylation reaction to attach a suitably substituted alkylating agent to the aromatic hydroxy group and finally a basic hydrolysis of the amino acid ester to the free amino acid:

| No. | Structure | Name | ESI+ or ESI− |
|---|---|---|---|
| 177 | 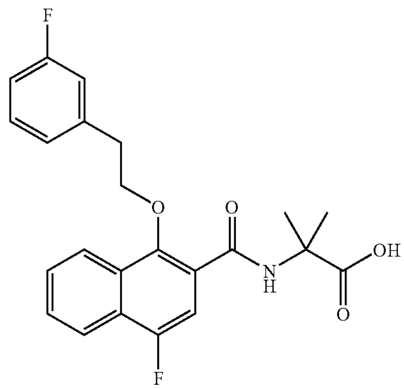 [SMILES: CC(C)(NC(=O)c1cc(F)c2ccccc2c1OCCc1cccc(F)c1)C(=O)O] | 2-({4-Fluoro-1-[2-(3-fluoro-phenyl)-ethoxy]-naphthalene-2-carbonyl}-amino)-2-methyl-propionic acid | 414.18 |
| 178 | 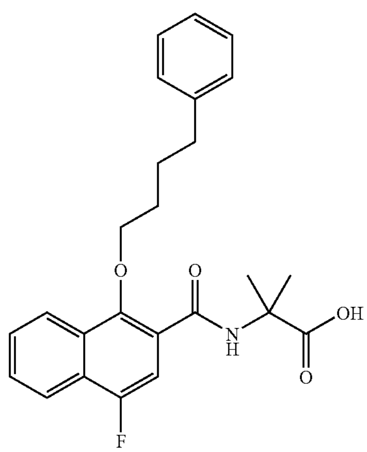 [SMILES: CC(C)(NC(=O)c1cc(F)c2ccccc2c1OCCCCc1ccccc1)C(=O)O] | 2-{[4-Fluoro-1-(4-phenyl-butoxy)-naphthalene-2-carbonyl]-amino}-3-methyl-propionic acid | 424.25 |
| 179 | 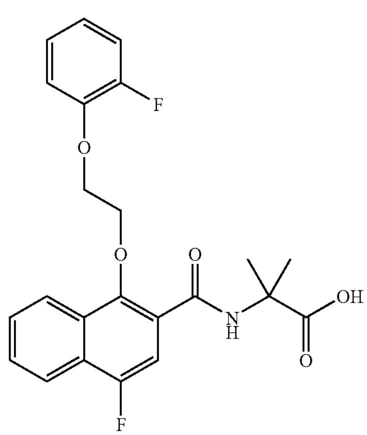 [SMILES: CC(C)(NC(=O)c1cc(F)c2ccccc2c1OCCOc1ccccc1F)C(=O)O] | 2-({4-Fluoro-1-[2-(2-fluoro-phenoxy)-ethoxy]-naphthalene-2-carbonyl}-amino)-2-methyl-propionic acid | 430.18 |

-continued
| No. | Structure | Name | ESI+ or ESI− |
|---|---|---|---|
| 180 | 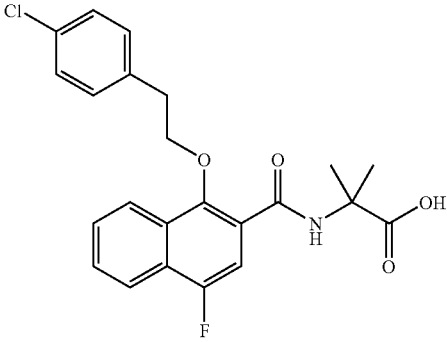 [SMILES: CC(C)(NC(=O)c1cc(F)c2ccccc2c1OCCc1ccc(Cl)cc1)C(=O)O] | 2-({1-[2-(4-Chloro-phenyl)-ethoxy]-4-fluoro-naphthalene-2-carbonyl}-amino)-2-methyl-propionic acid | 430.13 |
| 181 | 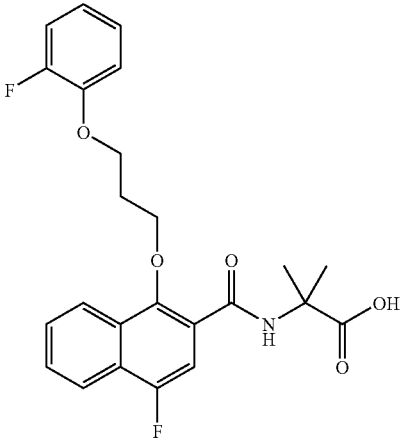 [SMILES: CC(C)(NC(=O)c1cc(F)c2ccccc2c1OCCCOc1ccccc1F)C(=O)O] | 2-({4-Fluoro-1-[3-(2-fluoro-phenoxy)-propoxy]-naphthalene-2-carbonyl}-amino)-2-methyl-propionic acid | 444.20 |
| 182 | 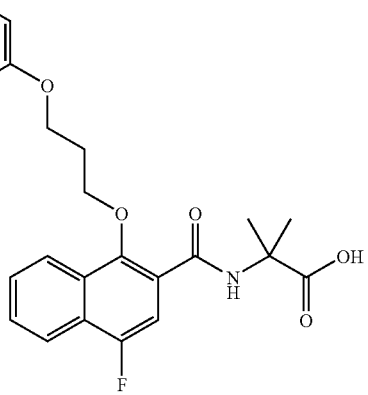 | 2-({4-Fluoro-1-[3-(4-fluoro-phenoxy)-propoxy]-naphthalene-2-carbonyl}-amino)-2-methyl-propionic acid | 444.17 |

| No. | Structure | Name | ESI+ or ESI− |
|---|---|---|---|
| 183 | 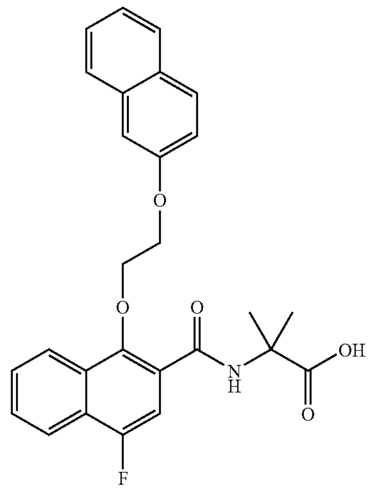 [SMILES: CC(C)(NC(=O)c1cc(F)c2ccccc2c1OCCOc1ccc2ccccc2c1)C(=O)O] | 2-({4-Fluoro-1-[2-(naphthalen-2-yloxy)-ethoxy]-naphthalene-2-carbonyl}-amino)-2-methyl-propionic acid | 462.17 |

The following example was prepared in analogy to example 2 via a sequence of a coupling of a suitable (ortho-)hydroxy-arene-carboxylic acid with a corresponding amino acid ester using coupling reagents as for example EDC/HOBT, DIC/HOBT, HATU, TBTU/DMAP, followed by a Mitsunobu reaction of a suitably substituted alcohol with the aromatic hydroxy group and finally a basic hydrolysis of the amino acid ester to the free amino acid:

| No. | Structure | Name | ESI+ or ESI− |
|---|---|---|---|
| 184 | 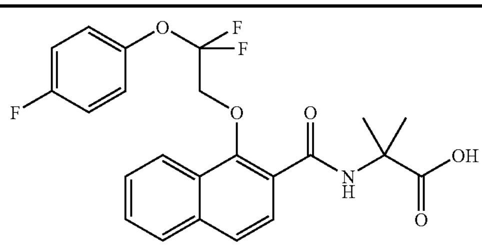 | 2-({1-[2,2-Difluoro-2-(4-fluoro-phenoxy)-ethoxy]-naphthalene-2-carbonyl}-amino)-2-methyl-propionic acid | 448.14 |

The following example was prepared in analogy to example 3 via a sequence of an alkylation of a suitable (ortho-)hydroxy-arene-carboxylic ester with a corresponding alkylating agent, followed by a basic hydrolysis of this ester, and a coupling of the resulting acid with a corresponding amino acid ester using coupling reagents as for example EDC/HOBT, DIC/HOBT, HATU, TBTU/DMAP, and finally a basic hydrolysis of the amino acid ester to the free amino acid:

| No. | Structure | Name | ESI+ or ESI− |
|---|---|---|---|
| 185 | 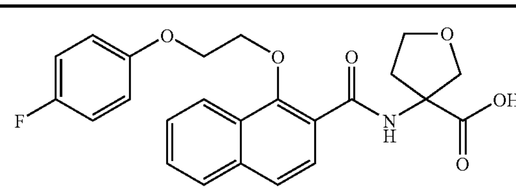 | 3-({1-[2-(4-Fluoro-phenoxy)-ethoxy]-naphthalene-2-carbonyl}-amino)-tetrahydro-furan-3-carboxylic acid | 440.05 |

Preparation of Intermediates

4-Fluoro-1-hydroxynaphthalene-2-carboxylic acid

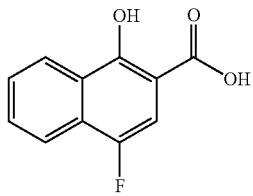

a) 4-Fluoro-naphthalene-1-carbaldehyde 19.9 g Dichloromethyl methyl ether and 45.7 g tin chloride were dissolved in 70 ml dichloromethane. The solution was cooled to +5° C. and 20.0 g fluoronapthalene in dichloromethane (49 ml) was added over a 60 min period, while keeping the temperature at 5° C. The reaction was brought to room temperature after the addition. After 4 h the reaction was quenched by slowly pouring it into an ice/water mixture. This mixture was stirred for 15 min and left standing overnight. The dichloromethane layer was washed with water, dried (sodium sulfate), filtered through celite and concentrated in vacuo to obtain 24.0 g of 4-fluoro-naphthalene-1-carbaldehyde as an off white solid.

b) 4-Fluoro-naphthalen-1-ol 23.3 g of 4-fluoro-naphthalene-1-carbaldehyde were dissolved in 200 ml dichloromethane. 65.9 g MCPBA was added neat in portions over a 15 min period, 70 ml additional dichloromethane was added and the reaction was stirred overnight at ambient temperature. Then, the reaction mixture was filtered and the solid was washed with dichloromethane. heptane was added and the mixture filtrated several times, then the combined filtrates were concentrated and taken up in ethyl acetate. This was shaken with 10% sodium thiosulfate (100 ml). The organic layer was separated, washed water and brine, dried over sodium sulfate, filtered and concentrated to yield 27.3 g of the formate ester as a viscous oil, which was dissolved in MeOH (80 ml), treated with KOH (7.5 g) in a methanol solution (30 ml) for 15 min at 5° C. and was then left stirring at ambient temperature for 3 h, before the solvent was removed in vacuo. The resulting oil was treated with 6N HCl (40 ml) to obtain a pH of 2-3. Water (60 ml) was added and the aqueous phase was extracted 3× with ethyl acetate (35 ml). The extracts were washed with water (2×20 ml) and concentrated to yield 23.7 g of 4-fluoro-naphthalen-1-ol, which was used without further purification.

c) 4-Fluoro-1-methoxynaphthalene 21.7 g of 4-Fluoro-naphthalen-1-ol were dissolved in 250 ml acetone. 39.0 g of potassium carbonate and 14.6 ml dimethyl sulfate were added at room temperature. The reaction was placed under nitrogen and stirred for 72 h. The mixture was filtrated, the solid washed with acetone, and the filtrate was concentrated to a viscous oil, which was taken up in ethyl acetate. This was washed with water and with brine, dried over sodium sulfate, filtered through celite and concentrated. The resulting oil was distilled using a Kugelrohr-apparatus, yielding 11.4 g of 4-fluoro-1-methoxynaphthalene.

d) 4-Fluoro-1-methoxynaphthalene-2-carbaldehyde 5.25 ml of dichloromethyl methyl ether were dissolved in 40 ml dichloromethane and cooled to +5° C. 6.75 ml tin(IV) chloride were added neat over 45 min to the solution. After the addition the mixture was stirred for 45 min at 5° C. 11.4 g 4-fluoro-1-methoxy-naphthalene in 30 ml dichloromethane was added over 1 h. Then the cooling bath was removed, and the mixture was stirred for 2 h at ambient temperature. It was then poured into ice/water. The dichloromethane layer was separated and the aqueous phase was extracted with dichloromethane. The combined dichloromethane layers were washed with water, dried over sodium sulfate, filtered through celite and concentrated in vacuo. The residue was treated with pentane to yield 9.3 g of 4-fluoro-1-methoxynaphthalene-2-carbaldehyde as a brown solid.

e) 4-Fluoro-1-methoxynaphthalene-2-carboxylic acid 9.3 g of 4-fluoro-1-methoxynaphthalene-2-carbaldehyde were dissolved in 100 ml of acetonitrile. 2.1 g sodium dihydrogenphsophate monohydrate in 10 ml of water were added, followed by the addition of 9.5 ml hydrogen peroxide (30%). 8.9 g sodium chlorite, dissolved in 20 ml water were added dropwise while maintaining an internal temperature between 5° C. and 15° C. The reaction was then allowed to come to room temp over 2.5 h. The precipitated solid was filtered with suction, and the solid was washed with water, and dried in vacuo at 40° C. to yield 9.4 g of 4-fluoro-1-methoxynaphthalene-2-carboxylic acid. The filtrate was treated with 60 ml of cold 10% aqueous sodium bisulfite solution. The aqueous layer was extracted with ethyl acetate. The combined organic layers were washed with water and brine. The organic layer was washed with 0.2 N NaOH twice. The washes were acidified with 6 N HCl to pH 3, whereupon crystallization occurred. The precipitating product was filtered, washed with water and dried in vacuo at 40° C. to yield a second batch of 1.0 g of 4-fluoro-1-methoxynaphthalene-2-carboxylic acid.

f) 4-Fluoro-1-hydroxynaphthalene-2-carboxylic acid

To 10.1 g 4-fluoro-1-methoxynaphthalene-2-carboxylic acid 55 ml HBr/HOAc were added and the mixture was stirred and heated. After 30 min at 60° C. another 7.5 ml of hBr/HOAc were added, and after an additional 30 min at 80° C. the mixture was cooled to ambient temperature and left standing overnight. The reaction was then poured into ice/water and the precipitated solid was filtered and washed with water, followed by 1% ether in heptane and then by heptane. The solid was dried in vacuo at 40° C. to yield 7.7 g 4-fluoro-1-hydroxynaphthalene-2-carboxylic acid.

$C_{11}H_7FO_3$ (206.18), LCMS: (ESI$^+$): 207.2 (MH$^+$).

4-Chloro-1-hydroxy-naphthalene-2-carboxylic acid

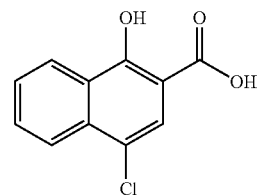 [SMILES: O=C(O)c1cc(Cl)c2ccccc2c1O]

To a suspension of 30.0 g 1-Hydroxy-naphthalene-2-carboxylic acid in 600 ml chloroform a mixture of 14.9 ml sulfuryl chloride and 20 ml chloroform was added dropwise. After stirring the reaction for 8 h at room temperature the precipitated product was isolated by filtration, washed with dichloromethane and recrystallized from isopropanol/water to yield 25.1 g of 4-chloro-1-hydroxy-naphthalene-2-carboxylic acid as off-white solid.

$C_{11}H_7ClO_3$ (222.63, LCMS (ESI): 223.00 (MH$^+$).

4-Bromo-1-hydroxy-naphthalene-2-carboxylic acid

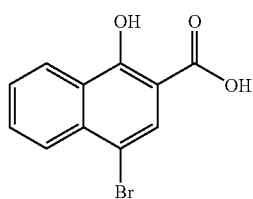 [SMILES: O=C(O)c1cc(Br)c2ccccc2c1O]

To a solution of 2.50 g 1-hydroxy-2-naphthoic acid in 50 ml chloroform a solution of 0.68 ml bromine in 5 ml chloroform was added dropwise. After 16 h the reaction was concentrated to yield 3.40 g 4-bromo-1-hydroxy-naphthalene-2-carboxylic acid.

$C_{11}H_7BrO_3$ (267.08, LCMS (ESI): 268.95 (MH$^+$).

The following intermediates were prepared in analogy to the preparation of Example 1, step a) (2-[(4-Bromo-1-hydroxy-naphthalene-2-carbonyl)-amino]-2-methyl-propionic acid methyl ester) from the corresponding 1-Hydroxy-naphthalene-2-carboxylic acids and the corresponding alpha-amino acid methyl or ethyl esters:

4,4,4-Trifluoro-2-[(1-hydroxy-naphthalene-2-carbonyl)-amino]-butyric acid methyl ester

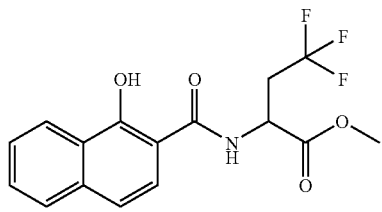 [SMILES: COC(=O)C(CC(F)(F)F)NC(=O)c1ccc2ccccc2c1O]

$C_{16}H_{14}F_3NO_4$ (341.29), LCMS (ESI): 342.35 (MH$^+$).

2-[(1-Hydroxy-naphthalene-2-carbonyl)-amino]-butyric acid ethyl ester

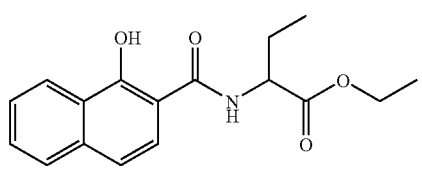 [SMILES: CCOC(=O)C(CC)NC(=O)c1ccc2ccccc2c1O]

$C_{17}H_{19}NO_4$ (301.35), LCMS (ESI): 302.08 (MH$^+$).

(S)-2-[(1-Hydroxy-naphthalene-2-carbonyl)-amino]-3-methyl-butyric acid methyl ester

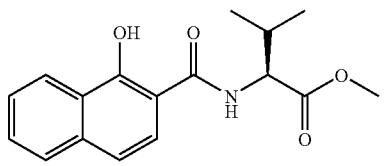 [SMILES: COC(=O)[C@@H](NC(=O)c1ccc2ccccc2c1O)C(C)C]

$C_{17}H_{19}NO_4$ (301.35), LCMS (ESI): 302.21 (MH$^+$).

(R)-2-[(1-Hydroxy-naphthalene-2-carbonyl)-amino]-3-methyl-butyric acid methyl ester

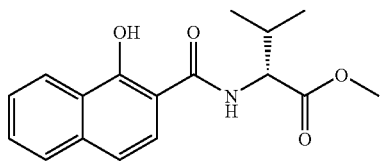 [SMILES: COC(=O)[C@H](NC(=O)c1ccc2ccccc2c1O)C(C)C]

$C_{17}H_{19}NO_4$ (301.35), LCMS (ESI): 302.17 (MH$^+$).

2-Ethyl-2-[(1-hydroxy-naphthalene-2-carbonyl)-amino]-hexanoic acid ethyl ester

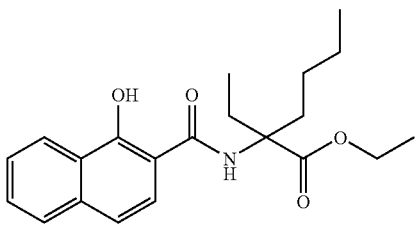 [SMILES: CCCCC(CC)(NC(=O)c1ccc2ccccc2c1O)C(=O)OCC]

$C_{21}H_{27}NO_4$ (357.45), LCMS (ESI): 358.21 (MH$^+$).

1-[(1-Hydroxy-naphthalene-2-carbonyl)-amino]-cyclobutanecarboxylic acid ethyl ester

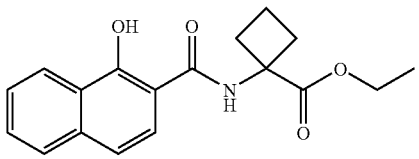 [SMILES: CCOC(=O)C1(NC(=O)c2ccc3ccccc3c2O)CCC1]

$C_{18}H_{19}NO_4$ (313.36), LCMS (ESI): 314.12 (MH$^+$).

1-[(4-Chloro-1-hydroxy-naphthalene-2-carbonyl)-amino]-cyclobutanecarboxylic acid ethyl ester

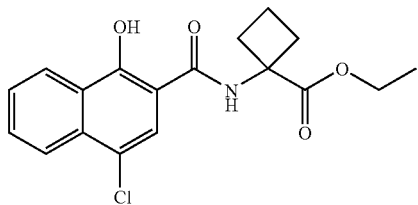 [SMILES: CCOC(=O)C1(NC(=O)c2cc(Cl)c3ccccc3c2O)CCC1]

$C_{18}H_{18}ClNO_4$ (347.80), LCMS (ESI): 348.05 (MH$^+$).

2-{[4-Fluoro-1-(hydroxy)naphthalene-2-carbonyl]-amino}-2-methyl-propionic acid methyl ester

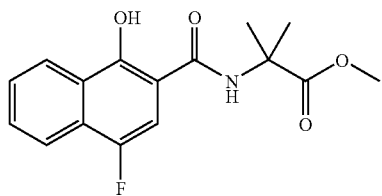 [SMILES: COC(=O)C(C)(C)NC(=O)c1cc(F)c2ccccc2c1O]

$C_{16}H_{16}FNO_4$ (305.31), LCMS: (ESI$^+$): 306.11 (MH$^+$).

2-[(4-Fluoro-1-hydroxy-naphthalene-2-carbonyl)-amino]-2-methyl-butyric acid methyl ester

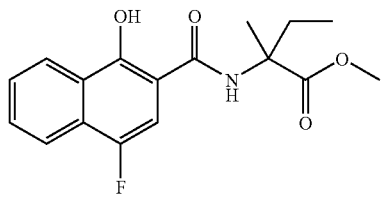 [SMILES: CCC(C)(NC(=O)c1cc(F)c2ccccc2c1O)C(=O)OC]

$C_{17}H_{18}FNO_4$ (319.34), LCMS: (ESI$^+$): 320.12 (MH$^+$).

1-[(4-Fluoro-1-hydroxy-naphthalene-2-carbonyl)-amino]-cyclopentanecarboxylic acid methyl ester

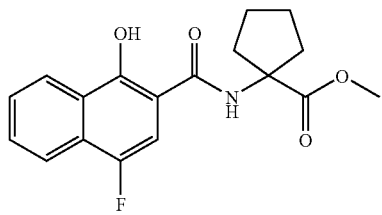 [SMILES: COC(=O)C1(NC(=O)c2cc(F)c3ccccc3c2O)CCCC1]

$C_{18}H_{18}FNO_4$ (331.35), LCMS: (ESI$^+$): 332.1 (MH$^+$).

Determination of CXCR2 inhibition: Calcium Fluorescence Assay (FLIPR)

The assay is based on the detection of intracellular calcium changes detected by the selective, calcium-chelating dye, Fluo-4 (Molecular Probes). A large fluorescence intensity increase is observed upon calcium association with Fluo-4. The dye is delivered to the cell interior using an acetoxymethylester form of Fluo-4, where the intracellular esterase activity results in the charged species being released and trapped within the cytoplasm of the cell. hence, influx of calcium to this cytoplasmic pocket, via release from intracellular pools and the phospholipase C cascade can be detected. By co-expressing the CXCR2 receptor and the promiscuous $G_{\alpha16}$ protein, activation of this chemokine receptor is directed into this phospholipase C cascade resulting in intracellular calcium mobilization.

The CHO—K1 cells stably transfected with human CXCR2 and the promiscuous $G_{\alpha16}$ protein were maintained in a log phase of growth at 37° C. and 5% $CO_2$ in the following media: Iscove's, 10% FBS, 1× Penicillin-Streptomycin, 400 µg/mL g418 and 350 µg/mL Zeocin. Approximately 24-48 hours prior to the assay, 20,000-30,000 cells/well were plated onto a 96-well black/clear bottomed assay plate (Becton Dickinson) with a well volume of 180 µl. For dye-loading the culture medium was carefully removed and replaced by 100 µl/well dye solution (4 µM Fluo-4 in 135 mM NaCl, 5 mM KCl, 1 mM magnesium sulphate, 5 mM glucose, 20 mM hepes, 2.5 mM probenecid; pH 7.4). Cells were incubated for 1 h at 37° C., and then washed 3× with buffer. After washing 90 µl buffer/well were left. Increasing concentrations of compound was added in 45 µl buffer (4× concentrated) followed by 10 min incubation at 37° C. Then the chemokine (10-100 nM) was applied in 45 µl buffer (4× concentrated) and the measurement performed for 2 min. The $IC_{50}$ value of a compound was determined by calculation of % inhibition of total calcium response to the chemokine.

Compounds of this invention exhibit activity in the CXCR2-calcium fluorescence (FLIPR) assay in a range of about 0.01 nM to 30000 nM. Some compounds of the invention may additionally exhibit activity as modulators of CXCR1 and CX3CR1.

Determination of CXCR2 Inhibition: Calcium Fluorescence Assay (FLIPR) CXCR2 Inhibition for Selected Example Compounds:

The compounds of examples 1-8, 12-15, 17, 18, 20, 22-31, 33-40, 43-60, 63-65, 67-70, 72-75, 77-89, 92-94, 97, 99, 100, 105, 106, 110-112, 116, 117, 119, 121-123, 126, 130, 140, 165, 166, 168-184 exhibited in the assay with chemokine IL-8 an $IC_{50}$ value of less than 10 µM.

More particular, the following compounds had the following activities:

| Example No. | IC50 [µM] |
|---|---|
| 46 | 1.76 |
| 52 | 0.92 |
| 55 | 2.56 |
| 73 | 1.25 |
| 105 | 3.23 |
| 166 | 1.67 |

The invention claimed is:
1. A compound of the formula I

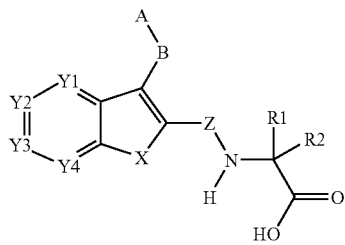

wherein

X is —CR3=CR4-;
R3 and R4 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR27R28, C(O)R29, C(O)NR30R31, $S(O)_oR32$, $S(O)_pNR33R34$, aryl, heteroaryl, arylalkyl with alkyl having 1, 2, 3 or 4 carbon atoms or heteroarylalkyl with alkyl having 1, 2, 3 or 4 carbon atoms;
R27 is hydrogen or alkyl having 1, 2, 3 or 4 carbon atoms;
R28 is hydrogen, alkyl having 1, 2, 3 or 4 carbon atoms, aryl, C(O)H, C(O)alkyl with alkyl having 1, 2, 3 or 4 carbon atoms or C(O)aryl;
R29 is hydrogen, OH, alkyl with 1, 2, 3 or 4 carbon atoms, alkoxy with 1, 2, 3 or 4 carbon atoms or aryl;
R30, R31, R33 and R34 are, independently of one another, hydrogen, alkyl having 1, 2, 3 or 4 carbon atoms or aryl;
R32 is OH, alkyl having 1, 2, 3 or 4 carbon atoms, alkoxy with 1, 2, 3 or 4 carbon atoms or aryl;
o and p are, independently of one another, 1 or 2;
Y1, Y2, Y3 and Y4 are, independently of one another, —CR8-;
R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR36R37, C(O)R38, C(O)NR39R40, $S(O)_qR41$, $S(O)_rNR42R43$, aryl, heteroaryl, arylalkyl with alkyl having 1, 2, 3 or 4 carbon atoms or heteroarylalkyl with alkyl having 1, 2, 3 or 4 carbon atoms;
R36 is hydrogen or alkyl having 1, 2, 3 or 4 carbon atoms;
R37 is hydrogen, alkyl having 1, 2, 3 or 4 carbon atoms, aryl, C(O)H, C(O)alkyl with alkyl having 1, 2, 3 or 4 carbon atoms or C(O)aryl;
R38 is hydrogen, OH, alkyl with 1, 2, 3 or 4 carbon atoms, alkoxy with 1, 2, 3 or 4 carbon atoms or aryl;
R39, R40, R42 and R43 are, independently of one another, hydrogen, alkyl having 1, 2, 3 or 4 carbon atoms or aryl;
R41 is OH, alkyl having 1, 2, 3 or 4 carbon atoms, alkoxy with 1, 2, 3 or 4 carbon atoms or aryl;
q and r are, independently of one another, 1 or 2;
Z is —C(O)—, —S(O)— or —$S(O)_2$—;
A is cycloalkyl having 3, 4, 5, 6, 7 or 8 carbon atoms or phenyl;
in which the said cycloalkyl or phenyl can be condensed to a cycloalkyl radical having 3, 4, 5, 6, 7 or 8 atoms or a phenyl radical,
and in which said cycloalkyl or phenyl and the optionally condensed cycloalkyl radical or phenyl radical are unsubstituted or substituted by 1, 2, 3, 4 or 5 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms and —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
B is a linear linker consisting of 3, 4 or 5 carbon atoms, in which 1 or 2 carbon atoms can be replaced by a member of a heteroatom containing group consisting of O, NR19 or $S(O)_y$, and which linker may contain 0, 1 or 2 double or triple bonds between carbon atoms within the linker, with the provisos, that 2 of said heteroatom containing groups are separated by at least 2 carbon atoms, that heteroatom containing groups are not adjacent to a double or triple bond within the linker or to a non-aromatic double bond, which might be part of A, that double or triple bonds are not cumulated, and that, if A is connected to the linker via a nitrogen atom being part of A, the atom of the linker which is connected to A is a carbon atom;

and in which linker saturated carbon atoms, which are not adjacent to heteroatom containing groups, which are not adjacent to double or triple bonds within the linker or which are not adjacent to a heteroatom, which might be part of A, can, independently of one another, be substituted by hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms; cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

and in which linker saturated carbon atoms, which are adjacent to heteroatom containing groups, which are adjacent to double or triple bonds in the linker, or which are adjacent to a heteroatom, which might be part of A, or carbon atoms being part of a double bond, can, independently of one another, be substituted by hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is hydrogen, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

R44, R45 and R46 are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms;

y is 0, 1 or 2;

R1 is alkyl having 1, 2, 3, 4, 5 or 6 carbon atoms;

which can be unsubstituted or substituted by 1, 2, 3, 4 or 5 radicals selected from the group consisting of F, Cl, Br, I, and $-O_m-(CH_2)_n-R26$;

and

R2 is alkyl having 1, 2, 3, 4, 5 or 6 carbon atoms, phenyl, heteroaryl having 5 or 6 atoms, cycloalkyl having 3, 4, 5, 6, 7 or 8 carbon atoms or heterocyclyl having 3, 4, 5, 6, 7 or 8 atoms;

wherein alkyl is unsubstituted or substituted by 1, 2, 3, 4 or 5 radicals selected from the group consisting of F, Cl, Br, I, and $-O_m-(CH_2)_n-R26$;

m is 0 or 1;

n is 0, 1, 2 or 3;

R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from the group consisting of F, Cl, Br and I;

and wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms and cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

or

R1 and R2 form, together with the carbon atom to which they are attached, a 3-, 4-, 5- or 6 membered carbon ring, wherein the formed ring can be saturated or partially unsaturated, and in which the formed ring can optionally be condensed to a phenyl or cycloalkyl radical having 3, 4, 5, 6, 7 or 8 atoms;

wherein the formed ring and the optionally condensed phenyl or cycloalkyl radical can be unsubstituted or substituted by 1, 2, 3, 4 or 5 radicals selected from the group consisting of F, Cl, Br, I, CN, $NO_2$, $SCF_3$, $SF_5$ and alkyl having 1, 2, 3 or 4 carbon atoms;

and/or a pharmaceutically acceptable salt thereof and/or an ester prodrug of a carboxylic acid group thereof.

2. A compound of the formula I as claimed in claim 1, wherein

R3 and R4 are, independently of one another, hydrogen, F, Cl, Br, I, alkyl having 1, 2, 3 or 4 carbon atoms or alkoxy having 1, 2, 3 or 4 carbon atoms;

and

R8 is hydrogen, F, Cl, Br, I or alkyl having 1, 2, 3 or 4 carbon atoms.

3. A compound of the formula I as claimed in claim 1, wherein

R3 and R4 are, independently of one another, hydrogen, F, Cl or Br;

and

R8 is hydrogen, F or Cl.

4. A compound of the formula I as claimed in claim 1, wherein

R3 and R4 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN or $NO_2$;

and

R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN or $NO_2$.

5. A compound of the formula I as claimed in claim 4, wherein

R3 and R4 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms; and R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms.

6. A compound of the formula I as claimed in claim 1, wherein

A is cycloalkyl having 3, 4, 5, 6, 7 or 8 carbon atoms or phenyl;

in which the said phenyl can be condensed to a cycloalkyl radical having 3, 4, 5, 6, 7 or 8 atoms or a phenyl radical;

and in which said cycloalkyl, heterocyclyl, phenyl or heteroaryl and the optionally condensed cycloalkyl radical, heterocyclyl radical, phenyl radical or heteroaryl radical are unsubstituted or substituted by 1, 2, 3, 4 or 5 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, and —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms.

7. A compound of the formula I as claimed in claim 1, wherein

A is cycloalkyl having 3, 4, 5, 6, 7 or 8 carbon atoms or phenyl or;

in which the said phenyl can be condensed to form a naphthyl or an indanyl, in which said cycloalkyl or phenyl or the optionally formed naphthyl or indanyl are unsubstituted or substituted by 1, 2, 3, 4 or 5 radicals selected from the group consisting of F, Cl, Br, I, OH, CN, $NO_2$, $SF_5$, $SCF_3$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, and alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms.

8. A compound of the formula I as claimed in claim 1, wherein

A is cyclohexyl, phenyl, naphthyl, or indanyl; in which the phenyl radical is unsubstituted or substituted by 1, 2 or 3 radicals selected from the group consisting of F, Cl, Br, methoxy, and alkyl having 1, 2 or 3 carbon atoms in which 1, 2, 3, 4, 5 6 or 7 hydrogen atoms may be substituted by fluorine atoms; and in which pyridinyl is unsubstituted or substituted by Cl.

9. A compound of the formula I as claimed in claim 1, wherein

A is cyclohexyl, phenyl, naphthyl, or indanyl; in which the phenyl radical is unsubstituted or substituted by 1, 2 or 3 radicals selected from the group consisting of F, Cl, Br, methoxy, methyl, ethyl, propyl, iso-propyl and trifluoromethyl.

10. A compound of the formula I as claimed in claim 1, wherein

B is —C(R11R12)-C(R13R14)-O—, —C(R11R12)-C(R15R16)-C(R15R16)-, —C(R13R14)-C≡C—, —C(R13R14)-C(R17)=C(R18)-, —C(R11R12)-C(R13R14)-NR19-, —C(R11R12)-C(R13R14)-S(O)$_y$—, —O—C(R13R14)-C(R15R16), —C≡C—C(R13R14)-, —C(R17)=C(R18)-C(R13R14)-, —C(R13R14)-O—C(R13R14)-, —C(R11R12)-C(R15R16)-C(R13R14)-O—, —C(R11R12)-C(R15R16)-C(R13R14)-NR19-, —C(R11R12)-C(R15R16)-C(R15R16)-C(R15R16)-, —O—C(R13R14)-C(R13R14)-O—, —O—C(R13R14)-C (R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R13R14)-O—C(R13R14)-C(R15R16)-, —C(R11R12)-C(R13R14)-O—C(R13R14)-, —C(R11R12)-C(R15R16)-C(R13R14)-S(O)$_y$—, —O—C(R13R14)-C(R13R14)-S(O)$_y$—, —O—C(R13R14)-C(R17)=C(R18)-, —C≡C—C(R13R14)-C(R15R16)-, —C(R17)=C(R18)-C(R13R14)-C(R15R16)-, —C(R13R14)-C≡C—C(R13R14)-, —C(R13R14)-C(R17)=C(R18)-C(R13R14)-, —C(R11R12)-C(R15R16)-C(R15R16)-C(R15R16)-, —C(R11R12)-C(R15R16)-C(R13R14)-O—, —O—C(R13R14)-C(R15R16)-C(R13R14)-O—, —C(R11R12)-C(R15R16)-C(R13R14)-C≡C—, —C(R13R14)-O—C(R13R14)-C(R13R14)-O—, —C(R13R14)-O—C(R13R14)-C(R15R16)-C(R15R16)-, —C(R11R12)-C(R15R16)-C(R13R14)-C(R17)=C(R18)-, —C(R13R14)-C(R17)=C(R18)-C(R13R14)-O—, —C(R13R14)-C≡C—C(R13R14)-O—, —C(R17)=C(R18)-C(R13R14)-C(R13R14)-O—, —C≡C—C(R13R14)-C(R13R14)-O—, —C(R11R12)-C(R15R16)-C(R13R14)-O—C(R13R14)-, —C(R11R12)-C(R13R14)-O—C(R13R14)-C(R15R16)-, —O—C(R13R14)-C(R15R16)-C(R15R16)-C(R15R16)- or —O—C(R13R14)-C(R13R14)-O—C(R13R14)-, with the proviso that, if A is connected to the linker B via a nitrogen atom being part of A, the atom of the linker which is connected to A is a carbon atom;

R11 and R12 are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14, R17 and R18 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16 are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is hydrogen, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

R44, R45 and R46 are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms;

y is 0, 1 or 2.

11. A compound of the formula I as claimed in claim 1, wherein

B is —C(R11R12)-C(R13R14)-O—, —C(R11R12)-C(R15R16)-C(R13R14)-O—, —C(R11R12)-C(R15R16)-C(R13R14)-NR19-, —C(R11R12)-C(R15R16)-C(R15R16)-C(R15R16)-, —O—C(R13R14)-C(R13R14)-O—, —O—C(R13R14)-C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R11R12)-C(R15R16)-C(R15R16)-C(R15R16)-, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C— or —C(R13R14)-O—C(R13R14)-C(R13R14)-O—, with the proviso that, if A is connected to the linker via a nitrogen atom being part of A, the atom of the linker which is connected to A is a carbon atom;

R11 and R12 are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14, R17 and R18 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16 are, independently of one another, hydrogen, F,

OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is H or alkyl having 1, 2, 3, 4, 5 or 6 carbon atoms.

12. A compound of the formula I as claimed in claim 1, wherein

B is —C(R11R12)-C(R13R14)-O—, —C(R11R12)-C(R15R16)-C(R13R14)-O—, —O—C(R13R14)-C(R13R14)-O—, —C(R17)=C(R18)-C(R13R14)-O—, —C≡C—C(R13R14)-O—, —C(R11R12)-C(R13R14)-C≡C—, —O—C(R13R14)-C≡C—, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C— or —C(R13R14)-O—C(R13R14)-C(R13R14)-O—, with the proviso that, if A is connected to the linker via a nitrogen atom being part of A, the atom of the linker which is connected to A is a carbon atom;

R11 and R12 are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14, R17 and R18 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16 are, independently of one another, hydrogen, F,

OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms.

13. A compound of the formula I as claimed in claim 10, wherein

R11-R18 are, independently of each other, hydrogen, F, or alkyl having 1, 2, 3, or 4 carbon atoms.

14. A compound of the formula I as claimed in claim 1, wherein

R19 is hydrogen or methyl.

15. A compound of the formula I as claimed in claim 1, wherein
   y is 0.
16. A compound of the formula I as claimed in claim 1, wherein
   R1 is alkyl having 1, 2, 3, 4, 5 or 6 carbon atoms
   which can be unsubstituted or substituted by 1, 2, 3, 4 or 5 radicals selected from the group consisting of F, Cl, Br, I, and —$O_m$—$(CH_2)_n$—R26;
   R2 is alkyl having 1, 2, 3, 4, 5 or 6 carbon atoms or phenyl, wherein alkyl is unsubstituted or substituted by 1, 2, 3, 4 or 5 radicals selected from the group consisting of F, Cl, Br, I, and —$O_m$—$(CH_2)_n$—R26;
   m is 0 or 1;
   n is 0, 1, 2 or 3;
   R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from the group consisting of F, Cl, Br and I;
   and wherein phenyl is unsubstituted or substituted by 1, 2, 3, 4 or 5 radicals selected from the group consisting of F, Cl, Br, I, OH, CN, $NO_2$, $SCF_3$, $SF_5$, and alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms,
   or
   R1 and R2 form, together with the carbon atom to which they are attached, a 3-, 4-, 5- or 6-membered saturated or partly saturated carbon ring, which can optionally be condensed to a phenyl radical; wherein the formed ring and the optionally condensed phenyl can be unsubstituted or substituted by 1, 2, 3, 4 or 5 radicals selected from the group consisting of F, Cl, Br, I, CN, $NO_2$, $SCF_3$, $SF_5$ and alkyl having 1, 2, 3 or 4 carbon atoms.
17. A compound of the formula I as claimed in claim 1, wherein
   R1 is alkyl having 1, 2, 3, 4, 5 or 6 carbon atoms
   and
   R2 is alkyl having 1, 2, 3, 4, 5 or 6 carbon atoms or phenyl, wherein alkyl is unsubstituted or substituted by 1, 2, 3, 4 or 5 radicals selected from the group consisting of F, Cl, Br, I, and —$O_m$—$(CH_2)_n$—R26;
   m is 0 or 1;
   n is 0, 1, 2 or 3;
   R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from the group consisting of F, Cl, Br and I;
   or
   R1 and R2 form, together with the carbon atom to which they are attached, a 3-, 4-, 5- or 6-membered saturated or partly saturated carbon ring, which can optionally be condensed to a phenyl radical.
18. A compound of the formula I as claimed in claim 1, wherein
   R1 is alkyl having 1, 2, 3 or 4 carbon atoms and
   R2 is alkyl having 1, 2, 3 or 4 carbon atoms, phenyl or benzyl;
   or
   R1 and R2 form, together with the carbon atom to which they are attached, a cyclopropane, cyclobutane, cyclopentane, cyclohexane, cyclopentene ring or indene.
19. A compound of the formula I as claimed in claim 1, wherein
   R1 is methyl or ethyl;
   and
   R2 is methyl or ethyl;
   or
   R1 and R2 form, together with the carbon atom to which they are attached, a cyclobutane or cyclopentane ring.
20. A compound of the formula I as claimed in claim 1, wherein
   Z is —$S(O)_2$ or —C(O)—.
21. A compound of the formula I as claimed in claim 1, wherein
   Z is —C(O)—.
22. A compound of formula I as claimed in claim 1, wherein
   R3 and R4 are, independently of one another, hydrogen, F, Cl or Br;
   Y1, Y2, Y3 and Y4 are, independently of one another, —CR8-, wherein R8 is hydrogen, F or Cl;
   Z is —C(O)—;
   A is cyclohexyl, phenyl, naphthyl, indanyl or thienyl;
   in which the phenyl radical is unsubstituted or substituted by 1, 2 or 3 radicals selected from the group consisting of F, Cl, Br, methoxy, methyl, ethyl, propyl, iso-propyl and trifluoromethyl;
   B is —C(R11R12)-C(R13R14)-O—, —C(R11R12)-C(R15R16)-C(R13R14)-O—, —O—C(R13R14)-C(R13R14)-O—, —C(R17)=C(R18)-C(R13R14)-O—, —C≡C—C(R13R14)-O—, —C(R11R12)-C(R13R14)-C≡C—, —O—C(R13R14)-C≡C—, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C— or —C(R13R14)-O—C(R13R14)-C(R13R14)-O—;
   R11-R18 are, independently of each other, hydrogen or methyl;
   R1 is methyl or ethyl; and
   R2 is methyl or ethyl;
   or
   R1 and R2 form, together with the carbon atom to which they are attached, a cyclobutane or cyclopentane ring.
23. A compound of the formula I as claimed in claim 1 selected from the group consisting of:
   2-{[1-(2-Phenoxy-ethoxy)-naphthalene-2-carbonyl]-amino}-2-propyl-pentanoic acid,
   2-Ethyl-2-({1-[2-(4-fluoro-phenyl)-ethoxy]-naphthalene-2-carbonyl}-amino)-hexanoic acid,
   2-Ethyl-2-[(1-phenethyloxy-naphthalene-2-carbonyl)-amino]-hexanoic acid,
   1-{[1-(3-Cyclohexyl-propoxy)-naphthalene-2-carbonyl]-amino}-cyclobutanecarboxylic acid,
   2-Methyl-2-({1-[2-(naphthalen-2-yloxy)-ethoxy]-naphthalene-2-carbonyl}-amino)-propionic acid,
   2-({1-[2-(2,3-Dichloro-phenoxy)-ethoxy]-naphthalene-2-carbonyl}-amino)-2-methyl-propionic acid,
   2-Methyl-2-({1-[2-(4-trifluoromethyl-phenoxy)-ethoxy]-naphthalene-2-carbonyl}-amino)-propionic acid,
   2-Methyl-2-{[1-((E)-3-phenyl-allyloxy)-naphthalene-2-carbonyl]amino}-propionic acid,
   2-Methyl-2-{[1-(3-phenoxy-propyl)-naphthalene-2-carbonyl]-amino}-propionic acid,
   2-({1-[2-(4-Methoxy-phenoxy)-ethoxy]-naphthalene-2-carbonyl}-amino)-2-methyl-propionic acid,
   2-({1-[2-(2,4-Dichloro-phenoxy)-ethoxy]-naphthalene-2-carbonyl}-amino)-2-methyl-propionic acid, 2-Methyl-2-{[1-(2-phenoxy-ethylamino)-naphthalene-2-carbonyl]-amino}-propionic acid,
2-Methyl-2-[1-(2-phenoxy-ethoxy)-naphthalene-2-sulfonylamino]-propionic acid,
2-{[1-(3-Cyclohexyl-propoxy)-naphthalene-2-carbonyl]-amino}-2-methyl-propionic acid,
2-Methyl-2-{[1-(3-pyridin-2-yl-propoxy)-naphthalene-2-carbonyl]-amino}-propionic acid,
1-{[1-(1-Methyl-3-phenyl-propoxy)-naphthalene-2-carbonyl]-amino}-cyclohexanecarboxylic acid,
2-({1-[2-(4-Fluoro-phenoxy)-ethoxy]-naphthalene-2-carbonyl}-amino)-2-phenyl-butyric acid,
1-{[1-(2-Phenoxy-ethoxy)-naphthalene-2-carbonyl]-amino}-cyclopent-3-enecarboxylic acid,
2,4-Dimethyl-2-{[1-(2-phenoxy-ethoxy)-naphthalene-2-carbonyl]-amino}-pentanoic acid,
2-{[4-Fluoro-1-(2-phenoxy-ethoxy)-naphthalene-2-carbonyl]-amino}-2-methyl-butyric acid,
1-{[1-(2-Phenoxy-ethoxy)-naphthalene-2-carbonyl]-amino}-indan-1-carboxylic acid,
1-{[1-(2-Cyclohexyl-ethoxy)-4-fluoro-naphthalene-2-carbonyl]-amino}-cyclopentanecarboxylic acid,
1-({4-Fluoro-1-[2-(4-fluoro-phenoxy)-ethoxy]-naphthalene-2-carbonyl}-amino)-cyclopentanecarboxylic acid,
1-{[4-Fluoro-1-(3-phenoxy-propoxy)-naphthalene-2-carbonyl]-amino}-cyclopentanecarboxylic acid,
1-{[4-Fluoro-1-(2-phenoxy-ethoxy)-naphthalene-2-carbonyl]-amino}-cyclopentanecarboxylic acid,
1-[(4-Fluoro-1-phenethyloxy-naphthalene-2-carbonyl)-amino]-cyclopentanecarboxylic acid,
1-{[4-Fluoro-1-(3-phenyl-propoxy)-naphthalene-2-carbonyl]-amino}-cyclopentanecarboxylic acid,
2-({1-[2-(4-Fluoro-phenoxy)-ethoxy]-naphthalene-2-carbonyl}-amino)-2-methyl-3-phenyl-propionic acid,
2-{[1-(2-Cyclohexyl-ethoxy)-naphthalene-2-carbonyl]-amino}-2-ethyl-hexanoic acid,
2-{[1-(3-Cyclohexyl-propoxy)-naphthalene-2-carbonyl]-amino}-2-ethyl-hexanoic acid,
2-Ethyl-2-{[1-(3-phenyl-propoxy)-naphthalene-2-carbonyl]-amino}-hexanoic acid,
2-({1-[2-(4-Chloro-phenoxy)-ethoxy]-naphthalene-2-carbonyl}-amino)-2-ethyl-hexanoic acid,
2-Ethyl-2-{[1-(2-phenoxy-ethoxy)-naphthalene-2-carbonyl]amino}-hexanoic acid,
2-Ethyl-2-({1-[2-(4-fluoro-phenoxy)-ethoxy]-naphthalene-2-carbonyl}-amino)-hexanoic acid,
1-({4-Chloro-1-[2-(4-fluoro-phenyl)-ethoxy]-naphthalene-2-carbonyl}-amino)-cyclobutanecarboxylic acid,
1-{[4-Chloro-1-(2-cyclohexyl-ethoxy)-naphthalene-2-carbonyl]-amino}-cyclobutanecarboxylic acid,
1-[(4-Chloro-1-phenethyloxy-naphthalene-2-carbonyl)-amino]-cyclobutanecarboxylic acid,
1-{[4-Chloro-1-(3-phenyl-propoxy)-naphthalene-2-carbonyl]-amino}-cyclobutanecarboxylic acid,
1-{[4-Chloro-1-(2-phenoxy-ethoxy)-naphthalene-2-carbonyl]-amino}-cyclobutanecarboxylic acid,
1-({4-Chloro-1-[2-(4-fluoro-phenoxy)-ethoxy]-naphthalene-2-carbonyl}-amino)-cyclobutanecarboxylic acid,
1-({1-[2-(4-Fluoro-phenyl)-ethoxy]-naphthalene-2-carbonyl}-amino)-cyclobutanecarboxylic acid,
1-{[1-(2-Cyclohexyl-ethoxy)-naphthalene-2-carbonyl]amino}-cyclobutanecarboxylic acid,
1-({1-[2-(4-Chloro-phenyl)-ethoxy]-naphthalene-2-carbonyl}-amino)-cyclobutanecarboxylic acid,
1-[(1-Phenethyloxy-naphthalene-2-carbonyl)-amino]-cyclobutanecarboxylic acid,
1-{[1-(3-Phenyl-propoxy)-naphthalene-2-carbonyl]-amino}-cyclobutanecarboxylic acid,
1-({1-[2-(4-Chloro-phenoxy)-ethoxy]-naphthalene-2-carbonyl}-amino)-cyclobutanecarboxylic acid,
1-{[1-(2-Phenoxy-ethoxy)-naphthalene-2-carbonyl]-amino}-cyclobutanecarboxylic acid,
1-({1-[2-(4-Fluoro-phenoxy)-ethoxy]-naphthalene-2-carbonyl}-amino)-cyclobutanecarboxylic acid,
2-{[4-Fluoro-1-(1-methyl-3-phenyl-propoxy)-naphthalene-2-carbonyl]-amino}-2-methyl-propionic acid,
2-({4-Fluoro-1-[2-(4-fluoro-phenoxy)-ethoxy]-naphthalene-2-carbonyl}-amino)-2-methyl-propionic acid,
2-{[4-Fluoro-1-(3-phenoxy-propoxy)-naphthalene-2-carbonyl]-amino}-2-methyl-butyric acid,
2-({4-Fluoro-1-[2-(4-fluoro-phenyl)-ethoxy]-naphthalene-2-carbonyl}-amino)-2-methyl-propionic acid,
2-{[4-Fluoro-1-(3-phenyl-propoxy)-naphthalene-2-carbonyl]-amino}-2-methyl-propionic acid,
2-{[4-Fluoro-1-(3-phenoxy-propoxy)-naphthalene-2-carbonyl]-amino}-2-methyl-propionic acid,
2-[(4-Fluoro-1-phenethyloxy-naphthalene-2-carbonyl)-amino]-2-methyl-propionic acid,
2-{[4-Fluoro-1-(2-phenoxy-ethoxy)-naphthalene-2-carbonyl]-amino}-2-methyl-propionic acid,
2-{[1-(2-Cyclohexyl-ethoxy)-naphthalene-2-carbonyl]-amino}-2-methyl-propionic acid,
2-({1-[3-(4-Chloro-phenyl)-propoxy]-naphthalene-2-carbonyl}-amino)-2-methyl-propionic acid,
1-{[1-((R)-1-Methyl-3-phenyl-propoxy)-naphthalene-2-carbonyl]-amino}-cyclopentanecarboxylic acid,
1-{[1-((S)-1-Methyl-3-phenyl-propoxy)-naphthalene-2-carbonyl]-amino}-cyclopentanecarboxylic acid,
(R)-2-Methyl-2-{[1-(2-phenoxy-ethoxy)-naphthalene-2-carbonyl]-amino}-butyric acid,
(S)-2-Methyl-2-{[1-(2-phenoxy-ethoxy)-naphthalene-2-carbonyl]-amino}-butyric acid,
2-({4-Chloro-1-[2-(4-fluoro-phenoxy)-ethoxy]-naphthalene-2-carbonyl}-amino)-2-methyl-butyric acid,
2-({4-Chloro-1-[2-(4-fluoro-phenoxy)-ethoxy]-naphthalene-2-carbonyl}-amino)-2-methyl-propionic acid,
2-({1-[2-(3-Chloro-4-fluoro-phenoxy)-ethoxy]-naphthalene-2-carbonyl}-amino)-2-methyl-propionic acid,
2-{[4-Bromo-1-(2-phenoxy-ethoxy)-naphthalene-2-carbonyl]-amino}-2-methyl-propionic acid,
2-({1-[2-(4-Fluoro-3-trifluoromethyl-phenoxy)-ethoxy]-naphthalene-2-carbonyl}-amino)-2-methyl-propionic acid,
2-({1-[2-(4-Bromo-phenoxy)-ethoxy]-naphthalene-2-carbonyl}-amino)-2-methyl-propionic acid,
2-({1-[2-(4-Fluoro-phenoxy)-ethoxy]-naphthalene-2-carbonyl}-amino)-2-methyl-butyric acid,
2-({4-Bromo-1-[2-(4-fluoro-phenoxy)-ethoxy]-naphthalene-2-carbonyl}-amino)-2-methyl-propionic acid,
2-Methyl-2-{[1-((S)-1-methyl-2-phenoxy-ethoxy)-naphthalene-2-carbonyl]-amino}-propionic acid,
2-Methyl-2-{[1-((R)-1-methyl-2-phenoxy-ethoxy)-naphthalene-2-carbonyl]-amino}-propionic acid,
2-({1-[2-(2-Isopropyl-phenoxy)-ethoxy]-naphthalene-2-carbonyl}-amino)-2-methyl-propionic acid,
2-Methyl-2-{[1-(2-m-tolyloxy-ethoxy)-naphthalene-2-carbonyl]-amino}-propionic acid,
2-({1-[2-(3-Methoxy-phenoxy)-ethoxy]-naphthalene-2-carbonyl}-amino)-2-methyl-propionic acid,
2-({1-[2-(3,5-Dichloro-phenoxy)-ethoxy]-naphthalene-2-carbonyl}-amino)-2-methyl-propionic acid,
2-({1-[2-(2,6-Dichloro-phenoxy)-ethoxy]-naphthalene-2-carbonyl}-amino)-2-methyl-propionic acid, 2-({1-[2-(3-Chloro-5-fluoro-phenoxy)-ethoxy]-naphthalene-2-carbonyl}-amino)-2-methyl-propionic acid,
2-({1-[2-(3,4-Dichloro-phenoxy)-ethoxy]-naphthalene-2-carbonyl}-amino)-2-methyl-propionic acid,
2-({1-[2-(Indan-5-yloxy)-ethoxy]-naphthalene-2-carbonyl}-amino)-2-methyl-propionic acid,
2-({1-[2-(2,4-Dimethyl-phenoxy)-ethoxy]-naphthalene-2-carbonyl}-amino)-2-methyl-propionic acid,
2-({1-[2-(2,3-Dimethyl-phenoxy)-ethoxy]-naphthalene-2-carbonyl}-amino)-2-methyl-propionic acid,
2-({1-[2-(3-Isopropyl-phenoxy)-ethoxy]-naphthalene-2-carbonyl}-amino)-2-methyl-propionic acid,
2-({1-[2-(2-Chloro-phenoxy)-ethoxy]-naphthalene-2-carbonyl}-amino)-2-methyl-propionic acid,
2-({1-[2-(3-Chloro-phenoxy)-ethoxy]-naphthalene-2-carbonyl}-amino)-2-methyl-propionic acid,
2-({1-[2-(2-Chloro-4-fluoro-phenoxy)-ethoxy]-naphthalene-2-carbonyl}-amino)-2-methyl-propionic acid,
2-({1-[2-(3,4-Difluoro-phenoxy)-ethoxy]-naphthalene-2-carbonyl}-amino)-2-methyl-propionic acid,
2-({1-[2-(3-Fluoro-phenoxy)-ethoxy]-naphthalene-2-carbonyl}-amino)-2-methyl-propionic acid,
2-({1-[2-(2-Methoxy-phenoxy)-ethoxy]-naphthalene-2-carbonyl}-amino)-2-methyl-propionic acid,
2-Methyl-2-{[1-(3-phenyl-prop-2-ynyloxy)-naphthalene-2-carbonyl]-amino}-propionic acid,
2-({1-[3-(4-Chloro-phenyl)-prop-2-ynyloxy]-naphthalene-2-carbonyl}-amino)-2-methyl-propionic acid,
2,3-Dimethyl-2-{[1-(2-phenoxy-ethoxy)-naphthalene-2-carbonyl]-amino}-butyric acid,
1-{[1-(1-Methyl-3-phenyl-propoxy)-naphthalene-2-carbonyl]-amino}-cyclopentanecarboxylic acid,
1-({1-[2-(4-Fluoro-phenoxy)-ethoxy]-naphthalene-2-carbonyl}-amino)-cyclopentanecarboxylic acid,
2,3-Dimethyl-2-{[1-(1-methyl-3-phenyl-propoxy)-naphthalene-2-carbonyl]-amino}-butyric acid,
2-({1-[2-(4-Chloro-phenoxy)-ethoxy]-naphthalene-2-carbonyl}-amino)-2,3-dimethyl-butyric acid,
2-({1-[2-(4-Fluoro-phenoxy)-ethoxy]-naphthalene-2-carbonyl}-amino)-2,3-dimethyl-butyric acid,
2-Methyl-2-{[1-(1-methyl-2-phenoxy-ethoxy)-naphthalene-2-carbonyl]-amino}-propionic acid,
2-Methyl-2-{[1-(5-phenyl-pentyl)-naphthalene-2-carbonyl]-amino}-propionic acid,
2-Methyl-2-{[1-(5-phenyl-pent-1-ynyl)-naphthalene-2-carbonyl]-amino}-propionic acid,
2-Methyl-2-{[1-(3-phenyl-butoxy)-naphthalene-2-carbonyl]-amino}-propionic acid,
2-({1-[2-(4-Chloro-phenoxy)-ethoxy]-naphthalene-2-carbonyl}-amino)-2-methyl-butyric acid,
2-({1-[2-(4-Chloro-phenoxy)-ethoxy]-naphthalene-2-carbonyl}-amino)-2-methyl-propionic acid,
2-({1-[2-(2,4-Dichloro-phenyl)-ethoxy]-naphthalene-2-carbonyl}-amino)-2-methyl-propionic acid,
2-Methyl-2-{[1-(3-phenoxy-prop-1-ynyl)-naphthalene-2-carbonyl]-amino}-propionic acid,
2-({1-[2-(4-Chloro-phenyl)-ethoxy]-naphthalene-2-carbonyl}-amino)-2-methyl-propionic acid,
2-Methyl-2-{[1-(2-p-tolyl-ethoxy)-naphthalene-2-carbonyl]-amino}-propionic acid,
2-{[1-(2-Benzyloxy-ethoxy)-naphthalene-2-carbonyl]-amino}-2-methyl-propionic acid,
2-Methyl-2-{[1-(2-phenoxy-ethoxy)-naphthalene-2-carbonyl]-amino}-butyric acid,
2-({1-[2-(3,5-Difluoro-phenoxy)-ethoxy]-naphthalene-2-carbonyl}-amino)-2-methyl-propionic acid,
2-Methyl-2-{[1-((E)-4-phenyl-but-1-enyl)-naphthalene-2-carbonyl]-amino}-propionic acid,
2-Methyl-2-{[1-(4-phenyl-butyl)-naphthalene-2-carbonyl]-amino}-propionic acid,
2-({1-[2-(4-Fluoro-phenoxy)-ethoxy]-naphthalene-2-carbonyl}-amino)-2-methyl-propionic acid,
2-Methyl-2-{[1-(1-methyl-3-phenyl-propoxy)-naphthalene-2-carbonyl]-amino}-butyric acid,
2-Methyl-2-{[1-(4-phenyl-but-1-ynyl)-naphthalene-2-carbonyl]-amino}-propionic acid,
2-[(4-Bromo-1-phenethyloxy-naphthalene-2-carbonyl)-amino]-2-methyl-propionic acid,
2-{[4-Bromo-1-(1-methyl-3-phenyl-propoxy)-naphthalene-2-carbonyl]-amino}-2-methyl-propionic acid,
2-Methyl-2-({1-[2-(3-trifluoromethyl-phenyl)-ethoxy]-naphthalene-2-carbonyl}-amino)-propionic acid,
2-({1-[2-(4-Fluoro-phenyl)-ethoxy]-naphthalene-2-carbonyl}-amino)-2-methyl-propionic acid,
2-({1-[2-(3-Bromo-phenyl)-ethoxy]-naphthalene-2-carbonyl}-amino)-2-methyl-propionic acid,
2-Methyl-2-{[1-(2-phenoxy-ethoxy)-naphthalene-2-carbonyl]-amino}-propionic acid,
2-Methyl-2-{[1-((S)-1-methyl-3-phenyl-propoxy)-naphthalene-2-carbonyl]-amino}-propionic acid,
2-Methyl-2-{[1-(3-phenyl-propoxy)-naphthalene-2-carbonyl]-amino}-propionic acid,
2-Methyl-2-{[1-((R)-1-methyl-3-phenyl-propoxy)-naphthalene-2-carbonyl]-amino}-propionic acid,
2-Methyl-2-[(1-phenethyloxy-naphthalene-2-carbonyl)-amino]-propionic acid, or
2-Methyl-2-{[1-(1-methyl-3-phenyl-propoxy)-naphthalene-2-carbonyl]-amino}-propionic acid,
2-({4-Fluoro-1-[2-(3-fluoro-phenyl)-ethoxy]-naphthalene-2-carbonyl}-amino)-2-methyl-propionic acid,
2-{[4-Fluoro-1-(4-phenyl-butoxy)-naphthalene-2-carbonyl]-amino}-2-methyl-propionic acid,
2-({4-Fluoro-1-[2-(2-fluoro-phenoxy)-ethoxy]-naphthalene-2-carbonyl}-amino)-2-methyl-propionic acid,
2-({1-[2-(4-Chloro-phenyl)-ethoxy]-4-fluoro-naphthalene-2-carbonyl}-amino)-2-methyl-propionic acid,
2-({4-Fluoro-1-[3-(2-fluoro-phenoxy)-propoxy]-naphthalene-2-carbonyl}-amino)-2-methyl-propionic acid,
2-({4-Fluoro-1-[3-(4-fluoro-phenoxy)-propoxy]-naphthalene-2-carbonyl}-amino)-2-methyl-propionic acid,
2-({4-Fluoro-1-[2-(naphthalen-2-yloxy)-ethoxy]-naphthalene-2-carbonyl}-amino)-2-methyl-propionic acid, and
2-({1-[2,2-Difluoro-2-(4-fluoro-phenoxy)-ethoxy]-naphthalene-2-carbonyl}-amino)-2-methyl-propionic acid
or a pharmaceutically acceptable salt thereof or an ester prodrug of a carboxylic acid group thereof.

24. A compound of the formula (I) as claimed in claim 1 selected from the group consisting of:
2-({1-[2-(4-Fluoro-phenoxy)-ethoxy]-naphthalene-2-carbonyl}-amino)-2-phenyl-butyric acid,
1-{[1-(2-Phenoxy-ethoxy)-naphthalene-2-carbonyl]-amino}-cyclopent-3-enecarboxylic acid,
2,4-Dimethyl-2-{[1-(2-phenoxy-ethoxy)-naphthalene-2-carbonyl]-amino}-pentanoic acid,
2-{[4-Fluoro-1-(2-phenoxy-ethoxy)-naphthalene-2-carbonyl]-amino}-2-methyl-butyric acid,
1-{[1-(2-Phenoxy-ethoxy)-naphthalene-2-carbonyl]-amino}-indan-1-carboxylic acid,
1-{[1-(2-Cyclohexyl-ethoxy)-4-fluoro-naphthalene-2-carbonyl]-amino}-cyclopentanecarboxylic acid,
1-({4-Fluoro-1-[2-(4-fluoro-phenoxy)-ethoxy]-naphthalene-2-carbonyl}-amino)-cyclopentanecarboxylic acid, 1-{[4-Fluoro-1-(3-phenoxy-propoxy)-naphthalene-2-carbonyl]-amino}-cyclopentanecarboxylic acid,
1-{[4-Fluoro-1-(2-phenoxy-ethoxy)-naphthalene-2-carbonyl]-amino}-cyclopentanecarboxylic acid,
1-[(4-Fluoro-1-phenethyloxy-naphthalene-2-carbonyl)-amino]-cyclopentanecarboxylic acid,
1-{[4-Fluoro-1-(3-phenyl-propoxy)-naphthalene-2-carbonyl]-amino}-cyclopentanecarboxylic acid,
2-({1-[2-(4-Fluoro-phenoxy)-ethoxy]-naphthalene-2-carbonyl}-amino)-2-methyl-3-phenyl-propionic acid,
2-{[1-(2-Cyclohexyl-ethoxy)-naphthalene-2-carbonyl]-amino}-2-ethyl-hexanoic acid,
2-{[1-(3-Cyclohexyl-propoxy)-naphthalene-2-carbonyl]-amino}-2-ethyl-hexanoic acid,
2-Ethyl-2-{[1-(3-phenyl-propoxy)-naphthalene-2-carbonyl]-amino}-hexanoic acid,
2-({1-[2-(4-Chloro-phenoxy)-ethoxy]-naphthalene-2-carbonyl}-amino)-2-ethyl-hexanoic acid,
2-Ethyl-2-{[1-(2-phenoxy-ethoxy)-naphthalene-2-carbonyl]-amino}-hexanoic acid,
2-Ethyl-2-({1-[2-(4-fluoro-phenoxy)-ethoxy]-naphthalene-2-carbonyl}-amino)-hexanoic acid,
1-({4-Chloro-1-[2-(4-fluoro-phenyl)-ethoxy]-naphthalene-2-carbonyl}-amino)-cyclobutanecarboxylic acid,
1-{[4-Chloro-1-(2-cyclohexyl-ethoxy)-naphthalene-2-carbonyl]-amino}-cyclobutanecarboxylic acid,
1-[(4-Chloro-1-phenethyloxy-naphthalene-2-carbonyl)-amino]-cyclobutanecarboxylic acid,
1-{[4-Chloro-1-(3-phenyl-propoxy)-naphthalene-2-carbonyl]-amino}-cyclobutanecarboxylic acid,
1-{[4-Chloro-1-(2-phenoxy-ethoxy)-naphthalene-2-carbonyl]-amino}-cyclobutanecarboxylic acid,
1-({4-Chloro-1-[2-(4-fluoro-phenoxy)-ethoxy]-naphthalene-2-carbonyl}-amino)-cyclobutanecarboxylic acid,
1-({1-[2-(4-Fluoro-phenyl)-ethoxy]-naphthalene-2-carbonyl}-amino)-cyclobutanecarboxylic acid,
1-{[1-(2-Cyclohexyl-ethoxy)-naphthalene-2-carbonyl]amino}-cyclobutanecarboxylic acid,
1-({1-[2-(4-Chloro-phenyl)-ethoxy]-naphthalene-2-carbonyl}-amino)-cyclobutanecarboxylic acid,
1-[(1-Phenethyloxy-naphthalene-2-carbonyl)-amino]-cyclobutanecarboxylic acid,
1-{[1-(3-Phenyl-propoxy)-naphthalene-2-carbonyl]-amino}-cyclobutanecarboxylic acid,
1-({1-[2-(4-Chloro-phenoxy)-ethoxy]-naphthalene-2-carbonyl}-amino)-cyclobutanecarboxylic acid,
1-{[1-(2-Phenoxy-ethoxy)-naphthalene-2-carbonyl]-amino}-cyclobutanecarboxylic acid,
1-({1-[2-(4-Fluoro-phenoxy)-ethoxy]-naphthalene-2-carbonyl}-amino)-cyclobutanecarboxylic acid,
2-{[4-Fluoro-1-(1-methyl-3-phenyl-propoxy)-naphthalene-2-carbonyl]-amino}-2-methyl-propionic acid,
2-({4-Fluoro-1-[2-(4-fluoro-phenoxy)-ethoxy]-naphthalene-2-carbonyl}-amino)-2-methyl-propionic acid,
2-{[4-Fluoro-1-(3-phenoxy-propoxy)-naphthalene-2-carbonyl]-amino}-2-methyl-butyric acid,
2-({4-Fluoro-1-[2-(4-fluoro-phenyl)-ethoxy]-naphthalene-2-carbonyl}-amino)-2-methyl-propionic acid,
2-{[4-Fluoro-1-(3-phenyl-propoxy)-naphthalene-2-carbonyl]-amino}-2-methyl-propionic acid,
2-{[4-Fluoro-1-(3-phenoxy-propoxy)-naphthalene-2-carbonyl]-amino}-2-methyl-propionic acid,
2-[(4-Fluoro-1-phenethyloxy-naphthalene-2-carbonyl)-amino]-2-methyl-propionic acid,
2-{[4-Fluoro-1-(2-phenoxy-ethoxy)-naphthalene-2-carbonyl]-amino}-2-methyl-propionic acid,
2-{[1-(2-Cyclohexyl-ethoxy)-naphthalene-2-carbonyl]amino}-2-methyl-propionic acid,
2-({1-[3-(4-Chloro-phenyl)-propoxy]-naphthalene-2-carbonyl}-amino)-2-methyl-propionic acid,
1-{[1-((R)-1-Methyl-3-phenyl-propoxy)-naphthalene-2-carbonyl]-amino}-cyclopentanecarboxylic acid,
1-{[1-((S)-1-Methyl-3-phenyl-propoxy)-naphthalene-2-carbonyl]-amino}-cyclopentanecarboxylic acid,
(R)-2-Methyl-2-{[1-(2-phenoxy-ethoxy)-naphthalene-2-carbonyl]amino}-butyric acid,
(S)-2-Methyl-2-{[1-(2-phenoxy-ethoxy)-naphthalene-2-carbonyl]-amino}-butyric acid,
2-({1-[2-(5-Chloro-pyridin-3-yloxy)-ethoxy]-naphthalene-2-carbonyl}-amino)-2-methyl-propionic acid,
2-({4-Chloro-1-[2-(4-fluoro-phenoxy)-ethoxy]-naphthalene-2-carbonyl}-amino)-2-methyl-butyric acid,
2-({4-Chloro-1-[2-(4-fluoro-phenoxy)-ethoxy]-naphthalene-2-carbonyl}-amino)-2-methyl-propionic acid,
2-({1-[2-(3-Chloro-4-fluoro-phenoxy)-ethoxy]-naphthalene-2-carbonyl}-amino)-2-methyl-propionic acid,
2-{[4-Bromo-1-(2-phenoxy-ethoxy)-naphthalene-2-carbonyl]-amino}-2-methyl-propionic acid,
2-({1-[2-(4-Fluoro-3-trifluoromethyl-phenoxy)-ethoxy]-naphthalene-2-carbonyl}-amino)-2-methyl-propionic acid,
2-({1-[2-(4-Bromo-phenoxy)-ethoxy]-naphthalene-2-carbonyl}-amino)-2-methyl-propionic acid,
2-({1-[2-(4-Fluoro-phenoxy)-ethoxy]-naphthalene-2-carbonyl}-amino)-2-methyl-butyric acid,
2-({4-Bromo-1-[2-(4-fluoro-phenoxy)-ethoxy]-naphthalene-2-carbonyl}-amino)-2-methyl-propionic acid,
2-Methyl-2-{[1-((S)-1-methyl-2-phenoxy-ethoxy)-naphthalene-2-carbonyl]-amino}-propionic acid,
2-Methyl-2-{[1-((R)-1-methyl-2-phenoxy-ethoxy)-naphthalene-2-carbonyl]-amino}-propionic acid,
2-({1-[2-(2-Isopropyl-phenoxy)-ethoxy]-naphthalene-2-carbonyl}-amino)-2-methyl-propionic acid,
2-Methyl-2-{[1-(2-m-tolyloxy-ethoxy)-naphthalene-2-carbonyl]-amino}-propionic acid,
2-({1-[2-(3-Methoxy-phenoxy)-ethoxy]-naphthalene-2-carbonyl}-amino)-2-methyl-propionic acid,
2-({1-[2-(3,5-Dichloro-phenoxy)-ethoxy]-naphthalene-2-carbonyl}-amino)-2-methyl-propionic acid,
2-({1-[2-(2,6-Dichloro-phenoxy)-ethoxy]-naphthalene-2-carbonyl}-amino)-2-methyl-propionic acid,
2-({1-[2-(3-Chloro-5-fluoro-phenoxy)-ethoxy]-naphthalene-2-carbonyl}-amino)-2-methyl-propionic acid,
2-({1-[2-(3,4-Dichloro-phenoxy)-ethoxy]-naphthalene-2-carbonyl}-amino)-2-methyl-propionic acid,
2-({1-[2-(Indan-5-yloxy)-ethoxy]-naphthalene-2-carbonyl}-amino)-2-methyl-propionic acid,
2-({1-[2-(2,4-Dimethyl-phenoxy)-ethoxy]-naphthalene-2-carbonyl}-amino)-2-methyl-propionic acid,
2-({1-[2-(2,3-Dimethyl-phenoxy)-ethoxy]-naphthalene-2-carbonyl}-amino)-2-methyl-propionic acid,
2-({1-[2-(3-Isopropyl-phenoxy)-ethoxy]-naphthalene-2-carbonyl}-amino)-2-methyl-propionic acid,
2-({1-[2-(2-Chloro-phenoxy)-ethoxy]-naphthalene-2-carbonyl}-amino)-2-methyl-propionic acid,
2-({1-[2-(3-Chloro-phenoxy)-ethoxy]-naphthalene-2-carbonyl}-amino)-2-methyl-propionic acid,
2-({1-[2-(2-Chloro-4-fluoro-phenoxy)-ethoxy]-naphthalene-2-carbonyl}-amino)-2-methyl-propionic acid,
2-({1-[2-(3,4-Difluoro-phenoxy)-ethoxy]-naphthalene-2-carbonyl}-amino)-2-methyl-propionic acid,
2-({1-[2-(3-Fluoro-phenoxy)-ethoxy]-naphthalene-2-carbonyl}-amino)-2-methyl-propionic acid, 2-({1-[2-(2-Methoxy-phenoxy)-ethoxy]-naphthalene-2-carbonyl}-amino)-2-methyl-propionic acid,
2-Methyl-2-{[1-(3-phenyl-prop-2-ynyloxy)-naphthalene-2-carbonyl]-amino}-propionic acid,
2-({1-[3-(4-Chloro-phenyl)-prop-2-ynyloxy]-naphthalene-2-carbonyl}-amino)-2-methyl-propionic acid,
2,3-Dimethyl-2-{[1-(2-phenoxy-ethoxy)-naphthalene-2-carbonyl]-amino}-butyric acid,
1-{[1-(1-Methyl-3-phenyl-propoxy)-naphthalene-2-carbonyl]-amino}-cyclopentanecarboxylic acid,
1-({1-[2-(4-Fluoro-phenoxy)-ethoxy]-naphthalene-2-carbonyl}-amino)-cyclopentanecarboxylic acid,
2,3-Dimethyl-2-{[1-(1-methyl-3-phenyl-propoxy)-naphthalene-2-carbonyl]-amino}-butyric acid,
2-({1-[2-(4-Chloro-phenoxy)-ethoxy]-naphthalene-2-carbonyl}-amino)-2,3-dimethyl-butyric acid,
2-({1-[2-(4-Fluoro-phenoxy)-ethoxy]-naphthalene-2-carbonyl}-amino)-2,3-dimethyl-butyric acid,
2-Methyl-2-{[1-(1-methyl-2-phenoxy-ethoxy)-naphthalene-2-carbonyl]-amino}-propionic acid,
2-Methyl-2-{[1-(5-phenyl-pentyl)-naphthalene-2-carbonyl]-amino}-propionic acid,
2-Methyl-2-{[1-(5-phenyl-pent-1-ynyl)-naphthalene-2-carbonyl]-amino}-propionic acid,
2-Methyl-2-{[1-(3-phenyl-butoxy)-naphthalene-2-carbonyl]-amino}-propionic acid,
2-({1-[2-(4-Chloro-phenoxy)-ethoxy]-naphthalene-2-carbonyl}-amino)-2-methyl-butyric acid,
2-({1-[2-(4-Chloro-phenoxy)-ethoxy]-naphthalene-2-carbonyl}-amino)-2-methyl-propionic acid,
2-({1-[2-(2,4-Dichloro-phenyl)-ethoxy]-naphthalene-2-carbonyl}-amino)-2-methyl-propionic acid,
2-Methyl-2-{[1-(3-phenoxy-prop-1-ynyl)-naphthalene-2-carbonyl]-amino}-propionic acid,
2-({1-[2-(4-Chloro-phenyl)-ethoxy]-naphthalene-2-carbonyl}-amino)-2-methyl-propionic acid,
2-Methyl-2-{[1-(2-p-tolyl-ethoxy)-naphthalene-2-carbonyl]-amino}-propionic acid,
2-{[1-(2-Benzyloxy-ethoxy)-naphthalene-2-carbonyl]-amino}-2-methyl-propionic acid,
2-Methyl-2-{[1-(2-phenoxy-ethoxy)-naphthalene-2-carbonyl]amino}-butyric acid,
2-({1-[2-(3,5-Difluoro-phenoxy)-ethoxy]-naphthalene-2-carbonyl}-amino)-2-methyl-propionic acid,
2-Methyl-2-{[1-((E)-4-phenyl-but-1-enyl)-naphthalene-2-carbonyl]-amino}-propionic acid,
2-Methyl-2-{[1-(4-phenyl-butyl)-naphthalene-2-carbonyl]-amino}-propionic acid,
2-({1-[2-(4-Fluoro-phenoxy)-ethoxy]-naphthalene-2-carbonyl}-amino)-2-methyl-propionic acid,
2-Methyl-2-{[1-(1-methyl-3-phenyl-propoxy)-naphthalene-2-carbonyl]-amino}-butyric acid,
2-Methyl-2-{[1-(4-phenyl-but-1-ynyl)-naphthalene-2-carbonyl]-amino}-propionic acid,
2-[(4-Bromo-1-phenethyloxy-naphthalene-2-carbonyl)-amino]-2-methyl-propionic acid,
2-{[4-Bromo-1-(1-methyl-3-phenyl-propoxy)-naphthalene-2-carbonyl]-amino}-2-methyl-propionic acid,
2-Methyl-2-({1-[2-(3-trifluoromethyl-phenyl)-ethoxy]-naphthalene-2-carbonyl}-amino)-propionic acid,
2-({1-[2-(4-Fluoro-phenyl)-ethoxy]-naphthalene-2-carbonyl}-amino)-2-methyl-propionic acid,
2-({1-[2-(3-Bromo-phenyl)-ethoxy]-naphthalene-2-carbonyl}-amino)-2-methyl-propionic acid,
2-Methyl-2-{[1-(2-phenoxy-ethoxy)-naphthalene-2-carbonyl]-amino}-propionic acid,
2-Methyl-2-{[1-((S)-1-methyl-3-phenyl-propoxy)-naphthalene-2-carbonyl]-amino}-propionic acid,
2-Methyl-2-{[1-(3-phenyl-propoxy)-naphthalene-2-carbonyl]-amino}-propionic acid,
2-Methyl-2-{[1-((R)-1-methyl-3-phenyl-propoxy)-naphthalene-2-carbonyl]-amino}-propionic acid,
2-Methyl-2-[(1-phenethyloxy-naphthalene-2-carbonyl)-amino]-propionic acid, or
2-Methyl-2-{[1-(1-methyl-3-phenyl-propoxy)-naphthalene-2-carbonyl]-amino}-propionic acid,
2-({4-Fluoro-1-[2-(3-fluoro-phenyl)-ethoxy]-naphthalene-2-carbonyl}-amino)-2-methyl-propionic acid,
2-{[4-Fluoro-1-(4-phenyl-butoxy)-naphthalene-2-carbonyl]-amino}-2-methyl-propionic acid,
2-({4-Fluoro-1-[2-(2-fluoro-phenoxy)-ethoxy]-naphthalene-2-carbonyl}-amino)-2-methyl-propionic acid,
2-({1-[2-(4-Chloro-phenyl)-ethoxy]-4-fluoro-naphthalene-2-carbonyl}-amino)-2-methyl-propionic acid,
2-({4-Fluoro-1-[3-(2-fluoro-phenoxy)-propoxy]-naphthalene-2-carbonyl}-amino)-2-methyl-propionic acid,
2-({4-Fluoro-1-[3-(4-fluoro-phenoxy)-propoxy]-naphthalene-2-carbonyl}-amino)-2-methyl-propionic acid,
2-({4-Fluoro-1-[2-(naphthalen-2-yloxy)-ethoxy]-naphthalene-2-carbonyl}-amino)-2-methyl-propionic acid, and
2-({1-[2,2-Difluoro-2-(4-fluoro-phenoxy)-ethoxy]-naphthalene-2-carbonyl}-amino)-2-methyl-propionic acid
or a pharmaceutically acceptable salt thereof or an ester prodrug of a carboxylic acid group thereof.

25. A method for the treatment of a chemokine mediated disease, the method comprising inhibiting CXCR2 by administering to a patient in need thereof an effective amount of a pharmaceutically acceptable salt and/or an ester prodrug of a carboxylic acid group thereof as claimed in claim 1 alone or in combination with other medicaments or active ingredients.

26. The method of claim 25, wherein said chemokine mediated disease is selected from acute and chronic inflammatory diseases.

27. The method of claim 25, wherein said chemokine mediated disease is selected from atherosclerosis, ischemia/reperfusion injuries, chronic obstructive pulmonary disease, asthma, and rheumatoid arthritis, adult respiratory distress syndrome, inflammatory bowel disease, ulcerative colitis, Crohn's disease, atopic dermatitis, cystic fibrosis, psoriasis, dermatitis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer.

28. A medicine for human, veterinary and/or phytoprotective use comprising an effective amount of a compound of the formula I and/or a pharmaceutically acceptable salt and/or an ester prodrug of a carboxylic acid group hereof as claimed in claim 1, together with pharmaceutically acceptable carriers and additives.

29. A medicine for human, veterinary and/or phytoprotective use comprising an effective amount of at least one compound of the formula I and/or a pharmaceutically acceptable salt and/or an ester prodrug of a carboxylic acid group thereof as claimed in claim 1, together with pharmaceutically acceptable carriers and additives in combination with at least one other pharmacological active ingredient or medicament.

30. A method for the treatment of a chemokine mediated disease, the method comprising inhibiting CXCR2 by administering to a patient in need thereof an effective amount of a compound of the formula I and/or a pharmaceutically acceptable salt thereof and/or an ester prodrug of a carboxylic acid group thereof alone or in combination with other medicaments or active ingredients, wherein said compound of the formula I has the following structure:

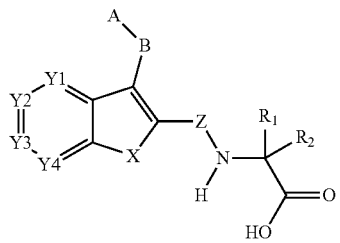

wherein
X is —CR3=CR4-;
R3 and R4 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR27R28, C(O)R29, C(O)NR30R31, $S(O)_oR32$, $S(O)_pNR33R34$, aryl, heteroaryl, arylalkyl with alkyl having 1, 2, 3 or 4 carbon atoms or heteroarylalkyl with alkyl having 1, 2, 3 or 4 carbon atoms;
R27 is hydrogen or alkyl having 1, 2, 3 or 4 carbon atoms;
R28 is hydrogen, alkyl having 1, 2, 3 or 4 carbon atoms, aryl, C(O)H, C(O)alkyl with alkyl having 1, 2, 3 or 4 carbon atoms or C(O)aryl;
R29 is hydrogen, OH, alkyl with 1, 2, 3 or 4 carbon atoms, alkoxy with 1, 2, 3 or 4 carbon atoms or aryl;
R30, R31, R33 and R34 are, independently of one another, hydrogen, alkyl having 1, 2, 3 or 4 carbon atoms or aryl;
R32 is OH, alkyl having 1, 2, 3 or 4 carbon atoms, alkoxy with 1, 2, 3 or 4 carbon atoms or aryl;
o and p are, independently of one another, 1 or 2;
Y1, Y2, Y3 and Y4 are, independently of one another, —CR8-;
R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR36R37, C(O)R38, C(O)NR39R40, $S(O)_qR41$, $S(O)_rNR42R43$, aryl, heteroaryl, arylalkyl with alkyl having 1, 2, 3 or 4 carbon atoms or heteroarylalkyl with alkyl having 1, 2, 3 or 4 carbon atoms;
R36 is hydrogen or alkyl having 1, 2, 3 or 4 carbon atoms;
R37 is hydrogen, alkyl having 1, 2, 3 or 4 carbon atoms, aryl, C(O)H, C(O)alkyl with alkyl having 1, 2, 3 or 4 carbon atoms or C(O)aryl;
R38 is hydrogen, OH, alkyl with 1, 2, 3 or 4 carbon atoms, alkoxy with 1, 2, 3 or 4 carbon atoms or aryl;
R39, R40, R42 and R43 are, independently of one another, hydrogen, alkyl having 1, 2, 3 or 4 carbon atoms or aryl;
R41 is OH, alkyl having 1, 2, 3 or 4 carbon atoms, alkoxy with 1, 2, 3 or 4 carbon atoms or aryl;
q and r are, independently of one another, 1 or 2;
Z is —C(O)—, S(O)— or —$S(O)_2$—;
A is cycloalkyl having 3, 4, 5, 6, 7 or 8 carbon atoms, or phenyl; in which the said cycloalkyl, or phenyl can be condensed to a cycloalkyl radical having 3, 4, 5, 6, 7 or 8 atoms, or a phenyl radical, and in which said cycloalkyl, or phenyl and the optionally condensed cycloalkyl radical, or phenyl radical or heteroaryl radical are unsubstituted or substituted by 1, 2, 3, 4 or 5 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, and —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
B is a linear linker consisting of 3, 4 or 5 carbon atoms, in which 1 or 2 carbon atoms can be replaced by a member of a heteroatom containing group consisting of O, NR19 or $S(O)_y$ and which linker may contain 0, 1 or 2 double or triple bonds between carbon atoms within the linker, with the provisos, that 2 of said heteroatom containing groups are separated by at least 2 carbon atoms, that heteroatom containing groups are not adjacent to a double or triple bond within the linker or to a non-aromatic double bond, which might be part of A, that double or triple bonds are not cumulated, and that, if A is connected to the linker via a nitrogen atom being part of A, the atom of the linker which is connected to A is a carbon atom;

and in which linker saturated carbon atoms, which are not adjacent to heteroatom containing groups, which are not adjacent to double or triple bonds within the linker or which are not adjacent to a heteroatom, which might be part of A, can, independently of one another, be substituted by hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms; cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

and in which linker saturated carbon atoms, which are adjacent to heteroatom containing groups, which are adjacent to double or triple bonds in the linker, or which are adjacent to a heteroatom, which might be part of A, or carbon atoms being part of a double bond, can, independently of one another, be substituted by hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is hydrogen, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

R44, R45 and R46 are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms;

y is 0, 1 or 2;

R1 is hydrogen;

and

R2 is alkyl having 1, 2, 3, 4, 5 or 6 carbon atoms, phenyl, heteroaryl having 5 or 6 atoms, cycloalkyl having 3, 4, 5, 6, 7 or 8 carbon atoms or heterocyclyl having 3, 4, 5, 6, 7 or 8 atoms;

wherein alkyl is unsubstituted or substituted by 1, 2, 3, 4 or 5 radicals selected from the group consisting of F, Cl, Br, I, and $-O_m-(CH_2)_n-R26$;

m is 0 or 1;

n is 0, 1, 2 or 3;

R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from the group consisting of F, Cl, Br and I;

and wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, and cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms.

31. The method of claim 30, wherein said chemokine mediated disease is selected from acute and chronic inflammatory diseases.

32. The method of claim 30, wherein said chemokine mediated disease is selected from atherosclerosis, ischemia/reperfusion injuries, chronic obstructive pulmonary disease, asthma, and rheumatoid arthritis, adult respiratory distress syndrome, inflammatory bowel disease, ulcerative colitis, Crohn's disease, atopic dermatitis, cystic fibrosis, psoriasis, dermatitis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer.

33. A compound of the formula I as claimed in claim 1, wherein:

R1 is alkyl having 1, 2, 3, 4, 5 or 6 carbon atoms, which can be unsubstituted or substituted by 1, 2, 3, 4 or 5 radicals selected from the group consisting of F, Cl, Br, I, and $-O_m-(CH_2)_n-R26$; and R2 is alkyl having 1, 2, 3, 4, 5 or 6 carbon atoms, or phenyl, wherein alkyl is unsubstituted or substituted by 1, 2, 3, 4 or 5 radicals selected from the group consisting of F, Cl, Br, I, and $-O_m-(CH_2)_n-R26$;

R26 is hydrogen, phenyl, or cycloalkyl having 3, 4, 5 or 6 carbon atoms, in which phenyl or cycloalkyl are unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, and cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

m is 0 or 1;

n is 0, 1, 2 or 3;

or

R1 and R2 form, together with the carbon atom to which they are attached, a 3-, 4-, 5- or 6-membered carbon ring, wherein the formed ring can be saturated or partially unsaturated, and in which the formed ring can optionally be condensed to a phenyl or cycloalkyl radical having 3, 4, 5, 6, 7 or 8 carbon atoms;

wherein the formed ring and the optionally condensed phenyl or cycloalkyl radical can be unsubstituted or substituted by 1, 2, 3, 4 or 5 radicals selected from the group consisting of F, Cl, Br, I, CN, $NO_2$, $SCF_3$, $SF_5$ and alkyl having 1, 2, 3 or 4 carbon atoms.

34. A compound of the formula I as claimed in claim 1, wherein:

A is cycloalkyl having 3, 4, 5, 6, 7 or 8 carbon atoms, or phenyl, in which said phenyl can be condensed to a cycloalkyl radical having 3, 4, 5, 6, 7 or 8 atoms, or a phenyl radical;

and in which said cycloalkyl or phenyl, and the optionally condensed cycloalkyl or phenyl radical are unsubstituted or substituted by 1, 2, 3, 4 or 5 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, and —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

R1 is alkyl having 1, 2, 3, 4, 5 or 6 carbon atoms, which can be unsubstituted or substituted by 1, 2, 3, 4 or 5 radicals selected from the group consisting of F, Cl, Br, I, and —$O_m$—$(CH_2)_n$—R26; and R2 is alkyl having 1, 2, 3, 4, 5 or 6 carbon atoms, or phenyl, wherein alkyl is unsubstituted or substituted by 1, 2, 3, 4 or 5 radicals selected from the group consisting of F, Cl, Br, I, and —$O_m$—$(CH_2)_n$—R26;

R26 is hydrogen, phenyl, or cycloalkyl having 3, 4, 5 or 6 carbon atoms, in which phenyl or cycloalkyl are unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, and cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

m is 0 or 1;

n is 0, 1, 2 or 3;

or

R1 and R2 form, together with the carbon atom to which they are attached, a 3-, 4-, 5- or 6-membered carbon ring, wherein the formed ring can be saturated or partially unsaturated, and in which the formed ring can optionally be condensed to a phenyl or cycloalkyl radical having 3, 4, 5, 6, 7 or 8 carbon atoms;

wherein the formed ring and the optionally condensed phenyl or cycloalkyl radical can be unsubstituted or substituted by 1, 2, 3, 4 or 5 radicals selected from the group consisting of F, Cl, Br, I, CN, $NO_2$, $SCF_3$, $SF_5$ and alkyl having 1, 2, 3 or 4 carbon atoms.

* * * * *